United States Patent
Kitano et al.

(10) Patent No.: US 6,248,772 B1
(45) Date of Patent: Jun. 19, 2001

(54) INDOLOYLGUANIDINE DERIVATIVES

(75) Inventors: Masahumi Kitano, Takatsuki; Kazuhiro Nakano; Hideki Yagi, both of Osaka; Naohito Ohashi, Takatsuki; Atsuyuki Kojima, Takarazuka; Tsuyoshi Noguchi, Toyonaka; Akira Miyagishi, Takatsuki, all of (JP)

(73) Assignee: Sumitomo Pharmaceuticals Co., Ltd., Osaka (JP)

( * ) Notice: Subject to any disclaimer, the term of this patent is extended or adjusted under 35 U.S.C. 154(b) by 0 days.

(21) Appl. No.: 09/604,826

(22) Filed: Jun. 27, 2000

Related U.S. Application Data

(60) Division of application No. 08/544,292, filed on Oct. 17, 1995, now Pat. No. 6,169,107, which is a continuation-in-part of application No. 08/230,223, filed on Apr. 20, 1994, now abandoned.

(30) Foreign Application Priority Data

| Apr. 28, 1993 | (JP) | 5-125085 |
| Oct. 18, 1994 | (JP) | 6-280025 |

(51) Int. Cl.[7] ............... A61K 31/404; C07D 209/14
(52) U.S. Cl. .......... 514/419; 514/414; 514/415; 548/492; 548/503
(58) Field of Search .................. 548/492, 503; 514/419, 414, 415

(56) References Cited

U.S. PATENT DOCUMENTS

| 3,313,813 | 4/1967 | Cragoe, Jr. .................. 260/250 |
| 3,780,027 | 12/1973 | Cragoe, Jr. et al. .......... 260/239.6 |
| 4,140,776 | 2/1979 | Cragoe, Jr. et al. .......... 424/281 |
| 4,728,650 | 3/1988 | Eziri et al. .................. 514/253 |
| 5,091,394 | 2/1992 | Englert et al. ................ 514/331 |
| 5,395,826 | 3/1995 | Naumann et al. .............. 514/107 |
| 5,559,127 | 9/1996 | Hartman et al. .............. 514/322 |
| 5,814,654 | 9/1998 | Kitano et al. ................ 514/411 |

FOREIGN PATENT DOCUMENTS

| 6884494 | 2/1995 | (AU) . |
| 2054850 | 5/1992 | (CA) . |
| 2089439 | 8/1993 | (CA) . |
| 2089440 | 8/1993 | (CA) . |
| 2089442 | 8/1993 | (CA) . |
| 275672 | 1/1990 | (DE) . |
| 4127026 | 2/1993 | (DE) . |
| 0116360 | 8/1984 | (EP) . |
| 0416499 | 3/1991 | (EP) . |
| 0483667 | 5/1992 | (EP) . |
| 0556672 | 8/1993 | (EP) . |
| 0556673 | 8/1993 | (EP) . |
| 0556674 | 8/1993 | (EP) . |
| 0600371 | 6/1994 | (EP) . |
| 0639573 | 7/1994 | (EP) . |
| 0622356 | 11/1994 | (EP) . |
| 59-05284 | 6/1984 | (JP) . |
| WO9109849 | 7/1991 | (WO) . |
| WO94/12478 | 6/1994 | (WO) . |

OTHER PUBLICATIONS

The Chemistry of Indoles, Richard J. Sundberg, Department of Chemistry, University of Virginia Charlottesville, Virginia, 1970, Academic Press, pp. 142–159, 160–163 and 176–183.

Comprehensive Heterocyclic Chemistry, The Structure, Reactions, Synthesis and Uses of Heterocyclic Compounds, vol. 4, Alan R. Katritzky, FRS, Charles W. Reefs, FRS, Part 3, Pergamon Press, 1980.

Organic Synthesis, Collective vol. 1, Being A Revised Edition of Annual vols. I–IX, Henry Gilman, Second Edition, Seventh Printing, New York, John Wiley & Sons, 1980.

Synthesis and antifungal evaluation of some 3–phenyl–2, 5–disubstituted indoles derived from new ethyl–2–benzyl–2–[–(aryl)hydrazono] ethanoates, N, Ergenc, A. Salman, A. Gursoy & G. Bankaoglu, Pharamize 45, 346 (1990) H5.

The Synthesis of 6–n–Amylindole and 6–n–Amyltryptophan, H.R. Snyder and Harry R. Beilfuss, Noyes Chemical Lab, University of Illinois, vol. 75, 4921 1953.

Experiments on the Synthesis of Bz–Substituted Indoles and Tryptophans, Part III—The Synthesis of Four Bz–Chloro–indoles and –tryptophans, H.N. Rydon and J.C. Tweddle, [Reprint Order No. 6430], 3499, 19.

Substituted Styrenes, VI. Syntheses of the Isomeric Formylstyrenes and o– and m–Vinylbenzoic Acid, Wesley J. Dale, Leon Starr and Charles W. Strobel, Dept of Chemistry, University of Wisconsin, 26, 2225, 1961.

Facile Synthesis of Ethynylated Benzoic Acid Derivatives and Aromatic Compounds via Ethynyltrimethylsilane, William B. Austin, Norman Bilow, William J. Kelleghan and Kreisler S.Y. Lau, J. Org. Chem. 46 (11), 2280 (1981).

(List continued on next page.)

*Primary Examiner*—Laura L. Stocton
(74) *Attorney, Agent, or Firm*—Sughrue, Mion, Zinn, Macpeak & Seas, PLLC

(57) ABSTRACT

Novel indoloylguanidine derivatives shown by formula (1), wherein $R_1$ represents one or more, the same or different substituent(s) which is selected from the group consisting of a hydrogen atom, an alkyl group, a substituted alkyl group, an alkenyl group, an alkynyl group, a cycloalkyl group, a halogen atom, nitro group, an acyl group, carboxyl group, an alkoxycarbonyl group, an aromatic group, and a group shown by formula: $-OR_3$, $-NR_6R_7$, $-SO_2NR_6R_7$ or $-S(O)_nR_{40}$; and $R_2$ represents a hydrogen atom, an alkyl group, a substituted alkyl group, a cycloalkyl group, hydroxy group, an alkoxy group or a group shown by formula: $-CH_2R_{20}$; and which inhibit the $Na^+/H^+$ exchanger activity and are useful for the treatment and prevention of a disease caused by increased $Na^+/H^+$ exchanger activity, such as hypertension, arrhythmia, angina pectoris, cardiac hypertrophy, diabetes, disorders associated with ischemia or ischemic reperfusion, cerebro-ischemic disorders; or diseases caused by excessive cell proliferation.

15 Claims, No Drawings

OTHER PUBLICATIONS

Julius V. Braun, Gerhard Irmisch and Johannes Nelles: Synthesen in der Di– und Terphenylreihe (LL Mitteil) Chem. Ber. 66, 1471 (1933).

Reactions of Phosphorus Compounds. XIII. Preparations and Reactions of Cyclopropyltriphenylphosphonium Bromide, E.E. Schweizer, C.J. Berninger and J.G. Thompson, Journal of Organic Chemistry, 33 (1), 336 (1968).

Helvetica Chimica Acta—vol. 54, Fasc. 7 (1971)—Nr. 188–189, Synthetic Studies on Damascenones, G. Büchi & H. Wüest.

Die Synthese von Cyanmethylen–triphenyl–phosphoran und seine Umstezung mit aromatischen Aldehyden Jul. 28, 1960, Chem. Ber. 94, 578 (1961).

Steroselective Synthesis of α–Substituted α,β–Unsaturated Esters, Herbert O. House and Gray H. Rasmusson, Dept. of Chemistry, MIT, 26, 4278 (1961).

Phosphinemethylenes. II. Triphenylphosphineacylmethylenes, Fausto Ramirez and Samuel Dershowitz, Dept. of Chemistry, Columbia University, 22, 41 (1957).

The Stereochemistry of the Wittig Reaction With Non–Stabilized And Semistabilized Ylids, L.D. Bergelson, L.I. Barsukov and M.M. Shemyakin, Tetrahedron, 23, 2709 (1967).

Synthesis of Novel 1–Phenyl–1H–indole–2–carboxylic Acids. I. Utilization of Ullmann and Dieckmann Reactions for the Preparation of 3–Hydroxy, 3–Alkoxy, and 3–Alkyl Derivatives, Paul C. Unangst, David T. Connor, S. Russell Stabler and Robert J. Weikert, J. Heterocyclic Chem 24, 811 (1987).

The Synthesis of Certain Substituted Indoleacetic Acids, Stephen P. Findlay and Gregg Dougherty, Dept. of Chemistry, Princeton University, 13, 560 (1948).

Nitration of Indoles V. Nitration of Electronegatively Substituted Indoles. Synthesis of the Four–b=,3–Dinitroindoles, Wayland E. Noland and Kent R. Rush, J.O.C., 31, 70 (1966).

Synthetic Studies on Indoles and Related Compounds. XII. A Simple General Method for the C–3 Acylation of Ethyl Indole–2–carboxylates, Yasuoki Murakami, Masanobu Tani, Michio Suzuki, Keizo Sudoh, Midori Uesato, Kenjiro Tanaka and Yuusaku Yokoyama, Chem Pharm Bull, 33 (II) 4707 (1985).

Indole Esters as Heterocyclic Synthons. II[1]. Preparation of 1,3–Oxazino[5,6,b]indoles and 3–Substituted–pyrano[3,2–b]indoles, Paul C. Unangst and Richard E. Brown, J. Heterocyclic Chem 21, 283 (1984).

Pyridol [1'2':1,2]pyrimido[5,4–d]indoles. A New Heterocyclic Ring System, Paul C. Unangst, J. Heterocyclic Chem, 20, 495 (1983).

Synthesis of Novel 1–Phenyl–1–H–indole 2–carboxylic Acids. II. Preparation of 3–Dialkylamino, 3–Alkylthio, 3–Alkylsulfinyl, and 3–Alkylsulfonyl Derivatives, Paul C. Unangst, David T. Connor and S. Russell Stable, J. Heterocyclic Chem. 24, 817 (1987).

The Phenylcarbene Rearrangement Revisited, Peter P. Gaspar, Jong–Pyng Hsu and Sarangan Chari, Tetrabedron, 41 (8), 1479 (1985).

Antimalarial Phenanthrene Amino Alcohols. 3. Halogen–Containing 9–Phenanthrenemethanols, Edward A. Nodiff, Andrew J. Saggiomo, Keiichi Tanabe, Eugene H. Chen, Masafu Shinbo, Mahesh P. Tyagi, Atsuto Kozuka, Hirotaka Otomasu, Basant L. Verna and David Goff, J. of Medicinal Chemistry, 18(10), 1011 (1975).

K. v. Anwers und W Mauss: Zur Kenntnis der Reaktionen von Friedel und Crafts, Fries und Gattermann, Chem. Ber., 61, 1495 (1928).

The Addition of Ethyl Diazoacetate to Prehnitene, Lee Irvin Smith and Courtland L. Agre J. Amer. Chem. Soc. 60, 648 (1938).

Arnold Reissert: Umwandlungen des o–Nitrobenzyl–malonsäureesters. L. Alkalische Verseifung, Synthese neuer Indolabkömmlinge, Chem. Ber. 29, 639, (1996).

Applicability of the Hammett Equation to the Indole System: Acidity of Indole–3–carboxylic Acids, Marvin S. Melzer, J.O.C., 27, 496 (1962).

The Chemistry of Indoles, Richard J. Sundberg, Department of Chemistry, University of Virginia, Charlottesville, Virginia, 1970, Academic Press, Organic Chemistry, A Series of Monographs, pp. 32–37.

An Efficient Synthesis of Indole, Journal of the American Chemical Society / 99 (10) 3532 (1977).

Organic Syntheses, Collective vol. 5, Henry E. Baumgarten, Copyright 1973 by John Wiley & Sons, Inc. pp. 1060–1063.

Condensed Heteroaromatic Ring Systems. XXIV.[1,2] Palladium–Catalyzed Cyclization of 2–Substituted Phenylacetylenes in the Presence of Carbon Monoxide, Yoshinori Kondo, Futoshi Shiga, Naoko Murata, Takao Sakamoto and Hiroshi Yamanaka, Tetrabebron, 50 (41), 11803 (1994).

Fischer Indole Synthesis of 3–Acyl–and–3–Alkoxy–carbonylindoles, Keith Mills, Ibtisam K. Al Khawaja, Fowzia S. Al–Saleh and John A. Joule, J.C.S. Perkins I, 636, 1981.

Condensed Heteraromatic Ring Systems: VXII: Palladium–Catalyzed Cyclization of β–(2–Halophenyl)amino Substituted α,β–Unsaturated Ketones and Esters to 2,3–Disubsituted Indoles, Takao Sakamoto, Tatsuo Nagano, Yoshinori Kondo, Hiroshi Yamanaka, Synthesis 215, (1990).

Reactivite D'Enediamines–1, Cycliques: Acylation Des Dialkylamino–2 Indoles; Tetrahedron Letters No. 32, 3049–3052 (1971).

Synthesis of Indoles by catalytic reduction of o–mitrodenzyl cyanides, 80,4622, 1958.

Protective Groups In Organic Synthesis, Second Edition, Theodora W. Greene and Peter G.M. Wuts, John Wiley & Sons, Inc., pp. 178–183, 1980.

New Synthesis and Some Selected Reactions of The Potential Ergot Alkaloid Precursor, Alan P. Korzikowski, Hitoshi Ishida and Yon–Yih Chen, J. Org. Chem, 45, 3350–3352 (1980).

Formylation of Phenols with Electron–withdrawing Groups in Strong Acids, Synthesis of Substituted Salicylaldehyde, Yuji Suzuki and Hiroshi Takahashi, Chem. Pharm. Bull. 31 (5), 1751 (1983).

Coordination in Solutions. II. Acid Dissociation Constants in Water and Structural Reassignments of the Isomeric Chlorosalicylaldehydes, J.O.C. 29, 2693 (1964).

P. Russel et al., "The Reaction of Aromatic Nitriles with Guanidine", Journal of the American Chemical Society, vol. 72, 1950, pp. 4922–2925.

J. Bicking et al., "Pyrazine Diuretics. III. 5– and 6–Alkyl, – Cycloalkyl, and –Aryl Derivatives of N–Amidino–3–aminopyrazinecarboxamides", J. Med. Chem., vol. 10, 1967, pp. 598–602.

T. George et al., "Synthesis of 3–Amino–2–ethoxycrbonyl–4–quinazolone & Related Compounds: Use of Diethyl Oxalate in Quinazolone Synthesis", *Indian Journal of Chemistry*, vol. 9, Aug. 1971, pp. 755–758.

E. Hawes et al., "2,3–Disubstituted 1,8–Naphthyridines as Potential Diuretic Agents. 2. 5,7–Dimethyl Derivatives", *Journal of Medicinal Chemistry*, vol. 20, No. 6, 1977, pp. 838–841.

D. Gorecki et al., "2,3–Disubstituted 1,8–Naphthyridines as Potential Diuretic Agents", *Journal of Medicinal Chemistry*, vol. 20, No. 1, 1977, pp. 124–128.

H. L. Davis et al., "2,3–Disubstituted 1,8–naphthyridines as potential diuretic agents. 3.4– and 7–Phenyl derivatives", *Eur. J. Med. Chem.—Chim. Ther.*, vol. 20, No. 4, 1985, pp. 381–383.

E. Hawes et al., "2,3–Disubstituted 1,6–Naphthyridines as Potential Diuretic Agents", *Journal of Medicinal Chemistry*, vol. 16, No. 7, 1973, pp. 849–853.

J. Clark et al., "Heterocyclic Studies. Part 43. Thieno[2,3–d:4,5–d']dipyrimidines", *J. Chem. Soc. Perkin Trans. I*, 1984, pp. 2005–2008.

A. Stolyarchuk et al., "Synthesis of furoylguanidines and comparison of their pharmacological . . . properties of furoylureas", *Khim.–Farm. Zh.*, vol. 10, No. 7, 1976, pp. 72–77 with Chemical Abstract.

W. Hoffman et al., "(Acylaryloxy)acetic Acid Diuretics. 3. 2,3–Dihydro–5–acyl–2– . . . New Class of Uricosuric Diuretics", *J. Med. Chem.*, vol. 24, 1981, pp. 865–873.

W. Ried et al., "Synthesis and reactions of novel 3–chloro–N–[chloro(dialkylamino) . . . carboxamides", *Chem. Ber.*, vol. 113, No. 7, 1980, pp. 2583–2588.

T. Kleyman et al., "Amiloride and Its Analogs as Tools in the Study of Ion Transport", *J. Membrane Biol.*, vol. 105, 1988, pp. 1–21.

*J. Mol. Cell. Cardiol.*, vol. 24, Suppl. I, 1992, S.92.

*J. Mol. Cell. Cardiol.*, vol. 24, Suppl. I, 1992, S.117.

Compound registered as No. 18322–34–4 in Chemical Abstract, 1993.

Merck Index, 11th Edition, 1987, p. 67.

M. Frankel et al., "The Synthesis of Gongrine and Some Other Amidinoureido–acids," Journal of the Chemical Society, 1967, pp. 2698–2699.

INDOLOYLGUANIDINE DERIVATIVES

This is a divisional of application Ser. No. 08/544,292 filed Oct. 17, 1995 now U.S. Pat. No. 6,169,107, which is a continuation-in-part of application Ser. No. 08/230,223 filed Apr. 20, 1994 now abandoned, the disclosures of which are incorporated herein by reference.

BACKGROUND OF THE INVENTION

1. Field of the Invention

The present invention relates to novel indoloylguanidine derivatives. The present invention also relates to sodium/proton ($Na^+/H^+$) exchanger inhibitors comprising the indoloylguanidine derivatives as the active component which are useful for the treatment and prevention of diseases caused by increased sodium/proton ($Na^+/H^+$) exchanger activity.

2. Related Art Statement

Certain polycyclic aroylguanidine derivatives are known as those having polycondensed rings, for example, a naphthalene, 9,10-dihydroanthracene, benzofuran, 2,3-dihydrobenzofuran, benzothiophene, benzothiazole, methylenedioxybenzene, pyridothiophene, pyrimidothiophene, quinoline, 1,6-naphthylidine, 1,8-naphthylidine, 3,4-dihydrobenzopyran, 3,4-dihydroquinazolin-4-one, 1,2,3,4-tetrahydroquinazolin-2-one, quinoxaline, 5,6,7,8-tetrahydroquinoxaline, benzoazepine, benzotriazepine, benzimidazolothiazine, benzopyranopyran or benzocarbazole ring. As one of the aroylguanidine derivatives having indole rings there is known 1-guanidinocarbonyltryptophane but this compound is merely registered in Chemical Abstracts under Registered No. 18322-34-4, without any reference to its source.

Turning to some monocyclic aroylguanidine derivatives, pyrazinoylguanidine derivatives represented by, e.g., Amiloride, are known to exhibit the sodium/proton ($Na^+/H^+$) exchanger inhibition activity and anti-arrhythmic activity, cf., J. Membrane Biol., Vol. 105, 1 (1988); and Circulation, Vol. 79, 1257 (1989). Recent reports also reveal that benzoylguanidine derivatives possess the sodium/proton ($Na^+/H^+$) exchanger inhibition and anti-arrhythmic activities, cf., J. Mol. Cell. Cardiol., Vol. 24, Supple. I, S. 92 (1992); ibid., Vol. 24, Suppl. I, S. 117 (1992); and Japanese Patent KOKAI Nos. 3-106858 and 5-339228.

SUMMARY OF THE INVENTION

An object of the present invention is to provide novel indoloylguanidine derivatives which inhibit the sodium/proton ($Na^+/H^+$) exchanger activity and are therefore useful for the treatment and prevention of diseases caused by increased sodium/proton ($Na^+/H^+$) exchanger activity, for example, hypertension, arrhythmia, angina pectoris, cardiac hypertrophy, diabetes mellitus, organ disorders associated with ischemia or ischemic reperfusion such as cardiac ischemic reperfusion injury (e.g., heart muscle ischemic reperfusion-associated disorders, acute renal failure, disorders induced by surgical treatment such as organ transplantation or percutaneous transluminal coronary angioplasty (PTCA), cerebro-ischemic disorders such as disorders associated with cerebral infarction, disorders caused after cerebral apoplexy as sequelae, or cerebral edema; or diseases caused by excessive cell proliferation such as proliferation of fibroblast, proliferation of smooth muscle cells or proliferation of mesangium cells, which diseases are, e.g., atherosclerosis, pulmonary fibrosis, hepatic fibrosis, renal fibrosis, glomerular nephrosclerosis, organ hypertrophy, prostatic hypertrophy, diabetic complications or recurrent stricture after PTCA, or diseases caused by endothelial cell injury.

Another object of the present invention is to provide compositions comprising the indoloylguanidine derivatives as the active component which inhibit the sodium/proton ($Na^+/H^+$) exchanger activity and are useful for the prevention and treatment of diseases caused by abnormal sodium/proton ($Na^+/H^+$) exchanger activity.

The present invention relates to indoloylguanidine derivatives represented by the following formula (1):

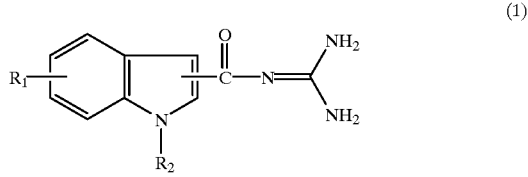

wherein:

$R_1$ represents one or more, the same or different substituent(s) which is selected from the group consisting of a hydrogen atom, a $C_1$–$C_8$ alkyl group, a substituted $C_1$–$C_8$ alkyl group, a $C_2$–$C_6$ alkenyl group, a $C_2$–$C_6$ alkynyl group, a $C_3$–$C_7$ cycloalkyl group, a halogen atom, nitro, a $C_2$–$C_8$ alkanoyl group, an arylalkanoyl group having carbon atoms up to 10, an aroyl group having carbon atoms up to 11, carboxyl, a $C_2$–$C_6$ alkoxycarbonyl group, an aromatic group, a group shown by formula: —$OR_3$, —$NR_6R_7$, —$SO_2NR_6R_7$ or —$S(O)_nR_{40}$, and a group shown by formula:

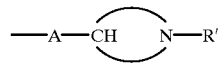

wherein A represents an oxygen atom or a group shown by formula: —$S(O)_n$— or —$N(R_{50})$— (in which $R_{50}$ is a hydrogen atom or a $C_1$–$C_8$ alkyl group; R' represents a hydrogen atom, a $C_1$–$C_8$ alkyl group or a substituted $C_1$–$C_8$ alkyl group); and the ring represents a saturated 3 to 8-membered hetero ring containing one nitrogen atom;

$R_2$ represents a hydrogen atom, a $C_1$–$C_8$ alkyl group, a substituted $C_1$–$C_8$ alkyl group, a $C_3$–$C_7$ cycloalkyl group, hydroxy, a $C_1$–$C_6$ alkoxy group, an aromatic group or a group shown by formula: —$CH_2R_{20}$;

$R_3$ represents a hydrogen atom, a $C_1$–$C_8$ alkyl group, a substituted $C_1$–$C_8$ alkyl group, a $C_3$–$C_7$ cycloalkyl group, an aromatic group or a group shown by formula: —$CH_2R_{30}$, in which $R_{30}$ represents an alkenyl group or an alkynyl group;

each of $R_6$ and $R_7$ independently represents a hydrogen atom, a $C_1$–$C_8$ alkyl group, a substituted $C_1$–$C_8$ alkyl group, a $C_3$–$C_7$ cycloalkyl group, a $C_2$–$C_8$ alkanoyl group, an arylalkanoyl group having carbon atoms up to 10, an aroyl group having carbon atoms up to 11, an aromatic group or a group shown by formula: —$CH_2R_{60}$ (in which $R_{60}$ represents a $C_2$–$C_6$ alkenyl group or a $C_2$–$C_6$ alkynyl group); or $R_6$ and $R_7$ are combined together to form a saturated 5- to 7-membered cyclic amino group which may contain other hetero atom(s) in the ring thereof;

$R_{40}$ represents a $C_1$–$C_8$ alkyl group, a substituted $C_1$–$C_8$ alkyl group or an aromatic group;

n represents 0, 1 or 2; and,

R$_{20}$ represents a C$_2$–C$_6$ alkenyl group or a C$_2$–C$_6$ alkynyl group;

in which:

the substituent(s) of the substituted C$_1$–C$_8$ alkyl group means a halogen atom, hydroxy, a C$_1$–C$_6$ alkoxy group, cyano, carboxyl, a C$_2$–C$_6$ alkoxycarbonyl group, a C$_2$–C$_8$ alkanoyl group, an arylalkanoyl group having carbon atoms up to 10, an aroyl group having carbon atoms up to 11, an aromatic group, —CONR$_4$R$_5$ in which each of R$_4$ and R$_5$ independently represents a hydrogen atom or a C$_1$–C$_8$ alkyl group or R$_4$ and R$_5$ are combined together to form a saturated 5- to 7-membered cyclic amino group which may contain other hetero atom(s) in the ring; —NR$_6$R$_7$; or a group shown by:

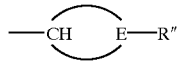

in which:

E represents a nitrogen atom or a CH group and

R" represents a hydrogen atom, a C$_1$–C$_8$ alkyl group or a substituted C$_1$–C$_8$ alkyl group substituted with hydroxy, a C$_1$–C$_6$ alkoxy group, cyano, carboxyl, a C$_2$–C$_6$ alkoxycarbonyl group, a C$_2$–C$_8$ alkanoyl group, an arylalkanoyl group having carbon atoms up to 10, an aroyl group having carbon atoms up to 11, an aromatic group, a group shown by —NR$_6$R$_7$, or a group shown by —CONR$_4$R$_5$, in which each of R$_4$ and R$_5$ independently represents a hydrogen atom or a C$_1$–C$_8$ alkyl group or R$_4$ and R$_5$ are combined together to form a saturated 5- to 7-membered cyclic amino group which may contain other hetero atom(s) therein; and the ring of

is a 3- to 8-membered saturated aliphatic ring or saturated hetero ring containing one nitrogen atom;

all of the aromatic groups hereinabove means an aryl group having carbon atoms up to 10, a 5- or 6-membered hetero-aryl group containing 1 to 4 nitrogen atom(s), a 5- or 6-membered hetero-aryl group containing 1 to 2 nitrogen atom(s) and one oxygen atom or one sulfur atom, or furyl; and, all of the aromatic groups hereinabove may be substituted with a substituent selected from the group consisting of a C$_1$–C$_8$ alkyl group, a substituted C$_1$–C$_8$ alkyl group, a halogen atom, nitro, a C$_2$–C$_6$ alkoxy-carbonyl group, carboxyl and a group selected from the group shown by formulae: —OR$_3$, —NR$_6$R$_7$, —CONR$_6$R$_7$, —SO$_2$NR$_6$R$_7$ and —S(O)$_n$R$_{40}$;

provided that R$_1$ and the guanidinocarbonyl group may be substituted at any one of the 5- and 6-membered rings of the indole nucleus; or, a pharmaceutically acceptable acid addition salt thereof.

The present invention also relates to pharmaceutical compositions comprising as an effective ingredient the indoloylguanidine derivatives described above, which inhibit the sodium/proton exchanger system.

DETAILED DESCRIPTION OF THE PREFERRED EMBODIMENTS

Among the indoloylguanidine derivatives of formula (1), the compounds represented by formulae (2) and (1') are particularly preferred; the compounds represented by the following general formulae (2) and (1') and the pharmaceutical compositions comprising these compounds are given below as the embodiments of the present invention.

The indoloylguanidine derivatives represented by general formula (2):

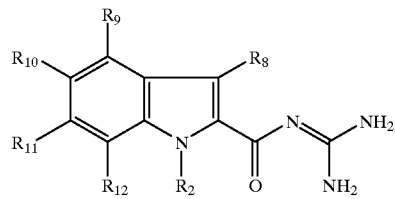

(2)

wherein:

each of R$_8$, R$_9$, R$_{10}$, R$_{11}$ and R$_{12}$ independently represents a hydrogen atom, a C$_1$–C$_8$ alkyl group, a substituted C$_1$–C$_8$ alkyl group, a C$_2$–C$_6$ alkenyl group, a C$_2$–C$_6$ alkynyl group, a C$_3$–C$_7$ cycloalkyl group, a halogen atom, nitro, a C$_2$–C$_8$ alkanoyl group, an arylalkanoyl group having carbon atoms up to 10, an aroyl group having carbon atoms up to 11, carboxyl, a C$_2$–C$_6$ alkoxycarbonyl group, an aromatic group, a group shown by formula: —OR$_3$, —NR$_6$R$_7$, —SO$_2$NR$_6$R$_7$ or —S(O)$_n$R$_{40}$, or a group shown by formula:

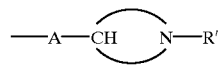

wherein A represents an oxygen atom or a group shown by formula: —S(O)$_n$— or —N(R$_{50}$)— (in which R$_{50}$ is a hydrogen atom or a C$_1$–C$_8$ alkyl group; R' represents a hydrogen atom, a C$_1$–C$_8$ alkyl group or a substituted C$_1$–C$_8$ alkyl group); and the ring represents a saturated 3 to 8-membered hetero ring containing one nitrogen atom;

R$_2$ represents a hydrogen atom, a C$_1$–C$_8$ alkyl group, a substituted C$_1$–C$_8$ alkyl group, a C$_3$–C$_7$ cycloalkyl group, hydroxy, a C$_1$–C$_6$ alkoxy group, an aromatic group or a group shown by formula: —CH$_2$R$_{20}$;

R$_3$ represents a hydrogen atom, a C$_1$–C$_8$ alkyl group, a substituted C$_1$–C$_8$ alkyl group, a C$_3$–C$_7$ cycloalkyl group, an aromatic group or a group shown by formula: —CH$_2$R$_{30}$ in which R$_{30}$ represents a C$_2$–C$_6$ alkenyl group or an alkynyl group;

each of R$_6$ and R$_7$ independently represents a hydrogen atom, a C$_1$–C$_8$ alkyl group, a substituted C$_1$–C$_8$ alkyl group, a C$_3$–C$_7$ cycloalkyl group, an aromatic group or a group shown by formula: —CH$_2$R$_{60}$ (in which R$_{60}$ represents a C$_2$–C$_6$ alkenyl group or a C$_2$–C$_6$ alkynyl group); or R$_6$ and R$_7$ are combined together to form a saturated 5- to 7-membered cyclic amino group which may contain other hetero atom(s) in the ring thereof;

R$_{40}$ represents an alkyl group or a substituted alkyl group;

n represents 0, 1 or 2; and,

R$_{20}$ represents a C$_2$–C$_6$ alkenyl group or a C$_2$–C$_6$ alkynyl group;

in which:

the substituent(s) of the substituted C$_1$–C$_8$ alkyl group means a halogen atom, hydroxy, a C$_1$–C$_6$ alkoxy group, cyano, carboxyl, a C$_2$–C$_6$ alkoxycarbonyl group, a C$_2$–C$_8$ alkanoyl group, an arylalkanoyl group having carbon atoms up to 10, an aroyl group having carbon atoms up to 11, an aromatic group, and —CONR$_4$R$_5$ in which each of R$_4$ and R$_5$ independently represents a hydrogen atom or a C$_1$–C$_8$ alkyl group or R$_4$ and R$_5$ are combined together to form a saturated 5- to 7-membered cyclic amino group which may contain other hetero atom(s) in the ring; —NR$_6$R$_7$; or a group shown by:

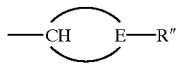

in which:

E represents a nitorgen atom or a CH group and

R" represents a hydrogen atom, a C$_1$–C$_8$ alkyl group or a substituted C$_1$–C$_8$ alkyl group substituted with hydroxy, a C$_1$–C$_6$ alkoxy group, cyano, carboxyl, a C$_2$–C$_6$ alkoxycarbonyl group, a C$_2$–C$_8$ alkanoyl group, an arylalkanoyl group having carbon atoms up to 10, an aroyl group having carbon atoms up to 11, an aromatic group, a group shown by —NR$_6$R$_7$, or a group shown by —CONR$_4$R$_5$, in which each of R$_4$ and R$_5$ independently represents a hydrogen atom or a C$_1$–C$_8$ alkyl group or R$_4$ and R$_5$ are combined together to form a saturated 5- to 7-membered cyclic amino group which may contain other hetero atom(s) therein; and the ring of

is a 3- to 8-membered saturated aliphatic ring or saturated hetero ring containing one nitrogen atom;

all of the aromatic groups hereinabove means an aryl group having carbon atoms up to 10, a 5- or 6-membered hetero-aryl group containing 1 to 4 nitrogen atom(s), a hetero-aryl group containing 1 to 2 nitrogen atom(s) and one oxygen atom or one sulfur atom, or furyl; and, all of the aromatic groups hereinabove may be substituted with a substituent selected from the group consisting of a C$_1$–C$_8$ alkyl group, a substituted C$_1$–C$_8$ alkyl group, a halogen atom, nitro, a C$_2$–C$_6$ alkoxycarbonyl group, carboxyl and a group selected from the group shown by formulae: —OR$_3$, —NR$_6$R$_7$, —CONR$_6$R$_7$, —SO$_2$NR$_6$R$_7$ and —S(O)$_n$R$_{40}$.

Indoloylguanidine derivative represented by general formula (1'):

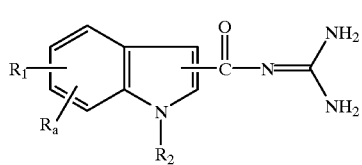

wherein:

R$_1$ represents one or more, the same or different substituent(s) which is selected from the group consisting of a hydrogen atom, a C$_1$–C$_8$ alkyl group, a substituted C$_1$–C$_8$ alkyl group, a C$_2$–C$_6$ alkenyl group, a C$_2$–C$_6$ alkynyl group, a C$_3$–C$_7$ cycloalkyl group, a halogen atom, nitro, a C$_2$–C$_8$ alkanoyl group, an arylalkanoyl group having carbon atoms up to 10, an aroyl group having carbon atoms up to 11, carboxyl, a C$_2$–C$_6$ alkoxycarbonyl group, an aromatic group, a group shown by formula: —OR$_3$, —NR$_6$R$_7$, —SO$_2$NR$_6$R$_7$ or —S(O)$_n$R$_{40}$, and a group shown by formula:

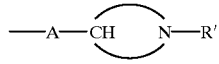

wherein A represents an oxygen atom or a group shown by formula: —S(O)$_n$— or —N(R$_{50}$)— (in which R$_{50}$ is a hydrogen atom or a C$_1$–C$_8$ alkyl group; R' represents a hydrogen atom, a C$_1$–C$_8$ alkyl group or a substituted C$_1$–C$_8$ alkyl group); and the ring represents a saturated 3 to 8-membered hetero ring containing one nitrogen atom;

R$_2$ represents a hydrogen atom, a C$_1$–C$_8$ alkyl group, a substituted C$_1$–C$_8$ alkyl group, a C$_3$–C$_7$ cycloalkyl group, hydroxy, a C$_1$–C$_6$ alkoxy group, a group shown by formula: —CH$_2$R$_{20}$ or an aromatic group;

when R$_2$ is an aromatic group, R$_a$ represents R$_1$;

when R$_2$ is a hydrogen atom, a C$_1$–C$_8$ alkyl group, a substituted C$_1$–C$_8$ alkyl group, a C$_3$–C$_7$ cycloalkyl group, hydroxy, a C$_1$–C$_6$ alkoxy group or —CH$_2$R$_{20}$;

R$_a$ may be one or more substituent(s), which may be the same or different and represents an aryl-C$_1$–C$_8$ alkyl group or a hetero-aryl-C$_1$–C$_8$ alkyl group, in which the aryl moiety in these groups contains a substituent(s) selected from the group consisting of a C$_1$–C$_8$ alkyl group, a substituted C$_1$–C$_8$ alkyl group, a C$_2$–C$_6$ alkoxycarbonyl group, carboxyl, —CONR$_6$R$_7$, —SO$_2$NR$_6$R$_7$ and —S(O)$_n$R$_{40}$; or, R$_a$ represents a group shown by formula: —A—R$_b$, in which A represents an oxygen atom or a group shown by formula: —S(O)$_n$— or —N(R$_{50}$)— (in which R$_{50}$ is a hydrogen atom or a C$_1$–C$_8$ alkyl group); R$_b$ represents an aryl group or a hetero-aryl group in which the aryl moiety and the hetero-aryl group may contain a substituent(s) selected from the group consisting of a C$_1$–C$_8$ alkyl group, a substituted C$_1$–C$_8$ alkyl group, a halogen atom, nitro, a C$_2$–C$_6$ alkoxycarbonyl group, carboxyl, —OR$_3$, —NR$_6$R$_7$, —CONR$_6$R$_7$, —SO$_2$NR$_6$R$_7$ and —S(O)$_n$R$_{40}$; or, R$_a$ represents a group shown by formula:

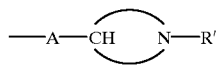

wherein A represents an oxygen atom or a group shown by formula: —S(O)$_n$— or —N(R$_{50}$)— (in which R$_{50}$ is a hydrogen atom or a C$_1$–C$_8$ alkyl group); R' represents a hydrogen atom, a C$_1$–C$_8$ alkyl group or a substituted C$_1$–C$_8$ alkyl group; and the ring represents a saturated 3 to 8-membered hetero ring containing one nitrogen atom; or, R$_a$ represents a group shown by formula:

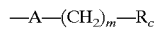

wherein A represents an oxygen atom or a group shown by formula: —S(O)$_n$— or —N(R$_{50}$)— (in which R$_{50}$ is a hydrogen atom or a C$_1$–C$_8$ alkyl group); R$_c$ represents an aryl group or a hetero-aryl group in which the aryl moiety and the hetero-aryl group contain a substituent(s) selected from the group consisting of a $C_1$–$C_8$ alkyl group, a substituted $C_1$–$C_8$ alkyl group, a $C_2$–$C_6$ alkoxycarbonyl group, carboxyl, —$CONR_6R_7$—, —$OR_{31}$, —$SO_2NR_6R_7$ and —$S(O)_nR_{40}$; m represents 1 to 8; and $R_{31}$ represents a substituted $C_1$–$C_8$ alkyl group, a $C_3$–$C_7$ cycloalkyl group or —$CH_2R_{30}$ (in which $R_{30}$ represents a $C_2$–$C_6$ alkenyl group or a $C_2$–$C_6$ alkynyl group);

$R_3$ represents a hydrogen atom, a $C_1$–$C_8$ alkyl group, a substituted $C_1$–$C_8$ alkyl group, a $C_3$–$C_7$ cycloalkyl group, an aromatic group, or a group shown by formula: —$CH_2R_{30}$ in which $R_{30}$ represents a $C_2$–$C_6$ alkenyl group or a $C_2$–$C_6$ alkynyl group;

each of $R_6$ and $R_7$ independently represents a hydrogen atom, a $C_1$–$C_8$ alkyl group, a substituted $C_1$–$C_8$ alkyl group, a $C_3$–$C_7$ cycloalkyl group, a $C_2$–$C_8$ alkanoyl group, an arylalkanoyl group having carbon atoms up to 10, an aroyl group having carbon atoms up to 11, an aromatic group or a group shown by formula: —$CH_2R_{60}$ (in which $R_{60}$ represents a $C_2$–$C_6$ alkenyl group or a $C_2$–$C_6$ alkynyl group); or $R_6$ and $R_7$ are combined together to form a saturated 5- to 7-membered cyclic amino group which may contain other hetero atom(s) in the ring thereof;

$R_{40}$ represents a $C_1$–$C_8$ alkyl group or a substituted $C_1$–$C_8$ alkyl group;

n represents 0, 1 or 2; and, $R_{20}$ represents a $C_2$–$C_6$ alkenyl group or a $C_2$–$C_6$ alkynyl group;

in which;

the substituent(s) of the substituted $C_1$–$C_8$ alkyl group means a halogen atom, hydroxy, a $C_1$–$C_6$ alkoxy group, cyano, carboxyl, a $C_2$–$C_6$ alkoxycarbonyl group, a $C_2$–$C_8$ alkanoyl group, an arylalkanoyl group having carbon atoms up to 10, an aroyl group having carbon atoms up to 11, an aromatic group, and —$CONR_4R_5$ in which each of $R_4$ and $R_5$ independently represents a hydrogen atom or a $C_1$–$C_8$ alkyl group or $R_4$ and $R_5$ are combined together to form a saturated 5- to 7-membered cyclic amino group which may contain other hetero atom(s) in the ring; —$NR_6R_7$; or a group shown by:

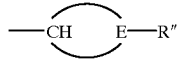—R″ in which:

E represents a nitorgen atom or a CH group and

R″ represents a hydrogen atom, a $C_1$–$C_8$ alkyl group or a substituted $C_1$–$C_8$ alkyl group substituted with hydroxy, a $C_1$–$C_6$ alkoxy group, cyano, carboxyl, a $C_2$–$C_6$ alkoxycarbonyl group, a $C_2$–$C_8$ alkanoyl group, an arylalkanoyl group having carbon atoms up to 10, an aroyl group having carbon atoms up to 11, an aromatic group, a group shown by —$NR_6R_7$, or a group shown by —$CONR_4R_5$, in which each of $R_4$ and $R_5$ independently represents a hydrogen atom or a $C_1$–$C_8$ alkyl group or R4 and $R_5$ are combined together to form a saturated 5- to 7-membered cyclic amino group which may contain other hetero atom(s) therein; and the ring of

is a 3- to 8-membered saturated aliphatic ring or saturated hetero ring containing one nitrogen atom;

all of the aromatic groups hereinabove means an aryl group having carbon atoms up to 10, a 5- or 6-membered hetero-aryl group containing 1 to 4 nitrogen atom(s), a hetero-aryl group containing 1 to 2 nitrogen atom(s) and one oxygen atom or one sulfur atom, or furyl; and, all of the aromatic groups hereinabove may be substituted with a substituent selected from the group consisting of a $C_1$–$C_8$ alkyl group, a substituted $C_1$–$C_8$ alkyl group, a halogen atom, nitro, a $C_2$–$C_6$ alkoxycarbonyl group, carboxyl and a group selected from the group shown by formulae: —$OR_3$, —$NR_6R_7$, —$CONR_6R_7$, —$SO_2NR_6R_7$ and —$S(O)_nR_{40}$; provided that $R_1$, $R_a$ and the guanidinocarbonyl group may be substituted at any one of the 5- and 6-membered rings of the indole nucleus.

A further preferred embodiment of the present invention is the indoloylguanidine derivatives represented by formula (2) above in which at least one of $R_8$, $R_9$, $R_{10}$, $R_{11}$ and $R_{12}$ is a group shown by $R_a$.

The respective groups in the indoloylguanidine derivatives of the present invention are described below in detail.

The alkyl group refers to a straight or branched alkyl group having carbon atoms of 8 or less, for example, methyl, ethyl, propyl, 2-propyl, butyl, 2-butyl, 2-methylpropyl, 1,1-dimethylethyl, pentyl, hexyl, heptyl and octyl.

The alkenyl group refers to an alkenyl group having carbon atoms up to 6, e.g., vinyl, allyl, propenyl, 2-propenyl, butenyl, pentenyl and hexenyl.

The alkynyl group refers to an alkynyl group having 2 to 6 carbon atoms, e.g., ethynyl, propargyl, butynyl and pentynyl.

The cycloalkyl group refers to a cycloalkyl group having 3 to 7 carbon atoms, e.g., cyclopropyl, cyclobutyl, cyclopentyl, cyclohexyl and cycloheptyl.

Typical examples of the halogen atom include fluorine, chlorine and bromine.

The acyl group refers to a straight or branched alkanoyl group having carbon atoms up to 8, e.g., acetyl, propanoyl and 2-methylpropanoyl; an arylalkanoyl group having carbon atoms up to 10, e.g., phenylacetyl and phenylpropanoyl; and an aroyl group having carbon atoms of 11 or less, e.g., benzoyl, 1-naphthoyl and 2-naphthoyl.

The alkoxycarbonyl group refers to a straight or branched alkoxycarbonyl group having carbon atoms up to 6, e.g., methoxycarbonyl, ethoxycarbonyl, propoxycarbonyl and 2-propoxycarbonyl.

The aromatic group refers to an aryl or hetero-aryl group which may have a substituent. Examples of the aryl group are those having carbon atoms up to 10, e.g., phenyl, tolyl or naphthyl, and examples of the hetero-aryl group are a 5- or 6-membered aromatic group containing 1 to 4 nitrogen atoms or a 5- or 6-membered aromatic ring containing 1 to 2 nitrogen atoms and one oxygen atom or one sulfur atom, e.g., 2-, 3- or 4-pyridyl, imidazolyl, triazolyl, tetrazolyl, 2- or 3-furyl, 2- or 3-thienyl, l-, 3- or 4-oxazolyl, and 3-, 4- or 5-isoxazolyl.

Examples of the substituent in the substituted aryl or hetero-aryl group include an alkyl group, a substituted alkyl group, a halogen atom, nitro, an alkoxycarbonyl group, carboxyl and a group shown by formula: —$OR_3$, —$NR_6R_7$, —$CONR_6R_7$, —$SO_2NR_6R_7$ or —$S(O)_nR_{40}$.

Where $R_1$ is a group shown by formula: —$OR_3$ wherein $R_3$ is an aromatic group, representative examples of the —$OR_3$ group include phenoxy and a substituted phenoxy group. Examples of the substituted phenoxy group are a phenoxy group substituted with nitro, —$NR_6R_7$ (in which $R_6$ and $R_7$ are typically a hydrogen atom or an alkyl group) or a substituted alkyl group (the substituent of which is exemplified by hydroxy or —$NR_6R_7$). Specific examples of the substituted phenoxy group are o-, m- or p-nitrophenoxy, o-, m- or p-aminophenoxy, o-, m- or p-(dimethylamino)phenoxy, o-, m- or p-(aminomethyl)phenoxy and o-, m- or p-(dimethylaminomethyl)-phenoxy.

The alkoxy group refers to a straight or branched alkoxy group having carbon atoms up to 6, e.g., methoxy, ethoxy, isopropoxy and tert-butoxy.

As the saturated 5- to 7-membered cyclic amino group which is formed by combining $R_6$ and R7 together and may contain other hetero atoms therein, there are, for example, a 5- to 7-membered cyclic group containing 1 to 3 nitrogen atoms and a 5- to 7-membered cyclic group containing one nitrogen atom and one oxygen atom. Specific examples of such cyclic amino group include 1-pyrrolidinyl, piperidino, 1-piperazinyl, morpholino, and 4-methylpiperazinyl.

Examples of the substituent in the substituted alkyl group include a cycloalkyl group, a halogen atom, hydroxy, an alkoxy group, cyano, carboxyl, an alkoxycarbonyl group, an acyl group, an aromatic group, or a group shown by formula: —$CONR_4R_5$, wherein each of $R_4$ and $R_5$ independently represents hydrogen atom or an alkyl group, or $R_4$ and $R_5$ are combined together to form a saturated 5- to 7-membered cyclic amino group which may contain other hetero atoms in the ring; —$NR_6R_7$; or a group shown by formula:

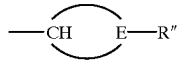

wherein:
E represents a nitrogen atom or a CH group and
R" represents a hydrogen atom, an alkyl group or a substituted alkyl group substituted with hydroxy, a $C_1$–$C_6$ alkoxy group, cyano, carboxy, a $C_2$–$C_6$ alkoxycarbonyl group, a $C_2$–$C_8$ alkanoyl group, an arylalkanoyl group having carbon atoms up to 10, an aroyl group having carbon atoms up to 11, an aromatic group, a group shown by —$NR_6R_7$, or a group shown by —$CONR_4R_5$, in which each of $R_4$ and $R_5$ independently represents a hydrogen atom or a $C_1$–$C_8$ alkyl group or $R_4$ and $R_5$ are combined together to form a saturated 5- to 7-membered cyclic amino group which may con a n other hetero atom(s) therein; and the ring of

is a 3- to 8-membered saturated aliphatic ring or saturated hetero ring containing one nitrogen atom. Particularly where $R_1$, $R_2$ and $R_3$ represent a substituted alkyl group, examples of the substituent include a cycloalkyl group, a halogen atom, hydroxy, an alkoxy group, carboxyl, an alkoxycarbonyl group, an acyl group, an aromatic group or a group shown by formula: —$CONR_4R_5$ or —$NR_6R_7$. Where $R_6$ and $R_7$ represent a substituted alkyl group, examples of the substituent include a cycloalkyl group, hydroxy, an alkoxy group, carboxyl, an alkoxycarbonyl group, an acyl group, an aryl group or a group shown by formula: —$CONR_4R_5$ or —$NR_4R_5$. As the alkyl moiety in the substituted alkyl group, the same examples as those for the alkyl group described above are given.

As such a substituted alkyl group, there are, for example, an alkyl group having 1 to 5 carbon atoms which is substituted with a cycloalkyl having 3 to 6 carbon atoms, a polyhaloalkyl group having 1 to 5 carbon atoms, a hydroxyalkyl group having 1 to 6 carbon atoms, an alkoxyalkyl group having 2 to 6 carbon atoms, a cyanoalkyl group having 2 to 6 carbon atoms, a carboxyalkyl group having 2 to 6 carbon atoms, an alkoxycarbonylalkyl group having 3 to 8 carbon atoms, an alkanoylalkyl group having 3 to 8 carbon atoms, an aralkyl group having carbon atoms up to 16, a phenyl- or naphthyl-$C_1$ to $C_5$ alkyl group which may be substituted, a carbamoyl-$C_1$ to $C_3$ alkyl group in which the nitrogen atom may be substituted with one or two $C_1$ to $C_3$ alkyl, an amino-$C_1$ to $C_5$ alkyl group in which the nitrogen atom may be substituted with one or two $C_1$ to $C_3$ alkyl or $C_7$ to $C_{11}$ aralkyl, and a saturated 5- to 7-membered cyclic amino-$C_1$ to $C_3$ alkyl group.

Representative examples of the substituted alkyl group include:

in the case of $R_1$: a polyhaloalkyl group having 1 to 3 carbon atoms such as trifluoromethyl, trifluoroethyl or trichloromethyl; a hydroxyalkyl group having 1 to 6 carbon atoms such as hydroxymethyl, hydroxyethyl or 1-hydroxyethyl; and an aminoalkyl group having 1 to 5 carbon atoms such as aminomethyl, aminoethyl or 1-aminoethyl;

in the case of $R_2$: a hydroxyalkyl group having 1 to 6 carbon atoms such as hydroxyethyl, hydroxypropyl, hydroxybutyl, 2-hydroxypropyl or 3,4-dihydroxybutyl; an alkoxyalkyl group having 1 to 6 carbon atoms such as methoxyethyl, ethoxyethyl or methoxypropyl; a carboxyalkyl group having 2 to 6 carbon atoms such as carboxyethyl or carboxypropyl; an alkoxycarbonylalkyl group having 3 to 7 carbon atoms such as methoxycarbonylmethyl, ethoxycarbonylmethyl or methoxycarbonylethyl; a phenyl- or naphthyl-$C_1$ to $C_5$ alkyl group (wherein a phenyl or naphthyl group may be substituted with a substituent, e.g., a $C_1$ to $C_3$ alkyl group, a halogen atom, nitro, amino, hydroxy or a $C_1$ to $C_3$ alkoxy group) such as benzyl, phenylethyl, phenylpropyl, phenylbutyl or, 1- or 2-naphthylmethyl; a carbamoyl-$C_1$ to $C_3$ alkyl group in which the nitrogen atom may be substituted with one or two $C_1$ to $C_3$ alkyl groups, such as carbamoylmethyl, carbamoylethyl or dimethylcarbamoylmethyl; or, an amino-$C_1$ to $C_5$ alkyl group in which the nitrogen atom may be substituted with one or two $C_1$ to $C_3$ alkyl, such as aminoethyl, aminopropyl, dimethylaminoethyl, dimethylaminopropyl or diethylaminoethyl;

in the case of $R_3$ and $R_{40}$: a hydroxyalkyl group having 1 to 6 carbon atoms such as hydroxyethyl, hydroxypropyl, 2-hydroxypropyl, hydroxybutyl or 2,3-dihydroxybutyl; a carboxyalkyl group having 2 to 6 carbon atoms such as carboxymethyl or carboxyethyl; a phenyl-$C_1$ to $C_5$ alkyl group such as benzyl, phenylethyl or phenylpropyl; a carbamoyl-$C_1$ to $C_3$ alkyl group such as carbamoylmethyl or carbamoylethyl; an amino-$C_1$ to $C_5$ alkyl group containing one or two nitrogen atoms in which the nitrogen atom may be substituted with one or two $C_1$ to $C_3$ alkyl or $C_7$ to $C_{11}$ aralkyl groups, such as aminoethyl, aminopropyl, dimethylaminoethyl, dimethylaminopropyl or benzylmethyl-aminoethyl; or a saturated 5- to 7-membered cyclic amino-$C_1$ to $C_3$ alkyl group such as 1-pyrrolidinyl-ethyl or piperidinoethyl; and, in the case of $R_6$ and $R_7$: a phenyl-$C_1$ to $C_5$ alkyl group such as phenylethyl.

Examples of the saturated 5- to 7-membered cyclic amino group which is formed by combining $R_4$ and $R_5$ together and may contain other hetero atoms in the ring thereof include the same groups as exemplified for the aforesaid cyclic amino group formed by $R_6$ and $R_7$.

Examples of the group shown by formula: $-S(O)_nR_{40}$ include an alkylsulfonyl group having carbon atoms up to 8, such as methylsulfonyl, ethylsulfonyl, propylsulfonyl or isopropylsulfonyl; and the corresponding alkylsulfinyl and alkylthio groups. Examples of the group of

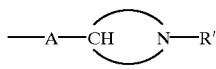

include the following groups:

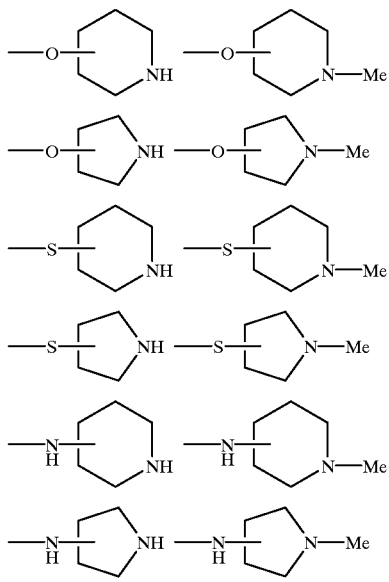

Among the above groups, there are preferable (piperidine-3-yl)oxy, (piperidine-4-yl)oxy, (1-methylpiperidine-3-yl)oxy, (1-methylpiperidine-4-yl)oxy, pyrrolidine-3-yl)oxy, (1-methylpyrrolidine-3-yl)oxy, piperidine-3-yl)thio, (piperidine-4-yl)thio, (1-methylpiperidine-3-yl)thio, (1-methylpiperidine-4-yl)thio, (pyrrolidine-3-yl)thio, (1-methylpyrrolidine-3-yl)thio, (piperidine-3-yl)amino, (piperidine-4-yl)amino, (1-methylpiperidine-3-yl)amino, (1-methylpiperidine-4-yl)amino, (pyrrolidine-3-yl)amino and (1-methylpyrrolidine-3-yl)amino.

The compounds of the present invention represented by the formula (1) above can be prepared by the following processes.

(a) The compounds (1) of the present invention can be obtained by reacting reactive derivatives of indolecarboxylic acid shown by formula (3) with guanidine in an inert solvent.

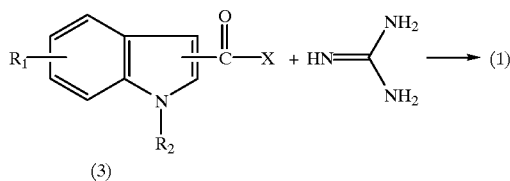

wherein X is a leaving group which can be readily replaced by a nucleophilic reagent and, $R_1$ and $R_2$ have the same significance as described above.

In this reaction, where the indolecarboxylic acid derivatives (3) contain reactive groups such as hydroxy or amino, these groups are previously protected by their protective groups. These protective groups are removed after the reaction is completed. The desired indoloylguanidine derivatives (1) can thus be prepared.

As the reactive derivatives of the carboxylic acid, there are acid halides, acid anhydrides (including mixed acid anhydrides) and ester derivatives. Specific examples are acid chlorides and acid bromides as the acid halides; as the mixed acid anhydrides, there are mixed acid anhydrides with alkyloxy chloride type such as ethyloxycarbonyl chloride or isobutyloxycarbonyl chloride and those with a-polyalkyl-substituted carboxylate type such as diethylacetyl chloride or trimethylacetyl chloride; as the ester derivatives there are activated esters such as p-nitrophenyl esters, N-hydroxysuccinimide esters or pentafluorophenyl esters, and ordinary esters such as methyl esters or ethyl esters. These reactive derivatives of the carboxylic acids can be readily obtained from the corresponding carboxylic acids in a conventional manner.

In the case of performing the reaction between the acid halides or the acid anhydrides (including the mixed acid anhydrides) and guanidine, the reaction can be carried out in a solvent under cooling or at room temperature, in the presence of a base or an excess of guanidine. Inorganic bases such as sodium hydroxide, potassium hydroxide, sodium carbonate, potassium carbonate or sodium hydrogencarbonate, or organic bases such as triethylamine or pyridine may be used as the base. Examples of the solvent include aromatic hydrocarbons such as benzene, toluene or xylene, ethers such as tetrahydrofuran or 1,4-dioxane, halogenated hydrocarbons such as dichloromethane, chloroform or 1,2-dichloro-ethane, amides such as dimethylformamide or dimethyl-acetamide, basic solvents such as pyridine, or a mixture of these solvents.

Where the ester derivatives are reacted, the reaction is carried out in a solvent usually at a elevated temperature, in the presence of an equimolar amount of or an excess of guanidine. In the case of using the activated esters, the reaction is performed preferably in an ethers such as tetrahydrofuran, 1,2-dimethoxyethane or 1,4-dioxane, an ester type solvent such as ethyl acetate, dimethylformamide or a solvent mixture thereof. In the case of using other esters, it is preferred to perform the reaction in an alcohol type solvent such as methanol, ethanol or isopropanol, an ether type solvent such as tetrahydrofuran, 1,2-dimethoxyethane or 1,4-dioxane, dimethylformamide or a solvent mixture thereof. After removal of the solvent, if necessary and desired, the reaction system may be heated at about 130° C. for a short period of time.

(b) The compounds (1) of the present invention can be obtained by reacting indolecarboxylic acids shown by formula (4) with guanidine in an inert solvent at room temperature or with heating, preferably in the presence of a condensing agent.

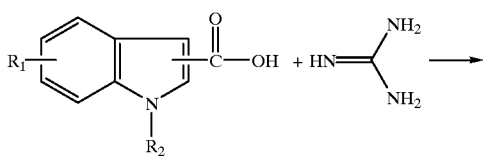

(4)

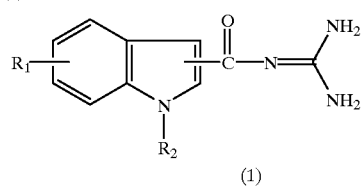

(1)

wherein $R_1$ and $R_2$ have the same significance as described above.

In this reaction, where the indolecarboxylic acid derivatives (4) contain reactive groups such as hydroxy or amino, these groups are previously protected by their protective groups. These protective groups are removed after the reaction is completed. The desired indoloylguanidine derivatives (1) can thus be prepared.

The reaction is carried out in a solvent, e.g., aromatic hydrocarbons such as benzene, toluene or xylene, ethers such as tetrahydrofuran or 1,4-dioxane, halogenated hydrocarbons such as dichloromethane, chloroform or 1,2-dichloroethane, amides such as dimethylformamide or dimethylacetamide, basic solvents such as pyridine, or a mixture of these solvents, in the presence of a condensing agent, e.g., dicyclohexylcarbodiimide (DCC), diisopropylcarbodiimide (DIPC), 1-ethyl-3-(3-dimethylaminopropyl) carbodiimide (WSC), benzotriazol-1-yl-tris(dimethylamino) phosphonium hexafluorophosphate (BOP), diphenylphosphonylazide (DPPA) or N,N-carbonyldiimidazole, cf., Angew. Chem. Int. Ed. Engl., Vol. 1, 351 (1962), and, if desired, in the presence of an additive such as N-hydroxysuccinimide (HONSu), 1-hydroxybenzotriazole (HOBt), 3-hydroxy-4-oxo-3,4-dihydro-1,2,3-benzotriazine (HOObt), etc.

(c) The compounds (1a) of the present invention can be obtained by debenzylation of benzyloxyindoloylguanidine derivatives shown by general formula (5).

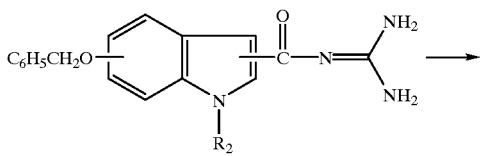

(5)

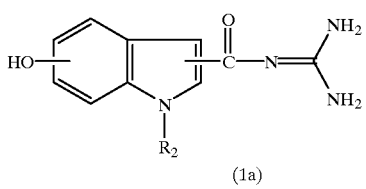

(1a)

wherein $R_2$ has the same significance as described hereinabove.

The debenzylation is carried out in a manner similar to the processes described in publications, such as catalytic hydrogenation using a palladium/carbon catalyst, cf., J. Chem. Soc., 1953, 4058 or decomposition under acidic conditions using hydrochloric acid/acetic acid, cf., J. Amer. Chem. Soc., Vol. 73, 5765 (1951).

(d) The compounds (1b) of the present invention can be obtained by reducing nitroindoloylguanidine derivatives represented by formula (6).

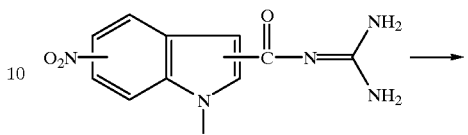

(6)

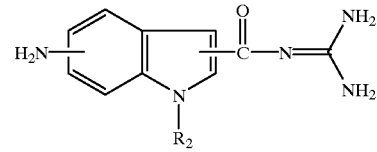

(1b)

wherein $R_2$ has the same significance as described hereinabove.

As the reducing conditions applicable, there are conditions, e.g., reduction under acidic conditions using zinc, iron, tin or tin (II) chloride, cf., Ann., 641, 81 (1961), J. Amer. Chem. Soc., Vol. 66, 1781 (1944); reducing using sulfides such as sodium dithionite (Na2S2O4), cf., J. Amer. Chem. Soc., Vol. 72, 1361 (1950); catalytic hydrogenation using catalysts such as palladium/carbon, cf., Synth. Commun., 1 47 (1971) or Raney nickel, cf., Org. Synth., IV, 226 (1963).

As the protective groups for the hydroxy, amino or carboxyl group reactive with the reaction in the process (a) or (b) described hereinabove, there may be used protective groups conventionally used in the field of organic synthesis chemistry. Introduction and removal of these protective groups can be made in a conventional manner, e.g., Protective Groups in Organic Synthesis, John Wiley & Sons, 1991.

Examples of the protective group for the hydroxy group include methoxymethyl and tetrahydropyranyl. Examples of the protective group for the amino group include tert-butyloxycarbonyl and the like. These protective groups for the hydroxy group can be removed by conducting the reaction in a solvent such as hydrated methanol, hydrated ethanol or hydrated tetrahydrofuran in the presence of an acid, e.g., hydrochloric acid, sulfuric acid or acetic acid. The amino protective groups can be removed by performing the reaction in a solvent such as hydrated tetrahydrofuran, methylene chloride, chloroform or hydrated methanol, in the presence of an acid, e.g., hydrochloric acid or trifluoroacetic acid.

For protecting the carboxyl group, the protection is effected in the form of tert-butyl esters, ortho-esters or acid amides. Such protective groups are removed, in the case of the tert-butyl esters, e.g., by performing the reaction in a hydrated solvent in the presence of hydrochloric acid; in the case of the ortho-esters, the protective groups are removed, e.g., by treating the protected compounds with an acid in a solvent such as hydrated methanol, hydrated tetrahydrofuran or hydrated 1,2-dimethoxyethane and then with an alkali such as sodium hydroxide. In the case of the acid amides, the protective groups are removed, e.g., by conducting the reaction in a solvent such as water, hydrated methanol or hydrated tetrahydrofuran in the presence of an acid such as hydrochloric acid or sulfuric acid.

The indolecarboxylic acids which are the starting compounds in the processes (a) and (b) described hereinabove are commercially available. Examples of such commercially available indolecarboxylic acids are indole-5-carboxylic acid, 5-chloro-2-indole carboxylic acid, indole-3-carboxylic acid, indole-2-carboxylic acid, indole-4-carboxylic acid, 5-methoxy-2-indolecarboxylic acid. Alternatively, the indolecarboxylic acids may be prepared by known methods.

According to, e.g., the method of Reissert (Reissert's indole synthesis), there can be prepared 4-chloro-2-indolecarboxylic acid, cf., J. Chem. Soc., 1955, 3490; 6-n-amyl-2-indolecarboxylic acid, cf., J. Amer. Chem. Soc., Vol. 75, 4921 (1953); 7-indolecarboxylic acid, cf., J. Amer. Chem. Soc., Vol. 77, 5700 (1955);, 5-cyano-2-indolecarboxylic acid, cf., J. Org. Chem., Vol. 18, 354 (1953); 6-cyano-2-indolecarboxylic acid, cf., J. Chem. Soc., 1924, 2285; 6-benzyloxy-2-indolecarboxylic acid, cf., J. Chem. Soc., 1937, 1726 and the like.

The method of Fischer (Fischer's indole synthesis) gives nitro-2-indolecarboxylic acids in J. Amer. Chem. Soc., Vol. 80, 4621 (1958), 7-chloro-2-indolecarboxylic acid in J. Chem. Soc., 1955, 3499, 4-trifluoromethyl-2-indolecarboxylic acid in J. Amer. Chem. Soc., Vol. 79, 1745 (1957) and the like.

The 2-indolecarboxylic acids may also be prepared by known methods using benzaldehyde derivatives as the starting compounds, see, e.g., Tetrahedron, Vol. 42, 3259 (1986).

The 4-indolecarboxylic acids, 5-indolecarboxylic acids and 6-indolecarboxylic acids can be prepared based on the methods described in, e.g., J. Chem. Tech. Biotechnol., Vol. 36, 562 (1986), Tetrahedron Letters, Vol. 27, 1653 (1986), etc.

The 1-hydroxyindolecarboxylic acids can be prepared based on the method described in Chem. Ber., Vol. 56, 1024 (1923).

The aryloxyindolecarboxylic acids can be prepared by reacting alkali metal salts (e.g., sodium or potassium salts) of hydroxyindolecarboxylic acids with aryl halides in an inert solvent such as dimethylformamide or tetrahydrofuran in the presence or absence of a catalyst such as copper or copper iodide. In case that the aryl halide employed for the reaction contains a reactive group(s) such as carboxyl, hydroxy or amino, these groups may be previously protected with appropriate protective groups. Then the coupling reaction is carried out and the reaction with guanidine follows. Thereafter the protective groups are removed to prepare the objective indoloylguanidine derivatives. The other indolecarboxylic acids are either commercially available or may be prepared with reference to the synthesis methods described in reviews (1), (2) and (3) given below:

(1) W. A. Remers, R. K. Brown, "Indoles", edited by W. J. Houlihan, Part I, Part II and Part III, Wiley-Interscience, New York, 1972

(2) R. J. Sundberg, "The Chemistry of Indoles", Academic Press, New York, 1970

(3) A. R. Kartritzky, C. W. Rees, "Comprehensive Heterocyclic Chemistry", edited by C. W. Bird, G. W. H. Cheeseman, Volume 4, Pergamon Press, Oxford, 1984

The compounds of formula (1) prepared as described above are illustratively given below.

1-methyl-2-indoloylguanidine
1-methyl-3-indoloylguanidine
1-methyl-4-indoloylguanidine
1-methyl-5-indoloylguanidine
1-methyl-6-indoloylguanidine
4-chloro-1-methyl-2-indoloylguanidine
5-chloro-1-methyl-2-indoloylguanidine
6-chloro-1-methyl-2-indoloylguanidine
7-chloro-1-methyl-2-indoloylguanidine
5-chloro-2-indoloylguanidine
1,4-dimethyl-2-indoloylguanidine
1,5-dimethyl-2-indoloylguanidine
1,6-dimethyl-2-indoloylguanidine
1,7-dimethyl-2-indoloylguanidine
4-methoxy-1-methyl-2-indoloylguanidine
5-methoxy-1-methyl-2-indoloylguanidine
6-methoxy-1-methyl-2-indoloylguanidine
7-methoxy-1-methyl-2-indoloylguanidine
1-methyl-4-nitro-2-indoloylguanidine
1-methyl-5-nitro-2-indoloylguanidine
1-methyl-6-nitro-2-indoloylguanidine
1-methyl-7-nitro-2-indoloylguanidine
4-amino-1-methyl-2-indoloylguanidine
5-amino-1-methyl-2-indoloylguanidine
6-amino-1-methyl-2-indoloylguanidine
7-amino-1-methyl-2-indoloylguanidine
1-benzyl-2-indoloylguanidine
1-benzyl-3-indoloylguanidine
1-benzyl-5-indoloylguanidine
1-isopropyl-2-indoloylguanidine
1-isopropyl-3-indoloylguanidine
1-isopropyl-5-indoloylguanidine
2-indoloylguanidine
3-indoloylguanidine
5-indoloylguanidine
4-hydroxy-1-methyl-2-indoloylguanidine
5-hydroxy-1-methyl-2-indoloylguanidine
6-hydroxy-1-methyl-2-indoloylguanidine
7-hydroxy-1-methyl-2-indoloylguanidine
1-(3-dimethylaminopropyl)-4-trifluoromethyl-2-indoloylguanidine
1-(3-diethylaminopropyl)-4-trifluoromethyl-2-indoloylguanidine
1-[3-(N-pyrrolidinyl)propyl]-4-trifluoromethyl-2-indoloylguanidine
6-(3-aminopropoxy)-1-methyl-4-trifluoromethyl-2-indoloylguanidine
6-(3-dimethylaminopropoxy)-1-methyl-4-trifluoromethyl-2-indoloylguanidine
6-(3-diethylaminopropoxy)-1-methyl-4-trifluoromethyl-2-indoloylguanidine
6-(2-aminoethoxy)-1-methyl-4-trifluoromethyl-2-indoloylguanidine
6-(2-dimethylaminoethoxy)-1-methyl-4-trifluoromethyl-2-indoloylguanidine
6-(2-diethylaminoethoxy)-1-methyl-4-trifluoromethyl-2-indoloylguanidine
1-methyl-6-[3-(N-pyrrolidinyl)propoxy]-4-trifluoromethyl-2-indoloylguanidine
1-methyl-6-[2-(N-pyrrolidinyl)ethoxy]-4-trifluoromethyl-2-indoloylguanidine
1-(3-dimethylaminopropyl)-4-methoxy-2-indoloylguanidine
1-(3-diethylaminopropyl)-4-methoxy-2-indoloylguanidine 1-(3-aminopropyl)-4-methoxy-2-indolyolguanidine
4-methoxy-1-[3-(N-pyrrolidinyl)propyl]-2-indoloylguanidine
6-(3-aminopropoxy)-4-methoxy-1-methyl-2-indoloylguanidine
6-(3-dimethylaminopropoxy)-4-methoxy-1-methyl-2-indoloylguanidine
6-(3-diethylaminopropoxy)-4-methoxy-1-methyl-2-indoloylguanidine
6-(2-aminoethoxy)-4-methoxy-1-methyl-2-indoloylguanidine
6-(2-dimethylaminoethoxy)-4-methoxy-1-methyl-2-indoloylguanidine
6-(2-diethylaminoethoxy)-4-methoxy-1-methyl-2-indoloylguanidine
4-methoxy-1-methyl-6-[3-(N-pyrrolidinyl)-propoxy]-2-indoloylguanidine
4-methoxy-1-methyl-6-[2-(N-pyrrolidinyl)-ethoxy]-2-indoloylguanidine
7-(3-aminopropoxy)-4-methoxy-1-methyl-2-indoloylguanidine
7-(3-dimethylaminopropoxy)-4-methoxy-1-methyl-2-indoloylguanidine
7-(3-diethylaminopropoxy)-4-methoxy-1-methyl-2-indoloylguanidine
4-methoxy-1-methyl-7-[3-(N-pyrrolidinyl)-propoxy]-2-indoloylguanidine
1-(3-dimethylaminopropyl)-4-isopropoxy-2-indoloylguanidine
1-(3-diethylaminopropyl)-4-isopropoxy-2-indoloylguanidine
1-(3-aminopropyl)-4-isopropoxy-2-indoloylguanidine
4-isopropoxy-1-[3-(N-pyrrolidinyl)propyl]-2-indoloylguanidine
6-(3-aminopropoxy)-4-isopropoxy-1-methyl-2-indoloylguanidine
6-(3-dimethylaminopropoxy)-4-isopropoxy-1-methyl-2-indoloylguanidine
6-(3-diethylaminopropoxy)-4-isopropoxy-1-methyl-2-indoloylguanidine
6-(2-aminoethoxy)-4-isopropoxy-1-methyl-2-indoloylguanidine
6-(2-dimethylaminoethoxy)-4-isopropoxy-1-methyl-2-indoloylguanidine
6-(2-diethylaminoethoxy)-4-isopropoxy-1-methyl-2-indoloylguanidine
4-isopropoxy-1-methyl-6-[3-(N-pyrrolidinyl)-propoxy]-2-indoloylguanidine
4-isopropoxy-1-methyl-6-[2-(N-pyrrolidinyl)-ethoxy]-2-indoloylguanidine
7-(3-aminopropoxy)-4-isopropoxy-1-methyl-2-indoloylguanidine
7-(3-dimethylaminopropoxy)-4-isopropoxy-1-methyl-2-indoloylguanidine
7-(3-diethylaminopropoxy)-4-isopropoxy-1-methyl-2-indoloylguanidine
4-isopropoxy-1-methyl-7-[3-(N-pyrrolidinyl)-propoxy]-2-indoloylguanidine
1-(3-aminopropyl)-4-methyl-2-indoloylguanidine
1-(3-dimethylaminopropyl)-4-methyl-2-indoloylguanidine
1-(3-diethylaminopropyl)-4-methyl-2-indoloylguanidine
4-methyl-1-[3-(N-pyrrolidinyl)propyl]-2-indoloylguanidine
6-(3-aminopropoxy)-1,4-dimethyl-2-indoloylguanidine
1,4-dimethyl-6-(3-dimethylaminopropoxy)-2-indoloylguanidine
6-(3-diethylaminopropoxy)-1,4-dimethyl-2-indoloylguanidine
1,4-dimethyl-6-(2-diethylaminoethoxy)-2-indoloylguanidine
6-(2-diethylaminoethoxy)-1,4-dimethyl-2-indoloylguanidine
6-(2-aminoethoxy)-1,4-dimethyl-2-indoloylguanidine
1,4-dimethyl-6-[3-(N-pyrrolidinyl)propoxy]-2-indoloylguanidine
1,4-dimethyl-6-[2-(N-pyrrolidinyl)ethoxy]-2-indoloylguanidine
7-(3-aminopropoxy)-1,4-dimethyl-2-indoloylguanidine
1,4-dimethyl-7-(3-dimethylaminopropoxy)-2-indoloylguanidine
7-(3-diethylaminopropoxy)-1,4-dimethyl-2-indoloylguanidine
1,4-dimethyl-7-[3-(N-pyrrolidinyl)propoxy]-2-indoloylguanidine
4-tert-butyl-1-methyl-2-indoloylguanidine
1-(3-aminopropyl)-4-tert-butyl-2-indoloylguanidine
4-tert-butyl-1-(3-dimethylaminopropyl)-2-indoloylguanidine
4-tert-butyl-1-(3-diethylaminopropyl)-2-indoloylguanidine
4-tert-butyl-1-[3-(N-pyrrolidinyl)propyl]-2-indoloylguanidine
6-(3-dimethylaminopropoxy)-1-methyl-2-indoloylguanidine
6-(3-diethylaminopropoxy)-1-methyl-2-indoloylguanidine
6-(2-aminoethoxy)-1-methyl-2-indoloylguanidine
6-(2-dimethylaminoethoxy)-1-methyl-2-indoloylguanidine
6-(2-diethylaminoethoxy)-1-methyl-2-indoloylguanidine
1-methyl-6-[3-(N-pyrrolidinyl)propoxy]-2-indoloylguanidine
1-methyl-6-[2-(N-pyrrolidinyl)ethoxy]-2-indoloylguanidine
7-(3-dimethylaminopropoxy)-1-methyl-2-indoloylguanidine
7-(3-diethylaminopropoxy)-1-methyl-2-indoloylguanidine
1-methyl-7-[3-(N-pyrrolidinyl)propoxy]-2-indoloylguanidine
1-methyl-6-phenoxy-2-indoloylguanidine
1-methyl-7-phenoxy-2-indoloylguanidine
1-methyl-6-(2-nitrophenoxy)-2-indoloylguanidine
1-methyl-7-(2-nitrophenoxy)-2-indoloylguanidine
1-methyl-6-(3-nitrophenoxy)-2-indoloylguanidine
1-methyl-7-(3-nitrophenoxy)-2-indoloylguanidine
1-methyl-6-(4-nitrophenoxy)-2-indoloylguanidine
1-methyl-7-(4-nitrophenoxy)-2-indoloylguanidine
6-(2-aminophenoxy)-1-methyl-2-indoloylguanidine
7-(2-aminophenoxy)-1-methyl-2-indoloylguanidine 6-(3-aminophenoxy)-1-methyl-2-indoloylguanidine
7-(3-aminophenoxy)-1-methyl-2-indoloylguanidine
6-(4-aminophenoxy)-1-methyl-2-indoloylguanidine
7-(4-aminophenoxy)-1-methyl-2-indoloylguanidine
6-[2-(aminomethyl)phenoxy]-1-methyl-2-indoloylguanidine
7-[2-(aminomethyl)phenoxy]-1-methyl-2-indoloylguanidine
6-[3-(aminomethyl)phenoxy]-1-methyl-2-indoloylguanidine
7-[3-(aminomethyl)phenoxy]-1-methyl-2-indoloylguanidine
6-[4-(aminomethyl)phenoxy]-1-methyl-2-indoloylguanidine
7-[4-(aminomethyl)phenoxy]-1-methyl-2-indoloylguanidine
6-[2-(dimethylaminomethyl)phenoxy]-1-methyl-2-indoloylguanidine
7-[2-(dimethylaminomethyl)phenoxy]-1-methyl-2-indoloylguanidine
6-[3-(dimethylaminomethyl)phenoxy]-1-methyl-2-indoloylguanidine
7-[3-(dimethylaminomethyl)phenoxy]-1-methyl-2-indoloylguanidine
6-[4-(dimethylaminomethyl)phenoxy]-1-methyl-2-indoloylguanidine
7-[4-(dimethylaminomethyl)phenoxy]-1-methyl-2-indoloylguanidine
4-chloro-1-methyl-6-phenoxy-2-indoloylguanidine
4-chloro-1-methyl-7-phenoxy-2-indoloylguanidine
4-chloro-1-methyl-6-(2-nitrophenoxy)-2-indoloylguanidine
4-chloro-1-methyl-7-(2-nitrophenoxy)-2-indoloylguanidine
4-chloro-1-methyl-6-(3-nitrophenoxy)-2-indoloylguanidine
4-chloro-1-methyl-7-(3-nitrophenoxy)-2-indoloylguanidine
4-chloro-1-methyl-6-(4-nitrophenoxy)-2-indoloylguanidine
4-chloro-1-methyl-7-(4-nitrophenoxy)-2-indoloylguanidine
6-(2-aminophenoxy)-4-chloro-1-methyl-2-indoloylguanidine
7-(2-aminophenoxy)-4-chloro-1-methyl-2-indoloylguanidine
6-(3-aminophenoxy)-4-chloro-1-methyl-2-indoloylguanidine
7-(3-aminophenoxy)-4-chloro-1-methyl-2-indoloylguanidine
6-(4-aminophenoxy)-4-chloro-1-methyl-2-indoloylguanidine
7-(4-aminophenoxy)-4-chloro-1-methyl-2-indoloylguanidine
6-[2-(aminomethyl)phenoxy]-4-chloro-1-methyl-2-indoloylguanidine
7-[2-(aminomethyl)phenoxy]-4-chloro-1-methyl-2-indoloylguanidine
6-[3-(aminomethyl)phenoxy]-4-chloro-1-methyl-2-indoloylguanidine
7-[3-(aminomethyl)phenoxy]-4-chloro-1-methyl-2-indoloylguanidine
6-[4-(aminomethyl)phenoxy]-4-chloro-1-methyl-2-indoloylguanidine
7-[4-(aminomethyl)phenoxy]-4-chloro-1-methyl-2-indoloylguanidine
4-chloro-6-[2-(dimethylaminomethyl)phenoxy]-1-methyl-2-indoloylguanidine
4-chloro-7-[2-(dimethylaminomethyl)phenoxy]-1-methyl-2-indoloylguanidine
4-chloro-6-[3-(dimethylaminomethyl)phenoxy]-1-methyl-2-indoloylguanidine
4-chloro-7-[3-(dimethylaminomethyl)phenoxy]-1-methyl-2-indoloylguanidine
4-chloro-6-[4-(dimethylaminomethyl)phenoxy]-1-methyl-2-indoloylguanidine
4-chloro-7-[4-(dimethylaminomethyl)phenoxy]-1-methyl-2-indoloylguanidine
1-methyl-6-phenoxy-4-trifluoromethyl-2-indoloylguanidine
1-methyl-7-phenoxy-4-trifluoromethyl-2-indoloylguanidine
1-methyl-6-(2-nitrophenoxy)-4-trifluoromethyl-2-indoloylguanidine
1-methyl-7-(2-nitrophenoxy)-4-trifluoromethyl-2-indoloylguanidine
1-methyl-6-(3-nitrophenoxy)-4-trifluoromethyl-2-indoloylguanidine
1-methyl-7-(3-nitrophenoxy)-4-trifluoromethyl-2-indoloylguanidine
1-methyl-6-(4-nitrophenoxy)-4-trifluoromethyl-2-indoloylguanidine
1-methyl-7-(4-nitrophenoxy)-4-trifluoromethyl-2-indoloylguanidine
6-(2-aminophenoxy)-1-methyl-4-trifluoromethyl-2-indoloylguanidine
7-(2-aminophenoxy)-1-methyl-4-trifluoromethyl-2-indoloylguanidine
6-(3-aminophenoxy)-1-methyl-4-trifluoromethyl-2-indoloylguanidine
7-(3-aminophenoxy)-1-methyl-4-trifluoromethyl-2-indoloylguanidine
6-(4-aminophenoxy)-1-methyl-4-trifluoromethyl-2-indoloylguanidine
7-(4-aminophenoxy)-1-methyl-4-trifluoromethyl-2-indoloylguanidine
6-[2-(aminomethyl)phenoxy]-1-methyl-4-trifluoromethyl-2-indoloylguanidine
7-[2-(aminomethyl)phenoxy]-1-methyl-4-trifluoromethyl-2-indoloylguanidine
6-[3-(aminomethyl)phenoxy]-1-methyl-4-trifluoromethyl-2-indoloylguanidine
7-[3-(aminomethyl)phenoxy]-1-methyl-4-trifluoromethyl-2-indoloylguanidine
6-[4-(aminomethyl)phenoxy]-1-methyl-4-trifluoromethyl-2-indoloylguanidine
7-[4-(aminomethyl)phenoxy]-1-methyl-4-trifluoromethyl-2-indoloylguanidine
6-[2-(dimethylaminomethyl)phenoxy]-1-methyl-4-trifluoromethyl-2-indoloylguanidine
7-[2-(dimethylaminomethyl)phenoxy]-1-methyl-4-trifluoromethyl-2-indoloylguanidine
6-[3-(dimethylaminomethyl)phenoxy]-1-methyl-4-trifluoromethyl-2-indoloylguanidine 7-[3-(dimethylaminomethyl)phenoxy]-1-methyl-4-trifluoromethyl-2-indoloylguanidine
6-[4-(dimethylaminomethyl)phenoxy]-1-methyl-4-trifluoromethyl-2-indoloylguanidine
7-[4-(dimethylaminomethyl)phenoxy]-1-methyl-4-trifluoromethyl-2-indoloylguanidine
6-[2-(diethylaminomethyl)phenoxy]-1-methyl-4-trifluoromethyl-2-indoloylguanidine
7-[2-(diethylaminomethyl)phenoxy]-1-methyl-4-trifluoromethyl-2-indoloylguanidine
6-[3-(diethylaminomethyl)phenoxy]-1-methyl-4-trifluoromethyl-2-indoloylguanidine
7-[3-(diethylaminomethyl)phenoxy]-1-methyl-4-trifluoromethyl-2-indoloylguanidine
6-[4-(diethylaminomethyl)phenoxy]-1-methyl-4-trifluoromethyl-2-indoloylguanidine
7-[4-(diethylaminomethyl)phenoxy]-1-methyl-4-trifluoromethyl-2-indoloylguanidine
1-methyl-6-[2-(N-pyrrolidinylmethyl)phenoxy]-2-indoloylguanidine
1-methyl-7-[2-(N-pyrrolidinylmethyl)phenoxy]-2-indoloylguanidine
1-methyl-6-[3-(N-pyrrolidinylmethyl)phenoxy]-2-indoloylguanidine
1-methyl-7-[3-(N-pyrrolidinylmethyl)phenoxy]-2-indoloylguanidine
1-methyl-6-[4-(N-pyrrolidinylmethyl)phenoxy]-2-indoloylguanidine
1-methyl-7-[4-(N-pyrrolidinylmethyl)phenoxy]-2-indoloylguanidine
1-methyl-6-[2-(N-piperidinylmethyl)phenoxy]-2-indoloylguanidine
1-methyl-7-[2-(N-piperidinylmethyl)phenoxy]-2-indoloylguanidine
1-methyl-6-[3-(N-piperidinylmethyl)phenoxy]-2-indoloylguanidine
1-methyl-7-[3-(N-piperidinylmethyl)phenoxy]-2-indoloylguanidine
1-methyl-6-[4-(N-piperidinylmethyl)phenoxy]-2-indoloylguanidine
1-methyl-7-[4-(N-piperidinylmethyl)phenoxy]-2-indoloylguanidine
6-[2-(aminomethyl)benzyloxy]-1-methyl-2-indoloylguanidine
7-[2-(aminomethyl)benzyloxy]-1-methyl-2-indoloylguanidine
6-[3-(aminomethyl)benzyloxy]-1-methyl-2-indoloylguanidine
7-[3-(aminomethyl)benzyloxy]-1-methyl-2-indoloylguanidine
6-[4-(aminomethyl)benzyloxy]-1-methyl-2-indoloylguanidine
7-[4-(aminomethyl)benzyloxy]-1-methyl-2-indoloylguanidine
6-[2-(dimethylaminomethyl)benzyloxy]-1-methyl-2-indoloylguanidine
7-[2-(dimethylaminomethyl)benzyloxy]-1-methyl-2-indoloylguanidine
6-[3-(dimethylaminomethyl)benzyloxy]-1-methyl-2-indoloylguanidine
7-[3-(dimethylaminomethyl)benzyloxy]-1-methyl-2-indoloylguanidine
6-[4-(dimethylaminomethyl)benzyloxy]-1-methyl-2-indoloylguanidine
7-[4-(dimethylaminomethyl)benzyloxy]-1-methyl-2-indoloylguanidine
4-chloro-6-[2-(diethylaminomethyl)phenoxy]-1-methyl-2-indoloylguanidine
4-chloro-7-[2-(diethylaminomethyl)phenoxy]-1-methyl-2-indoloylguanidine
4-chloro-6-[3-(diethylaminomethyl)phenoxy]-1-methyl-2-indoloylguanidine
4-chloro-7-[3-(diethylaminomethyl)phenoxy]-1-methyl-2-indoloylguanidine
4-chloro-6-[4-(diethylaminomethyl)phenoxy]-1-methyl-2-indoloylguanidine
4-chloro-7-[4-(diethylaminomethyl)phenoxy]-1-methyl-2-indoloylguanidine
4-chloro-1-methyl-6-[2-(N-pyrrolidinylmethyl)-phenoxy]-2-indoloylguanidine
4-chloro-1-methyl-7-[2-(N-pyrrolidinylmethyl)-phenoxy]-2-indoloylguanidine
4-chloro-1-methyl-6-[3-(N-pyrrolidinylmethyl)-phenoxy]-2-indoloylguanidine
4-chloro-1-methyl-7-[3-(N-pyrrolidinylmethyl)-phenoxy]-2-indoloylguanidine
4-chloro-1-methyl-6-[4-(N-pyrrolidinylmethyl)-phenoxy]-2-indoloylguanidine
4-chloro-1-methyl-7-[4-(N-pyrrolidinylmethyl)-phenoxy]-2-indoloylguanidine
4-chloro-1-methyl-6-[2-(N-piperidinylmethyl)-phenoxy]-2-indoloylguanidine
4-chloro-1-methyl-7-[2-(N-piperidinylmethyl)-phenoxyl-2-indoloylguanidine
4-chloro-1-methyl-6-[3-(N-piperidinylmethyl)-phenoxy]-2-indoloylguanidine
4-chloro-1-methyl-7-[3-(N-piperidinylmethyl)-phenoxy]-2-indoloylguanidine
4-chloro-1-methyl-6-[4-(N-piperidinylmethyl)-phenoxy]-2-indoloylguanidine
4-chloro-1-methyl-7-[4-(N-piperidinylmethyl)-phenoxy]-2-indoloylguanidine
4-chloro-6-[2-(aminomethyl)benzyloxy]-1-methyl-2-indoloylguanidine
4-chloro-7-[2-(aminomethyl)benzyloxy]-1-methyl-2-indoloylguanidine
4-chloro-6-[3-(aminomethyl)benzyloxy]-1-methyl-2-indoloylguanidine
4-chloro-7-[3-(aminomethyl)benzyloxy]-1-methyl-2-indoloylguanidine
4-chloro-6-[4-(aminomethyl)benzyloxy]-1-methyl-2-indoloylguanidine
4-chloro-7-[4-(aminomethyl)benzyloxy]-1-methyl-2-indoloylguanidine
4-chloro-6-[2-(dimethylaminomethyl)benzyloxy]-1-methyl-2-indoloylguanidine
4-chloro-7-[2-(dimethylaminomethyl)benzyloxy]-1-methyl-2-indoloylguanidine
4-chloro-6-[3-(dimethylaminomethyl)benzyloxy]-1-methyl-2-indoloylguanidine
4-chloro-7-[3-(dimethylaminomethyl)benzyloxy]-1-methyl-2-indoloylguanidine
4-chloro-6-[4-(dimethylaminomethyl)benzyloxy]-1-methyl-2-indoloylguanidine 4-chloro-7-[4-(dimethylaminomethyl)benzyloxy]-1-methyl-2-indoloylguanidine
6-[2-(diethylaminomethyl)phenoxy]-1-methyl-4-trifluoromethyl-2-indoloylguanidine
7-[2-(diethylaminomethyl)phenoxy]-1-methyl-4-trifluoromethyl-2-indoloylguanidine
6-[3-(diethylaminomethyl)phenoxy]-1-methyl-4-trifluoromethyl-2-indoloylguanidine
7-[3-(diethylaminomethyl)phenoxy]-1-methyl-4-trifluoromethyl-2-indoloylguanidine
6-[4-(diethylaminomethyl)phenoxy]-1-methyl-4-trifluoromethyl-2-indoloylguanidine
7-[4-(diethylaminomethyl)phenoxy]-1-methyl-4-trifluoromethyl-2-indoloylguanidine
1-methyl-6-[2-(N-pyrrolidinylmethyl)phenoxy]-4-trifluoromethyl-2-indoloylguanidine
1-methyl-7-[2-(N-pyrrolidinylmethyl)phenoxy]-4-trifluoromethyl-2-indoloylguanidine
1-methyl-6-[3-(N-pyrrolidinylmethyl)phenoxy]-4-trifluoromethyl-2-indoloylguanidine
1-methyl-7-[3-(N-pyrrolidinylmethyl)phenoxy]-4-trifluoromethyl-2-indoloylguanidine
1-methyl-6-[4-(N-pyrrolidinylmethyl)phenoxy]-4-trifluoromethyl-2-indoloylguanidine
1-methyl-7-[4-(N-pyrrolidinylmethyl)phenoxy]-4-trifluoromethyl-2-indoloylguanidine
1-methyl-6-[2-(N-piperidinylmethyl)phenoxy]-4-trifluoromethyl-2-indoloylguanidine
1-methyl-7-[2-(N-piperidinylmethyl)phenoxy]-4-trifluoromethyl-2-indoloylguanidine
1-methyl-6-[3-(N-piperidinylmethyl)phenoxy]-4-trifluoromethyl-2-indoloylguanidine
1-methyl-7-[3-(N-piperidinylmethyl)phenoxy]-4-trifluoromethyl-2-indoloylguanidine
1-methyl-6-[4-(N-piperidinylmethyl)phenoxy]-4-trifluoromethyl-2-indoloylguanidine
1-methyl-7-[4-(N-piperidinylmethyl)phenoxy]-4-trifluoromethyl-2-indoloylguanidine
6-[2-(aminomethyl)benzyloxy]-1-methyl-4-trifluoromethyl-2-indoloylguanidine
7-[2-(aminomethyl)benzyloxy]-1-methyl-4-trifluoromethyl-2-indoloylguanidine
6-[3-(aminomethyl)benzyloxy]-1-methyl-4-trifluoromethyl-2-indoloylguanidine
7-[3-(aminomethyl)benzyloxy]-1-methyl-4-trifluoromethyl-2-indoloylguanidine
6-[4-(aminomethyl)benzyloxy]-1-methyl-4-trifluoromethyl-2-indoloylguanidine
7-[4-(aminomethyl)benzyloxy]-1-methyl-4-trifluoromethyl-2-indoloylguanidine
6-[2-(dimethylaminomethyl)benzyloxy]-1-methyl-4-trifluoromethyl-2-indoloylguanidine
7-[2-(dimethylaminomethyl)benzyloxy]-1-methyl-4-trifluoromethyl-2-indoloylguanidine
6-[3-(dimethylaminomethyl)benzyloxy]-1-methyl-4-trifluoromethyl-2-indoloylguanidine
7-[3-(dimethylaminomethyl)benzyloxy]-1-methyl-4-trifluoromethyl-2-indoloylguanidine
6-[4-(dimethylaminomethyl)benzyloxy]-1-methyl-4-trifluoromethyl-2-indoloylguanidine
7-[4-(dimethylaminomethyl)benzyloxy]-1-methyl-4-trifluoromethyl-2-indoloylguanidine
6-[2-(diethylaminomethyl)benzyloxy]-1-methyl-2-indoloylguanidine
7-[2-(diethylaminomethyl)benzyloxy]-1-methyl-2-indoloylguanidine
6-[3-(diethylaminomethyl)benzyloxy]-1-methyl-2-indoloylguanidine
7-[3-(diethylaminomethyl)benzyloxy]-1-methyl-2-indoloylguanidine
6-[4-(diethylaminomethyl)benzyloxy]-1-methyl-2-indoloylguanidine
7-[4-(diethylaminomethyl)benzyloxy]-1-methyl-2-indoloylguanidine
1-methyl-6-[(pyridin-2-yl)oxy]-2-indoloylguanidine
1-methyl-7-[(pyridin-2-yl)oxy]-2-indoloylguanidine
1-methyl-6-[(4-nitropyridin-2-yl)oxy]-2-indoloylguanidine
1-methyl-7-[(4-nitropyridin-2-yl)oxy]-2-indoloylguanidine
6-[(4-aminopyridin-2-yl)oxy]-1-methyl-2-indoloylguanidine
7-[(4-aminopyridin-2-yl)oxy]-1-methyl-2-indoloylguanidine
6-[[4-(aminomethyl)pyridin-2-yl]oxy]-1-methyl-2-indoloylguanidine
7-[[4-(aminomethyl)pyridin-2-yl]oxy]-1-methyl-2-indoloylguanidine
6-[[4-(dimethylaminomethyl)pyridin-2-yl]oxy]-1-methyl-2-indoloylguanidine
7-[[4-(dimethylaminomethyl)pyridin-2-yl]oxy]-1-methyl-2-indoloylguanidine
6-[[4-(diethylaminomethyl)pyridin-2-yl]oxy]-1-methyl-2-indoloylguanidine
7-[[4-(diethylaminomethyl)pyridin-2-yl]oxy]-1-methyl-2-indoloylguanidine
1-methyl-6-[[4-(N-pyrrolidinylmethyl)pyridin-2-yl]oxy]-2-indoloylguanidine
1-methyl-7-[(4-(N-pyrrolidinylmethyl)pyridin-2-yl]oxy]-2-indoloylguanidine
1-methyl-6-[(pyridin-3-yl)oxy]-2-indoloylguanidine
1-methyl-7-[(pyridin-3-yl)oxy]-2-indoloylguanidine
1-methyl-6-[(5-nitropyridin-3-yl)oxy]-2-indoloylguanidine
1-methyl-7-[(5-nitropyridin-3-yl)oxy]-2-indoloylguanidine
6-[(5-aminopyridin-3-yl)oxy]-1-methyl-2-indoloylguanidine
7-[(5-aminopyridin-3-yl)oxy]-1-methyl-2-indoloylguanidine
6-[[(5-aminomethyl)pyridin-3-yl]oxy]-1-methyl-2-indoloylguanidine
7-[[(5-aminomethyl)pyridin-3-yl]oxy]-1-methyl-2-indoloylguanidine
6-[[5-(dimethylaminomethyl)pyridin-3-yl]oxy]-methyl-2-indoloylguanidine
7-[[5-(dimethylaminomethyl)pyridin-3-yl]oxy]-1-methyl-2-indoloylguanidine
4-chloro-6-[2-(diethylaminomethyl)benzyloxy]-1-methyl-2-indoloylguanidine
4-chloro-7-[2-(diethylaminomethyl)benzyloxy]-methyl-2-indoloylguanidine
4-chloro-6-[3-(diethylaminomethyl)benzyloxy]-1-methyl-2-indoloylguanidine 4-chloro-7-[3-(diethylaminomethyl)benzyloxy]-1-methyl-2-indoloylguanidine
4-chloro-6-[4-(diethylaminomethyl)benzyloxy]-1-methyl-2-indoloylguanidine
4-chloro-7-[4-(diethylaminomethyl)benzyloxy]-1-methyl-2-indoloylguanidine
4-chloro-1-methyl-6-[(pyridin-2-yl)oxy]-2-indoloylguanidine
4-chloro-1-methyl-7-[(pyridin-2-yl)oxy]-2-indoloylguanidine
4-chloro-1-methyl-6-[(4-nitropyridin-2-yl)oxy]-2-indoloylguanidine
4-chloro-1-methyl-7-[(4-nitropyridin-2-yl)oxy]-2-indoloylguanidine
6-[(4-aminopyridin-2-yl)oxy]-4-chloro-1-methyl-2-indoloylguanidine
7-[(4-aminopyridin-2-yl)oxy]-4-chloro-1-methyl-2-indoloylguanidine
6-[[4-(aminomethyl)pyridin-2-yl]oxy]-4-chloro-1-methyl-2-indoloylguanidine
7-[[4-(aminomethyl)pyridin-2-yl]oxy]-4-chloro-1-methyl-2-indoloylguanidine
4-chloro-6-[[4-(dimethylaminomethyl)pyridin-2-yl]oxy]-1-methyl-2-indoloylguanidine
4-chloro-7-[[4-(dimethylaminomethyl)pyridin-2-yl]oxy]-1-methyl-2-indoloylguanidine
4-chloro-6-[[4-(diethylaminomethyl)pyridin-2-yl]oxy]-1-methyl-2-indoloylguanidine
4-chloro-7-[[4-(diethylaminomethyl)pyridin-2-yl]oxy]-1-methyl-2-indoloylguanidine
4-chloro-1-methyl-6-[[4-(N-pyrrolidinyl-methyl)pyridin-2-yl]oxy]-2-indoloylguanidine
4-chloro-1-methyl-7-[[4-(N-pyrrolidinyl-methyl)pyridin-2-yl]oxy]-2-indoloylguanidine
4-chloro-1-methyl-6-[(pyridin-3-yl)oxy]-2-indoloylguanidine
4-chloro-1-methyl-7-[(pyridin-3-yl)oxy]-2-indoloylguanidine
4-chloro-1-methyl-6-[(5-nitropyridin-3-yl)oxy]-2-indoloylguanidine
4-chloro-1-methyl-7-[(5-nitropyridin-3-yl)oxy]-2-indoloylguanidine
6-[(5-aminopyridin-3-yl)oxy]-4-chloro-1-methyl-2-indoloylguanidine
7-[(5-aminopyridin-3-yl)oxy]-4-chloro-1-methyl-2-indoloylguanidine
6-[[5-(aminomethyl)pyridin-3-yl]oxy]-4-chloro-1-methyl-2-indoloylguanidine
7-[[5-(aminomethyl)pyridin-3-yl]oxy]-4-chloro-1-methyl-2-indoloylguanidine
4-chloro-6-[[5-(dimethylaminomethyl)pyridin-3-yl]oxy]-1-methyl-2-indoloylguanidine
4-chloro-7-[[5-(dimethylaminomethyl)pyridin-3-yl]oxy]-1-methyl-2-indoloylguanidine
6-[2-(diethylaminomethyl)benzyloxy]-1-methyl-4-trifluoromethyl-2-indoloylguanidine
7-[2-(diethylaminomethyl)benzyloxy]-1-methyl-4-trifluoromethyl-2-indoloylguanidine
6-[3-(diethylaminomethyl)benzyloxy]-1-methyl-4-trifluoromethyl-2-indoloylguanidine
7-[3-(diethylaminomethyl)benzyloxy]-1-methyl-4-trifluoromethyl-2-indoloylguanidine
6-[4-(diethylaminomethyl)benzyloxy]-1-methyl-4-trifluoromethyl-2-indoloylguanidine
7-[4-(diethylaminomethyl)benzyloxy]-1-methyl-4-trifluoromethyl-2-indoloylguanidine
1-methyl-6-[(pyridin-2-yl)oxy]-4-trifluoromethyl-2-indoloylguanidine
1-methyl-7-[(pyridin-2-yl)oxy]-4-trifluoromethyl-2-indoloylguanidine
1-methyl-6-[(4-nitropyridin-2-yl)oxy]-4-trifluoromethyl-2-indoloylguanidine
1-methyl-7-[(4-nitropyridin-2-yl)oxy]-4-trifluoromethyl-2-indoloylguanidine
1-methyl-6-[(4-aminopyridin-2-yl)oxy]-4-trifluoromethyl-2-indoloylguanidine
1-methyl-7-[(4-aminopyridin-2-yl)oxy]-4-trifluoromethyl-2-indoloylguanidine
6-[[(4-aminomethyl)pyridin-2-yl]oxy]-1-methyl-4-trifluoromethyl-2-indoloylguanidine
7-[[(4-aminomethyl)pyridin-2-yl]oxy]-1-methyl-4-trifluoromethyl-2-indoloylguanidine
6-[[4-(dimethylaminomethyl)pyridin-2-yl]oxy]-1-methyl-4-trifluoromethyl-2-indoloylguanidine
7-[[4-(dimethylaminomethyl)pyridin-2-yl]oxy]-1-methyl-4-trifluoromethyl-2-indoloylguanidine
6-[[4-(diethylaminomethyl)pyridin-2-yl]oxy]-1-methyl-4-trifluoromethyl-2-indoloylguanidine
7-[[4-(diethylaminomethyl)pyridin-2-yl]oxy]-1-methyl-4-trifluoromethyl-2-indoloylguanidine
1-methyl-6-[[4-(N-pyrrolidinylmethyl)-pyridin-2-yl]oxy]-4-trifluoromethyl-2-indoloylguanidine
1-methyl-7-[[4-(N-pyrrolidinylmethyl)-pyridin-2-yl]oxy]-4-trifluoromethyl-2-indoloylguanidine
1-methyl-6-[(pyridin-3-yl)oxy]-4-trifluoromethyl-2-indoloylguanidine
1-methyl-7-[(pyridin-3-yl)oxy]-4-trifluoromethyl-2-indoloylguanidine
1-methyl-6-[(5-nitropyridin-3-yl)oxy]-4-trifluoromethyl-2-indoloylguanidine
1-methyl-7-[(5-nitropyridin-3-yl)oxy]-4-trifluoromethyl-2-indoloylguanidine
6-[(5-aminopyridin-3-yl)oxy]-1-methyl-4-trifluoromethyl-2-indoloylguanidine
7-[(5-aminopyridin-3-yl)oxy]-1-methyl-4-trifluoromethyl-2-indoloylguanidine
6-[[5-(aminomethyl)pyridin-3-yl]oxy]-1-methyl-4-trifluoromethyl-2-indoloylguanidine
7-[[5-(aminomethyl)pyridin-3-yl]oxy]-1-methyl-4-trifluoromethyl-2-indoloylguanidine
6-[[5-(dimethylaminomethyl)pyridin-3-yl]oxy]-1-methyl-4-trifluoromethyl-2-indoloylguanidine
7-[[5-(dimethylaminomethyl)pyridin-3-yl]oxy]-1-methyl-4-trifluoromethyl-2-indoloylguanidine
6-[[5-(diethylaminomethyl)pyridin-3-yl]oxy]-1-methyl-2-indoloylguanidine
7-[[5-(diethylaminomethyl)pyridin-3-yl]oxy]-1-methyl-2-indoloylguanidine
1-methyl-6-[[5-(N-pyrrolidinylmethyl)pyridin-3-yl]oxy]-2-indoloylguanidine
1-methyl-7-[[5-(N-pyrrolidinylmethyl)pyridin-3-yl]oxy]-2-indoloylguanidine
1-methyl-6-[(pyridin-4-yl)oxy]-2-indoloylguanidine 1-methyl-7-[(pyridin-4-yl)oxy]-2-indoloylguanidine
1-methyl-6-[(2-nitropyridin-4-yl)oxy]-2-indoloylguanidine
1-methyl-7-[(2-nitropyridin-4-yl)oxy]-2-indoloylguanidine
6-[(2-aminopyridin-4-yl)oxy]-1-methyl-2-indoloylguanidine
7-[(2-aminopyridin-4-yl)oxy]-1-methyl-2-indoloylguanidine
6-[[2-(dimethylaminomethyl)pyridin-4-yl]oxy]-1-methyl-2-indoloylguanidine
7-[[2-(dimethylaminomethyl)pyridin-4-yl]oxy]-1-methyl-2-indoloylguanidine
6-[[2-(diethylaminomethyl)pyridin-4-yl]oxy]-1-methyl-2-indoloylguanidine
7-[[2-(diethylaminomethyl)pyridin-4-yl]oxy]-1-methyl-2-indoloylguanidine
1-methyl-6-[[2-(N-pyrrolidinylmethyl)pyridin-4-yl]oxy]-2-indoloylguanidine
1-methyl-7-[[2-(N-pyrrolidinylmethyl)pyridin-4-yl]oxy]-2-indoloylguanidine
1-methyl-6-[(thiophen-2-yl)oxy]-2-indoloylguanidine
1-methyl-7-[(thiophen-2-yl)oxy]-2-indoloylguanidine
1-methyl-6-[(5-nitrothiophen-2-yl)oxy1-2-indoloylguanidine
1-methyl-7-[(5-nitrothiophen-2-yl)oxy]-2-indoloylguanidine
6-[(5-aminothiophen-2-yl)oxy]-1-methyl-2-indoloylguanidine
7-[(5-aminothiophen-2-yl)oxy]-1-methyl-2-indoloylguanidine
6-[[5-(dimethylaminomethyl)thiophen-2-yl]oxy]-1-methyl-2-indoloylguanidine
7-[[5-(dimethylaminomethyl)thiophen-2-yl]oxy]-1-methyl-2-indoloylguanidine
6-[[5-(diethylaminomethyl)thiophen-2-yl]oxy]-1-methyl-2-indoloylguanidine
7-[[5-(diethylaminomethyl)thiophen-2-yl]oxy]-1-methyl-2-indoloylguanidine
6-[[5-(aminomethyl)thiophen-2-yl]oxy]-1-methyl-2-indoloylguanidine
7-[[5-(aminomethyl)thiophen-2-yl]oxy]-1-methyl-2-indoloylguanidine
1-methyl-6-[[5-(N-pyrrolidinylmethyl)-thiophen-2-yl]oxy]-2-indoloylguanidine
1-methyl-7-[[5-(N-pyrrolidinylmethyl)-thiophen-2-yl]oxy]-2-indoloylguanidine
4-chloro-6-[[5-(diethylaminomethyl)pyridin-3-yl]oxy]-1-methyl-2-indoloylguanidine
4-chloro-7-[[5-(diethylaminomethyl)pyridin-3-yl]oxy]-1-methyl-2-indoloylguanidine
4-chloro-1-methyl-6-[[5-(N-pyrrolidinyl-methyl)pyridin-3-yl]oxy]-2-indoloylguanidine
4-chloro-1-methyl-7-[[5-(N-pyrrolidinyl-methyl)pyridin-3-yl]oxy]-2-indoloylguanidine
4-chloro-1-methyl-6-[(pyridin-4-yl)oxy]-2-indoloylguanidine
4-chloro-1-methyl-7-[(pyridin-4-yl)oxy]-2-indoloylguanidine
4-chloro-1-methyl-6-[(2-nitropyridin-4-yl)oxy]-2-indoloylguanidine
4-chloro-1-methyl-7-[(2-nitropyridin-4-yl)oxy]-2-indoloylguanidine
6-[(2-aminopyridin-4-yl)oxyl-4-chloro-1-methyl-2-indoloylguanidine
7-[(2-aminopyridin-4-yl)oxy]-4-chloro-1-methyl-2-indoloylguanidine
4-chloro-6-[[2-(dimethylaminomethyl)pyridin-4-yl]oxy]-1-methyl-2-indoloylguanidine
4-chloro-7-[[2-(dimethylaminomethyl)pyridin-4-yl]oxy]-1-methyl-2-indoloylguanidine
4-chloro-6-[[2-(diethylaminomethyl)pyridin-4-yl]oxy]-1-methyl-2-indoloylguanidine
4-chloro-7-[[2-(diethylaminomethyl)pyridin-4-yl]oxy]-1-methyl-2-indoloylguanidine
4-chloro-1-methyl-6-[[2-(N-pyrrolidinyl-methyl)pyridin-4-yl]oxy]-2-indoloylguanidine
4-chloro-1-methyl-7-[[2-(N-pyrrolidinyl-methyl)pyridin-4-yl]oxy]-2-indoloylguanidine
4-chloro-1-methyl-6-[(thiophen-2-yl)oxy]-2-indoloylguanidine
4-chloro-1-methyl-7-[(thiophen-2-yl)oxy]-2-indoloylguanidine
4-chloro-1-methyl-6-[(5-nitrothiophen-2-yl)oxy]-2-indoloylguanidine
4-chloro-1-methyl-7-[(5-nitrothiophen-2-yl)oxy]-2-indoloylguanidine
6-[(5-aminothiophen-2-yl)oxy]-4-chloro-1-methyl-2-indoloylguanidine
7-[(5-aminothiophen-2-yl)oxy]-4-chloro-1-methyl-2-indoloylguanidine
6-[[5-(aminomethyl)thiophen-2-yl]oxy]-4-chloro-1-methyl-2-indoloylguanidine
7-[[5-(aminomethyl)thiophen-2-yl]oxy]-4-chloro-1-methyl-2-indoloylguanidine
4-chloro-6-[[5-(dimethylaminomethyl)thiophen-2-yl]oxy]-1-methyl-2-indoloylguanidine
4-chloro-7-[[5-(dimethylaminomethyl)thiophen-2-yl]oxy]-1-methyl-2-indoloylguanidine
4-chloro-6-[[5-(diethylaminomethyl)thiophen-2-yl]oxy]-1-methyl-2-indoloylguanidine
4-chloro-7-[[5-(diethylaminomethyl)thiophen-2-yl]oxy]-1-methyl-2-indoloylguanidine
4-chloro-1-methyl-6-[[5-(N-pyrrolidinyl-methyl)thiophen-2-yl]oxy]-2-indoloylguanidine
4-chloro-1-methyl-7-[[5-(N-pyrrolidinyl-methyl)thiophen-2-yl]oxy]-2-indoloylguanidine
6-[[5-(diethylaminomethyl)pyridin-3-yl]oxy]-1-methyl-4-trifluoromethyl-2-indoloylguanidine
7-[[5-(diethylaminomethyl)pyridin-3-yl]oxy]-1-methyl-4-trifluoromethyl-2-indoloylguanidine
1-methyl-6-[[5-(N-pyrrolidinylmethyl)-pyridin-3-yl]oxy]-4-trifluoromethyl-2-indoloylguanidine
1-methyl-7-[[5-(N-pyrrolidinylmethyl)-pyridin-3-yl]oxy]-4-trifluoromethyl-2-indoloylguanidine
1-methyl-6-[(pyridin-4-yl)oxy]-4-trifluoromethyl-2-indoloylguanidine
1-methyl-7-[(pyridin-4-yl)oxy]-4-trifluoromethyl-2-indoloylguanidine
1-methyl-6-[(2-nitropyridin-4-yl)oxy]-4-trifluoromethyl-2-indoloylguanidine
1-methyl-7-[(2-nitropyridin-4-yl)oxy]-4-trifluoromethyl-2-indoloylguanidine 6-[(2-aminopyridin-4-yl)oxy]-1-methyl-4-trifluoromethyl-2-indoloylguanidine 7-[(2-aminopyridin-4-yl)oxy]-1-methyl-4-trifluoromethyl-2-indoloylguanidine 6-[[2-(dimethylaminomethyl)pyridin-4-yl]oxy]-1-methyl-4-trifluoromethyl-2-indoloylguanidine 7-[[2-(dimethylaminomethyl)pyridin-4-yl]oxy]-1-methyl-4-trifluoromethyl-2-indoloylguanidine 6-[[2-(dimethylaminomethyl)pyridin-4-yl]oxy]-1-methyl-4-trifluoromethyl-2-indoloylguanidine 7-[[2-(dimethylaminomethyl)pyridin-4-yl]oxy]-1-methyl-4-trifluoromethyl-2-indoloylguanidine 1-methyl-6-[[2-(N-pyrrolidinylmethyl)-pyridin-4-yl]oxy]-4-trifluoromethyl-2-indoloylguanidine 1-methyl-7-[[2-(N-pyrrolidinylmethyl)-pyridin-4-yl]oxy]-4-trifluoromethyl-2-indoloylguanidine 1-methyl-6-[(thiophen-2-yl)oxy]-4-trifluoromethyl-2-indoloylguanidine 1-methyl-7-[(thiophen-2-yl)oxy]-4-trifluoromethyl-2-indoloylguanidine 1-methyl-6-[(5-nitrothiophen-2-yl)oxy]-4-trifluoromethyl-2-indoloylguanidine 1-methyl-7-[(5-nitrothiophen-2-yl)oxy]-4-trifluoromethyl-2-indoloylguanidine 6-[(5-aminothiophen-2-yl)oxy]-1-methyl-4-trifluoromethyl-2-indoloylguanidine 7-[(5-aminothiophen-2-yl)oxy]-1-methyl-4-trifluoromethyl-2-indoloylguanidine 6-[[5-(aminomethyl)thiophen-2-yl]oxy]-1-methyl-4-trifluoromethyl-2-indoloylguanidine 7-[[5-(aminomethyl)thiophen-2-yl]oxy]-1-methyl-4-trifluoromethyl-2-indoloylguanidine 6-[[5-(dimethylaminomethyl)thiophen-2-yl]oxy]-1-methyl-4-trifluoromethyl-2-indoloylguanidine 7-[[5-(dimethylaminomethyl)thiophen-2-yl]oxy]-1-methyl-4-trifluoromethyl-2-indoloylguanidine 6-[[5-(diethylaminomethyl)thiophen-2-yl]oxy]-1-methyl-4-trifluoromethyl-2-indoloylguanidine 7-[[5-(diethylaminomethyl)thiophen-2-yl]oxy]-1-methyl-4-trifluoromethyl-2-indoloylguanidine 1-methyl-6-[[5-(N-pyrrolidinylmethyl)-thiophen-2-yl]oxy]-4-trifluoromethyl-2-indoloylguanidine 1-methyl-7-[[5-(N-pyrrolidinylmethyl)-thiophen-2-yl]oxy]-4-trifluoromethyl-2-indoloylguanidine 6-[[5-(aminomethyl)thiophen-2-yl]methoxy]-1-methyl-2-indoloylguanidine 7-[[5-(aminomethyl)thiophen-2-yl]methoxy]-1-methyl-2-indoloylguanidine 6-[[5-(aminomethyl)furan-2-yl]methoxy]-1-methyl-2-indoloylguanidine 7-[[5-(aminomethyl)furan-2-yl]methoxy]-1-methyl-2-indoloylguanidine 6-[[5-(aminomethyl)thiophen-2-yl]methoxy]-4-chloro-1-methyl-2-indoloylguanidine 7-[[5-(aminomethyl)thiophen-2-yl]methoxy]-4-chloro-1-methyl-2-indoloylguanidine 6-[[5-(aminomethyl)furan-2-yl]methoxy]-4-chloro-1-methyl-2-indoloylguanidine 7-[[5-(aminomethyl)furan-2-yl]methoxy]-4-chloro-1-methyl-2-indoloylguanidine 4-chloro-6-[[5-(dimethylaminomethyl)thiophen-2-yl]methoxy]-1-methyl-2-indoloylguanidine 4-chloro-7-[[5-(dimethylaminomethyl)thiophen-2-yl]methoxy]-1-methyl-2-indoloylguanidine 4-chloro-6-[[5-(dimethylaminomethyl)furan-2-yl]methoxy]-1-methyl-2-indoloylguanidine 4-chloro-7-[[5-(dimethylaminomethyl)furan-2-yl]methoxy]-1-methyl-2-indoloylguanidine 6-[[5-(aminomethyl)thiophen-2-yl]methoxy]-1-methyl-4-trifluoromethyl-2-indoloylguanidine 7-[[5-(aminomethyl)thiophen-2-yl]methoxy]-1-methyl-4-trifluoromethyl-2-indoloylguanidine 6-[[5-(aminomethyl)furan-2-yl]methoxy]-1-methyl-4-trifluoromethyl-2-indoloylguanidine 7-[[5-(aminomethyl)furan-2-yl]methoxy]-1-methyl-4-trifluoromethyl-2-indoloylguanidine 6-[[5-(dimethylaminomethyl)thiophen-2-yl]methoxy]-1-methyl-4-trifluoromethyl-2-indoloylguanidine 7-[[5-(dimethylaminomethyl)thiophen-2-yl]methoxy]-1-methyl-4-trifluoromethyl-2-indoloylguanidine 6-[[5-(dimethylaminomethyl)furan-2-yl]-methoxy]-1-methyl-4-trifluoromethyl-2-indoloylguanidine 7-[[5-(dimethylaminomethyl)furan-2-yl]-methoxy]-1-methyl-4-trifluoromethyl-2-indoloylguanidine 6-[[5-(aminomethyl)furan-2-yl]oxy]-1-methyl-2-indoloylguanidine 7-[[5-(aminomethyl)furan-2-yl]oxy]-1-methyl-2-indoloylguanidine 6-[[5-(dimethylaminomethyl)furan-2-yl]oxy]-1-methyl-2-indoloylguanidine 7-[[5-(dimethylaminomethyl)furan-2-yl]oxy]-1-methyl-2-indoloylguanidine 6-[[5-(diethylaminomethyl)furan-2-yl]oxy]-1-methyl-2-indoloylguanidine 7-[[5-(diethylaminomethyl)furan-2-yl]oxy]-1-methyl-2-indoloylguanidine 6-[[5-(N-pyrrolidinylmethyl)furan]-2-yl]oxy]-1-methyl-2-indoloylguanidine 7-[[5-(N-pyrrolidinylmethyl)furan]-2-yl]oxy]-1-methyl-2-indoloylguanidine 6-[[5-(aminomethyl)furan-2-yl]oxy]-4-chloro-1-methyl-2-indoloylguanidine 7-[[5-(aminomethyl)furan-2-yl]oxy]-4-chloro-1-methyl-2-indoloylguanidine 4-chloro-6-[[5-(dimethylaminomethyl)furan-2-yl]oxy]-1-methyl-2-indoloylguanidine 4-chloro-7-[[5-(dimethylaminomethyl)furan-2-yl]oxy]-1-methyl-2-indoloylguanidine 4-chloro-6-[[5-(diethylaminomethyl)furan-2-yl]oxy]-1-methyl-2-indoloylguanidine 4-chloro-7-[[5-(diethylaminomethyl)furan-2-yl]oxy]-1-methyl-2-indoloylguanidine 4-chloro-1-methyl-6-[[5-(N-pyrrolidinylmethyl)furan-2-yl]oxy]-2-indoloylguanidine 4-chloro-1-methyl-7-[[5-(N-pyrrolidinylmethyl)furan-2-yl]oxy]-2-indoloylguanidine 6-[[5-(aminomethyl)furan-2-yl]oxy]-1-methyl-4-trifluoromethyl-2-indoloylguanidine 7-[[5-(aminomethyl)furan-2-yl]oxy]-1-methyl-4-trifluoromethyl-2-indoloylguanidine 6-[[5-(dimethylaminomethyl)furan-2-yl]oxy]-1-methyl-4-trifluoromethyl-2-indoloylguanidine 7-[[5-(dimethylaminomethyl)furan-2-yl]oxy]-1-methyl-4-trifluoromethyl-2-indoloylguanidine 6-[[5-(diethylaminomethyl)furan-2-yl]oxy]-1-methyl-4-trifluoromethyl-2-indoloylguanidine 7-[[5-(diethylaminomethyl)furan-2-yl]oxy]-1-methyl-4-trifluoromethyl-2-indoloylguanidine 1-methyl-6-[[5-(N-pyrrolidinylmethyl)furan-2-yl]oxy]-4-trifluoromethyl-2-indoloylguanidine 1-methyl-7-[[5-(N-pyrrolidinylmethyl)furan-2-yl]oxy]-4-trifluoromethyl-2-indoloylguanidine 6-[[5-(dimethylaminomethyl)thiophen-2-yl]methoxy]-1-methyl-2-indoloylguanidine 7-[[5-(dimethylaminomethyl)thiophen-2-yl]methoxy]-1-methyl-2-indoloylguanidine 6-[[5-(dimethylaminomethyl)furan-2-yl]methoxy]-1-methyl-2-indoloylguanidine 7-[[5-(dimethylaminomethyl)furan-2-yl]methoxy]-1-methyl-2-indoloylguanidine The compounds represented by formula (1) may be converted into acid addition salts with pharmaceutically acceptable inorganic acids or organic acids, if necessary and desired. Examples of such acid addition salts are salts with inorganic acids such as hydrochloric acid, hydrobromic acid, sulfuric acid or phosphoric acid; salts with organic acids such as formic acid, acetic acid, fumaric acid, maleic acid, oxalic acid, citric acid, malic acid, tartaric acid, aspartic acid or glutamic acid; salts with sulfonic acids such as methanesulfonic acid, benzenesulfonic acid, p-toluenesulfonic acid, hydroxybenzenesulfonic acid, dihydroxybenzenesulfonic acid, etc.

The compounds of the present invention inhibit the sodium/proton ($Na^+/H^+$) exchanger system and are thus useful for the treatment and prevention of the diseases caused by increased sodium/proton ($Na^+/H^+$) exchanger activity, for example, hypertension, organ disorders associated with ischemia or ischemic reperfusion, arrhythmia, angina pectoris, diabetes mellitus, cardiac hypertrophy, cerebro-ischemic disorders, diseases caused by excessive cell proliferation, diseases induced by endothelial cell injury.

The compounds of the present invention can be prepared in the form of pharmaceutical preparations which are suitable for oral or parenteral administration. These pharmaceutical preparations can be administered orally in the form of powders, granules, tablets, capsules, syrup or suspensions; alternatively, parenterally in the form of injections using its solution, emulsion or suspension. The pharmaceutical preparations may also be administered rectally in the form of suppositories.

These pharmaceutical compositions can be prepared by mixing the compound of the present invention as the active ingredient with a conventionally acceptable carrier, a recipient, a binder, a stabilizer and a diluent. In the case of using the compound of the present invention in the form of injection, a pharmaceutically acceptable buffer, a dissolution aid or an isotonic agent may also be incorporated in the composition.

Dosage and time of administration may vary depending upon the disease, condition, age, body weight and mode of administration but the composition is administered in a daily dose of 0.1 to 2000 mg, preferably 1 to 200 mg, for adult at once or by dividing into several times.

The present invention is described below more specifically by referring to Reference Examples, Examples and Experiments but not deemed to be limited thereto.

REFERENCE EXAMPLE 1

Preparation of 7-chloro-2-indolecarboxylic acid
(Fischer's indole synthesis)

a) Preparation of Ethyl 2-(2-chlorophenyl)hydrazonopropionate

To a solution of 14.4 g (0.10 mol) of ethyl 2-methylacetacetate in 100 ml of ethanol was added dropwise 50 g of 50% potassium hydroxide aqueous solution at 0° C. After 70 g of ice was added to the solution, a diazonium salt solution prepared by mixing 12.8 g (0.10 mol) of o-chloroaniline, 13.6 g (0.20 mol) of sodium nitrite and 60 g of conc. hydrochloric acid was added to the mixture at once. The reaction mixture was stirred at 0° C. for 30 minutes. The precipitates were collected and dried under reduced pressure to give 9.10 g (37.7%) of the desired ethyl 2-(2-chlorophenyl)-hydrazonopropionate.

b) Preparation of Ethyl 7-chloro-2-indolecarboxylate

After 8.00 g (33.2 mmol) of ethyl 2-(2-chlorophenyl)hydrazonopropionate obtained above was added to 20 g of polyphosphoric acid, the mixture was gradually heated to 190° C., which was kept for 5 minutes. The reaction mixture was cooled to 60° C. and water was then added thereto. The mixture was extracted three times with ethyl acetate. The combined extracts were washed with water. After drying over anhydrous magnesium sulfate, the solvent was distilled off under reduced pressure. The resulting residue was purified by silica gel column chromatography to obtain 3.40 g (45.7%) of the desired ethyl 7-chloro-2-indole-carboxylate.

$^1$H NMR (CDCl$_3$) δ: 1.40–1.46 (3H, m), 4,43 (2H, dd, J=7.3, 14.2 Hz), 7.09 (1H, t, J=7.9 Hz), 7.25 (1H, d, J=2.3 Hz), 7.32 (1H, dd, J=1.0, 7.6 Hz), 7.58–7.61 (1H, m), 9.02 (1H, br-s).

The following compounds were prepared by carrying out the reaction in a manner similar to Reference Example 1.

(1) Ethyl 5-nitro-2-indolecarboxylate:

$^1$H NMR (CDCl$_3$) δ: 1.42–1.47 (3H, m), 4.45 (2H, dd, J=7.3, 14.2 Hz), 7.38 (1H, dd, J=0.7, 2.0 Hz), 7.50 (1H, d, J=9.3 Hz), 8.21–8.25 (1H, m), 8.69 (1H, d, J=2.0 Hz), 9.3 (1H, br-s).

(2) Ethyl 7-nitro-2-indolecarboxylate:

$^1$H NMR (CDCl$_3$) δ: 1.42–1.48 (3H, m), 4.43–4.51 (2H, m), 7.25–7.28) (1H, m), 7.37 (1H, d, J=2.3 Hz), 8.04–8.08 (1H, m), 8.31 (1H, dd, J=1.0, 7.9 Hz), 10.4 (1H, br-s).

(3) Ethyl 4-methoxy-2-indolecarboxylate:

$^1$H NMR (CDCl$_3$) δ: 1.38–1.43 (3H, m), 3.96 (3H, s), 4.36–4.44 (2H, m), 6.51 (1H, d, J=7.9 Hz), 7.01 (1H, d, J=8.3 Hz), 7.22 (1H, d, J=7.9 Hz), 7.34–7.35 (1H, m), 8.9 (1H, br-s).

(4) Ethyl 6-methoxy-2-indolecarboxylate:

$^1$H NMR (CDCl$_3$) δ: 1.38–1.43 (3H, m), 3.85 (3H, s), 4.39 (2H, dd, J=7.3, 14.2 Hz), 6.80–6.84 (2H, m), 7.16–7.17 (1H, m), 7.52–7.56 (1H, m), 8.9 (1H, br-s).

(5) Ethyl 4-nitro-2-indolecarboxylate:

$^1$H NMR (CDCl$_3$) δ: 1.44–1.49 (3H, m), 4.43–4.51 (2H, m), 7.41–7.47 (1H, m), 7.77–7.80 (1H, m), 7.92 (1H, dd, J=1.0, 2.3 Hz), 8.20 (1H, dd, J=0.7, 7.9 Hz), 9.4 (1H, br-s).

(6) Ethyl 6-nitro-2-indolecarboxylate:

$^1$H NMR (CDCl$_3$) δ: 1.46 (3H, t, J=7.3 Hz), 4.48 (2H, dd, J=7.3, 14.2 Hz), 7.29–7.30 (1H, m), 7.78 (1H, d, J=8.9 Hz), 8.05 (1H, dd, J=2.0, 8.9 Hz), 8.42 (1H, t, J=1.0 Hz), 9.6 (1H, br-s).

(7) Ethyl 4-trifluoromethyl-2-indolecarboxylate:

$^1$H NMR (CDCl$_3$) δ: 1.42–1.47 (3H, m), 4.45 (2H, dd, J=6.9, 14.2 Hz), 7.35–7.41 (2H, m), 7.46–7.49 (1H, m), 7.62 (1H, d, J=8.3 Hz), 9.32 (1H, br-s).

(8) Ethyl 6-trifluoromethyl-2-indolecarboxylate:

$^1$H NMR (CDCl$_3$) δ: 1.41–1.47 (3H, m), 4.41–4.49 (2H, m), 7.26–7.27 (1H, m), 7.36–7.40 (1H, m), 7.73–7.81 (2H, m), 9.26 (1H, br-s).

(9) Ethyl 7-phenyl-2-indolecarboxylate:

$^1$H NMR (CDCl$_3$) δ: 1.28–1.43 (3H, m), 4.41 (2H, dd, J=6.9, 14.2 Hz), 7.20–7.26 (1H, m), 7.35–7.57 (6H, m), 7.66–7.70 (2H, m), 9.11 (1H, br-s).

(10) Ethyl 4-acetyl-2-indolecarboxylate:
$^1$H NMR (CDCl$_3$) δ: 1.41–1.47 (3H, m), 2.72 (3H s), 4.40–4.48 (2H, m), 7.38 (1H, dd, J=7.3, 8.2 Hz), 7.66 (1H, dd, J=1.0, 8.3 Hz), 7.78 (1H, dd, J=1.0, 7.3 Hz), 7.99–8.00 (1H, m), 9.42 (1H, br-s).

REFERENCE EXAMPLE 2

Preparation of 4-methyl-2-indolecarboxylic Acid (Reissert's Indole Synthesis)

a) Preparation of (6-methyl-2-nitrophenyl)pyruvic Acid

A solution of 15.1 g (0.10 mol) of 2-methyl-3-nitrotoluene and 14.6 g (0.10 mol) of diethyl oxalate in 10 ml of ethanol was added to a solution of 11.2 g (0.10 mol) of potassium tert-butoxide in 50 ml of ethanol. After stirring at room temperature for 1.5 hour, the reaction mixture was refluxed for 1.5 hour. After 60 ml of water was added to the reaction mixture, the mixture was refluxed for further an hour. After cooling, ice water was poured onto the reaction mixture followed by washing twice with ethyl acetate. The aqueous layer was acidified with conc. hydrochloric acid and then extracted three times with chloroform. The combined extracts were washed with water. After drying over anhydrous magnesium sulfate, the solvent was distilled off under reduced pressure to give 10.4 g (46.6%) of the desired 6-methyl-2-nitrophenylpyruvic acid.

b) Preparation of 4-methyl-2-indolecarboxylic Acid

A 5% aqueous ammonia of 10.4 g (46.6 mmol) of 6-methyl-2-nitrophenylpyruvic acid obtained above was added to a suspension of 96.4 g (0.33 mol) of ferric sulfate heptahydrate in 324 ml of water containing 37 ml of 28% aqueous ammonia. The mixture was refluxed for 10 minutes. After insoluble matters were filtered off, the filtrate was acidified with conc. hydrochloric acid followed by extracting three times with ethyl acetate. The combined extracts were washed with saturated sodium chloride solution and dried over anhydrous magnesium sulfate. The solvent was distilled off under reduced pressure to give 4.30 g (24.5%, yield based on 2-methyl-3-nitrotoluene) of the desired 4-methyl-2-indole-carboxylic acid.

$^1$H NMR (DMSO-d$_6$) δ: 2.49 (3H, s), 6.83 (1H, d, J=6.3 Hz), 7.08–7.14 (2H, m), 7.25 (1H, d, J=8.3 Hz), 11.7 (1H, br-s), 12.8 (1H, br-s).

The following compounds were prepared in a manner similar to Reference Example 2.

(1) 4-Chloro-2-indolecarboxylic Acid:
$^1$H NMR (DMSO-d$_6$) δ: 7.06 (1H, d, J=2.0 Hz), 7.16 (1H, d, J=7.6 Hz), 7.22–7.28 (1H, m), 7.42 (1H, d, J=7.9 Hz), 12.2 (1H, br-s), 13.2 (1H, br-s).

(2) 6-Chloro-2-indolecarboxylic Acid:
$^1$H NMR (DMSO-d$_6$) δ: 7.04–7.10 (2H, m), 7.43 (1H, d, J=0.7 Hz), 7.65 (1H, d, J=8.6 Hz), 11.9 (1H, br-s), 13.0 (1H, br-s).

(3) 5-Methyl-2-indolecarboxylic Acid:
$^1$H NMR (DMSO-d$_6$) δ: 2.36 (3H, s), 6.98 (1H, dd, J=1.0, 2.0 Hz), 7.04–7.08 (1H, m), 7.30–7.33 (1H, m), 7.40 (1H, s), 11.6 (1H, br-s), 12.9 (1H, br-s).

(4) 6-Methyl-2-indolecarboxylic Acid:
$^1$H NMR (DMSO-d$_6$) δ: 2.40 (3H, s), 6.87–6.90 (1H, m), 7.00–7.01 (1H, m), 7.21 (1H, s), 7.50 (1H, d, J=8.3 Hz), 11.6 (1H, br-s), 12.7 (1H, br-s).

(5) 7-Methyl-2-indolecarboxylic Acid:
$^1$H NMR (DMSO-d$_6$) δ: 2.52 (3H, s), 6.93–7.02 (2H, m), 7.09 (1H, d, J=2.0 Hz), 11.5 (1H, br-s), 12.8 (1H, br-s).

(6) 7-Benzyloxy-2-indolecarboxylic Acid:
$^1$H NMR (DMSO-d$_6$) δ: 5.27 (2H, s), 6.86 (1H, d, J=7.3 Hz), 6.94–7.00 (1H, m), 7.07 (1H, dd, J=2.0, 7.3 Hz), 7.17–7.23 (1H, m), 7.31–7.43 (3H, m), 7.65 (2H, d, J=6.9 Hz), 11.82 (1H, br-s), 12.81 (1H, br-s).

(7) 4-Benzyloxy-2-indolecarboxylic Acid:
$^1$H NMR (DMSO-d$_6$) δ: 5.24 (2H, s), 6.62 (1H, d, J=6.9 Hz), 7.00–7.17 (3H, m), 7.31–7.44 (3H, m), 7.50–7.53 (2H, m), 11.78 (1H, br-s), 12.85 (1H, br-s).

REFERENCE EXAMPLE 3

Preparation of Methyl 6-indolecarboxylate a) Preparation of Methyl 4-chloro-3-nitrobenzoate To a solution of 10.0 g (49.6 mmol) of 4-chloro-3-nitrobenzoic acid in 100 ml of methanol was added dropwise 11.8 g (99.2 mmol) of thionyl chloride at 0° C. The reaction mixture was refluxed for 2 hours and the solvent was then distilled off under reduced pressure. Ice water was added to the resulting residue. The mixture was made basic by the addition of concentrated ammonium hydroxide. The mixture was extracted three times with ethyl acetate. The combined extracts were washed with water and dried over anhydrous magnesium sulfate. The solvent was then distilled off under reduced pressure to give 10.9 g (>99%) of the desired methyl 4-chloro-3-nitro-benzoate.

b) Preparation of Methyl 3-nitro-4-trimethylsilylethynylbenzoate

A mixture of 10.7 g (49.6 mmol) of methyl 4-chloro-3-nitrobenzoate obtained above, 8.77 g (89.3 mmols) of trimethylsilylacetylene, 0.4 g of dichloro-bis(triphenylphosphine)palladium and 120 ml of triethylamine was heated at 75° C. for 3 hours with stirring. The reaction mixture was cooled. After insoluble matters were filtered off, the extract was distilled off under reduced pressure. The resulting residue was purified by silica gel column chromatography to obtain 8.40 g (61.0%) of methyl 3-nitro-4-trimethylsilylethynylbenzoate.

c) Preparation of Methyl 4-(2,2-dimethoxyethyl)-3-nitrobenzoate

To a methanol solution of 2.92 g (54.1 mmol) of sodium methoxide was added 3.00 g (10.8 mmol) of methyl 3-nitro-4-trimethylsilylethynylbenzoate prepared above. The mixture was refluxed for 30 minutes. After cooling to 0° C., 5.52 g (54.1 mmol) of acetic acid was added to the reaction mixture and the solvent was then distilled off under reduced pressure. Ice water was poured onto the resulting residue followed by extraction three times with dichloromethane. After drying over anhydrous magnesium sulfate, the solvent was distilled off under reduced pressure and the residue was purified by silica gel column chromatography to give 2.40 g (82.4%) of methyl 4-(2,2-dimethoxyethyl)-3-nitrobenzoate.

d) Preparation of Methyl 3-amino-4-(2,2-dimethoxyethyl)benzoate

To a mixture of 4.40 g (16.3 mmol) of methyl 4-(2,2-dimethoxyethyl)-3-nitrobenzoate in a solvent mixture of 200 ml of methanol and 2 ml of acetic acid was added 0.50 g of 5% palladium-carbon to perform catalytic hydrogenation at ambient temperature under normal.pressure and then treat the reaction mixture in a conventional manner. Thus, 4.16 g of methyl 3-amino-4-(2,2-dimethoxyethyl)benzoate was obtained.

e) Preparation of Methyl 6-indolecarboxylate

After 4.00 g (16.7 mmol) of methyl 3-amino-4-(2,2-dimethoxyethyl)benzoate obtained above was added to a solution of 5 ml of 1N hydrochloric acid in 15 ml of ethanol, the mixture was heated at 60° C. for an hour. The reaction mixture was poured onto ice water followed by extraction three times with ethyl acetate. The combined extracts were then washed with water. After drying over anhydrous magnesium sulfate, the solvent was then distilled off under reduced pressure to give 3.00 g (>99%) of methyl 6-indolecarboxylate.

¹H NMR (CDCl₃) δ: 3.95 (3H, s), 7.13–7.45 (4H, m), 7.68–7.72 (1H, m), 8.94 (1H, br-s).

REFERENCE EXAMPLE 4

Preparation of Methyl 1-methyl-2-indolecarboxylate

After 2.00 g (12.4 mmol) of 2-indolecarboxylic acid was added to a suspension of 0.99 g (24.8 mmol) of 60% sodium hydride in 40 ml of dimethylformamide, the mixture was stirred at room temperature until the mixture became a transparent solution. A solution of 7.05 g (49.6 mmol) of methyl iodide in 10 ml of dimethylformamide was then added dropwise to the transparent solution at room temperature followed by stirring at the same temperature for 5 hours. The reaction mixture was poured onto ice water. The resulting mixture was then extracted three times with ethyl acetate. The combined extracts were washed with water. After drying over anhydrous magnesium sulfate, the solvent was distilled off under reduced pressure and the residue was recrystallized from n-hexane to give 1.70 g (72.4%) of methyl 1-methyl-2-indolecarboxylate.

¹H NMR (CDCl₃) δ: 3.91 (3H, s), 4.08 (3H, s), 7.12–7.18 (1H, m), 7.30 (1H, s), 7.32–7.41 (2H, m), 7.66–7.70 (1H, m).

The following compounds were prepared in a manner similar to Reference Example 4.

(1) Methyl 1-methyl-5-indolecarboxylate:
¹H NMR (CDCl₃) δ: 3.82 (3H, s), 3.93 (3H, s), 6.58 (1H, dd, J=1.0, 3.3 Hz), 7.11 (1H, d, J=3.3 Hz), 7.32 (1H, d, J=8.6 Hz), 7.91–7.95 (1H, m), 8.39–8.40 (1H, m).

(2) Methyl 1-methyl-3-indolecarboxylate
¹H NMR (CDCl₃) δ: 3.82 (3H, s), 3.91 (3H, s), 7.24–7.37 (3H, m), 7.77 (1H, s), 8.14–8.20 (1H, m).

(3) Methyl 1-methyl-4-indolecarboxylate:
¹H NMR (CDCl₃) δ: 3.84 (3H, s), 3.98 (3H, s), 7.10–7.11 (1H, m), 7.20 (1H, d, J=3.0 Hz), 7.24–7.29 (1H, m), 7.53 (1H, d, J=8.2 Hz), 7.91 (1H, dd, J=1.0, 7.6 Hz).

(4) Methyl 4-chloro-1-methyl-2-indolecarboxylate:
¹H NMR (CDCl₃) δ: 3.60 (3H, s), 3.75 (3H, s), 6.80–6.83 (1H, m), 6.89–6.95 (2H, m), 7.05 (1H, d, J=0.7 Hz).

(5) Methyl 5-chloro-1-methyl-2-indolecarboxylate;
¹H NMR (CDCl₃) δ: 3.64 (3H, s), 3.78 (3H, s), 6.93 (1H, s), 6.97–7.02 (2H, m), 7.36 (1H, t, J=1.3 Hz).

(6) Methyl 6-chloro-1-methyl-2-indolecarboxylate:
¹H NMR (CDCl₃) δ: 3.91 (3H, s), 4.04 (3H, s), 7.09–7.13 (1H, m), 7.25–7.26 (1H, m), 7.38–7.39 (1H, m), 7.56–7.59 (1H, m).

(7) Methyl 7-chloro-1-methyl-2-indolecarboxylate:
¹H NMR (CDCl₃) δ: 3.91 (3H, s), 4.47 (3H, s), 6.99 (1H, m), 7.26–7.30 (2H, m), 7.52–7.56 (1H, m).

(8) Methyl 1,4-dimethyl-2-indolecarboxylate:
¹H NMR (CDCl₃) δ: 2.56 (3H, s), 3.92 (3H, s), 4.07 (3H, s), 6.93–6.96 (1H, m), 7.17–7.29 (2H, m), 7.33 (1H, d, J=0.7 Hz).

(9) Methyl 1,5-dimethyl-2-indolecarboxylate:
¹H NMR (CDCl₃) δ: 2.44 (3H, s), 3.90 (3H, s), 4.05 (3H, s), 7.16–7.29 (3H, m), 7.42–7.45 (1H, m).

(10) Methyl 1,6-dimethyl-2-indolecarboxylate:
¹H NMR (CDCl₃) δ: 2.51 (3H, s), 3.90 (3H, s), 4.05 (3H, s), 6.99 (1H, dd, J=1.0, 8.3 Hz), 7.12–7.16 (1H, m), 7.24–7.26 (1H, m), 7.55 (1H, d, J=8.2 Hz), 7.42–7.45 (1H, m).

(11) Methyl 1,7-dimethyl-2-indolecarboxylate:
¹H NMR (CDCl₃) δ: 2.80 (3H, s), 3.89 (3H, s), 4.35 (3H, s), 6.97 (2H, m), 7.25–7.27 (1H, m), 7.26 (1H, d, J=7.3 Hz), 7.48 (1H, d, J=7.3 Hz).

(12) Methyl 1-methyl-5-methoxy-2-indolecarboxylate:
¹H NMR (CDCl₃) δ: 3.85 (3H, s), 3.90 (3H, s), 4.05 (3H, s), 7.00–7.09 (2H, m), 7.19–7.30 (2H, m).

(13) Benzyl 1-benzyl-5-indolecarboxylate:
¹H NMR (CDCl₃) δ: 5.33 (2H, s), 5.38 (2H, 5), 6.64 (1H, d, J=3.3 Hz), 7.06–7.49 (12H, m), 7.92 (1H, dd, J=1.7, 8.9 Hz), 8.45–8.46 (1H, m).

(14) Isopropyl 1-isopropyl-5-indolecarboxylate:
¹H NMR (CDCl₃) δ: 1.38 (6H, d, J=6.3 Hz), 1.53 (6H, d, J=6.6 Hz), 4.62–4.75 (1H, m), 5.21–5.35 (1H, m), 6.60 (1H, d, J=3.3 Hz), 7.27 (1H, d, J=3.3 Hz), 7.36 (1H, d, J=8.6 Hz), 7.90 (1H, dd, J=1.7, 8.6 Hz), 8.38 (1H, d, J=1.7 Hz).

REFERENCE EXAMPLE 5

Preparation of Methyl 1-methyl-6-indolecarboxylate

The reaction was carried out in a manner similar to Reference Example 4 except for using 3.00 (17.1 mmol) of methyl 6-indolecarboxylate, 0.68 g (17.1 mmol) of 60% sodium hydroxide, 4.86 g (34.4 mmol) of methyl iodide and 60 ml of dimethylformamide. Thus 2.75 g (86.9%) of methyl 1-methyl-6-indolecarboxylate was obtained.

¹H NMR (CDCl₃) δ: 3.86 (3H, s), 3.95 (3H, s), 6.51–6.53 (1H, m), 7.21 (1H, d, J=3.3 Hz), 7.63 (1H, d, J=8.6 Hz), 7.78–7.82 (1H, m), 8.10 (1H, s).

The following compounds were prepared in a manner similar to Reference Example 5.

(1) Ethyl 4-methoxy-1-methyl-2-indolecarboxylate:
¹H NMR (CDCl₃) δ: 1.39 (3H, t, J=7.3 Hz), 3.96 (3H, s), 4.06 (3H, s), 4.35 (2H, dd, J=7.3, 14.2 Hz), 6.50 (1H, d, J=7.6 Hz), 6.98 (1H, d, J=8.6 Hz), 7.24–7.30 (1H, m), 7.42 (1H, d, J=0.7 Hz).

(2) Ethyl 6-methoxy-1-methyl-2-indolecarboxylate:
¹H NMR (CDCl₃) δ: 1.37–1.42 (3H, m), 3.89 (3H, s), 4.03 (3H, s), 4.31–4.39 (2H, m), 6.75 (1H, s), 6.80–6.84 (1H, m), 7.25 (1H, s), 7.53 (1H, d, J=8.9 Hz).

(3) Ethyl 1-methyl-4-nitro-2-indolecarboxylate:
¹H NMR (CDCl₃) δ: 1.45 (3H, t, J=7.3 Hz), 4.17 (3H, s), 4.39–4.47 (2H, m), 7.41–7.48 (1H, m), 7.74–7.77 (1H, m), 7.96 (1H, d, J=1.0 Hz), 8.18–8.21 (1H, m).

(4) Ethyl 1-methyl-6-nitro-2-indolecarboxylate:
¹H NMR (CDCl₃) δ: 1.41–1.46 (3H, m), 4.17 (3H, s), 4.38–4.46 (2H, m), 7.34 (1H, d, J=1.0 Hz), 7.75 (1H, dd, J=0.7, 8.9 Hz), 8.03 (1H, dd, J=2.0, 8.9 Hz), 8.39 (1H, d, J=2.0 Hz).

(5) Ethyl 1-methyl-5-nitro-2-indolecarboxylate:
¹H NMR (CDCl₃) δ: 1.41–1.46 (3H, m), 4.14 (3H, s), 4.41 (2H, dd, J=7.3, 14.2 Hz), 7.42–7.46 (2H, m), 8.22–8.26 (1H, m), 8.66 (1H, d, J=2.0 Hz).

(6) Ethyl 1-methyl-7-nitro-2-indolecarboxylate:
¹H NMR (CDCl₃) δ: 1.43 (3H, t, J=7.3 Hz), 4.00 (3H, s), 4.37–4.45 (2H, m), 7.20 (1H, t, J=7.9 Hz), 7.43 (1H, s), 7.85–7.93 (2H, m).

(7) Methyl 1-benzyl-2-indolecarboxylate:
¹H NMR (CDCl₃) δ: 3.86 (3H, s), 5.84 (2H, s), 7.02–7.06 (2H, m), 7.13–7.44 (7H, m), 7.70–7.73 (1H, m).

(8) Methyl 1-benzyl-3-indolecarboxylate:
¹H NMR (CDCl₃) δ: 3.91 (3H, s), 5.34 (2H, s), 7.13–7.17 (2H, m), 7.20–7.36 (6H, m), 7.85 (1H, s), 8.17–8.21 (1H, m).

(9) Methyl 1-isopropyl-3-indolecarboxylate:
¹H NMR (CDCl₃) δ: 1.56 (6H, d, J=6.9 Hz), 3.92 (3H, s), 4.64–4.74 (1H, m), 7.24–7.31 (2H, m), 7.39–7.42 (2H, m), 7.96 (1H, s), 8.15–8.20 (1H, m).

(10) Ethyl 1,3-dimethyl-2-indolecarboxylate:
¹H NMR (CDCl₃) δ: 1.42–1.47 (3H, m), 2.59 (3H, s), 4.01 (3H, s), 4.37–4.45 (2H, m), 7.10–7.18 (1H, m), 7.31–7.38 (2H, m), 7.64–7.67 (1H, m).

(11) Ethyl 1-methyl-4-methylsulfonyl-2-indolecarboxylate:
$^1$H NMR (CDCl$_3$) δ: 1.41–1.46 (3H, m), 3.14 (3H, s), 4.16 (3H, s), 4.41 (2H, dd, J=7.3, 14.2 Hz), 7.48 (1H, dd, J=7.3, 8.3 Hz), 7.68–7.71 (2H, m), 7.81–7.84 (1H, m).

(12) Ethyl 1-methyl-6-methylsulfonyl-2-indolecarboxylate:
$^1$H NMR (CDCl$_3$) δ: 1.41–1.46 (3H, m), 3.11 (3H, s), 4.16 (3H, s), 4.37–4.45 (2H, m), 7.34 (1H, d, J=0.7 Hz), 7.62–7.70 (2H, m), 7.83 (1H, dd, J=0.7, 8.6 Hz), 8.07 (1H, d, J=0.7 Hz).

(13) Methyl 4-fluoro-1-methyl-2-indolecarboxylate:
$^1$H NMR (CDCl$_3$) δ: 3.92 (3H, s), 4.09 (3H, s), 6.77–6.83 (1H, m), 7.16 (1H, d, J=8.3 Hz), 7.23–7.31 (1H, m), 7.36 (1H, s).

(14) Methyl 4-bromo-1-methyl-2-indolecarboxylate:
$^1$H NMR (CDCl$_3$) δ: 3.93 (3H, s), 4.08 (3H, s), 7.16–7.26 (1H, m), 7.31–7.35 (3H, m).

(15) Methyl 1-(2-naphthylmethyl)-2-indolecarboxylate:
$^1$H NMR (CDCl$_3$) δ: 3.86 (3H, s), 6.00 (2H, s), 7.14–7.32 (3H, m), 7.37–7.43 (5H, m), 7.66–7.78 (4H, m).

(16) Methyl 1-(2-phenylethyl)-2-indolecarboxylate:
$^1$H NMR (CDCl$_3$) δ: 3.06 (2H, t, J=7.9 Hz), 3.90 (3H, s), 4.74–4.80 (2H, m), 7.11–7.33 (9H, m), 7.66–7.69 (1H, m).

(17) Methyl 1-(4-bromobenzyl)-2-indolecarboxylate:
$^1$H NMR (CDCl$_3$) δ: 3.87 (3H, s), 5.79 (2H, s), 6.92 (2H, dd, J=2.0, 6.6 Hz), 7.15–7.23 (1H, m), 7.31–7.38 (5H, m), 7.70–7.74 (1H, m).

(18) Methyl 1-(4-nitrobenzyl)-2-indolecarboxylate:
$^1$H NMR (CDCl$_3$) δ: 3.87 (3H, s), 5.93 (2H, s), 7.14–7.41 (5H, m), 7.42 (1H, d, J=0.7 Hz), 7.73–7.77 (1H, m), 8.09–8.14 (2H, m).

(19) Methyl 1-(3-phenylpropyl)-2-indolecarboxylate:
$^1$H NMR (CDCl$_3$) δ: 2.06–2.22 (2H, m), 2.69 (2H, d, J=8.0 Hz), 3.90 (3H, s), 4.60 (2H, t, J=8.0 Hz), 7.05–7.40 (9H, m), 7.66 (1H, d, J=8.0 Hz).

(20) Methyl 1-(2-methoxyethyl)-2-indolecarboxylate:
$^1$H NMR (CDCl$_3$) δ: 3.28 (3H, s), 3.73 (2H, t, J=5.9 Hz), 3.91 (3H, s), 4.74 (2H, t, J=5.9 Hz), 7.14 (1H, ddd, J=1.0, 6.9, 7.4 Hz), 7.31 (1H, d, J=0.7 Hz), 7.36 (1H, dd, J=1.3, 6.9 Hz), 7.48 (1H, dd, J=0.7, 8.6 Hz), 7.66 (1H, dd, J=1.1, 8.3 Hz).

(21) Methyl 1-(2-diethylaminoethyl)-2-indolecarboxylate:
$^1$H NMR (CDCl$_3$) δ: 1.03 (6H, t, J=7.3 Hz), 2.61 (4H, q, J=7.3 Hz), 2.70–2.82 (2H, m), 3.91 (3H, s), 4.58–4.70 (2H, m), 7.14 (1H, ddd, J=1.3, 6.7, 8.6 Hz), 7.27 (1H, d, J=1.0 Hz), 7.34 (1H, ddd, J=1.0, 6.7, 7.1 Hz), 7.43 (1H, dd, J=1.0, 8.6 Hz), 7.61–7.71 (1H, m).

(22) Ethyl 4-chloro-1-(2-diethylaminoethyl)-2-indolecarboxylate:
$^1$H NMR (CDCl$_3$) δ: 1.00 (6H, t, J=7.3 Hz), 1.42 (3H, t, J=7.3 Hz), 2.59 (4H, q, J=7.3 Hz), 2.69–2.80 (2H, m), 4.38 (2H, q, J=7.3 Hz), 4.56–4.68 (2H, m), 7.14 (1H, dd, J=1.0, 7.3 Hz), 7.18–7.28 (1H, m), 7.29–7.35 (1H, m), 7.37 (1H, d, J=0.7 Hz).

(23) Preparation of Methyl 1-[2-(2-tetrahydropyranyl)oxyethyl]-2-indolecarboxylate:

The reaction was carried out in a manner similar to Reference Example 5 except for using 2.0 g (11.4 mmol) of methyl 2-indolecarboxylate, 0.55 g (13.7 mmol) of 60% sodium hydroxide, 3.63 g (13.7 mmol) of 2-(2-iodo-ethoxy)tetrahydropyran (prepared from 2-iodoethanol and 3,4-dihydro-2H-pyran) and 50 ml of dimethylformamide. Thus, 2.87 g (83.0%) of methyl 1-[2-(2-tetrahydro-pyranyl)oxyethyl]-2-indolecarboxylate was obtained.

$^1$H NMR (CDCl$_3$) δ: 1.27–1.75 (6H, m), 3.26–3.54 (2H, m), 3.75 (1H, dt, J=4.6, 10.2 Hz), 4.03 (1H, dt, J=4.6, 10.2 Hz), 4.47 (1H, t, J=3.0 Hz), 4.80 (2H, t, J=3.7 Hz), 7.13 (1H, t, J=7.0 Hz), 7.22–7.38 (2H, m), 7.53 (1H, d, J=8.0 Hz), 7.65 (1H, d, J=8.0 Hz).

(24) Methyl 1-[3-(2-tetrahydropyranyl)oxypropyl]-2-indolecarboxylate:

The title compound was prepared in a manner similar to Reference Example 5 (23) except that 2-(3-iodopropoxy)tetrahydropyran was used in place of 2-(2-iodoethoxy)tetrahydrophyran.

$^1$H NMR (CDCl$_3$) δ: 1.42–1.97 (6H, m), 2.11 (2H, dt, J=5.9, 11.2 Hz), 3.33 (1H, dt, J=7.9, 8.3 Hz), 3.40–3.55 (1H, m), 3.72–3.88 (2H, m), 3.94 (3H, s), 4.52 (1H, dd, J=3.0, 4.3 Hz), 4.69 (2H, dt, J=0.9, 1.7 Hz), 7.14 (1H, ddd, J=1.0, 7.0, 7.9 Hz), 7.27–7.37 (2H, m), 7.48 (1H, dd, J=0.9, 8.5 Hz), 7.66 (1H, dt, J=1.0, 7.9 Hz).

(25) Synthesis of Methyl 1-(3-tert-butoxycarbonylaminopropyl)-2-indolecarboxylate:

The reaction was carried out in a manner similar to Reference Example 5 except for using 5.00 g (28.5 mmol) of methyl 2-indolecarboxylate, 1.26 g (31.4 mmol) of 60% sodium hydroxide, 12.3 g (43.2 mmol) of tert-butyl N-(3-iodopropyl)carbamate (prepared from 3-iodopropyl-amine and di-tert-butyl dicarbonate) and 60 ml of dimethylformamide. Thus, 2.54 g (27%) of methyl 1-(3-tert-butoxycarbonylaminopropyl)-2-indolecarboxylate was obtained.

$^1$H NMR (CDCl$_3$) δ: 1.45 (9H, s), 1.90–2.10 (2H, m), 3.00–3.20 (2H, m), 3.91 (3H, s), 4.62 (2H, t, J=6.9 Hz), 4.98 (1H, br-s), 7.06–7.20 (1H, m), 7.28–7.44 (3H, m), 7.68 (1H, d, J=7.3 Hz).

(26) Methyl 1-(2-tert-butoxycarbonylaminoethyl)-2-indolecarboxylate:

The title compound in a manner similar to Reference Example 5 (25) except that tert-butyl N-(2-iodopropyl)carbamate was used in place of tert-butyl N-(3-iodopropyl)carbamate.

$^1$H NMR (CDCl$_3$) δ: 1.41 (9H, s), 3.53 (2H, t, J=5.9 Hz), 3.90 (3H, s), 4.68 (2H, t, J=6.3 Hz), 4.60–4.80 (1H, m), 7.15 (1H, ddd, 1H, J=1.0, 6.9, 7.4 Hz), 7.27–7.38 (2H, m), 7.48 (1H, d, J=8.3 Hz), 7.66 (1H, d, J=7.9 Hz).

(27) Ethyl 1-methyl-4-(2-tetrahydropyranyl)oxymethyl-2-indolecarboxylate:

The title compound was prepared in a manner imilar to Reference Example 5.

$^1$H NMR (CDCl$_3$) δ: 1.39–1.44 (3H, m), 1.53–1.91 (6H, m), 3.50–3.61 (1H, m), 3.84–4.03 (1H, m), 4.09 (3H, s), 4.34–4.42 (2H, m), 4.75 (1H, t, J=3.6 Hz), 4.83 (1H, d, J=12.2 Hz), 5.08 (1H, d, J=12.2 Hz), 7.18 (1H, t, J=4.0 Hz), 7.32–7.33 (2H, m), 7.42 (1H, s).

(28) Ethyl 4-chloro-1-[4-(2-tetrahydropyranyl)oxybutyl]-2-indolecarboxylate:

The title compound was prepared in a manner similar to Reference Example 5 (23) except that 2-(4-iodobutoxy)tetrahydropyran and ethyl 4-chloro-2-indolecarboxylate was used in place of 2-(2-iodoethoxy)tetrahydropyran and methyl 2-indolecarboxylate.

$^1$H NMR (CDCl$_3$) δ: 1.42 (3H, t, J=7.3 Hz), 1.41–2.00 (10H, m), 3.32–3.56 (2H, m), 3.68–3.90 (2H, m), 4.38 (2H, q, J=7.3 Hz), 4.55 (1H, t, J=4.0 Hz), 4.60 (2H, t, J=7.6 Hz), 7.13 (1H, dd, J=1.0, 7.6 Hz), 7.22 (1H, d, J=8.2 Hz), 7.32 (1H, d, J=8.3 Hz), 7.39 (1H, s).

(29) Methyl 1-(3:4-isopropylidenedioxybutyl)-2-indolecarboxylate:

The title compound was prepared in a manner similar to Reference Example 5 except that 3,4-isopropylidenedioxybutyl iodide was used in place of methyl iodide.

$^1$H NMR (CDCl$_3$) δ: 1.34 (3H, s), 1.46 (3H, s), 1.90–2.18 (2H, m), 3.52 (1H, dd, J=6.9, 7.9 Hz), 3.91 (3H, s), 3.97 (1H, dd, J=5.9, 7.9 Hz), 4.01–4.17 (1H, m), 4.58–4.80 (2H, m), 7.15 (1H, ddd, J=1.0, 6.9, 7.4 Hz), 7.31 (1H, d, J=0.7 Hz), 7.35 (1H, ddd, J=1.3, 6.9, 7.6 Hz), 7.47–7.55 (1H, m), 7.63–7.70 (1H, m).

(30) Methyl-1-[2-[1-(4-methyl-2,6,7-trioxabicyclo-[2.2.2]octyl)]ethyl]-2-indolecarboxylate:

The title compound was prepared in a manner similar to Reference Example 5 except that 2-[1-(4-methyl-2,6,7-trioxabicyclo[2.2.2]octyl]ethyl iodide was used in place of methyl iodide.

$^1$H NMR (CDCl$_3$) δ: 0.79 (3H, s), 2.17 (2H, ddd, J=2.6, 5.3, 7.9 Hz), 3.89 (6H, s), 3.90 (3H, s), 5,87 (2H, ddd, J=2.3, 5.6, 7.9 Hz), 7.12 (1H, ddd, J=1.0, 6.9, 7.4 Hz), 7.27 (1H, d, J=0.7 Hz), 7.32 (1H, ddd, J=1.3, 6.9, 7.6 Hz), 7.48 (1H, dd, J=0.7, 8.6 Hz), 7.65 (1H, ddd, J=1.0, 1.5, 8.3 Hz).

The following compounds were prepared in a manner similar to Reference Example 5.

(31) Methyl 4-benzyloxy-1-methyl-2-indolecarboxylate:

$^1$H NMR (CDCl$_3$) δ: 3.89 (3H, s), 4.06 (3H, s), 5.22 (2H, s), 6.57 (1H, d, J=7.6 Hz), 6.99 (1H, d, J=8.6 Hz), 7.22–7.28 (1H, m), 7.30–7.51 (6H, m).

(32) Methyl 6-benzyloxy-1-methyl-2-indolecarboxylate:

$^1$H NMR (CDCl$_3$) δ: 3.89 (3H, s), 4.02 (3H, s), 5.15 (2H, s), 6.85 (1H, d, J=2.31 Hz), 6.91 (1H, dd, J=2.3, 8.6 Hz), 7.24 (1H, d, J=1.0 Hz), 7.34–7.44 (3H, m), 7.47–7.52 (2H, m), 7.53–7.57 (1H, m).

(33) Methyl 7-benzyloxy-1-methyl-2-indolecarboxylate:

$^1$H NMR (CDCl$_3$) δ: 3.89 (3H, s), 4.38 (3H, s), 5.19 (2H, s), 6.78 (1H, d, J=8.6 Hz), 6.97–7.03 (1H, m), 7.24–7.27 (2H, m), 7.33–7.51 (5H, m).

REFERENCE EXAMPLE 6

Preparation of Methyl 2-indolecarboxylate

To 300 ml of a methanol solution of 30.0 g (186.2 mmol) of 2-indolecarboxylic acid was dropwise added 44.3 g (372.3 mmol) of thionyl chloride at 0° C. The reaction mixture was refluxed for 2 hours and the solvent was then distilled off under reduced pressure. Ice water was poured onto the resulting residue. The mixture was made basic by the addition of concentrated ammonium hydroxide. The mixture was extracted three times with ethyl acetate. The extract was washed with water and dried over anhydrous magnesium sulfate. The solvent was then distilled off under reduced pressure to give 32.34 g (99.2%) of methyl 2-indolecarboxylate.

$^1$H NMR (CDCl$_3$) δ: 3.95 (3H, s), 7.13–7.45 (4H, m), 7.69 (1H, dd, J=1.0, 7.9 Hz), 8.91 (1H, br-s).

The following compounds were prepared in a manner similar to Reference Example 6.

(1) Methyl 3-indolecarboxylate:

$^1$H NMR (CDCl$_3$) δ: 3.93 (3H, s), 7.24–7.31 (2H, m), 7.38–7.45 (1H, m), 7.93 (1H, d, J=3.0 Hz), 8.17–8.22 (1H, m), 8.63 (1H, br-s).

(2) Methyl 4-fluoro-2-indolecarboxylate:

$^1$H NMR (CDCl$_3$) δ: 3.96 (3H, s), 6.78–6.85 (1H, m), 7.18–7.30 (3H, m), 8.99 (1H, br-s).

(3) Methyl 4-bromo-2-indolecarboxylate:

$^1$H NMR (CDCl$_3$) δ: 3.97 (3H, s), 7.17 (1H, dd, J=7.6, 8.3 Hz), 7.28 (1H, dd, J=1.0, 2.3 Hz), 7.32–7.39 (2H, m), 9.05 (1H, br-s).

(4) Methyl 7-benzyloxy-2-indolecarboxylate:

$^1$H NMR (CDCl$_3$) δ: 3.93 (3H, s), 5.21 (2H, s), 6.80 (1H, d, J=6.9 Hz), 7.01–7.08 (1H, m), 7.19 (1H, dd, J=2.3, 4.3 Hz), 7.24–7.31 (1H, m), 7.35–7.51 (5H, m), 9.07 (1H, br-s).

(5) Methyl 4-benzyloxy-2-indolecarboxylate:

$^1$H NMR (CDCl$_3$) δ: 3.93 (3H, s), 5.22 (2H, s), 6.58 (1H, d, J=7.6 Hz), 7.03 (1H, d, J=8.3 Hz), 7.19–7.26 (1H, m), 7.31–7.44 (4H, m), 7.50 (2H, d, J=7.3 Hz), 8.84 (1H, br-s).

REFERENCE EXAMPLE 7

Preparation of Methyl 5-indolecarboxylate

A mixture of 1.00 g (6.21 mmol) of 5-indolecarboxylic acid and 50 ml of 10% hydrogen chloride/methanol was refluxed for 2 hours. The reaction mixture was then poured onto ice water followed by neutralization with sodium bicarbonate. The mixture was extracted three times with ethyl acetate. The combined extracts were washed with aqueous sodium bicarbonate solution. After drying over anhydrous magnesium sulfate, the solvent was distilled off under reduced pressure to give 0.42 g (38.6%) of methyl 5-indole-carboxylate.

$^1$H NMR (CDCl$_3$) δ: 3.93 (3H, s), 6.64–6.66 (1H, m), 7.26–7.29 (1H, m), 7.40 (1H, dd, J=0.7, 8.6 Hz), 7.91 (1H, dd, J=1.7, 8.6 Hz), 8.3–8.6 (2H, m).

REFERENCE EXAMPLE 8

Preparation of Methyl 1-isopropyl-5-indolecarboxylate

A mixture of 2.20 g (8.97 mmol) of isopropyl 1-isopropyl-5-indolecarboxylate, 100 ml of 2N sodium hydroxide solution and 100 ml of ethanol was refluxed for an hour. The solvent was then distilled off under reduced pressure. Thereafter water was added to the residue and the resulting mixture was acidified with conc. hydrochloric acid. The precipitated solid was filtered and dried under reduced pressure to give 2.00 g of crude 1-isopropyl-5-indolecarboxylic acid. The reaction was carried out in a manner similar to Reference Example 4 using 2.00 g of the crude 1-isopropyl-5-indolecarboxylic acid, 0.44 g (11.1 mmol) of 60% sodium hydride, 2.87 g (20.2 mmol) of methyl iodide and 50 ml of dimethyl-formamide. Thus, 1.64 g (84.2%; yield based on isopropyl 1-isopropyl-5-indolecarboxylic acid) was obtained.

$^1$H NMR (CDCl$_3$) δ: 1.54 (6H, d, J=6.9 Hz), 3.93 (3H, s), 4.65–4.75 (1H, m), 6.61 (1H, d, J=3.3 Hz), 7.28 (1H, d, J=3.3 Hz), 7.37 (1H, d, J=8.6 Hz), 7.9 (1H, dd, J=1.7, 8.6 Hz), 8.39 (1H, d, J=1.7 Hz).

REFERENCE EXAMPLE 9

Preparation of 7-chloro-2-indolecarboxylic Acid

A mixture of 3.40 g (15.2 mmol) of ethyl 7-chloro-2-indolecarboxylate, 100 ml of 2N sodium hydroxide solution and 100 ml of ethanol was refluxed for an hour. The solvent was then distilled off under reduced pressure. Thereafter ice water was added to the residue and the resulting mixture was acidified with conc. hydrochloric acid and extracted three times with ethyl acetate. After drying over anhydrous magnesium sulfate, the solvent was distilled off under reduced pressure to give 2.85 g (95.8%) of 7-chloro-2-indolecarboxylic acid.

$^1$H NMR (DMSO-d$_6$) δ: 7.04–7.09 (1H, m), 7.19 (1H, d, J=2.0 Hz), 7.30 (1H, dd, J=1.0, 7.6 Hz), 7.62 (1H, d, J=8.3 Hz), 11.9 (1H, br-s), 13.1 (1H, br-s).

REFERENCE EXAMPLE 10

Preparation of 1-isopropyl-2-indolecarboxylic Acid

The reaction was carried out in a manner similar to Reference Example 4, using 6.00 g (34.2 mmol) of methyl 2-indolecarboxylate, 1.36 g (34.2 mmol) of 60% sodium hydroxide, 6.40 g (37.7 mmol) of isopropyl iodide and 100 ml of dimethylformamide. The mixture of methyl 1-isopropyl-2-indolecarboxylate and isopropyl 1-isopropyl-2-indolecarboxylate was obtained. The reaction was carried out in a manner similar to Reference Example 9, using the thus obtained mixture, 150 ml of 2N sodium hydroxide solution and 150 ml of ethanol. Thus 3.71 g (53.3%) of 1-isopropyl-2-indolecarboxylic acid was obtained.

$^1$H NMR (DMSO-$d_6$) δ: 1.58 (6H, d, J=6.9 Hz), 5.74–5.85 (1H, m), 7.05–7.11 (1H, m), 7.19–7.28 (2H, m), 7.64–7.72 (2H, m), 12.9 (1H, br-s).

REFERENCE EXAMPLE 11

Preparation of Methyl 1-methyl-7-indolecarboxylate a) Preparation of Ethyl 7-carbomethoxy-1-methyl-2-indolecarboxylate After 5.00 g (20.2 mmol) of ethyl 7-carbomethoxy-2-indolecarboxylate obtained in a manner similar to Reference Example 1 was added to a suspension of 0.81 g (20.2 mmol) of 60% sodium hydride in 80 ml of dimethylformamide, the mixture was stirred at room temperature. After the mixture became a transparent solution, 5.74 g (40.4 mmol) of methyl iodide was then added dropwise to the transparent solution at room temperature followed by stirring at 50° C. for an hour. The reaction solution was poured onto ice water. The resulting mixture was then extracted three times with ethyl acetate and the combined extracts were washed with water. After drying over anhydrous magnesium sulfate, the solvent was distilled off under reduced pressure and the residue was isolated and purified by silica gel column chromatography to give 5.20 g (98.5%) of ethyl carbomethoxy-1-methyl-2-indolecarboxylate.

b) Preparation of 1-methylindole-2,7-dicarboxylic Acid

A mixture of 5.20 g (19.9 mmol) of ethyl 7-carbomethoxy-1-methyl-2-indolecarboxylate, 90 ml of 2N sodium hydroxide and 150 ml of ethanol was refluxed for 3 hours. The reaction mixture was concentrated under reduced pressure and ice water was added to the residue. 2N hydrochloric acid was added to acidify the reaction mixture. The precipitated solid was filtered and dried under reduced pressure to give 4.70 g (>99%) of 1-methylindole-2,7-dicarboxylic acid.

c) Preparation of 1-methyl-7-indolecarboxylic acid

A mixture of 4.60 g (21.0 mmol) of 1-methyl-indole-2,7-dicarboxylic acid, 0.5 g of copper (II) oxide and 50 ml of quinoline was stirred for an hour with heating at 180° C. After cooling, the reaction mixture was poured onto 200 ml of 2N hydrochloric acid. The mixture was extracted three times with ethyl acetate and the combined extracts were washed with saturated sodium chloride solution. After drying over anhydrous magnesium sulfate, the solvent was distilled off under reduced pressure. The residue was isolated and purified by silica gel column chromatography to give 1.82 g (49.0%) of 1-methyl-7-indolecarboxylic acid.

d) Preparation of Methyl 1-methyl-7-indolecarboxylate

To 70 ml of a methanol solution of 1.82 g (10.4 mmol) of 1-methyl-7-indolecarboxylic acid was added dropwise 3.09 g (26.0 mmol) of thionyl chloride at 0° C. The reaction mixture was refluxed for 2 hours and the solvent was then distilled off under reduced pressure. Ice water was poured onto the resulting residue and ammonium hydroxide was added to render the mixture alkaline. The mixture was extracted three times with ethyl acetate. The combined extracts were washed with water and dried over anhydrous magnesium sulfate. The solvent was then distilled off under reduced pressure. The residue was isolated and purified by silica gel column chromatography to give 1.16 g (59.0%) of methyl 1-methyl-7-indolecarboxylate.

$^1$H NMR (CDCl$_3$) δ: 3.88 (3H, S), 3.96 (3H, s), 6.54 (1H, d, J=3.3 Hz), 7.10 (1H, t, J=7.6 Hz), 7.67 (1H, d, J=7.3 Hz), 7.75–7.78 (1H, m).

REFERENCE EXAMPLE 12

Preparation of Ethyl 7-benzyloxy-4-chloro-2-indolecarboxylate a) Preparation of 3-benzyloxy-6-chloro-2-nitrotoluene A mixture of 1.50 g (8.00 mmols) of 4-chloro-3-methyl-2-nitrophenol, 1.50 g (8.80 mmols) of benzyl bromide, 2.43 g (17.6 mmols) of potassium carbonate and 70 ml of acetone was refluxed for 2 hours. Thereafter insoluble matters were filtered off and the filtrate was concentrated under reduced pressure. The residue was isolated and purified by silica gel column chromato- graphy to give 2.22 g (>99%) of 3-benzyloxy-6-chloro-2-nitrotoluene.

b) Preparation of Ethyl (3-benzyloxy-6-chloro-2-nitrophenyl)pyruvate

Diethyl oxalate, 1.20 g (7.92 mmol), was added dropwise to a suspension of 0.67 g (7.92 mmol) of potassium ethoxide in diethyl ether (50 ml) at room temperature. Subsequently 2.00 g (7.20 mmol) of 3-benzyloxy-6-chloro-2-nitrotoluene was added to the mixture followed by stirring for 4 hours at room temperature. The reaction solution was poured onto 1N hydrochloric acid and the mixture was extracted twice with diethyl ether. The combined extracts were washed with saturated sodium chloride solution. After drying over anhydrous magnesium sulfate, the solvent was distilled off under reduced pressure. The residue was isolated and purified by silica gel column chromatography to give 1.60 g (53.5%) of ethyl (3-benzyloxy-6-chloro-2-nitrophenyl)pyruvate.

c) Preparation of Ethyl 7-benzyloxy-4-chloro-2-indolecarboxylate

A mixture of 1.60 g (4.24 mmol) of ethyl (3-benzyloxy-4-chloro-2-nitrophenyl)pyruvate, 22.9 g (29.7 mmol) of 20% titanium trichloride solution and 60 ml of acetone was stirred at room temperature for 3 hours. The reaction mixture was poured onto ice water and the mixture was extracted three times with ethyl acetate. The combined extracts were washed with saturated sodium hydrogencarbonate solution. After drying over anhydrous magnesium sulfate, the solvent was distilled off under reduced pressure. The residue was purified by silica gel column chromatography to give 0.50 g (35.8%) of ethyl 7-benzyloxy-4-chloro-2-indolecarboxylate.

$^1$H NMR (CDCl$_3$) δ: 1.39–1.44 (3H, m), 4.40 (2H, dd, J=6.9, 14.2 Hz), 5.18 (2H, s), 6.69 (1H, d, J=8.3 Hz), 7.01 (1H, d, J=8.3 Hz), 7.26–7.27 (1H, m), 7.35–7.48 (5H, m), 9.15 (1H, br-s).

REFERENCE EXAMPLE 13

Preparation of Ethyl 6-benzyloxy-4-chloro-2-indolecarboxylate a) Preparation of Ethyl 3-(4-benzyloxy-2-chlorophenyl)-2-azidopropenoate An ethanol solution, 70 ml, containing 5.40 g (21.9 mmol) of 4-benzyloxy-2-chlorobenzaldehyde and 11.3 g (87.6 mmol) of ethyl azide acetate was gradually added dropwise to 70 ml of an ethanol solution of 5.95 g (87.6 mmol) of sodium ethoxide at −10° C. After stirring at −10° C. for further 5 hours, the reaction temperature was slowly elevated to room temperature. The reaction mixture was poured onto 200 ml of saturated ammonium chloride aqueous solution and the mixture was extracted three times with ethyl acetate. The combined extracts were then washed with saturated ammonium chloride solution and next with saturated sodium chloride solution. After drying over anhydrous magnesium sulfate, the solvent was distilled off under reduced pressure. The resulting residue was purified by silica gel column chromatography to give 4.50 g (57.5%) of ethyl 3-(4-benzyloxy-2-chlorophenyl)-2-azidopropenoate.

b) Preparation of Ethyl 6-benzyloxy-4-chloro-2-indolecarboxylate

A solution of 4.50 g (12.6 mmols) of ethyl 3-(4-benzyloxy-2-chlorophenyl)-2-azidopropenoate in 100 ml of toluene was refluxed for 3 hours. The reaction mixture was concentrated under reduced pressure. The resulting residue was purified by silica gel column chromatography to give 3.73 g (89.8%) of ethyl 6-benzyloxy-4-chloro-2-indolecarboxylate.

$^1$H NMR (CDCl$_3$) δ: 1.38–1.43 (3H, m), 4.35–4.43 (2H, m), 5.09 (2H, s), 6.79 (1H, dd, J=0.7, 2.0 Hz), 6.95 (1H, d, J=2.0 Hz), 7.23–7.24 (1H, m), 7.31–7.45 (5H, m), 8.94 (1H, br-s).

REFERENCE EXAMPLE 14

Preparation of methyl 1-(2-carbamoylethyl)-2-indolecarboxylate a) Preparation of Methyl 1-(2-cyanoethyl)-2-indolecarboxylate After 3.63 g (68.4 mmol) of acrylonitrile and 2.2 ml of 40% methanol solution of N-benzyltrimethylammonium hydroxide was added to a solution of 10.0 g (57.1 mmol) of methyl 2-indolecarboxylate in 150 ml of 1,4-dioxane, the mixture was stirred at 55° C. for an hour. The reaction mixture was concentrated under reduced pressure. The resulting residue was added to a mixture of 5 ml of acetic acid and 500 ml of water. The aqueous layer was extracted twice with methylene chloride and the combined extracts were washed with water. After drying over anhydrous magnesium sulfate, the solvent was distilled off under reduced pressure. The residue was purified by silica gel column chromatography to give 13.0 g of methyl 1-(2-cyano-ethyl)-2-indolecarboxylate.

b) Preparation of Methyl 1-(2-carbamoylethyl)-2-indolecarboxylate

A mixture of 3.12 g (13.7 mmol) of methyl 1-(2-cyanoethyl)-2-indolecarboxylate, 30 ml of 10% sodium carbonate solution, 30 ml of 30% hydrogen peroxide and 100 ml of acetone was stirred at room temperature for 4 hours. Next, the reaction mixture was cooled to 0° C. and 10% sodium sulfite solution was added dropwise to decompose an excess of the peroxide. The most of acetone in the reaction mixture was then distilled off and the concentrate was extracted three times with ethyl acetate. The combined extracts were washed with saturated sodium chloride solution. After drying over anhydrous magnesium sulfate, the solvent was distilled off under reduced pressure. The resulting residue was purified by silica gel column chromatography to give 2.30 g (68%) of methyl 1-(2-carbamoylethyl)-2-indolecarboxylate.

$^1$H NMR (CDCl$_3$) δ: 2.75 (2H, ddd, J=1.7, 5.9, 7.6 Hz), 3.92 (3H, s), 4.85 (2H, ddd, J=1.7, 5.9, 7.6 Hz), 5.37 (1H, br-s), 5.72 (1H, br-s), 7.16 (1H, ddd, J=1.0, 6.9, 7.4 Hz), 7.32 (1H, d, J=1.0 Hz), 7.37 (1H, ddd, J=1.0, 7.3, 7.8 Hz), 7.53 (1H, dd, J=0.8, 8.4 Hz), 7.67 (1, dt, J=1.0, 7.9 Hz).

The following compound was prepared in a manner similar to Reference Example 14.

(1) Ethyl 1-(2-carbamoylethyl)-4-chloro-2-indolecarboxylate:

$^1$H NMR (CDCl$_3$) δ: 1.43 (3H, t, J=7.3 Hz), 2.65–2.82 (1H, m), 4.39 (2H, q, J=7.3 Hz), 4.84 (2H, ddd, J=1.0, 6.3, 7.3 Hz), 5.45 (1H, br-s), 5.68 (1H, br-s), 7.14 (1H, d, J=7.9 Hz), 7.26 (1H, dd, J=7.6, 8.2 Hz), 7.41 (1H, d, J=1.0 Hz), 7.45 (1H, d, J=8.6 Hz).

REFERENCE EXAMPLE 15

Preparation of Methyl 7-carbamoylmethoxy-1-methyl-2-indolecarboxylate a) Preparation of Methyl 7-hydroxy-1-methyl-2-indolecarboxylate In a solvent mixture of 50 ml of tetrahydrofuran and 50 ml of methanol was dissolved 2.31 g (7.82 mmol) of methyl 7-benzyloxy-1-methyl-2-indolecarboxylate. After 0.5 g of 10% palladium/carbon was added to the solution, catalytic hydrogenation was performed at ambient temperature under normal pressure. After completion of the reaction, the catalyst was filtered off and the filtrate was concentrated under reduced pressure. The resulting residue was purified by silica gel column chromatography to give 1.63 g (>99%) of methyl 7-hydroxy-1-methyl-2-indolecarboxylate.

b) Preparation of Methyl 7-carbamoylmethoxy-1-methyl-2-indolecarboxylate

After 0.50 g (2.44 mmol) of methyl 7-hydroxy-1-methyl-2-indolecarboxylate was added to a suspension of 0.01 g (2.44 mmol) of 60% sodium hydride in 25 ml of dimethylformamide, the mixture was stirred at room temperature until the mixture became a transparent solution. Then 0.25 g (2.68 mmols) of 2-chloroacetamide as added dropwise to the transparent solution at room temperature followed by stirring at 50° C. for an hour. The reaction mixture was poured onto ice water. The resulting mixture was then extracted three times with ethyl acetate. The combined extracts were washed with water. After drying over anhydrous magnesium sulfate, the solvent was distilled off under reduced pressure. The residue was purified by silica gel column chromatography to give 0.54 g (84.4%) of methyl 7-carbamoylmethoxy-1-methyl-2-indolecarboxylate.

$^1$H NMR (CDCl$_3$) δ: 3.91 (3H, s), 4.41 (3H, s), 4.67 (2H, s), 5.70 (1H, br-s), 6.41 (1H, br-s), 6.70–6.73 (1H, m), 7.03 (1H, t, J=7.9 Hz), 7.26 (1H, s), 7.31–7.34 (1H, m).

The following compounds were synthesized in a manner similar to Reference Example 15.

(1) Methyl 1-Methyl-7-(2-phenylethoxy)-2-indolecarboxylate:

$^1$H NMR (CDCl$_3$) δ: 3.17–3.22 (2H, m), 3.87 (3H, s), 4.24 (3H, s), 4.31–4.36 (2H, m), 6.68 (1H, d, J=7.6 Hz), 6.94–7.00 (1H, m), 7.18–7.35 (7H, m).

(2) Methyl 1-methyl-7-(3-phenylpropoxy)-2-indolecarboxylate:

$^1$H NMR (CDCl$_3$) δ: 2.16–2.26 (2H, m), 2.84–2.90 (2H, m), 3.89 (3H, s), 4.07–4.12 (2H, m), 4.43 (3H, s), 6.64 (1H, d, J=6.9 Hz), 6.97 (1H, t, J=7.9 Hz), 7.18–7.23 (5H, m), 7.25–7.33 (2H, m).

(3) Ethyl 7-carbamoylmethoxy-4-chloro-1-methyl-2-indolecarboxylate:

$^1$H NMR (CDCl$_3$) δ: 1.33–1.36 (3H, m), 4.29–4.37 (5H, m), 4.60 (2H, s), 6.69 (1H, d, J=8.3 Hz), 7.06 (1H, dd, J=0.7, 8.2 Hz), 7.15 (1H, d, J=0.7 Hz), 7.38 (1H, br-s), 7.54 (1H, br-s).

(4) Ethyl 4-chloro-7-(2-dimethylaminoethoxy)-1-methyl-2-indolecarboxylate:

$^1$H NMR (CDCl$_3$) δ: 1.39–1.44 (3H, m), 2.36 (6H, s), 2.82 (2H, t, J=5.9 Hz), 4.17 (2H, t, J=5.9 Hz), 4.33–4.40 (5H, m), 6.59 (1H, d, J=8.3 Hz), 6.96 (1H, d, J=7.9 Hz), 7.30 (1H, s).

(5) Ethyl 6-carbamoylmethoxy-1-methyl-2-indolecarboxylate:

$^1$H NMR (CDCl$_3$) δ: 1.38–1.43 (3H, m), 4.03 (3H, s), 4.32–4.40 (2H, m), 4.60 (2H, s), 5.61 (1H, br-s), 6.59 (1H, br-s), 6.79 (1H, d, J=2.3 Hz), 6.84 (1H, dd, J=2.3, 8.6 Hz), 7.26–7.27 (1H, m), 7.57–7.60 (1H, m).

(6) Ethyl 4-chloro-1-methyl-7-[2-(N-pyrrolidinyl)-ethoxy]-2-indolecarboxylate:
$^1$H NMR (CDCl$_3$) δ: 1.39–1.44 (3H, m), 1.79–1.84 (4H, m), 2.63–2.68 (4H, m), 2.97–3.02 (2H, m), 4.20–4.24 (2H, m), 4.33–4.41 (5H, m), 6.60 (1H, d, J=8.6 Hz), 6.97 (1H, d, J=8.3 Hz), 7.31 (1H, s).

(7) Methyl 7-(3-tert-butoxycarbonylaminopropoxy)-1-methyl-2-indolecarboxylate:
$^1$H NMR (CDCl$_3$) δ: 1.43 (9H, s), 2.09 (2H, t, J=6.3 Hz), 3.35–3.42 (2H, m), 3.89 (3H, s), 4.13–4.18 (2H, m), 4.39 (3H, s), 4.73 (1H, br-s), 6.69 (1H, d, J=7.9 Hz), 6.96–7.02 (1H, m), 7.21–7.26 (2H, m).

(8) Ethyl 7-(3-tert-butoxycarbonylaminopropoxy)-4-chloro-1-methyl-2-indolecarboxylate:
$^1$H NMR (CDCl$_3$) δ: 1.38–1.44 (12H, m), 2.03–2.13 (2H, m), 3.33–3.40 (2H, m), 4.12 (2H, t, J=5.9 Hz), 4.33–4.41 (5H, m), 4.70 (1H, br-s), 6.58 (1H, d, J=8.3 Hz), 6.96 (1H, d, J=8.3 Hz), 7.31 (1H, s).

(9) Ethyl 6-(3-tert-butoxycarbonylaminopropoxy)-1-methyl-2-indolecarboxylate:
$^1$H NMR (CDCl$_3$) δ: 1.37–1.42 (3H, m), 1.45 (9H, s), 2.02 (2H, dd, J=6.3, 12.5 Hz), 3.33–3.40 (2H, m), 4.02 (3H, s), 4.10 (2H, t, J=5.9 Hz), 4.35 (2H, dd, J=6.9, 14.2 Hz), 4.78 (1H, br-s), 6.76 (1H, s), 6.78–6.83 (1H, m), 7.24–7.26 (1H, m), 7.53 (1H, d, J=8.6 Hz).

(10) Ethyl 7-(2-tert-butoxycarbonylaminoethoxy)-4-chloro-1-methyl-2-indolecarboxylate:
$^1$H NMR (CDCl$_3$) δ: 1.39–1.44 (3H, m), 1.45 (9H, s), 3.63 (2H, dd, J=5.3, 10.6 Hz), 4.13 (2H, t, J=5.3 Hz), 4.30–4.41 (5H, m), 4.63–4.89 (1H, m), 6.58 (1H, d, J=8.3 Hz), 6.97 (1H, d, J=8.3 Hz), 7.31 (1H, s).

(11) Methyl 1-methyl-7-[2-(2-tetrahydropyranyl)oxyethoxy]-2-indolecarboxylate:
$^1$H NMR (CDCl$_3$) δ: 1.52–1.85 (6H, m), 3.50–3.58 (1H, m), 3.83–3.90 (5H, m), 4.11–4.19 (1H, m), 4.26–4.30 (2H, m), 4.42 (3H, s), 4.73–4.75 (1H, m), 6.70–6.73 (1H, m), 7.01 (1H, t, J=7.9 Hz), 7.22–7.26 (2H, m).

(12) Ethyl 4-chloro-1-methyl-7-[2-(2-tetrahydropyranyl)-oxyethoxy]-2-indolecarboxylate:
$^1$H NMR (CDCl$_3$) δ: 1.42 (3H, t, J=7.3 Hz), 1.52–1.85 (6H, m), 3.51–3.56 (1H, m), 3.81–3.91 (2H, m), 4.10–4.17 (1H, m), 4.23–4.27 (2H, m), 4.33–4.40 (5H, m), 4.72–4.73 (1H, m), 6.61 (1H, d, J=8.2 Hz), 6.96 (1H, d, J=8.3 Hz), 7.30 (1H, s).

(13) Ethyl 4-chloro-7-(2:3-isopropylidenedioxypropoxy)-1-methyl-2-indolecarboxylate:
$^1$H NMR (CDCl$_3$) δ: 1.39–1.47 (9H, m), 3.91–3.99 (1H, m), 4.06–4.23 (3H, m), 4.33–4.41 (1H, m), 4.51–4.63 (1H, m), 6.60 (1H, d, J=8.3 Hz), 6,97 (1H, d, J=8.3 Hz), 7.31 (1H, s).

(14) Ethyl 4-chloro-1-methyl-7-[4-(2-tetrahydropyranyl)-oxybutoxy]-2-indolecarboxylate:
$^1$H NMR (CDCl$_3$) δ: 1.39–1.44 (3H, m), 1.52–1.85 (8H, m), 1.87–2.04 (2H, m), 3.44–3.55 (2H, m), 3.79–3.91 (2H, m), 4.10 (2H, t, J=6.3 Hz), 4.33–4.41 (5H, m), 4.58–4.61 (1H, m), 6,56 (1H, d, J=8.3 Hz), 6.96 (1H, d, J=8.3 Hz), 7.30 (1H, s).

REFERENCE EXAMPLE 16

Preparation of Ethyl 4-carboxy-1-methyl-2-indolecarboxylate a) Preparation of Ethyl 4-hydroxymethyl-1-methyl-2-indolecarboxylate In a solvent mixture of 20 ml of 2N hydrochloric acid and 60 ml of tetrahydrofuran was dissolved 4.00 g (12.6 mmol) of ethyl 1-methyl-4-(2-tetrahydropyranyl)-oxymethyl-2-indolecarboxylate. The solution was stirred at 50° C. for an hour. The reaction mixture was poured onto ice water and the aqueous layer was extracted three times with ethyl acetate. The combined extracts were washed with saturated sodium hydrogencarbonate solution. After drying over anhydrous magnesium sulfate, the solvent was distilled off under reduced pressure. The residue was purified by silica gel column chromatography to give 2.90 g (99%) of ethyl 4-hydroxymethyl-1-methyl-2-indolecarboxylate.

b) Preparation of Ethyl 4-carboxy-1-methyl-2-indolecarboxylate

In 30 ml of acetone was dissolved 0.70 g (3.00 mmols) of ethyl 4-hydroxymethyl-1-methyl-2-indolecarboxylate. After 3.3 ml of Jones' reagent, which was prepared by dissolving 26.7 g of chromium (VI) oxide in a mixture of 23 ml of conc. sulfuric acid and 40 ml of water and adding water to make the whole volume 100 ml, was added dropwise to the above solution at room temperature, the mixture was stirred at room temperature for an hour. The reaction mixture was poured onto ice water and the aqueous layer was extracted three times with chloroform. The combined extracts were washed with saturated sodium hydrogencarbonate solution. After drying over anhydrous magnesium sulfate, the solvent was distilled off under reduced pressure. The residue was purified by silica gel column chromatography to give 0.38 g (51.2%) of ethyl 4-carboxy-1-methyl-2-indolecarboxylate.

$^1$H NMR (DMSO-d$_6$) δ: 1.34–1.40 (3H, m), 4.08 (3H, s), 4.35 (2H, dd, J=7.3, 14.2 Hz), 7.41–7.47 (1H, m), 7.72 (1H, s), 7.82–7.89 (2H, m), 12.7 (0.5H, br-s).

REFERENCE EXAMPLE 17

Preparation of Ethyl 6-benzyloxy-4-methyl-2-indolecarboxylate a) Preparation of 4-benzyloxy-2-methylbenzoic Acid A mixture of 5.00 g (18.9 mmol) of 5-benzyloxy-2-bromotoluene, 0.46 g (18.9 mmol) of metallic magnesium, a catalytic amount of iodine and 20 ml of tetrahydrofuran was refluxed for 2 hours. After cooling to −50° C., carbon dioxide was bubbled into the reaction solution for 30 minutes. The reaction temperature was then elevated to room temperature and stirring was continued at the same temperature for further 2 hours. Next the reaction mixture was poured into 1N hydrochloric acid followed by extraction twice with ethyl acetate. The combined extracts were washed with water. After drying over anhydrous magnesium sulfate, the solvent was distilled off under reduced pressure. The resulting residue was purified by silica gel column chromatography to give 1.40 g of 4-benzyloxy-2-methylbenzoic acid.

b) Preparation of Methyl 4-benzyolxy-2-methylbenzoate

Using 1.40 g (5.78 mmol) of 4-benzyloxy-2-methylbenzoic acid, 1.37 g (11.6 mmol) of thionyl chloride and 50 ml of methanol, the reaction was carried out in a manner similar to Reference Example 6 to obtain 0.77 g of methyl 4-benzyloxy-2-methylbenzoate.

c) Preparation of 4-benzyloxy-2-methylbenzyl Alcohol

A suspension of 0.11 g (2.93 mmol) of lithium aluminum hydride in 20 ml of tetrahydrofuran was cooled to 0° C. A solution of 0.75 g (2.93 mmol) of methyl 4-benzyloxy-2-methylbenzoate in 20 ml of tetrahydrofuran was added dropwise to the suspension at 0° C. After stirring at 0° C. for 2 hours, the reaction mixture was treated in a conventional manner to give 0.66 g of 4-benzyloxy-2-methylbenzyl alcohol.

d) Preparation of 4-benzyloxy-2-methylbenzaldehyde

A mixture of 0.70 g (3.07 mmol) of 4-benzyl-oxy-2-methylbenzyl alcohol, 2.67 g (30.7 mmol) of manganese dioxide, 0.5 ml of methanol and 20 ml of chloroform was stirred at room temperature for 11 hours. Then insoluble matters were filtered off and the filtrate was concentrated under reduced pressure. The resulting residue was purified by silica gel column chromatography to give 0.60 g of 4-benzyloxy-2-methylbenzaldehyde.

e) Preparation of Ethyl 3-(4-benzyloxy-2-methylphenyl)-2-azidopropenoate

The reaction was carried out in a manner similar to Reference Example 13 a) except for using 2.80 g (12.4 mmol) of 4-benzyloxy-2-methylbenzaldehyde, 6.39 g (49.5 mmol) of ethyl azide acetate, 3.37 g (49.5 mmol) of sodium ethoxide and 50 ml of ethanol. Ethyl 3-(4-benzyloxy-2-methylphenyl)-2-azidopropenoate was thus obtained in the yield of 3.24 g.

f) Preparation of Ethyl 6-benzyloxy-4-methyl-2-indolecarboxylate

The reaction was carried out in a manner similar to Reference Example 13 b) except for using 3.22 g of ethyl 3-(4-benzyloxy-2-methylphenyl)-2-azidopropenoate and 100 ml of toluene. Ethyl 6-benzyloxy-4-methyl-2-indolecarboxylate was thus obtained in the yield of 2.66 g.

$^1$H NMR (CDCl$_3$) δ: 1.38–1.43 (3H, m), 2.51 (3H, s), 4.38 (2H, dd, J=6.9, 14.2 Hz), 5.09 (2H, s), 6.72 (2H, s), 7.19 (1H, d, J=2.3 Hz), 7.29–7.46 (5H, m), 8.71 (1H, br-s).

The following compound was prepared in a manner similar to Reference Example 17.

(1) Ethyl 6-benzyloxy-4-trifluoromethyl-2-indolecarboxylate:

$^1$H NMR (CDCl$_3$) δ: 1.39–1.44 (3H, m), 4.37–4.45 (2H, m), 5.14 (2H, s), 7.05 (1H, s), 7.23–7.24 (1H, m), 7.30 (1H, s), 7.35–7.47 (5H, m), 8.92 (1H, br-s).

REFERENCE EXAMPLE 18

Preparation of Ethyl 4-chloro-6-hydroxy-1-methyl-2-indolecarboxylate a) Preparation of Ethyl 6-benzyloxy-4-chloro-1-methyl-2-indolecarboxylate After 3.70 g (11.2 mmol) of ethyl 6-benzyloxy-4-chloro-2-indolecarboxylate was added to a suspension of 0.45 g (11.2 mmol) of 60% sodium hydride in 70 ml of dimethylformamide, the mixture was stirred at room temperature. After the mixture became an almost transparent solution, a solution of 3.18 g (22.4 mmcol) of methyl iodide in 10 ml of dimethylformamide was dropwise added to the transparent solution at room temperature followed by stirring for 5 hours at the same temperature. The reaction solution was poured onto ice water. The resulting mixture was then extracted three times with ethyl acetate and the combined extracts were washed with water. After drying over anhydrous magnesium sulfate, the solvent was distilled off under reduced pressure and the residue was isolated and purified by silica gel column chromatography to give 3.72 g (96.4%) of ethyl 6-benzyloxy-4-chloro-1-methyl-2-indolecarboxylate.

b) Preparation of Ethyl 4-chloro-6-hydroxy-1-methyl-2-indolecarboxylate

In 60 ml of tetrahydrofuran was dissolved 2.20 g (6.40 mmol) of ethyl 6-benzyloxy-4-chloro-1-methyl-2-indolecarboxylate. After 0.3 g of 10% palladium/carbon was added to the solution, catalytic hydrogenation was performed at ambient temperature under normal pressure. After completion of the reaction, the catalyst was filtered off and the filtrate was concentrated under reduced pressure. The resulting residue was purified by silica gel column chromatography to give 1.50 g (92.4%) of ethyl 4-chloro-6-hydroxy-1-methyl-2-indolecarboxylate. $^1$H NMR (CDCl$_3$) δ: 1.38–1.44 (3H, m), 3.98 (3H, s), 4.33–4.40 (2H, m), 5.07 (1H, s), 6.67 (1H, t, J=0.99 Hz), 6.78 (1H, d, J=1.98 Hz), 7.30 (1H, d, J=0.99 Hz)

REFERENCE EXAMPLE 19

Preparation of Ethyl 4-chloro-7-hydroxy-1-methyl-2-indolecarboxylate a) Preparation of Ethyl 7-benzyloxy-4-chloro-1-methyl-2-indolecarboxylate The reaction was carried out in a manner similar to Reference Example 18 a) except for using 8.00 g (24.3 mmol) of ethyl 7-benzyloxy-4-chloro-2-indolecarboxylate, 0.97 g (24.3 mmol) of 60% sodium hydride, 10.3 g (72.8 mmol) of methyl iodide and 200 ml of dimethylformamide. Ethyl 7-benzyloxy-4-chloro-1-methyl-2-indolecarboxylate was thus obtained in the yield of 7.71 g (92.4%).

b) Preparation of Ethyl 4-chloro-7-hydroxy-1-methyl-2-indolecarboxylate

The reaction was carried out in a manner similar to Reference Example 18 b) except for using 7.71 g (22.4 mmol) of ethyl 7-benzyloxy-4-chloro-1-methyl-2-indolecarboxylate, 0.50 g of 10% palladium/carbon and 150 ml of tetrahydrofuran. Ethyl 4-chloro-7-hydroxy-1-methyl-2-indolecarboxylate was thus obtained in the yield of 4.70 g (82.6%).

$^1$H NMR (CDCl$_3$) δ: 1.40–1.45 (3H, m), 4.34–4.42 (5H, m), 5.20 (1H, s), 6.50 (1H, d, J=7.92 Hz), 6.88 (1H, d, J=7.92 Hz), 7.31 (1H, s).

REFERENCE EXAMPLE 20

Preparation of Ethyl 7-hydroxy-1-methyl-4-trifluoromethyl-2-indolecarboxylate a) Preparation of 4-bromo-3-methyl-2-nitrophenol A mixture of 10.0 g (53.5 mmol) of 4-bromo-3-methylphenol, 50 ml of acetic acid and 10 ml of water was stirred under cooling at 0 to 5° C. To the resulting mixture was dropwise added 3.71 g (58.8 mmol) of 70% nitric acid. After completion of the dropwise addition, the mixture was stirred at room temperature for about an hour. The reaction solution was then poured onto ice water. The mixture was extracted three times with diethyl ether. The combined extracts were washed with water. After drying over anhydrous magnesium sulfate, the solvent was distilled off under reduced pressure. The resulting residue was purified by silica gel column chromatography to obtain 1.70 g (13.7%) of 4-bromo-3-methyl-2-nitrophenol.

b) Preparation of 3-benzyloxy-6-bromo-2-nitrotoluene

The reaction was carried out in a manner similar to Reference Example 12 a) except for using 5.11 g (29.9 mmol) of 4-bromo-3-methyl-2-nitrophenol, 6.30 g (27.2 mmol) of benzyl bromide, 8.26 g (59.7 mmol) of potassium carbonate and 150 ml of acetone. 3-Benzyloxy-6-bromo-2-nitrotoluene was thus obtained in the yield of 5.10 g (58.3%).

c) Preparation of 3-benzyloxy-6-trifluoromethyl-2-nitrotoluene

A mixture of 1.50 g (4.66 mmol) of 3-benzyloxy-6-bromo-2-nitrotoluene, 6.33 g (46.6 mmol) of sodium trifluoroacetate, 4.43 g (23.3 mmol) of copper (I) iodide and 80 ml of N-methylpyrrolidone was heated at 160° C. for 7 hours while stirring. Next, the solvent was distilled off under reduced pressure and ethyl acetate was added to the resulting residue. Insoluble matters were then filtered off. The filtrate was washed twice with water. After drying over anhydrous magnesium sulfate, the solvent was distilled off under reduced pressure and the residue was isolated and purified by silica gel column chromatography to give 0.70 (48.3%) of 3-benzyloxy-6-trifluoromethyl-2-nitrotoluene.

d) Preparation of Ethyl (3-benzyloxy-6-trifluoromethyl-2-nitrophenyl)pyruvate

The reaction was carried out in a manner similar to Reference Example 12 b) except for using 14.6 g (46.9 mmol) of 3-benzyloxy-6-trifluoromethyl-2-nitrotoluene, 13.7 g (93.8 mmol) of diethyl oxalate, 7.90 g (93.8 mmol) of potassium ethoxide and 300 ml of diethyl ether. Ethyl (3-benzyloxy-6-trifluoromethyl-2-nitrophenyl)pyruvate was thus obtained in the yield of 10.9 g (56.9%).

e) Preparation of Ethyl 7-benzyloxy-4-trifluoromethyl-2-indolecarboxylate

The reaction was carried out in a manner similar to Reference Example 12 c) except for using 10.9 g (26.7 mmol) of ethyl (3-benzyloxy-6-trifluoromethyl-2-nitrophenyl)pyruvate, 165 g (213 mmol) of 20% titanium chloride aqueous solution and 100 ml of ethanol. Ethyl 7-benzyloxy-4-trifluoromethyl-2-indolecarboxylate was thus obtained in the yield of 8.00 g (82.6%).

$^1$H NMR (CDCl$_3$) δ: 1.40–1.45 (3H, m), 4.38–4.46 (2H, m), 5.26 (2H, s), 6.79 (1H, d, J=7.59 Hz), 7.32–7.49 (7H, m), 9.25 (1H, br-s).

f) Preparation of Ethyl 7-benzyloxy-1-methyl-4-trifluoromethyl-2-indolecarboxylate The reaction was carried out in a manner similar to Reference Example 18 a) except for using 8.00 g (22.0 mmol) of ethyl 7-benzyloxy-4-trifluoromethyl-2-indolecarboxylate, 0.88 9 (22.0 mmol) of 60% sodium hydride, 6.25 g (44.0 mmol) of methyl iodide and 150 ml of dimethylformamide. Ethyl 7-benzyloxy-1-methyl-4-trifluoromethyl-2-indolecarboxylate was thus obtained in the yield of 7.40 g (89.1%).

g) Preparation of Ethyl 7-hydroxy-1-methyl-4-trifluoromethyl-2-indolecarboxylate The reaction was carried out in a manner similar to Reference Example 18 b) except for using 6.50 g (17.2 mmol) of ethyl 7-benzyloxy-1-methyl-4-trifluoromethyl-2-indolecarboxylate, 1.0 g of 10% palladium/carbon and 150 ml of ethanol. Ethyl 7-hydroxy-1-methyl-4-trifluoromethyl-2-indolecarboxylate was thus obtained in the yield of 4.95 g (97.0%).

$^1$H NMR (CDCl$_3$) δ: 1.39–1.45 (3H, m), 4.33–4.41 (2H, m), 6.69 (1H, dd, J=0.66, 7.92 Hz), 7.20 (1H, dd, J=0.99, 7.92 Hz), 7.31–7.33 (1H, m), 9.69 (1H, br-s).

REFERENCE EXAMPLE 21

Preparation of Ethyl 1,4-dimethyl-7-hydroxy-2-indolecarboxylate a) Preparation of 3,4-dimethyl-2-nitrophenol The reaction was carried out in a manner similar to Reference Example 20 a) except for using 15.7 g (129 mmol) of 3,4-dimethylphenol, 130 ml of acetic acid, 8 ml of water and 12.2 g (135 mmol) of 70% nitric acid. 3,4-Dimethyl-2-nitrophenol was thus obtained in the yield of 7.01 g (26.0%).

b) Preparation of Ethyl 7-benzyloxy-4-methyl-2-indolecarboxylate

The reaction was carried out in a manner similar to Reference Example 12 a) through c) except for using 7.01 g (41.9 mmol) of 3,4-dimethyl-2-nitrophenol as the starting material. Ethyl 7-benzyloxy-4-methyl-2-indolecarboxylate was thus obtained in the yield of 3.68 g.

$^1$H NMR (CDCl$_3$) δ: 1.39–1.44 (3H, m), 2.49 (3H, s) 4.40 (2H, dd, J=7.26, 14.19 Hz), 5.18 (2H, s), 6.69 (1H, d, J=7.92 Hz), 6.78–6.82 (1H, m), 7.22 (1H, J=2.31 Hz), 7.33–7.50 (5H, m), 9.05 (1H, br-s).

c) Preparation of Ethyl 1,4-dimethyl-7-hydroxy-2-indolecarboxylate

The reaction was carried out in a manner similar to Reference Example 19 a) and b) except for using 4.30 g (13.9 mmol) of ethyl 7-benzyolxy-4-methyl-2-indolecarboxylate as the starting material. Ethyl 1,4-dimethyl-7-hydroxy-2-indolecarboxylate was thus obtained in the yield of 2.95 g.

$^1$H NMR (CDCl$_3$) δ: 1.39–1.44 (3H, m), 2.45 (3H, m) 4.33–4.41 (5H, m), 4.76 (1H, s), 6.49 (1H, d, J=7.59 Hz), 6.65–6.69 (1H, m), 7.26 (1H, s).

REFERENCE EXAMPLE 22

Preparation of 4-(tert-butoxycarbonylaminomethyl) benzyl Chloride a) Preparation of 4-(tert-butoxycarbonylaminomethyl)-benzoic Acid To a mixture of 2.65 g (66.2 mmol) of sodium hydroxide, 50 ml of 1,4-dioxane and 50 ml of water was added 5.00 g (33.1 mmol) of 4-(aminomethyl)benzoic acid. Subsequently, a solution of 10.8 g (49.6 mmol) of di-tert-butyl dicarbonate in 10 ml of 1,4-dioxane was dropwise added to the mixture. After stirring at room temperature for 2 hours, the reaction mixture was poured onto ice water and 10% hydrochloric acid was added thereto to render weakly acidic (pH=5 to 6). The precipitated crystals were taken out by filtration and dried under reduced pressure to give 7.90 g (95.1%) of 4-(tert-butoxycarbonylaminomethyl)benzoic acid. b) Preparation of Methyl 4-(tert-butoxycarbonylaminomethyl) benzoate A mixture of 16.2 g (64.5 mmol) of 4-(tert-butoxycarbonylaminomethyl)benzoic acid, 13.6 g (70.9 mmol) of 1-ethyl-3-(3-dimethylaminopropyl)carbodiimide hydrochloride, 1.00 g of 4-dimethylaminopyridine and 200 ml of methanol was stirred at room temperature for 4 hours. Methanol was distilled off under reduced pressure and ice water was poured to the residue thus obtained. The mixture was extracted twice with ethyl acetate and the extract was washed with 10% citric acid aqueous solution and then with saturated sodium hydrogencarbonate aqueous solution and finally with saturated sodium chloride aqueous solution. After drying over anhydrous magnesium sulfate, the solvent was distilled off under reduced pressure to give 14.3 g (83.6%) of methyl 4-(tert-butoxycarbonylaminomethyl)-benzoate.

c) Preparation of 4-(tert-butoxycarbonylaminomethyl)-benzyl Alcohol

A suspension of 1.40 g (36.8 mmol) of lithium aluminum hydride in 150 ml of tetrahydrofuran was stirred at 0° C. A solution of 13.0 g (49.0 mmol) of 4-(tert-butoxycarbonylaminomethyl)benzoate in 50 ml of tetrahydrofuran was dropwise added slowly to the suspension. After completion of the dropwise addition, the solution was heated to reflux for 2 hours and then cooled to 0° C. After 20 ml of 50% tetrahydrofuran was dropwise added to the reaction mixture, 100 ml of ethyl acetate was added thereto. Insoluble matters were filtered off and the resulting filtrate was concentrated under reduced pressure. The concentrate was isolated and purified by silica gel column chromatography to obtain 8.80 g (75.7%) of 4-(tert-butoxycarbonylaminomethyl)benzyl alcohol.

d) Preparation of 4-(tert-butoxycarbonylaminomethyl)-benzyl Chloride

A mixture of 8.80 g (37.1 mmol) of 4-(tert-butoxycarbonylaminomethyl)benzyl alcohol, 120 ml of carbon tetrachloride and 50 ml of dimethylformamide was stirred at room temperature. After 12.2 g (44.5 mmol) of triphenylphosphine was added to the solution portionwise, the mixture was stirred at room temperature for 2 hours. The reaction solution was concentrated under reduced pressure and ice water was poured to the resulting concentrate. The mixture was extracted twice with ethyl acetate and the extract was washed with saturated sodium hydrogencarbonate aqueous solution and then with saturated sodium chloride aqueous solution. After drying over anhydrous magnesium sulfate, the solvent was distilled off under reduced pressure. The residue was isolated and purified by silica gel column chromatography to give 7.50 g (79.1%) of 4-(tert-butoxyarbonylaminomethyl)benzyl chloride.

$^1$H NMR (CDCl$_3$) δ: 1.46 (9H, s), 4.31 (2H, d, J=5.94 Hz), 4.57 (2H, s), 4.85 (1H, br-s), 7.27 (2H, d, J=7.26 Hz), 7.35 (2H, d, J=7.25).

EXAMPLE 1

Preparation of 1-methyl-2-indoloylquanidine Hydrochloride

After 8.58 g (89.8 mmol) of guanidine hydrochloride was added to 70 ml of a methanol solution of 4.85 g (89.8 mmol) of sodium methoxide, the mixture was stirred at room temperature. The precipitated sodium chloride was filtered off to obtain the solution. Then 1.70 g (8.97 mmol) of methyl 1-methyl-2-indole-carboxylate was added to the thus obtained solution. Subsequently methanol was distilled off under reduced pressure. The resulting residue was heated at 130° C. for minutes and then allowed to stand at room temperature for an hour. Thereafter water was poured onto the reaction solution and the mixture was extracted three times with ethyl acetate. The combined extracts were washed with water. After drying over anhydrous magnesium sulfate, the solvent was distilled off under reduced pressure. The resulting residue was isolated and purified by silica gel column chromatography to give the desired 1-methyl-2-indoloylguanidine. The compound was dissolved in chloroform and treated with hydrogen chloride/ether. Thus 0.70 g (30.8%) of 1-methyl-2-indoloylguanidine hydrochloride was obtained.

M.P.: 250° C. or higher; $^1$H NMR (DMSO-d$_6$) δ: 4.04 (3H, s), 7.12–7.21 (1H, m), 7.31–7.44 (1H, m), 7.61 (1H, d, J=8.6 Hz), 7.73 (1H, d, J=7.9 Hz), 7.89 (1H, s), 8.5 (2H, br-s), 8.7 (2H, br-s), 11.9 (1H, br-s).

EXAMPLE 2

Preparation of 1-methyl-5-indoloylquanidine Hydrochloride

The reaction was carried out in a manner similar to Example 1 except for using 1.00 g (5.29 mmol) of methyl 1-methyl-5-indolecarboxylate, 5.05 g (52.9 mmol) of guanidine hydrochloride and 50 ml of a methanol solution of 2.85 g (52.9 mmol) of sodium methoxide. Thus 0.92 g (68.9%) of 1-methyl-5-indoloylguanidine hydrochloride was obtained.

M.P.: 260° C. or higher; $^1$H NMR (DMSO-d$_6$) δ: 3.86 (3H, s), 6.62–6.64 (1H, m), 7.50 (1H, d, J=3.3 Hz), 7.61 (1H, d, J=8.9 Hz), 7.91–7.95 (1H, m), 8.44 (2H, br-s), 8.47 (1H, d, J=1.3 Hz), 8.7 (2H, br-s), 11.7 (1H, br-s).

EXAMPLE 3

Preparation of 1-methyl-3-indoloylquanidine Hydrochloride

The reaction was carried out in a manner similar to Example 1 except for using 1.00 g (5.29 mmol) of methyl 1-methyl-3-indolecarboxylate, 5.05 g (52.9 mmol) of guanidine hydrochloride and 50 ml of a methanol solution of 2.85 g (52.9 mmol) of sodium methoxide. Thus 0.48 g (35.9%) of 1-methyl-3-indoloylguanidine hydrochloride was obtained.

M.P.: 252–253° C.;

$^1$H NMR (DMSO-d$_6$) δ: 3.91 (3H, s), 7.25–7.37 (2H, m), 7.58–7.61 (1H, m), 8.15 (1H, dd, J=1.3, 6.6 Hz), 8.3 (2H, br-s), 8.6 (2H, br-s), 8.78 (1H, s), 11.8 (1H, br-s).

EXAMPLE 4

Preparation of 1-methyl-4-indoloylquanidine Hydrochloride

The reaction was carried out in a manner similar to Example 1 except for using 0.85 g (4.49 mmol) of methyl 1-methyl-4-indolecarboxylate, 4.29 g (44.9 mmol) of guanidine hydrochloride and 50 ml of a methanol solution of 2.43 g (44.9 mmol) of sodium methoxide. Thus 0.75 g (66.1%) of 1-methyl-4-indoloylguanidine hydrochloride was obtained.

M.P.: 186–187° C.; $^1$H NMR (DMSO-d$_6$) δ: 3.88 (3H, s), 6.97 (1H, d, J=3.0 Hz), 7.92–7.35 (1H, m), 7.56 (1H, d, J=3.0 Hz), 7.84 (1H, d, J=7.9 Hz), 7.98 (1H, d, J=7.6 Hz), 8.5 (2H, br-s), 8.7 (2H, br-s), 11.7 (1H, br-s).

EXAMPLE 5

Preparation of 4-chloro-1-methyl-2-indoloylquanidine Hydrochloride

The reaction was carried out in a manner similar to Example 1 except for using 2.00 g (8.94 mmol) of methyl 4-chloro-1-methyl-2-indolecarboxylate, 8.54 g (89.4 mmol) of guanidine hydrochloride and 50 ml of a methanol solution of 4.83 g (89.4 mmol) of sodium methoxide. Thus 1.06 g (41.3%) of 4-chloro-1-methyl-2-indoloylguanidine hydrochloride was obtained.

M.P.: 288–290° C.; $^1$H NMR (DMSO-d$_6$) δ: 4.05 (3H, s), 7.24 (1H, d, J=7.6 Hz), 7.35–7.41 (1H, m), 7.62 (1H, d, J=8.6 Hz), 7.98 (1H, s), 8.56 (2H, br-s), 8.63 (2H, br-s), 12.0 (1H, br-s).

The compounds of Examples 6 through 81 were prepared in a manner similar to Example 1.

EXAMPLE 6

5-Chloro-1-methyl-2-indoloylguanidine Hydrochloride

Yield: 43.6%, M.P.: 281–282° C.; $^1$H NMR (DMSO-d$_6$) δ: 4.03 (3H, s), 7.39 (1H, dd, J=2.0, 8.9 Hz), 7.67 (1H, d, J=8.9 Hz), 7.77 (1H, s), 7.81 (1H, d, J=1.7 Hz), 8.5 (2H, br-s), 8.6 (2H, br-s), 11.9 (1H, br-s).

EXAMPLE 7

6-Chloro-1-methyl-2-indoloylguanidine Hydrochloride

Yield: 59.6%, M.P.: 290–294° C.; $^1$H NMR (DMSO-d$_6$) δ: 4.02 (3H, s), 7.17 (1H, dd, J=2.0, 8.6 Hz), 7.74–7.77 (2H, m), 7.84 (1H, s), 8.5 (2H, br-s), 8.6 (2H, br-s), 11.9 (1H, br-s).

EXAMPLE 8

7-Chloro-1-methyl-2-indoloylguanidine Hydrochloride

Yield: 56.5%, M.P.: 243–244° C.; $^1$H NMR (DMSO-d$_6$) δ: 4.33 (3H, s), 7.11–7.17 (1H, m), 7.41 (1H, d, J=7.6 Hz), 7.71 (1H, d, J=7.9 Hz), 7.81 (1H, s), 8.5 (2H, br-s), 8.6 (2H, br-s), 12.0 (1H, br-s).

EXAMPLE 9

1,4-Dimethyl-2-indoloylguanidine Hydrochloride

Yield: 32.5%, M.P.: 279–280° C.; $^1$H NMR (DMSO-$d_6$) δ: 2.53 (3H, s), 4.02 (3H, s), 6.96 (1H, d, J=6.9 Hz), 7.26–7.32 (1H, m), 7.41 (1H, d, br-s), 11.9 (1H, br-s).

EXAMPLE 10

1,5-Dimethyl-2-indoloylguanidine Hydrochloride

Yield: 30.5%, M.P.: 281–282° C.; $^1$H NMR DMSO-d6) δ: 2.41 (3H, s), 4.00 (3H, s), 7.23 (1H, d, J=8.9 Hz), 7.48–7.51 (2H, m), 7.79 (1H, s), 8.5 (2H, br-s), 8.7 (2H, br-s), 11.9 (1H, br-s).

EXAMPLE 11

1,6-Dimethyl-2-indoloylguanidine Hydrochloride

Yield: 63.1%, M.P.: 267–269° C.; $^1$H NMR (DMSO-$d_6$) δ: 2.47 (3H, s), 3.99 (3H, s), 7.02 (1H, d, J=8.3 Hz), 7.41 (1H, s), 7.61–8.00 (2H, m), 8.4 (2H, br-s), 8.5 (2H, br-s), 11.6 (1H, br-s).

EXAMPLE 12

1,7-Dimethyl-2-indoloylguanidine Hydrochloride

Yield: 27.3%, M.P.: 271–273° C.; $^1$H NMR (DMSO-$d_6$) δ: 2.78 (3H, s), 4.25 (3H, s), 6.99–7.11 (2H, m), 7.53 (1H, d, J=7.6 Hz), 7.70 (1H, s), 8.4 (2H, br-s), 8.6 (2H, br-s), 11.8 (1H, br-s).

EXAMPLE 13

5-Methoxy-1-methyl-2-indoloylguanidine Hydrochloride

Yield: 50.1%, M.P.: 235–236° C.; $^1$H NMR (DMSO-$d_6$) δ: 3.80 (3H, s), 4.01 (3H, s), 7.03–7.07 (1H, m), 7.16 (1H, d, J=2.3 Hz), 7.52 (1H, d, J=8.9 Hz), 7.75 (1H, s), 8.4 (2H, br-s), 8.7 (2H, br-s), 11.8 (1H, br-s).

EXAMPLE 14

1-Methyl-6-indoloylguanidine Hydrochloride

Yield: 62.1%, M.P.: 297–298° C.; $^1$H NMR (DMSO-$d_6$) δ: 3.94 (3H, s), 6.55 (1H, dd, J=0.7, 3.0 Hz), 7.61 (1H, d, J=3.0 Hz), 7.67–7.78 (2H, m), 8.4 (2H, br-s), 8.6 (1H, br-s), 8.9 (2H, br-s), 12.0 (1H, br-s).

EXAMPLE 15

1-Benzyl-2-indoloylguanidine Hydrochloride

Yield: 54.9%, M.P.: 228–229° C.; $^1$H NMR (DMSO-$d_6$) δ: 5.86 (2H, s), 7.03 (2H, d, J=6.6 Hz), 7.17–7.39 (4H, m), 7.57 (1H, d, J=8.3 Hz), 7.78 (1H, d, J=7.9 Hz), 7.98 (1H, s), 8.4 (2H, br-s), 8.6 (2H, br-s), 11.9 (1H, br-s).

EXAMPLE 16

1-Benzyl-3-indoloylguanidine hydrochloride

Yield: 66.2%, M.P.: 252–253° C.; $^1$H NMR (DMSO-$d_6$) δ: 5.53 (2H, s), 7.23–7.37 (7H, m), 7.62–7.66 (1H, m), 8.15–8.18 (1H, m), 8.3 (2H, br-s), 8.6 (2H, br-s), 8.95 (1H, s), 11.8 (1H, br-s).

EXAMPLE 17

1-Isopropyl-3-indoloylguanidine Hydrochloride

Yield: 49.7%, M.P.: 221–223° C.; $^1$H NMR (DMSO-$d_6$) δ: 1.51 (6H, d, J=6.6 Hz), 4.85–4.90 (1H, m), 7.24–7.34 (2H, m), 7.67 (1H, d, J=7.6 Hz), 8.14–8.17 (1H, m), 8.3 (2H, br-s), 8.6 (2H, br-s), 9.12 (1H, s), 11.9 (1H, br-s).

EXAMPLE 18

2-Indoloylguanidine Hydrochloride

Yield: 61.9%, M.P.: 192–194° C.; $^1$H NMR (DMSO-$d_6$) δ: 7.09–7.14 (1H, m), 7.28–7.34 (1H, m), 7.49 (1H, d, J=8.3 Hz), 7.71 (1H, d, J=8.3 Hz), 8.5 (2H, br-s), 8.7 (2H, br-s), 12.06 (1H, br-s), 12.13 (1H, br-s).

EXAMPLE 19

3-Indoloylguanidine Hydrochloride

Yield: 42.2%, M.P.: 287° C.; $^1$H NMR (DMSO-$d_6$) δ: 7.20–7.29 (2H, m), 7.53 (1H, dd, J=1.7, 6.6 Hz), 8.12–8.16 (1H, m), 8.3 (2H, br-s), 8.7 (2H, br-s), 8.83 (1H, d, J=3.3 Hz), 11.8 (1H, br-s), 12.2 (1H, br-s).

EXAMPLE 20

5-Indoloylguanidine Hydrochloride

Yield: 55.9%, M.P.: 219–222° C.; $^1$H NMR (DMSO-$d_6$) δ: 6.61–6.63 (1H, m), 7.50–7.56 (2H, m), 7.85–7.89 (1H, m), 8.45 (2H, br-s), 8.49 (1H, d, J=1.7 Hz), 8.75 (2H, br-s), 11.6 (1H, br-s), 11.7 (1H, br-s).

EXAMPLE 21

1-Isopropyl-5-indoloylguanidine Hydrochloride

Yield: 72.5%, M.P.: 219° C.; $^1$H NMR (DMSO-$d_6$) δ: 1.48 (6H, d, J=6.6 Hz), 4.81–4.88 (1H, m), 6.67 (1H, d, J=3.3 Hz), 7.68–7.71 (2H, m), 7.89–7.93 (1H, m), 8.3–8.6 (3H, m), 8.7 (2H, br-s), 11.7 (1H, br-s).

EXAMPLE 22

4-Methoxy-1-methyl-2-indoloylguanidine Hydrochloride

Yield: 54.5%, M.P.; 281–282° C.; $^1$H NMR (DMSO-$d_6$) δ: 3.93 (3H, s), 4.01 (3H, s), 6.62 (1H, d, J=7.9 Hz), 7.16 (1H, d, J=8.6 Hz), 7.30–7.36 (1H, m), 7.83 (1H, s), 8.5 (2H, br-s), 8.6 (2H, br-s), 11.7 (2H, br-s).

EXAMPLE 23

6-Methoxy-1-methyl-2-indoloylguanidine Hydrochloride

Yield: 75.5%, M.P.: 272° C.; $^1$H NMR (DMSO-$d_6$) δ: 3.87 (3H, s), 4.00 (3H, s), 6.81 (1H, dd, J=2.0, 8.9 Hz), 7.05 (1H, d, J=2.0 Hz), 7.59 (1H, d, J=8.9 Hz), 7.84 (1H, s), 8.4 (2H, br-s), 8.7 (2H, br-s), 11.8 (1H, br-s).

EXAMPLE 24

1-Methyl-4-nitro-2-indoloylguanidine Hydrochloride

Yield: 97.7%, M.P.: 292–293° C.; $^1$H NMR (DMSO-$d_6$) δ: 4.14 (3H, s), 7.59–7.65 (1H, m), 8.16 (1H, m), 8.20–8.28 (2H, m), 8.5 (4H, br-s), 11.8 (1H, br-s).

EXAMPLE 25

1-Methyl-6-nitro-2-indoloylguanidine Hydrochloride

Yield: 68.4%, M.P.: 279–283° C.; $^1$H NMR (DMSO-$d_6$) δ: 4.15 (3H, s), 7.89 (1H, s), 7.95–8.03 (2H, m), 8.51–8.66 (5H, m), 12.1 (1H, br-s).

EXAMPLE 26

1-Methyl-7-nitro-2-indoloylguanidine Hydrochloride

Yield: 66.8%, M.P.: 268–270° C.; $^1$H NMR (DMSO-$d_6$) δ: 3.83 (3H, s), 7.36 (1H, t, J=7.9 Hz), 7.98 (1H, s), 8.06 (1H, dd, J=1.0, 7.9 Hz), 8.19 (1H, dd, J=1.0, 7.9 Hz), 8.44–8.74 (4H, m), 12.2 (1H, br-s).

EXAMPLE 27

1-Methyl-5-nitro-2-indoloylguanidine Hydrochloride

Yield: 73.6%, M.P.: 294–295° C.; $^1$H NMR (DMSO-$d_6$) δ: 4.09 (3H, s), 7.86–7.91 (2H, m), 8.23 (1H, dd, J=2.3, 9.2 Hz), 8.49 (4H, br-s), 8.83 (1H, d, J=2.3 Hz), 11.9 (1H, br-s).

EXAMPLE 28

1-Methyl-7-indoloylguanidine Hydrochloride

Yield: 37.4%, M.P.: 203–204° C.; $^1$H NMR (DMSO-$d_6$) δ: 3.78 (3H, s), 6.60 (1H, d, J=3.3 Hz), 7.16 (1H, t, J=7.6 Hz), 7.44 (1H, d, J=3.0 Hz), 7.53 (1H, d, J=7.6 Hz), 7.85 (1H, d, J=7.9 Hz), 8.44 (2H, br-s), 8.52 (2H, br-s), 11.90 (1H, br-s).

EXAMPLE 29

1-Methyl-4-trifluoromethyl-2-indoloylguanidine Hydrochloride

Yield: 57.8%, M.P.: 283–285° C.; $^1$H NMR (DMSO-$d_6$) δ: 4.10 (3H, 5), 7.52–7.58 (2H, m), 7.91 (1H, s), 7.98–8.01 (1H, m), 8.4–8.8 (4H, m), 11.99 (1H, br-s).

EXAMPLE 30

5-Fluoro-1-methyl-2-indoloylguanidine Hydrochloride

Yield: 60.8%, M.P.: 278–281° C.; $^1$H NMR (DMSO-$d_6$) δ: 4.03 (3H, t), 7.25–7.33 (1H, m), 7.54 (1H, dd, J=2.3, 9.6 Hz), 7.69 (1H, dd, J=4.6, 9.2 Hz), 7.82 (1H, s), 8.51 (2H, br-s), 8.69 (2H, br-s), 11.9 8 (1H, br-s).

EXAMPLE 31

5-Ethoxy-1-methyl-2-indoloylguanidine Hydrochloride

Yield; 30.9%, M.P.: 234–236° C.; $^1$H NMR (DMSO-$d_6$) δ: 1.35 (3H, t, J=6.9 Hz), 3.99 (3H, s), 4.05 (2H, dd, J=6.9, 14.2 Hz), 7.05 (1H, dd, J=2.3, 9.2 Hz), 7.16 (1H, d, J=2.3 Hz), 7.54 (1H, d, J=8.9 Hz), 7.73 (1H, s), 8.42 (2H, br-s), 8.65 (2H, br-s), 11.81 (1H, br-s).

EXAMPLE 32

5-Benzyloxy-4-methyl-2-indoloylguanidine Hydrochloride

Yield: 45.2%, M.P.: 249–251° C.; $^1$H NMR (DMSO-$d_6$) δ: 3.99 (3H, s), 5.14 (2H, s), 7.12–7.16 (1H, m), 7.28–7.58 (7H, m), 7.67 (1H, s), 8.28–8.68 (4H, m), 11.71 (1H, br-s).

EXAMPLE 33

1-Methyl-6-trifluoromethyl-2-indoloylguanidine Hydrochloride

Yield: 44.4%, M.P.: 255–257° C.; $^1$H NMR (DMSO-$d_6$) δ: 4.11 (3H, s), 7.44 (1H, dd, J=1.3, 8.6 Hz), 7.97 (1H, d, J=8.6 Hz), 8.10 (1H, s), 8.48 (2H, br-s), 8.63 (2H, br-s), 12.03 (1H, br-s).

EXAMPLE 34

7-Benzyloxy-1-methyl-2-indoloylguanidine Hydrochloride

Yield: 53.5%, M.P.: 221–222° C.; $^1$H NMR (DMSO-$d_6$) δ: 4.27 (3H, s), 5.26 (2H, s), 6.97–7.08 (2H, m), 7.27–7.56 (5H, m), 7.72 (1H, s), 8.43 (2H, br-s), 8.60 (2H, br-s), 11.80 (1H, br-s).

EXAMPLE 35

1-(2-Naphthylmethyl)-2-indoloylguanidine Hydrochloride

Yield: 56.4%, M.P.: 254–255° C.; $^1$H NMR (DMSO-$d_6$) δ: 6.02 (2H, s), 7.17–7.27 (2H, m), 7.32–7.38 (1H, m), 7.43–7.48 (3H, m), 7.60 (1H, d, J=7.9 Hz), 7.73–7.86 (4H, m), 8.07 (1H, s), 8.43 (2H, br-s), 8.67 (2H, br-s), 12.04 (1H, br-s).

EXAMPLE 36

1-(2-Phenylethyl)-2-indoloylguanidine Hydrochloride

Yield: 55.1%, M.P.: 262–264° C.; $^1$H NMR (DMSO-$d_6$) δ: 2.97–3.03 (2H, m), 4.73–4.79 (2H, m), 7.13–7.24 (6H, m), 7.32–7.38 (1H, m), 7.59 (1H, d, J=7.9 Hz), 7.73 (1H, d, J=7.9 Hz), 7.84 (1H, s), 8.43 (2H, br-s), 8.62 (2H, br-s), 11.78 (2H, br-s).

EXAMPLE 37

1-(4-Bromobenzyl)-2-indoloylguanidine Hydrochloride

Yield: 53.3%, M.P.: 260–263° C. $^1$H NMR (DMSO-$d_6$) δ: 5.82 (2H, s), 6.99 (2H, d, J=8.3 Hz), 7.17–7.23 (1H, s), 7.35–7.40 (1H, m) 7.47 (2H, d, J=8.3 Hz), 7.57 (1H, d, J=8.3 Hz), 7.79 (1H, d, J=7.9 Hz), 8.06 (1H, s), 8.47 (2H, br-s), 8.69 (2H, br-s), 12.07 (1H, br-s).

EXAMPLE 38

1-(4-Nitrobenzyl)-2-indoloylguanidine Hydrochloride

Yield: 42.7%, M.P.: 245–247° C.; $^1$H NMR (DMSO-$d_6$) δ: 5.98 (2H, s), 7.20–7.27 (3H, m), 7.39 (1H, t, J=7.3 Hz), 7.56 (1H, d, J=8.3 Hz), 7.82 (1H, d, J=7.9 Hz), 8.05 (1H, s), 8.16 (2H, d, J=8.6 Hz), 8.41 (2H, br-s), 8.61 (2H, br-s), 12.02 (1H, br-s).

EXAMPLE 39

1-(4-Methoxybenzyl)-2-indoloylguanidine Hydrochloride

Yield: 54.8%, M.P.: 239–240° C.; $^1$H NMR (DMSO-$d_6$) δ: 3.68 (3H, s), 5.78 (2H, s), 6.82 (2H, d, J=8.6 Hz), 7.18 (1H, t, J=7.3 Hz), 7.34–7.40 (1H, m), 7.61 (1H, d, J=8.6 Hz), 7.77 (1H, d, J=7.9 Hz), 7.92 (1H, s), 8.43 (2H, br-s), 8.60 (2H, br-s), 11.89 (1H, br-s).

EXAMPLE 40

1-(3-Phenylpropyl)-2-indoloylguanidine Hydrochloride

Yield: 39.0%, M.P.: 147–148° C.; $^1$H NMR (DMSO-$d_6$) δ: 1.97–2.13 (2H, m), 5.62 (2H, t, J=8.0 Hz), 4.59 (2H, t, J=7.0 Hz), 7.11–7.34 (6H, m), 7.40 (1H, dt, J=1.0, 8.0 Hz), 7.57 (1H, d, J=8.0 Hz), 7.76 (1H, d, J=8.0 Hz), 7.81 (1H, s), 8.25–8.70 (4H, m), 11.75 (1H, br-s).

EXAMPLE 41

1-(4-Phenylbutyl)-2-indoloylguanidine Hydrochloride

Yield: 51.0%, M.P.: 154–155° C.; $^1$H NMR (DMSO-$d_6$) δ: 1.43–1.65 (2H, m), 1.65–1.68 (2H, m), 2.57 (2H, t, J=8.0 Hz), 4.58 (1H, t, J=7.0 Hz), 7.03–7.32 (6H, m), 7.39 (1H, dt, J=1.0, 8.0 Hz), 7.63 (1H, d, J=8.0 Hz), 7.73 (1H, d, J=8.0 Hz), 7.92 (1H, s), 8.20–9.00 (4H, m), 11.95 (1H, br-s).

EXAMPLE 42

1-Isopropyl-6-indoloylguanidine Hydrochloride

Yield: 37.7%, M.P.: 218–220° C.; $^1$H NMR (DMSO-$d_6$) δ: 1.51 (6H, d, J=6.6 Hz), 4.92–5.02 (1H, m), 6.59 (1H, d, J=3.0 Hz), 7.66–7.81 (3H, m), 8.41 (2H, br-s), 8.66 (1H, s), 8.86 (2H, br-s), 12.04 (1H, br-s).

EXAMPLE 43

1-Benzyl-6-indoloylguanidine Hydrochloride

Yield: 44.5%, M.P.: 227–228° C.; $^1$H NMR (DMSO-$d_6$) δ: 5.57 (2H, s), 6.62 (1H, d, J=3.0 Hz), 7.24–7.32 (5H, m), 7.69–7.79 (2H, m), 7.81 (1H, d, J=3.0 Hz), 8.43 (2H, br-s), 8.71 (1H, s), 8.86 (2H, br-s), 12.06 (1H, br-s).

EXAMPLE 44

1-Isopropyl-4-indoloylguanidine Hydrochloride

Yield: 49.0%, M.P.: 95–97° C.; $^1$H NMR (DMSO-$d_6$) δ: 1.48 (6H, d, J=6.6 Hz), 4.87 (1H, m), 7.01 (1H, d, J=3.0 Hz), 7.26–7.31 (1H, m), 7.72 (1H, d, J=3.3 Hz), 7.91 (1H, d, J=8.3 Hz), 8.02 (1H, d, J=7.6 Hz), 8.54 (2H, br-s), 8.83 (2H, br-s), 11.85 (1H, br-s).

EXAMPLE 45

1-Benzyl-4-indoloylguanidine Hydrochloride

Yield: 42.6%, M.P.: 203–205° C.; $^1$H NMR (DMSO-$d_6$) δ: 5.52 (2H, s), 7.03 (1H, d, J=3.0 Hz), 7.17–7.32 (6H, m), 7.74 (1H, t, J=1.7 Hz), 7.84 (1H, d, J=7.9 Hz ), 7.98 (1H, d, J=7.6 Hz), 8.48 (2H, br-s), 8.77 (2H, br-s), 11.79 (1H, br-s).

EXAMPLE 46

4-Benzyloxy-1-methyl-2-indoloylguanidine Hydrochloride

Yield: 57.6%, M.P.: 260° C.; $^1$H NMR (DMSO-$d_6$) δ: 4.01 (3H, s), 5.26 (2H, s), 6.75 (1H, d, J=7.6 Hz), 7.20 (1H, d, J=8.6 Hz), 7.30–7.54 (6H, m), 7.75 (1H, s), 8.40 (4H, br-s), 11.41 (1H, br-s).

EXAMPLE 47

1,3-Dimethyl-2-indoloylguanidine Hydrochloride

Yield: 55.5%, M.P.: 228–229° C.; $^1$H NMR (DMSO-$d_6$) δ: 2.56 (3H, s), 3.84 (3H, S), 7.12–7.18 (1H, m), 7.34–7.40 (7H, m), 7.53 (1H, d, J=8.3 Hz), 7.69 (1H, d, J=7.9 Hz), 8.61–8.68 (4H, m), 11.67 (1H, br-s).

EXAMPLE 48

1-Methyl-7-phenyl-2-indoloylguanidine Hydrochloride

Yield: 58.9%, M.P.: 265–267° C.; $^1$H NMR (DMSO-$d_6$) δ: 4.07 (3H, s), 7.27 (1H, d, J=7.3 Hz), 7.41–7.75 (7H, m), 7.89 (1H, s), 8.50 (4H, br-s), 11.77 (1H, br-s).

EXAMPLE 49

4-Acetyl-1-methyl-2-indoloylguanidine Hydrochloride

Yield: 45.4%, M.P.: 288–289° C.; $^1$H NMR (DMSO-$d_6$) δ: 2.71 (3H, s), 4.07 (3H, s), 7.50–7.56 (1H, m), 7.91–7.97 (2H, m), 8.25 (1H, s), 8.53 (4H, br-s), 11.71 (1H, br-s).

EXAMPLE 50

6-Benzyloxy-1-methyl-2-indoloylguanidine Hydrochloride

Yield: 42.7%, M.P.: 269–270° C.; $^1$H NMR (DMSO-$d_6$) δ: 3.99 (3H, s), 5.20 (2H, s), 6.89 (1H, d, J=l0.6 Hz), 7.22 (1H, s), 7.35–7.58 (6H, m), 7.62–7.67 (1H, m), 8.4 (4H, br-s), 11.35 (1H, br-s).

EXAMPLE 51

4-Ethoxy-1-methyl-2-indoloylguanidine Hydrochloride

Yield: 69.8%, M.P.: 262–263° C.; $^1$H NMR (DMSO-$d_6$) δ: 1.42 (3H, t, J=6.9 Hz), 3.99 (3H, s), 4.19 (2H, q, J=6.9 Hz), 6.62 (1H, d, J=7.6 Hz), 7.16 (1H, d, J=8.6 Hz), 7.28–7.34 (1H, m), 7.77 (1H, s), 8.51 (4H, br-s), 11.60 (1H, br-s).

EXAMPLE 52

1-(2-Carbamoylethyl)-2-indoloylguanidine Hydrochloride

Yield: 30.0%, M.P.: 285–286° C.; $^1$H NMR (DMSO-$d_6$) δ: 2.55 (2H, t, J=7.3 Hz), 4.74 (2H, t, J=7.3 Hz), 6.85 (1H, br-s), 7.17 (1H, t, J=6.9 Hz), 7.33 (1H, br-s), 7.39 (1H, ddd, J=1.0, 7.3, 7.8 Hz), 7.70 (2H, dd, J=8.4, 17.7 Hz), 7.82 (1H, s), 8.46 (2H, br-s), 8.64 (2H, br-s), 11.85 (1H, br-s).

EXAMPLE 53

1-Propyl-2-indoloylguanidine Hydrochloride

Yield: 53.2%, M.P.: 218–219° C.; $^1$H NMR (DMSO-$d_6$) δ: 0.85 (3H, t, J=7.6 Hz), 1.66–1.77 (2H, m), 4.51 (2H, dd, J=6.9, 7.6 Hz), 7.10–7.23 (1H, m), 7.32–7.45 (1H, m), 7.65 (1H, d, J=8.6 Hz), 7.73 (1H, d, J=7.9 Hz), 7.97 (1H, s), 8.52 (2H, br-s), 8.77 (2H, br-s), 12.01 (1H, br-s).

EXAMPLE 54

1-(2-Methoxyethyl)-2-indoloylguanidine Hydrochloride

Yield: 15.0%, M.P.: 174–176° C.; $^1$H NMR (DMSO-$d_6$) δ: 3.16 (3H, s), 3.63 (2H, t, J=5.3 Hz), 4.72 (2H, t, J=5.3 Hz), 7.11–7.22 (1H, m), 7.31–7.44 (1H, m), 7.66 (1H, d, J=8.6 Hz), 7.72 (1H, d, J=7.9 Hz), 7.89 (1H, s), 8.49 (2H, br-s), 8.70 (2H, br-s), 11.96 (1H, br-s).

EXAMPLE 55

4-Fluoro-1-methyl-2-indoloylguanidine Hydrochloride

Yield: 53.1%, M.P.: 281–282° C.; $^1$H NMR (DMSO-$d_6$) δ: 4.04 (3H, s), 6.97 (1H, dd, J=7.6, 10.2 Hz), 7.35–7.43 (1H, m), 7.50 (1H, d, J=8.3 Hz), 7.89 (1H, s), 8.48–8.60 (4H, m), 11.92 (1H, br-s).

EXAMPLE 56

4-Bromo-1-methyl-2-indoloylguanidine Hydrochloride

Yield: 58.2%, M.P.: 306–307° C.; $^1$H NMR (DMSO-$d_6$) δ: 4.04 (3H, s), 7.30–7.36 (1H, m), 7.42 (1H, d, J=7.6 Hz), 7.69 (1H, d, J=8.6 Hz), 7.78 (1H, s), 8.56 (4H br-s), 11.91 (1H, br-s).

EXAMPLE 57

4-Isobutyloxy-1-methyl-2-indoloylguanidine Hydrochloride

Yield: 58.1%, M.P.: 245–247° C.; $^1$H NMR (DMSO-$d_6$) δ: 1.05 (6H, d, J=6.9 Hz), 2.06–2.16 (1H, m), 3.90 (2H, d, J=6.3 Hz), 3.99 (3H, s), 6.61 (1H, d, J=7.9 Hz), 7.16 (1H, d, J=8.6 Hz), 7.28–7.34 (1H, m), 7.84 (1H, s), 8.51 (4H, br-s), 11.65 (1H, br-s).

EXAMPLE 58

4-Isopropoxy-1-methyl-2-indoloylguanidine Hydrochloride

Yield: 62.3% M.P.: 269–270° C.; $^1$H NMR (DMSO-$d_6$) δ: 1.35 (6H, d, J=5.9 Hz), 3.99 (3H, s), 4.75–4.84 (1H, m), 6.65 (1H, d, J=7.6 Hz), 7.14 (1H, d, J=8.6 Hz), 7.28–7.34 (1H, m), 7.75 (1H, s), 8.53 (4H, br-s), 11.59 (1H, br-s).

EXAMPLE 59

1-Methyl-7-(2-phenylethoxy)-2-indoloylguanidine Hydrochloride

Yield: 24.3%, M.P.: 155–156° C.; $^1$H NMR (DMSO-$d_6$) δ: 3.21 (2H, t, J=6.3 Hz), 4.13 s), 4.43 (2H, t, J=6.3 Hz), 6.95 (1H, d, J=7.9 Hz),(3H, 7.08 (1H, t, J=7.9 Hz), 7.25–7.44 (6H, m), 7.60 (1H, s), 8.44 (4H, br-s), 11.62 (1H, br-s).

EXAMPLE 60

1-Methyl-7-(3-phenylpropoxy)-2-indoloylguanidine Hydrochloride

Yield: 46.1%, M.P.: 165–166° C.; $^1$H NMR (DMSO-$d_6$) δ: 2.12–2.17 (2H, m), 2.79–2.85 (2H, m), 4.09–4.13 (2H, m), 4.31 (3H, s), 6.83 (1H, m), 7.00–7.05 (1H, m), 7.19–7.32 (6H, m), 7.67 (1H, s), 8.56 (4H, br-s), 11.75 (1H, br-s).

EXAMPLE 61

7-Benzyloxy-4-chloro-1-methyl-2-indoloylguanidine Hydrochloride

Yield: 54.4%, M.P.: 264° C.; $^1$H NMR (DMSO-$d_6$) δ: 4.27 (3H, s), 5.26 (2H, s), 6.96 (1H, d, J=8.6 Hz), 7.11 (1H, d, J=8.3 Hz), 7.32–7.54 (5H, m), 7.78 (1H, s), 8.5–8.6 (4H, m), 11.94 (1H, br-s).

EXAMPLE 62

4-Carboxy-1-methyl-2-indoloylguanidine Hydrochloride

Yield: 40.5%, M.P.: 302–303° C.; $^1$H NMR (DMSO-$d_6$) δ: 4.07 (3H, s), 7.48–7.54 (1H, m), 7.86–7.95 (2H, m), 8.10 (1H, s), 8.3–8.7 (4H, m), 11.58 (1H, br-s), 13.0 (0.7H, br-s).

EXAMPLE 63

7-Carbamoylmethoxy-1-methyl-2-indoloylguanidine Hydrochloride

Yield: 56.7%, M.P.: 268–269° C.; $^1$H NMR (DMSO-$d_6$) δ: 4.32 (3H, s), 4.61 (2H, s), 6.76 (1H, d, J=7.9 Hz), 7.03 (1H, t, J=7.9 Hz), 7.30 (1H, d, J=7.6 Hz), 7.40 (1H, br-s), 7.58 (1H, br-s), 7.68 (1H, s), 8.54 (4H, m), 11.74 (1H, br-s).

EXAMPLE 64

7-Carbamoylmethoxy-4-chloro-1-methyl-2-indoloylguanidine Hydrochloride

Yield: 29.7%, M.P.: 270–271° C.; $^1$H NMR (DMSO-$d_6$) δ: 4.33 (3H, s), 4.61 (2H, s), 6.73 (1H, d, J=8.3 Hz), 7.10 (1H, d, J=8.3 Hz), 7.39 (1H, br-s), 7.58 (1H, br-s), 7.74 (1H, s), 8.57 (4H, br-s), 11.93 (1H, br-s).

EXAMPLE 65

4-Chloro-7-(2-dimethylaminoethoxy)-1-methyl-2-indoloylguanidine Dihydrochloride Yield: 50.8%, M.P.: 287–288° C.; $^1$H NMR (DMSO-$d_6$) δ: 2.86 (6H, d, J=5.0 Hz), 3.62–3.64 (2H, m), 4.29 (3H, s), 4.51–4.55 (2H, m), 6.92 (1H, d, J=8.2 Hz), 7.14 (1H, d, J=8.3 Hz), 7.88 (1H, s), 8.6–8.9 (4H, m), 11.01 (1H, br-s), 12.13 (1H, br-s).

EXAMPLE 66

6-Carbamoylmethoxy-1-methyl-2-indoloylguanidine Dihydrochloride

Yield: 26.8%, M.P.: 275° C.; $^1$H NMR (DMSO-$d_6$) δ: 3.98 (3H, s), 4.53 (2H, s), 6.90–6.95 (1H, m), 7.11 (1H, d, J=2.0 Hz), 7.45 (1H, br-s), 7.58 (1H, br-s), 7.65 (1H, d, J=8.9 Hz), 7.77 (1H, s), 8.38–8.58 (4H, m), 11.72 (1H, br-s).

EXAMPLE 67

1-Methyl-6-(2-phenylethoxy)-2-indoloylguanidine Hydrochloride

Yield: 48.6%, M.P.: 219–221° C.; $^1$H NMR (DMSO-d6) δ: 3.07–3.12 (2H, m), 3.97 (3H, s), 4.29 (2H, t, J=6.9 Hz), 6.79–6.83 (1H, m), 7.11 (1H, d, J=2.0 Hz), 7.23–7.39 (5H, m), 7.60 (1H, d, J=8.6 Hz), 7.74 (1H, s), 8.36–8.56 (4H, m), 11.67 (1H, br-s).

EXAMPLE 68

1-Methyl-6-(3-phenylpropoxy)-2-indoloylguanidine Hydrochloride

Yield: 72.4%, M.P.: 232–233° C.; $^1$H NMR (DMSO-$d_6$) δ: 2.02–2.13 (2H, m), 2.75–2.81 (2H, m), 3.97 (3H, s), 4.07 (2H, t, J=6.3 Hz), 6.82–6.86 (1H, m), 7.06 (1H, d, J=1.7 Hz), 7.16–7.33 (5H, m), 7.61 (1H, d, J=8.9 Hz), 7.75 (1H, s), 8.36–8.58 (4H, m), 11.69 (1H, br-s).

EXAMPLE 69

1-Methyl-6-methylsulfonyl-2-indoloylguanidine Hydrochloride

Yield: 30.7%, M.P.: 303–304° C.; $^1$H NMR (DMSO-$d_6$) δ: 3.25 (3H, s), 4.12 (3H, s), 7.65 (1H, dd, J=1.3, 8.6 Hz), 7.97–8.00 (2H, m), 8.24 (1H, s), 8.57 (2H, br-s), 8.74 (2H, br-s), 12.23 (1H, br-s).

EXAMPLE 70

1-Methyl-4-methylsulfonyl-2-indoloylguanidine Hydrochloride

Yield: 19.4%, M.P.: 313–314° C.; $^1$H NMR (DMSO-$d_6$) δ: 3.30 (3H, s), 4.10 (3H, s), 7.60 (1H, dd J=7.6, 8.3 Hz), 7.72–7.75 (1H, m), 8.04–8.07 (2H, m), 8.63 (4H, br-s), 12.29 (1H, br-s).

EXAMPLE 71

4-Chloro-1-(2-methoxyethyl)-2-indoloylguanidine Hydrochloride

Yield: 27.0%, M.P.: 147–150° C.; $^1$H NMR (DMSO-$d_6$) δ: 3.15 (3H, s), 3.63 (2H, t, J=5.3 Hz), 4.73 (2H, t, J=5.3 Hz), 7.26 (1H, d, J=6.9 Hz), 7.31–7.44 (1H, m), 7.66 (1H, d, J=8.6 Hz), 7.94 (1H, s), 8.60 (2H, br-s), 8.67 (2H, br-s), 12.05 (1H, br-s).

EXAMPLE 72

1-(2-carbamoylethyl)-4-chloro-2-indoloylguanidine Hydrochloride

Yield: 11.0%, M.P.; 295° C.; $^1$H NMR (DMSO-$d_6$) δ:2.56 (2H, t, J=6.9 Hz), 4.76 (2H, t, J=6.9 Hz), 6.84 (1H, br-s), 7.26 (1H, d, J=7.7 Hz), 7.30–7.46 (2H, m), 7.68 (1H, d, J=8.2 Hz), 7.89 (1H, s), 8.56 (2H, br-s), 8.62 (2H, br-s), 11.95 (1H, br-s).

EXAMPLE 73

4-Chloro-1-methyl-7-[2-(N-pyrrolidinyl)ethoxy]-2-indoloylguanidine Dihydrochloride Yield: 53.8%, M.P.: 250° C.; $^1$H NMR (DMSO-$d_6$) δ: 1.93–2.03 (4H, m), 3.0–3.2 (2H, m), 3.61–3.71 (4H, m), 4.30 (3H, s), 4.51–4.54 (2H, m), 6.92 (1H, d, J=8.2 Hz), 7.14 (1H, d, J=8.3Hz), 7.85 (1H, s), 8.6–8.7 (4H, m), 11.20 (1H, br-s), 12.07 (1H, br-s).

EXAMPLE 74

4-Chloro-7-(3-dimethylaminopropoxy)-1-methyl-2-indoloylguanidine Dihydrochloride Yield: 35.4%, M.P.: 250° C.; $^1$H NMR (DMSO-$d_6$) δ: 2.24–2.30 (2H, m), 2.78 (6H, s), 3.2–3.3 (2H, m), 4.20 (2H, t, J=5.9 Hz), 4.29 (3H, s), 6.85 (1H, d, J=8.3 Hz), 7.11 (1H, d, J=8.3 Hz), 7.82 (1H, s), 8.5–8.7 (4H, m), 10.74 (1H, br-s), 12.04 (1H, br-s).

EXAMPLE 75

7-[2-(N-Benzyl-N-methylamino)ethoxy]-4-chloro-1-methyl-2-indoloylguanidine Dihydrochloride Yield: 43.5%, M.P.: 230° C.; $^1$H NMR (DMSO-$d_6$) δ: 2.80 (3H, s), 3.61 (2H, br-s), 4.20 (3H, s), 4.40–4.57 (4H, m), 6.89 (1H, d, J=8.3 Hz), 7.13 (1H, d, J=8.3 Hz), 7.45–7.47 (3H, m), 7.6–7.7 (2H, m), 7.82 (1H, s), 8.5– 8.7 (4H, m), 11.10 (1H, br-s), 12.04 (1H, br-s).

EXAMPLE 76

4-Isopropenyl-1-methyl-2-indoloylguanidine Hydrochloride

Yield: 41.5%, M.P.: 235° C.; $^1$H NMR (DMSO-$d_6$) δ: 2.24 (3H, s), 4.03 (3H, s), 5.35–5.36 (1H, m), 5.48 (1H, d, J=1.0 Hz), 7.15 (1H, dd, J=0.7, 7.3 Hz), 7.38 (1H, dd, J=7.3, 8.6 Hz), 7.56 (1H, d, J=8.6 Hz), 8.07 (1H, s), 8.45–8.70 (4H, m), 12.03 (1H, br-s).

EXAMPLE 77

4-Isopropenyl-1-methyl-2-indoloylguanidine Hydrochloride

Yield; 75.6%, M.P.: 255° C.; $^1$H NMR (DMSO-$d_6$) δ: 1.35 (6H, d, J=6.9 Hz), 3.27–3.37 (1H, m), 4.02 (3H, s), 7.03 (1H, d, J=6.9 Hz), 7.31–7.37 (1H, m), 7.44 (1H, d, J=8.6 Hz), 8.08 (1H, s), 8.42–8.70 (4H, m), 11.97 (1H, br-s).

EXAMPLE 78

1-(2-Diethylaminoethyl)-2-indoloylguanidine Dihydrochloride

Yield: 19.3%, M.P.: 250° C.; $^1$H NMR (DMSO-$d_6$) δ: 1.28 (6H, t, J=7.3 Hz), 3.10– 3.43 (6H, m), 4.88–5.10 (2H, m), 7.23 (1H, t, J=7.6 Hz), 7.46 (1H, ddd, J=1.0, 8.3, 8.7 Hz), 7.76 (1H, d, J=7.6 Hz), 7.94 (1H, d, J=8.7 Hz), 8.09 (1H, br-s), 8.61 (2H, br-s), 8.79 (2H, br-s), 11.27 (1H, br-s), 12.3 (1H, br-s).

EXAMPLE 79

4-Chloro-1-(2-diethylaminoethyl)-2-indoloylguanidine Dihydrochloride

Yield: 36.0%, M.P.: 260–261° C.; $^1$H NMR (DMSO-$d_6$) δ: 1.28 (6H, t, J=7.3 Hz), 3.10–3.48 (6H, m), 4.90–5.15 (2H, m), 7.31 (1H, d, J=7.7 Hz), 7.45 (1H, dd, J=7.7, 8.3 Hz), 7.98 (1H, d, J=8.3 Hz), 8.14 (1H, br-s), 8.72 (2H, br-s), 8.75 (2H, br-s), 11.38 (1H, br-s), 12.33 (1H, br-s).

EXAMPLE 80

1-(2-Dimethylaminoethyl)-2-indoloylguanidine Dihydrochloride

Yield: 27.0%, M.P.: 239–242° C.; $^1$H NMR (DMSO-$d_6$) δ: 2.84 (6H, s), 3.23–3.53 (2H, m), 4.85–5.08 (2H, m), 7.23 (1H, dd, J=7.3, 7.9 Hz), 7.41–7.43 (1H, m), 7.77 (1H, d, J=7.9 Hz), 7.88 (1H, d, J=8.3 Hz), 8.11 (1H, s), 8.64 (2H, br-s), 8.81 (2H, br-s), 11.09 (1H, br-s), 12.26 (1H, br-s).

EXAMPLE 81

4-Chloro-1(2-dimethylaminoethyl)-2-indoloylguanidine Dihydrochloride

Yield: 26.0%, M.P.: 245–248° C.; $^1$H NMR (DMSO-$d_6$) δ: 2.84 (6H, m), 3.31–3.52 (2H, m), 4.88–5.08 (2H, m), 7.32 (1H, d, J=7.6 Hz), 7.46 (1H, dd,) J=7.6, 8.3 Hz), 7.91 (1H, d, J=8.3 Hz), 8.16 (1H, s), 8.71 (2H, br-s), 8.77 (2H, br-s), 11.19 (1H, m), 12.32 (1H, br-s).

EXAMPLE 82

Preparation of 1-benzyl-5-indoloylquanidine Hydrochloride

After 2.24 g (23.4 mmol) of guanidine hydrochloride was added to 50 ml of a methanol solution of 1.26 g (23.4 mmol) of sodium methoxide, 0.80 g (2.34 mmol) of benzyl 1-benzyl-5-indolecarboxylate was added to the resulting mixture. The mixture was then stirred for 30 hours while heating at 50 to 60° C. Methanol was distilled off under reduced pressure and the residue was purified by silica gel column chromatography followed by treatment with 2N hydrochloric acid to give 0.08 g (10.4%) of 1-benzyl-5-indoloylguanidine hydrochloride.

M.P.: 216–222° C.; $^1$H NMR (DMSO-d$_6$) δ: 5.51 (2H, s), 6.69 (1H, d, J=2.6 Hz), 7.20–7.34 (5H, m), 7.62–7.68 (2H, m), 7.88 (1H, dd, J=1.7, 8.9 Hz), 8.43–8.48 (3H, m), 8.72 (2H, br-s), 11.7 (1H, br-s).

EXAMPLE 83

Preparation of 7-methoxy-1-methyl-2-indoloylquanidine Hydrochloride a) The reaction was carried out in a manner similar to Reference Example 1-a) except for using 24.6 g (0.20 mmol) of 2-methoxyaniline, 15.2 g (0.22 mol) of sodium nitrite, 84 ml of conc. hydrochloric acid, 28.8 g (0.20 mmol) of ethyl 2-methylacetacetate and 20 ml of ethanol. Crude ethyl 2-(2-methoxyphenylhydrazono)-propionate was obtained in an amount of 23.0 g.

b) After 23.0 g of the crude ethyl 2-(2-methoxyphenylhydrazono)propionate obtained above was added to 150 ml of 10% hydrogen chloride/ethanol, the mixture was refluxed for 30 minutes. After cooling, the reaction mixture was poured onto ice water and the mixture was extracted three times with ether. After washing with water and then with aqueous sodium bicarbonate solution, the extract was dried over anhydrous magnesium sulfate. The solvent was then distilled off under reduced pressure. The resulting residue was roughly purified by silica gel column chromatography to give 8.00 g of crude ethyl 7-methoxy-2-indolecarboxylate.

c) The reaction was carried out in a manner similar to Reference Example 5 except for using 8.00 g (36.5 mmol) of the crude ethyl 7-methoxy-2-indolecarboxylate obtained above, 1.44 g (36 mmol) of 60% sodium hydride, 7.76 g (54.7 mmol) of methyl iodide and 50 ml of dimethylformamide. Thus 4.4 g of crude ethyl 7-methoxy-1-methyl-2-indolecarboxylate was obtained.

d) The reaction was carried out in a manner similar to Example 1 except for using 4.40 g (18.9 mmol) of the crude ethyl 7-methoxy-1-methyl-2-indolecarboxylate obtained above, 18.0 g (189 mmol) of guanidine hydrochloride and 150 ml of a methanol solution of 10.2 g (189 mmol) of sodium methoxide. Thus 1.58 g of 7-methoxy-1-methyl-2-indoloylguanidine hydrochloride was obtained;

yield: 5.6%, based on 2-methoxyaniline. M.P.: 252–253° C.; $^1$H NMR (DMSO-d$_6$) δ: 3.93 (3H, s), 4.28 (3H, s), 6.86 (1H, d, J=7.6 Hz), 7.05 (1H, t, J=7.9 Hz), 7.26 (1H, d, J=7.6 Hz), 7.74 (1H, s), 8.5 (2H, br-s), 8.6 (2H, br-s), 11.8 (1H, br-s).

EXAMPLE 84

Preparation of 1-isopropyl-2-indoloylquanidine Hydrochloride

A tetrahydrofuran solution, 60 ml, containing 2.00 g (9.84 mmol) of 1-isopropyl-2-indolecarboxylic acid and 2.39 g (14.8 mmol) of carbonyldiimidazole was stirred at room temperature for 2 hours and then at 45 to 50° C. for an hour. After cooling to room temperature, 30 ml of a dimethylformamide solution of 5.64 g (59.0 mmol) of guanidine hydrochloride and 5.97 g (59.0 mmol) of triethylamine was added to the reaction mixture followed by stirring at room temperature for 12 hours. The mixture was then distilled off under reduced pressure and water was added to the resulting residue. After adjusting pH in the range of 5 to 6 with 2N hydrochloric acid, the mixture was extracted three times with ethyl acetate. After drying over anhydrous magnesium sulfate, the extract was acidified with hydrogen chloride/ether. The precipitated crystals were filtered and dried to give 1.31 g (47.4%) of the desired 1-isopropyl-2-indoloylguanidine hydrochloride.

M.P.: 150–151° C.; $^1$H NMR (DMSO-d$_6$) δ: 1.61 (6H, d, J=7.3 Hz), 5.46–5.57 (1H, m), 7.15 (1H, t, J=7.9 Hz), 7.32–7.38 (1H, m), 7.68–7.78 (3H, m), 8.5 (2H, br-s), 8.7 (2H, br-s), 11.8–11.9 (1H, m).

The reaction was carried out in a manner similar to Example 84 to obtain the compound of Example 85.

EXAMPLE 85

1-Carbamoylmethyl-2-indoloylguanidine Hydrochloride

Yield: 2.1%, M.P.: 261–262° C.; $^1$H NMR (DMSO-d$_6$) δ: 5.17 (2H, s), 7.10–7.28 (2H, m), 7.32–7.45 (1H, m), 7.56 (1H, d, J=8.6 Hz), 7.59 (1H, br-s), 7.75 (1H, dd, J=0.7, 7.0 Hz), 7.81 (1H, s), 8.45 (2H, br-s), 8.61 (2H, br-s), 11.90 (1H, br-s).

EXAMPLE 86

Preparation of 5-chloro-2-indoloylquanidine Hydrochloride

The reaction was carried out in a manner similar to Example 84 except for using 2.00 g (10.2 mmol) of 5-chloro-2-indolecarboxylic acid, 1.82 g (11.3 mmol) of carbonyldiimidazole, 5.86 g (61.3 mmol) of guanidine hydrochloride, 6.20 g (61.3 mmol) of triethylamine, 50 ml of tetrahydrofuran and 50 ml of dimethylformamide. Thus 1.85 g (66.2%) of 5-chloro-2-indoloylguanidine hydrochloride was obtained.

M.P.: 250° C. or higher; $^1$H NMR (DMSO-d$_6$) δ: 7.32 (1H, dd, J=2.0, 8.9 Hz), 7.51(1H, d, J=8.9 Hz), 7.82 (2H, s), 8.53 (2H, br-s), 8.68 (2H, br-s), 12.2 (1H, br-s), 12.3 (1H, br-s).

EXAMPLE 87

Preparation of 6-amino-1-methyl-2-indoloylquanidine Hydrochloride

After 1.10 g (4.21 mmol) of 1-methyl-6-nitro-2-indoloylguanidine was dissolved in a solvent mixture of 100 ml of tetrahydrofuran and 100 ml of methanol, 0.50 g of 10% palladium/carbon was added to the solution at room temperature in a nitrogen flow, while stirring. Catalytic hydrogenation was then performed at ambient temperature under normal pressure. After completion of the reaction, the catalyst was filtered off and the filtrate was then concentrated under reduced pressure. Hydrogen chloride/methanol was added to the resulting residue to convert the compound into the hydrochloride, whereby 0.73 g (64.7%) of 6-amino-1-methyl-2-indoloylguanidine hydrochloride was obtained.

M.P.: 282–283° C.; $^1$H NMR (DMSO-d$_6$) δ: 4.00 (3H, s), 7.06 (1H, dd, J=1.7, 8.6 Hz), 7.39 (1H, s), 7.76 (1H, d, J=8.6 Hz), 7.93 (1H, s), 8.5 (2H, br-s), 8.7 (2H, br-s), 9.0–10.3 (2H, br), 12.0 (1H, br-s).

The reaction was carried out in a manner similar to Example 87 to prepare the compounds of Examples 88 through 90 shown below.

EXAMPLE 88

4-Amino-1-methyl-2-indoloylguanidine Hydrochloride

Yield: >99%, M.P.: 279–283° C.; $^1$H NMR (DMSO-d$_6$) δ: 4.00 (3H, s), 6.80 (1H, d, J=7.6 Hz), 7.20–7.31 (2H, m), 7.84 (1H, s), 8.5 (2H, br-s), 8.6 (2H, br-s), 11.9 (1H, br-s).

EXAMPLE 89

5-Amino-1-methyl-2-indoloylguanidine Hydrochloride

Yield: 89.8%, M.P.: 301–302° C.; $^1$H NMR (DMSO-$d_6$) δ: 4.04 (3H, s), 7.35–7.39 (1H, m), 7.72–7.79 (2H, m), 7.93 (1H, s), 8.5 (2H, br-s), 8.7 (2H, br-s), 10.1 (2H, br-s), 12.1 (1H, br).

EXAMPLE 90

7-Amino-1-methyl-2-indoloylguanidine Hydrochloride

Yield: 66.7%, M.P.: 299–300° C.; $^1$H NMR (DMSO-$d_6$) δ: 4.28 (3H, s), 7.08–7.14 (1H, m), 7.24 (1H, d, J=7.3 Hz), 7.55 (1H, d, J=7.9 Hz), 7.76 (1H, s), 8.5 (2H, br-s), 8.6 (2H, br-s), 12.0 (1H, br-s).

EXAMPLE 91

Preparation of 5-hydroxy-1-methyl-2-indoloylquanidine Hydrochloride

In 50 ml of methanol was dissolved 0.83 g (2.58 mmol) of 5-benzyloxy-1-methyl-2-indoloylguanidine obtained in Example 32. While stirring at room temperature, 0.30 g of 10% palladium/carbon was added to the solution in a nitrogen flow and catalytic hydrogenation was then conducted at ambient temperature under normal pressure. After completion of the reaction, the catalyst was filtered off and the filtrate was then concentrated under reduced pressure. The resulting residue was purified by silica gel column chromatography to give 5-hydroxy-1-methyl-2-indoloylguanidine. The 5-hydroxy-1-methyl-2-indoloylguanidine was further treated with hydrogen chloride/methanol to give 0.37 g (68.6%) of 5-hydroxy-1-methyl-2-indoloylguanidine hydrochloride.

M.P.: 288–289° C.; $^1$H NMR (DMSO-$d_6$) δ: 3.96 (3H, s), 6.93–6.98 (2H, m), 7.43–7.47 (1H, m), 7.65 (1H, s), 8.43 (2H, br-s), 8.65 (2H, br-s), 9.18 (1H, s), 11.76 (1H, br-s).

The reaction was carried out in a manner similar to Example 91 to prepare the compounds of Examples 92 through 96 shown below.

EXAMPLE 92

7-Hydroxy-1-methyl-2-indoloylguanidine Hydrochloride

Yield: 53.0%, M.P.: 244–246° C.; $^1$H NMR (DMSO-$d_6$) δ: 4.29 (3H, s), 6.71 (1H, d, J=7.6 Hz), 6.88–6.94 (1H, m), 7.12 (1H, d, J=7.9 Hz), 7.65 (1H, s), 8.42–8.56 (4H, m), 10.08 (1H, s), 11.70 (1H, br-s).

EXAMPLE 93

4-Hydroxy-1-methyl-2-indoloylguanidine Hydrochloride

Yield: 27.4%, M.P.: 267–268° C.; $^1$H NMR (DMSO-$d_6$) δ: 3.96 (3H, s), 6.50 (1H, d, J=7.6 Hz), 7.00 (1H, d, J=8.3 Hz), 7.16–7.22 (1H, m), 7.71 (1H, s), 8.42 (4H, br-s), 10.14 (1H, br-s), 11.51 (1H, br-s).

EXAMPLE 94

6-Hydroxy-1-methyl-2-indoloylguanidine Hydrochloride

Yield: 73.4%, M.P.: 270–271° C. $^1$H NMR (DMSO-$d_6$) δ: 3.90 (3H, s), 6.72–6.76 (1H, m), 6.81 (1H, s), 7.53–7.61 (2H, m), 8.4 (4H, br-s), 9.76 (1H, br-s), 11.39 (1H, br-s).

EXAMPLE 95

4-Chloro-7-hydroxy-1-methyl-2-indoloylguanidine Hydrochloride

Yield: 23.9%, M.P.: 280° C.; $^1$H NMR (DMSO-$d_6$) δ: 4.30 (3H, s), 6.70 (1H, d, J=7.9 Hz), 6.96 (1H, d, J=8.3 Hz), 7.68 (1H, 5), 8.54 (4H, br-s), 10.37 (1H, s), 11.79 (1H, br-s).

EXAMPLE 96

4-Chloro-6-hydroxy-1-methyl-2-indoloylguanidine Hydrochloride

Yield: 40.1%, M.P.: 270° C.; $^1$H NMR (DMSO-$d_6$) δ: 3.91 (3H, s), 6.83–6.84 (2H, m), 7.77 (1H, s), 8.3–8.7 (4H, m), 10.14 (1H, s), 11.72 (1H, br-s).

EXAMPLE 97

Preparation of 4-acetamido-1-methyl-2-indoloylguanidine Hydrochloride a) Preparation of Ethyl 4-amino-1-methyl-2-indolecarboxylate In a solvent mixture of 50 ml of tetrahydrofuran and 50 ml of methanol was dissolved 1.37 g (5.52 mmol) of ethyl 1-methyl-4-nitro-2-indolecarboxylate. Thereafter 0.30 g of 10% palladium/carbon was added to the solution and catalytic hydrogenation was then conducted at ambient temperature under normal pressure. After completion of the reaction, the catalyst was filtered off and the filtrate was then concentrated under reduced pressure. The resulting residue was purified by silica gel column chromatography to give 1.2 g (>99%) of ethyl 4-amino-1-methyl-2-indolecarboxylate.

b) Preparation of Ethyl-4-acetamido-1-methyl-2-indolecarboxylate

In 20 ml of pyridine was dissolved 1.2 g (5.52 mmol) of ethyl 4-amino-1-methyl-2-indolecarboxylate. While stirring at room temperature, 10 ml of anhydrous acetic acid was added to the solution. After stirring for 2 hours at room temperature, the reaction mixture was poured onto ice water. The mixture was extracted three times with ethyl acetate. The combined extracts were washed with 1N hydrochloric acid and then with saturated sodium hydrogencarbonate solution. The solvent was then distilled off under reduced pressure and the residue was purified by silica gel column chromatography to give 1.40 g (97.9%) of ethyl 4-acetamido-1-methyl-2-indolecarboxylate.

c) Preparation of 4-acetamido-1-methyl-2-indoloylquanidine Hydrochloride

The reaction was carried out in a manner similar to Example 1 except for using 1.40 g (5.38 mmol) of ethyl 4-acetamido-1-methyl-2-indole-carboxylate, 5.14 g (53.8 mmol) of guanidine hydrochloride and 50 ml of a methanol solution of 2.91 g (53.8 mmol) of sodium methoxide. Thus 1.15 g (69.0%) of 4-acetamido-1-methyl-2-indoloylguanidine hydrochloride was obtained.

M.P.: 277–279° C.; $^1$H NMR (DMSO-$d_6$) δ: 2.15 (3H, s), 3.99 (3H, s), 7.30–7.35 (2H, m), 7.5–7.6 (1H, m), 7.79 (1H, s), 8.4–8.7 (4H, m), 10.00 (1H, br-s), 11.68 (1H, br-s).

The reaction was carried out in a manner similar to Example 97 to prepare the compounds of Examples 98 through 100 shown below.

EXAMPLE 98

5-Acetamido-1-methyl-2-indoloylguanidine Hydrochloride

Yield: 49.2%, M.P.: 260–261° C.; $^1$H NMR (DMSO-$d_6$) δ: 2.06 (3H, s), 3.99 (3H, s), 7.46 (1H, dd, J=2.0, 8.9 Hz), 7.56 (1H, d, J=8.9 Hz), 7.83 (1H, s), 8.09 (1H, d, J=1.7 Hz), 8.47 (2H, br-s), 8.71 (2H, br-s), 9.97 (1H, br-s), 11.92 (1H, br-s).

EXAMPLE 99

7-Acetamido-1-methyl-2-indoloylguanidine Hydrochloride

Yield: 17.1%, M.P.: 285° C.; $^1$H NMR (DMSO-$d_6$) δ: 2.10 (3H, s), 4.07 (3H, s), 7.07–7.15 (2H, m), 7.61–7.64 (1H, m), 7.76 (1H, s), 8.45 (2H, br-s), 8.60 (2H, br-s), 9.90 (1H, br-s), 11.86 (1H, br-s).

EXAMPLE 100

6-Acetamido-1-methyl-2-indoloylguanidine Hydrochloride

Yield: 63.8%, M.P.: 280–281° C.; $^1$H NMR (DMSO-d6) δ: 2.09 (3H, s), 3.95 (3H, s), 7.18 (1H, dd, J=1.7, 8.6 Hz), 7.64 (1H, d, J=8.9 Hz), 7.72 (1H, s), 8.09 (1H, s), 8.2–8.8 (4H, m), 10.17 (1H, br-s), 11.75 (1H, br-s).

EXAMPLE 101

Preparation of 1-hydroxy-2-indoloylguanidine Hydrochloride a) Preparation of Methyl 1-hydroxy-2-indolecarboxylate The reaction was carried out in a manner similar to Reference Example 6 except for using 3.99 g (22.5 mmol) of 1-hydroxy-2-indolecarboxylic acid, 5.36 g (45.0 mmol) of thionyl chloride and 100 ml of methanol. Thus 2.56 g (59.5%) of methyl 1-hydroxy-2-indolecarboxylate was obtained.

b) Preparation of 1-hydroxy-2-indoloylquanidine

The reaction was carried out in a manner similar to Example 1 except for using 1.00 g (5.23 mmol) of methyl 1-hydroxy-2-indolecarboxylate, 5.00 g (52.3 mmol) of guanidine hydrochloride and 50 ml of a methanol solution of 2.82 g (52.3 mmol) of sodium methoxide. 1-Hydroxy-2-indoloylguanidine hydrochloride was obtained in an amount of 0.56 g (42.0%).

M.P.: 217° C.; $^1$H NMR (DMSO-$d_6$) δ: 7.13–7.19 (1H, m), 7.37–7.52 (2H, m), 7.69–7.73 (1H, m), 8.45 (2H, br-s), 8.70 (2H, br-s), 11.4–11.8 (2H, m).

EXAMPLE 102

Preparation of 1-methoxy-2-indoloylguanidine Hydrochloride a) Preparation of Methyl 1-methoxy-2-indolecarboxylate In a nitrogen flow 0.56 g (2.93 mmol) of methyl 1-hydroxy-2-indolecarboxylate was added to a suspension of 0.12 g (2.93 mmol) of 60% sodium hydride in 20 ml of tetrahydrofuran at room temperature. After it was confirmed that the reaction mixture became transparent, 0.83 g (5.86 mmol) of methyl iodide was added to the reaction mixture. The mixture was then refluxed for 2 hours. After cooling to room temperature, the reaction mixture was poured onto ice water followed by extraction three times with ethyl acetate. The combined extracts were washed with saturated sodium chloride solution. After drying over anhydrous magnesium sulfate, the solvent was distilled off under reduced pressure. The resulting residue was purified by silica gel column chromatography to give 0.46 g (76.5%) of methyl 1-methoxy-2-indolecarboxylate.

b) Preparation of 1-methoxy-2-indoloylquanidine Hydrochloride

The reaction was carried out in a manner similar to Example 1 except for using 0.46 g (2.24 mmol) of methyl 1-methoxy-2-indolecarboxylate, 2.14 g (22.4 mmol) of guanidine hydrochloride and 15 ml of a methanol solution of 1.21 g (22.4 mmol) of sodium methoxide. Thus 0.15 g (24.9%) of 1-methoxy-2-indoloylguanidine hydrochloride was obtained.

M.P.: 214° C.; $^1$H NMR (DMSO-$d_6$) δ: 4.16 (3H, s), 7.21–7.26 (1H, m), 7.44–7.50 (1H, m), 7.62 (1H, d, J=8.6 Hz), 7.74–7.79 (2H, m), 8.48 (2H, br-s), 8.66 (2H, br-s), 11.93 (1H, br-s).

EXAMPLE 103

Preparation of 5-benzamido-1-methyl-2-indoloylguanidine Hydrochloride a) Preparation of Ethyl-5-benzamido-1-methyl-2-indolecarboxylate In 20 ml of pyridine was dissolved 0.80 g (3.67 mmol) of ethyl 5-amino-1-methyl-2-indolecarboxylate. While stirring at room temperature, 0.57 g (4.03 mmol) of benzoyl chloride was added to the solution. After stirring for 2 hours at 70° C., the reaction mixture was cooled to room temperature and then poured onto ice water. The mixture was then extracted three times with ethyl acetate. The combined extracts were washed with 1N hydrochloric acid and then with saturated sodium hydrogencarbonate solution. After drying over anhydrous magnesium sulfate, the solvent was distilled off under reduced pressure. The residue was purified by silica gel column chromatography to give 0.62 g (52.5%) of ethyl 5-benzamido-1-methyl-2-indolecarboxylate.

b) Preparation of 5-benzamido-1-methyl-2-indoloylquanidine

The reaction was carried out in a manner similar to Example 1 except for using 0.62 g (1.92 mmol) of ethyl 5-benzamido-1-methyl-2-indole-carboxylate, 3.68 g (38.4 mmol) of guanidine hydrochloride and 50 ml of a methanol solution of 2.08 g (38.4 mmol) of sodium methoxide. 5-Benzamido-1-methyl-2-indoloylguanidine hydrochloride was obtained in an amount of 0.38 g (53.1%).

M.P.: 185–190° C.; $^1$H NMR (DMSO-$d_6$) δ: 4.03 (3H, s), 7.50–7.60 (4H, m), 7.63–7.74 (1H, m), 7.81 (1H, s), 7.96–8.00 (2H, m), 8.25 (1H, d, J=1.7 Hz), 8.44 (2H, br-s), 8.62 (2H, br-s), 10.26 (1H, br-s), 11.82 (1H, br-s).

The reaction was carried out in a manner similar to Example 103 to prepare the compounds of Examples 104 through 106 shown below.

EXAMPLE 104

4-Benzamido-1-methyl-2-indoloylguanidine Hydrochloride

Yield: 54.7%, M.P.: 302–303° C.; $^1$H NMR (DMSO-$d_6$) δ: 4.04 (3H, s), 7.37–7.64 (6H, m), 7.87 (1H, s), 8.05–8.09 (2H, m), 8.52 (4H, br-s), 10.35 (1H, br-s), 11.70 (1H, br-s).

EXAMPLE 105

7-Benzamido-1-methyl-2-indoloylguanidine Hydrochloride

Yield: 45.7%, M.P.: 318–319° C.; $^1$H NMR (DMSO-$d_6$) δ: 4.07 (3H, s), 7.16–7.24 (2H, m), 7.53–7.72 (4H, m), 7.80 (1H, m), 8.04–8.06 (2H, m), 8.45 (2H, br-s), 8.61 (2H, br-s), 10.44 (1H, br-s), 11.88 (1H, br-s).

EXAMPLE 106

6-Benzamido-1-methyl-2-indoloylguanidine Hydrochloride

Yield: 40.1%, M.P.: 309° C.; $^1$H NMR (DMSO-$d_6$) δ: 4.00 (3H, s), 7.48–7.62 (4H, m), 7.70–7.75 (2H, m), 7.98–8.01

(2H, m), 8.27 (1H, s), 8.2–8.8 (4H, m), 10.45 (1H, br-s), 11.73 (1H, br-s).

EXAMPLE 107

Preparation of 1-(4-aminobenzyl)-2-indoloylquanidine Hydrochloride

The reaction was carried out in a manner similar to Example 87 except for using 0.45 g (1.20 mmol) of 1-(4-nitrobenzyl)-2-indoloylguanidine, 0.50 g of 10% palladium/carbon, 25 ml of tetrahydrofuran and 25 ml of methanol. Thus 0.33 g (79.7%) of 1-(4-aminobenzyl)-2-indoloylguanidine hydrochloride was obtained.

M.P.: 226–228° C.; $^1$H NMR (DMSO-$d_6$) δ: 5.83 (2H, s), 7.00–7.13 (4H, m), 7.17–7.23 (1H, m), 7.34–7.40 (1H, m), 7.58 (1H, d, J=8.3 Hz), 7.79 (1H, d, J=7.9 Hz), 8.02 (1H, s), 8.50 (2H, br-s), 8.66 (2H, br-s), 9.0–9.8 (2H, m), 12.01 (1H, br-s).

EXAMPLE 108

Preparation of 1-(2-hydroxyethyl)-2-indoloylquanidine

The reaction was carried out in a manner similar to Example 1 except for using 1.00 g (3.30 mmol) of methyl 1-[2-(2-tetrahydropyranyl)oxyethyl]-2-indolecarboxylate, 3.15 g (33.0 mmol) of guanidine hydrochloride and a methanol solution of 1.78 g (33.0 mmol) of sodium methoxide. 1-[2-(2-Tetrahydropyranyl)-oxyethyl]-2-indoloylguanidine was obtained in an amount of 0.85 g. Thereafter 0.69 g of the thus obtained compound was dissolved in hydrochloric acid/methanol. The solution was stirred at room temperature for 5.5 hours. The reaction mixture was concentrated under reduced pressure and a solvent mixture of methanol and diethyl ether was added to the resulting residue. The precipitates formed were filtered and dried under reduced pressure to give 0.49 g (65%) of 1-(2-hydroxyethyl)-2-indoloylguanidine hydrochloride.

M.P.: 190–193° C.; $^1$H NMR (DMSO-$d_6$) δ: 3.60–3.82 (2H, m), 4.60 (2H, t, J=5.0 Hz), 4.74–4.97 (1H, br-s), 7.17 (1H, dt, J=7.0, 7.8 Hz), 7.38 (1H, dt, J=7.0, 7.8 Hz), 7.66 (1H, d, J=8.0 Hz), 7.72 (1H, d, J=8.0 Hz), 7.84 (1H, s), 8.20–8.90 (4H, m), 11.87 (1H, br-s).

The reaction was carried out in a manner similar to Example 108 to prepare the compounds of Examples 109 and 110 shown below.

EXAMPLE 109

1-(3-Hydroxypropyl)-2-indoloylguanidine Hydrochloride

Yield: 81.0%, M.P.: 206–207° C.; $^1$H NMR (DMSO-$d_6$) δ: 1.90 (2H, dt, J=6.9, 7.3 Hz), 3.39 (2H, t, J=6.3 Hz), 4.60 (2H, t, J=6.9 Hz), 7.18 (1H, dd, J=7.0, 7.8 Hz), 7.41 (1H, dd, J=7.1, 8.5 Hz), 7.65 (1H, d, J=8.2 Hz), 7.74 (1H, d, J=7.8 Hz), 7.88 (1H, s), 8.28–8.85 (4H, m), 11.87 (1H, br-s).

EXAMPLE 110

1-(4-Hydroxybutyl)-2-indoloylguanidine Hydrochloride

Yield: 84.0%, M.P.: 226° C.; $^1$H NMR (DMSO-$d_6$) δ: 1.30–1.50 (2H, m), 1.62–1.86 (2H, m), 3.38 (2H, t, J=6.4 Hz), 4.43 (1H, br-s), 4.56 (2H, t, J=7.3 Hz), 7.17 (1H, t, J=7.4 Hz), 7.40 (1H, ddd, J=1.0, 6.9, 7.4 Hz), 7.65 (1H, d, J=8.3 Hz), 7.73 (1H, d, J=7.9 Hz), 7.96 (1H, s), 8.52 (2H, br-s), 8.76 (2H, br-s), 12.00 (1H, s).

EXAMPLE 111

Preparation of 3-methyl-2-indoloylguanidine a) Preparation of Ethyl 2-phenylhydrazonobutyronate Ethyl 2-Phenylhydrazonobutyronate was obtained in a manner similar to Reference Example 1 a) except that aniline and ethyl 2-ethylacetacetate were used in place of o-chloroaniline and ethyl 2-methylacetacetate.

b) Preparation of Ethyl 3-methyl-2-indolecarboxylate

After 25.0 g of ethyl 2-phenylhydrazonobutyronate was dissolved in 80 ml of hydrochloric acid/methanol, the solution was refluxed for an hour. After cooling to room temperature, the reaction mixture was poured onto ice water. The mixture was then extracted three times with diethyl ether. The combined extracts were washed with water and next with saturated sodium hydrogen-carbonate solution. After drying over anhydrous magnesium sulfate, the solvent was distilled off under reduced pressure. The resulting residue was purified by silica gel column chromatography to give 14.0 g (69.0%) of ethyl 3-methyl-2-indolecarboxylate.

c) Preparation of 3-methyl-2-indoloylguanidine Hydrochloride

The reaction was carried out in a manner similar to Example 1 except for using 1.50 g (7.38 mmol) of ethyl 3-methyl-2-indolecarboxylate, 7.05 g (73.8 mmol) of guanidine hydrochloride and 50 ml of a methanol solution of 3.99 g (73.8 mmol) of sodium methoxide. Thus 1.61 g (86.3%) of 3-methyl-2-indoloylguanidine hydrochloride.

M.P.: 285–286° C.; $^1$H NMR (DMSO-$d_6$) δ: 2.60 (3H, s), 7.12 (1H, t, J=7.9 Hz), 7.31–7.44 (2H, m), 7.70 (1H, d, J=7.9 Hz), 8.46 (4H, br-s), 11.78 (1H, br-s), 11.94 (1H, br-s).

EXAMPLE 112

Preparation of 1-methyl-7-(3-phenylpropionamido)-2-indoloylguanidine Hydrochloride a) Preparation of Ethyl 1-methyl-7-(3-phenylpropionamido)-2-indolecarboxylate A suspension of 0.20 g (0.92 mmol) of ethyl 7-amino-1-methyl-2-indolecarboxylate, 0.14 g (0.94 mmol) of 3-phenylpropionic acid, 0.11 g (0.94 mmol) of 4-dimethylaminopyridine and 0.19 g (0.94 mmol) of dicyclohexylcarbodiimide in 5 ml of methylene chloride was stirred at room temperature for 24 hours. The reaction solution was poured onto ice water and the resulting mixture was extracted three times with ethyl acetate. The combined extracts were washed with 1N hydrochloric acid and next with 5% sodium hydrogencarbonate solution. After drying over anhydrous magnesium sulfate, the solvent was distilled off under reduced pressure. The resulting residue was purified by silica gel column chromatography to give ethyl 1-methyl 7-(3-phenylpropionamido)-2-indolecarboxylate.

b) Preparation of 1-methyl-7-(3-phenylpropionamido)-2-indoloylguanidine Hydrochloride The reaction was carried out in a manner similar to Example 1 except for using 0.42 g (1.21 mmol) of ethyl 1-methyl-7-(3-phenylpropionamido)-2-indolecarboxylate, 2.31 g (24.2 mmols) of guanidine hydrochloride and a solution of 1.31 g (24.2 mmols) of sodium methoxide in 30 ml of methanol. 1-Methyl-7-(3-phenylpropionamido)-2-indoloylguanidine hydrochloride was obtained in an amount of 0.16 g (34.9%).

M.P.: 279–280° C.; $^1$H NMR (DMSO-$d_6$) δ: 2.72 (2H, t, J=7.6 Hz), 2.96 (2H, t, J=7.6 Hz), 3.34 (3H, s), 7.03–7.14 (2H, m), 7.20–7.24 (1H, m), 7.29–7.31 (4H, m), 7.62 (1H, d, J=6.9 Hz), 7.69 (1H, s), 8.53 (4H, m), 9.89 (1H, s), 11.76 (1H, br-s).

The compound of Example 113 was prepared in a manner similar to Example 112.

EXAMPLE 113

1-Methyl-6-(3-phenylpropionamido)-2-indoloylguanidine Hydrochloride

Yield: 34.6%, M.P.: 245–247° C.; $^1$H NMR (DMSO-d$_6$) δ: 2.66–2.71 (2H, m), 2.91–2.97 (2H, m), 2.91–2.97 (2H, m), 3.95 (3H, s), 7.16–7.30 (6H, m), 7.63–7.71 (2H, m), 8.13 (1H, s), 8.36–8.52 (4H, m), 10.16 (1H, br-s), 11.67 (1H, br-s).

EXAMPLE 114

Preparation of 1-(3-aminopropyl)-2-indoloylquanidine Dihydrochloride

The reaction was carried out in a manner similar to Example 1 except for using 1.50 g (4.51 mmol) of methyl 1-(3-tert-butoxycarbonylaminopropyl)-2-indolecarboxylate, 4.31 g (45.1 mmol) of guanidine hydrochloride and 60 ml of a methanol solution of 2.44 g (45.1 mmol) of sodium methoxide. 1-(3-tert-Butoxycarbonylaminopropyl)-2-indoloylguanidine hydrochloride was obtained in an amount of 1.57 g. After 1.55 g of the compound was dissolved in hydrochloric acid/methanol, the solution was stirred at 70° C. for 3.5 hours. The reaction mixture was concentrated under reduced pressure. The resulting residue was recrystallized from water to give 0.65 g (46.0%) of 1-(3-aminopropyl)-2-indoloylguanidine dihydrochloride.

M.P.: 296–297° C.; $^1$H NMR (DMSO-d$_6$) δ: 2.05 (2H, ddd, J=7.6, 11.4, 14.5 Hz), 2.63–2.86 (2H, m), 4.65 (2H, t, J=7.3 Hz), 7.19 (1H, t, J=7.9 Hz), 7.42 (1H, t, J=7.6 Hz), 7.74 (2H, d, J=8.6 Hz), 7.83–8.16 (4H, m), 8.27–9.03 (4H, m), 12.00–12.30 (1H, br-s).

The compound of Example 115 was prepared in a manner similar to Example 114.

EXAMPLE 115

1-(2-Aminoethyl)-2-indoloylguanidine Dihydrochloride

Yield: 54.0%, M.P.: 240° C.; $^1$H NMR (DMSO-d$_6$) δ: 3.14–3.30 (2H, m), 4.77 (2H, t, J=6.3 Hz), 7.22 (1H, dd, J=7.3, 7.6 Hz), 7.45 (1H, dd, J=7.3, 7.6 Hz), 7.77 (1H, d, J=7.6 Hz), 7.83 (1H, d, J=7.6 Hz), 8.03 (1H, br-s), 8.20 (3H, br-s), 8.58 (2H, br-s), 8.74 (2H, br-s), 12.14 (1H, br-s).

EXAMPLE 116

Preparation of 4-aminomethyl-1-methyl-2-indoloylquanidine Dihydrochloride

The reaction was carried out in a manner similar to Example 1 except for using 1.40 g (4.21 mmol) of ethyl 1-methyl-4-tert-butyloxycarbonylaminomethyl-2-indolecarboxylate, 4.02 g (42.1 mmol) of guanidine hydrochloride and 60 ml of a methanol solution of 2.27 g (42.1 mmol) of sodium methoxide. 1-Methyl-4-tert-butyloxycarbonylaminomethyl-2-indoloylguanidine hydrochloride was obtained in an amount of 1.50 g. After the compound was dissolved in 35 ml of trifluoroacetic acid and 70 ml of methylene chloride, the solution was stirred at room temperature for 2 hours. The reaction mixture was concentrated under reduced pressure. Thereafter ice water was poured onto the resulting residue and the aqueous layer was rendered alkaline with 28% aqueous ammonia. The mixture was then extracted three times with ethyl acetate. The combined extracts were washed with saturated sodium chloride solution. After drying over anhydrous magnesium sulfate, the solvent was distilled off under reduced pressure. The resulting residue was converted with hydrogen chloride/ether into the hydrochloride. Thus 0.58 g (43.2%) of 4-aminomethyl-1-methyl-2-indoloylguanidine dihydrochloride was obtained.

M.P.: 283–284° C.; $^1$H NMR (DMSO-d$_6$) δ: 4.06 (3H, s), 4.28 (2H, d, J=6.6 Hz), 7.32 (1H, d, J=6.9 Hz), 7.43–7.49 (1H, m), 7.66 (1H, d, J=8.3 Hz), 8.28 (1H, s), 8.5–8.7 (5H, m), 8.79 (2H, br-s), 12.28 (1H, br-s).

The following compounds of Examples 117 to 122 were prepared in a manner similar to Example 116.

EXAMPLE 117

7-(3-Aminopropoxy)-1-methyl-2-indoloylguanidine Dihydrochloride

Yield: 51.8%, M.P.: 287–288° C.; $^1$H NMR (DMSO-d$_6$) δ: 2.09–2.17 (2H, m), 3.32 (2H, br-s), 4.21 (2H, t, J=5.9 Hz), 4.28 (3H, s), 6.86 (1H, d, J=6.9 Hz), 7.05 (1H, t, J=7.9 Hz), 7.28 (1H, d, J=7.9 Hz), 7.76 (1H, s), 7.98 (3H, br-s), 8.47–8.67 (4H, m), 11.92 (1H, br-s).

EXAMPLE 118

7-(3-Aminopropoxy)-4-chloro-1-methyl-2-indoloylguanidine Dihydrochloride

Yield: 41.7%, M.P.: 299–300° C.; $^1$H NMR (DMSO-d$_6$) δ: 2.14–2.19 (2H, m), 3.00–3.02 (2H, m), 4.21–4.26 (2H, m), 4.28 (3H, s), 6.83 (1H, d, J=8.3 Hz), 7.10 (1H, d, J=8.3 Hz), 7.88 (1H, s), 8.18 (3H, br-s), 8.6–8.7 (4H, m), 12.12 (1H, br-s).

EXAMPLE 119

6-(3-Aminopropoxy)-1-methyl-2-indoloylguanidine Dihydrochloride

Yield: 61.3%, M.P.: 280–281° C.; $^1$H NMR (DMSO-d$_6$) δ: 2.09–2.16 (2H, m), 3.01 (2H, t, J=6.3 Hz), 4.02 (3H, S), 4.19–4.24 (2H, m), 6.87 (1H, dd, J=2.0, 8.9 Hz), 7.15 (1H, s), 7.75 (1H, d, J=8.9 Hz), 7.95 (1H, s), 8.07 (3H, br-s), 8.51–8.80 (4H, m), 12.00 (1H, br-s).

EXAMPLE 120

1-(3-Aminopropyl)-4-chloro-2-indoloylguanidine Dihydrochloride

Yield: 46.0%, M.P.: 280–282° C.; $^1$H NMR (DMSO-d$_6$) δ: 1.95–2.16 (2H, m), 2.65–2.88 (2H, m), 4.66 (2H, t, J=6.6 Hz), 7.29 (1H, d, J=7.6 Hz), 7.42 (1H, dd, J=7.6, 8.3 Hz), 7.79 (1H, d, J=3.0 Hz), 8.02 (3H, br-s), 8.11 (1H, s), 8.68 (2H, br-s), 8.78 (2H, br-s), 12.2 (1H, br-s).

EXAMPLE 121

7-(2-Aminoethoxy)-4-chloro-1-methyl-2-indoloylguanidine Dihydrochloride

Yield: 31.9%, M.P.: 285° C.; $^1$H NMR (DMSO-d$_6$) δ: 3.2–3.4 (2H, m), 4.30 (3H, s), 4.33–4.37 (2H, m), 6.89 (1H, d, J=8.3 Hz), 7.13 (1H, d, J=8.3 Hz), 7.83 (1H, s), 8.33 (3H, br-s), 8.6–8.7 (4H, m), 12.06 (1H, br-s).

EXAMPLE 122

6-(3-Aminopropoxy)-4-chloro-1-methyl-2-indoloylguanidine Dihydrochloride

Yield: 38.7%, M.P.: 230° C.; $^1$H NMR (DMSO-d$_6$) δ: 2.06–2.11 (2H, m), 2.97–2.99 (2H, m), 4.00 (3H, s), 4.18–4.23 (2H, m), 6.96 (1H, d, J=1.7 Hz), 7.14 (1H, s), 7.95 (1H, s), 8.09 (3H, br-s), 8.5–8.7 (4H, m), 12.03 (1H, br-s).

EXAMPLE 123

Synthesis of 4-hydroxymethyl-1-methyl-2-indoloylquanidine Hydrochloride

The reaction was carried out in a manner similar to Example 1 except for using 1.50 g (4.73 mmol) of ethyl 1-methyl-4-(2-tetrahydropyranyl)oxymethyl-2-indolecarboxylate, 6.02 g (63.0 mmol) of guanidine hydrochloride and a solution of 3.40 g (63.0 mmol) of sodium methoxide in 60 ml of methanol. 1-Methyl-4-(2-tetrahydropyranyl)oxymethyl-2-indoloylguanidine was obtained. After the compound was dissolved in a mixture of 30 ml of 2N hydrochloric acid and 60 ml of tetrahydrofuran, the mixture was stirred at room temperature for an hour. The reaction mixture was poured onto ice water and the aqueous layer was rendered alkaline with 28% aqueous ammonia. The mixture was then extracted three times with ethyl acetate. The combined extracts were washed with saturated sodium chloride solution. After drying over anhydrous magnesium sulfate, the solvent was distilled off under reduced pressure. The resulting residue was purified by silica gel column chromatography to give 4-hydroxymethyl-1-methyl-2-indoloylguanidine. Next, the compound was treated with hydrogen chloride/methanol to convert into the hydrochloride. 4-Hydroxymethyl-1-methyl-2-indoloylguanidine hydrochloride was thus obtained in an amount of 0.58 g (44.2%).

M.P.: 226–229° C.; $^1$H NMR (DMSO-$d_6$) δ: 4.03 (3H, s), 4.80 (2H, s), 5.26 (1H, br-s), 7.17 (1H, d, J=6.9 Hz), 7.34–7.39 (1H, m), 7.48 (1H, d, J=8.3 Hz), 7.93 (1H, s), 8.48–8.60 (4H, m), 11.81 (1H, br-s).

The following compounds of Examples 124 to 133 were prepared in a manner similar to Example 123.

EXAMPLE 124

7-(2-Hydroxyethoxy)-1-methyl-2-indoloylguanidine Hydrochloride

Yield: 62.5%, M.P.: 243–244° C.; $^1$H NMR (DMSO-$d_6$) δ: 3.82 (2H, br-s), 4.12–4.15 (2H, m), 4.31 (3H, s), 4.94 (1H, br-s), 6.86 (1H d, J=7.3 Hz), 7.03 (1H, t, J=7.9 Hz), 7.26 (1H, d, J=7.3 Hz), 7.73 (1H, s), 8.45–8.63 (4H, m), 11.82 (1H, br-s).

EXAMPLE 125

4-Chloro-7-(2-hydroxyethoxy)-1-methyl-2-indoloylguanidine Hydrochloride

Yield; 17.7%, M.P.: 277–279° C.; $^1$H NMR (DMSO-$d_6$) δ: 3.79–3.83 (2H, m), 4.12–4.15 (2H, m), 4.31 (3H, s), 4.9 (1H, br-s), 6.85 (1H, d, J=8.3 Hz), 7.10 (1H, d, J=8.3 Hz), 7.75 (1H, s), 8.58 (4H, br-s), 11.88 (1H, br-s).

EXAMPLE 126

6-(2-Hydroxyethoxy)-1-methyl-2-indoloylguanidine Hydrochloride

Yield: 59.8%, M.P.: 265–268° C.; $^1$H NMR (DMSO-$d_6$) δ: 3.32–3.77 (2H, m), 3.98 (3H, s), 4.08–4.11 (2H, m), 4.91 (2H, m), 4.91 (1H, br-s), 6.81–6.85 (1H, m), 7.08 (1H, s), 7.61 (1H, d, J=8.9 Hz), 7.81 (1H, s), 8.39–8.64 (4H, m), 11.77 (1H, br-s).

EXAMPLE 127

4-Chloro-7-(2,3-dihydroxypropoxy)-1-methyl-2-indoloylguanidine Hydrochloride

Yield: 40.2%, M.P.: 237–238° C.; $^1$H NMR (DMSO-$d_6$) δ: 3.50 (2H, t, J=5.9 Hz), 3.88–3.91 (1H, m), 4.03 (1H, dd, J=5.6, 9.9 Hz), 4.15 (1H, dd, J=4.0, 9.9 Hz), 4.30 (3H, s), 6.85 (1H, d, J=8.3 Hz), 7.11 (1H, d, J=8.3 Hz), 7.68 (1H, s), 8.50 (4H, br-s), 11.76 (1H, br-s).

EXAMPLE 128

4-Chloro-7-(3-hydroxypropoxy)-1-methyl-2-indoloylguanidine Hydrochloride

Yield: 53.2%, M.P.: 210–212° C.; $^1$H NMR (DMSO-$d_6$) δ: 1.93–2.02 (2H, m), 3.60–3.64 (2H, m), 4.15–4.20 (2H, m), 4.28 (3H, s), 6.84 (1H, d, J=8.6 Hz), 7.09 (1H, d, J=8.3 Hz), 7.77 (1H, s), 8.5–8.6 (4H, m), 11.92 (1H, br-s).

EXAMPLE 129

4-Chloro-7-(4-hydroxybutoxy)-1-methyl-2-indoloylguanidine Hydrochloride

Yield: 69.5%, M.P.: 220–222° C.; $^1$H NMR (DMSO-$d_6$) δ: 1.59–1.67 (2H, m), 1.84–1.89 (2H, m), 3.45–3.50 (2H, m), 4.10–4.15 (2H, m), 4.29 (3H, s), 6.84 (1H, d, J=8.3 Hz), 7.10 (1H, d, J=8.3 Hz), 7.10 (1H, d, J=8.3 Hz), 7.71 (1H, s), 8.52 (4H, br-s), 11.80 (1H, br-s).

EXAMPLE 130

4-Chloro-1-(3-hydroxypropyl)-2-indoloylguanidine Hydrochloride

Yield: 60.0%, M.P.: 213–215° C.; $^1$H NMR (DMSO-$d_6$) δ: 1.78–1.98 (2H, m), 3.30–3.45 (2H, m), 4.61 (2H, t, J=7.3 Hz), 4.68 (1H, br-s), 7.27 (1H, d, J=7.6 Hz), 7.39 (1H, dd, J=7.3, 8.6 Hz), 7.66 (1H, d, J=8.6 Hz), 7.93 (1H, s), 8.55 (2H, br-s), 8.64 (2H, br-s), 11.96 (1H, br-s).

EXAMPLE 131

4-Chloro-1-(4-hydroxybutyl)-2-indoloylguanidine Hydrochloride

Yield: 48.0%, M.P.: 226–227° C.; $^1$H NMR (DMSO-$d_6$) δ: 1.28–1.51 (2H, m), 1.60–1.84 (2H, m), 3.37 (2H, t, J=6.6 Hz), 4.44 (1H, br-s), 4.58 (1H, t, J=7.3 Hz), 7.28 (1H, d, J=7.6 Hz), 7.39 (1H, dd, J=7.6, 8.6 Hz), 7.68 (1H, d, J=8.6 Hz), 7.92 (1H, s), 8.53 (2H, br-s), 8.63 (2H, br-s), 11.92 (1H, br-s).

EXAMPLE 132

4-Chloro-6-(2-hydroxyethoxy)-1-methyl-2-indoloylguanidine Hydrochloride

Yield: 51.9%, M.P.: 250–252° C.; $^1$H NMR (DMSO-$d_6$) δ: 3.74–3.77 (2H, m), 3.99 (3H, s), 4.11 (2H, t, J=5.0 Hz), 6.94 (1H, d, J=2.0 Hz), 7.13 (1H, s), 7.80 (1H, s), 8.3–8.7 (4H, m), 11.76 (1H, br-s).

EXAMPLE 133

1-(3,4-Dihydroxybutyl)-2-indoloylguanidine Hydrochloride

Yield: 73.0%, M.P.: 219–222° C.; $^1$H NMR (DMSO-$d_6$) δ: 1.53–1.73 (1H, m), 1.85–2.04 (1H, m), 3.12–3.55 (3H, m), 4.37–4.88 (4H, m), 7.18 (1H, t, J=7.3 Hz), 7.40 (1H, ddd, J=1.0, 7.3, 7.8 Hz), 7.65 (1H, d, J=8.3 Hz), 7.74 (1H, d, J=7.9 Hz), 7.86 (1H, s), 8.21 (2H, br-s), 8.67 (2H, br-s), 11.87 (1H, br-s).

EXAMPLE 134

Preparation of 1-(2-carboxyethyl)-2-indoloylquanidine Hydrochloride

After 0.80 g (2.23 mmol) of 1-[2-[1-(4-methyl-2,6,7-trioxabicyclo[2.2.2]octyl)]ethyl]-2-indoloylguanidine was suspended in 80 ml of 1,2-dimethoxyethane, 8 ml of 1N hydrochloric acid was added to the suspension. The mixture was stirred at room temperature for 20 minutes. Subsequently 10 ml of 4N sodium hydroxide solution was added to the mixture followed by stirring at room temperature for 40 minutes. Then 10 ml of 4N hydrochloric acid was added to the mixture followed by stirring at room temperature for an hour. The reaction mixture was concentrated under reduced pressure. After the resulting residue was washed with water, water was filtered off. The filtered matter was recrystallized from 0.5 N hydrochloric acid to give 0.44 g (64.0%) of 1-(2-carboxyethyl)-2-indoloylguanidine hydrochloride.

M.P.: 254° C.; $^1$H NMR (DMSO-$d_6$) δ: 2.72 (2H, t, J=7.3 Hz), 4.76 (2H, t, J=7.4 Hz), 7.17 (1H, t, J=7.9 Hz), 7.40 (1H, ddd, J=1.0, 6.9, 7.4 Hz), 7.68 (1H, d, J=8.6 Hz), 7.73 (1H, d, J=7.9 Hz), 7.91 (1H, s), 8.50 (2H, br-s), 8.72 (2H, br-s), 12.22 (1.5H, br-s).

EXAMPLE 135

Preparation of 7-carboxymethoxy-4-chloro-1-methyl-2-indoloylquanidine Hydrochloride A suspension of 0.40 g (1.11 mmol) of 7-carbamoylmethoxy-4-chloro-1-methyl-2-indoloylguanidine obtained in Example 64 in 100 ml of 2N hydrochloric acid was refluxed for an hour. The reaction mixture was gradually cooled. The precipitated crystals were filtered and dried under reduced pressure to give 0.39 g (97.2%) of 7-carboxymethoxy-4-chloro-1-methyl-2-indoloylguanidine hydrochloride.

M.P.: 283–284° C.; $^1$H NMR (DMSO-$d_6$) δ: 4.34 (3H, s), 4.84 (2H, s), 6.82 (1H, d, J=8.3 Hz), 7.09 (1H, d, J=8.3 Hz), 7.69 (1H, s), 8.48 (4H, br-s), 11.5–13.5 (1.3H, br-s).

The following compounds of Examples 136 and 137 were prepared in a manner similar to Example 135.

EXAMPLE 136

7-Carboxymethoxy-1-methyl-2-indoloylguanidine Hydrochloride

Yield: 41.5%, M.P.: 264° C.; $^1$H NMR (DMSO-$d_6$) δ: 4.34 (3H, s), 4.84 (2H, s), 6.83 (1H, d, J=7.6 Hz), 7.03 (1H, t, J=7.9 Hz), 7.30 (1H, d, J=7.9 Hz), 7.74 (1H, s), 8.47–8.63 (4H, m), 11.71–12.07 (1H, m), 12.6–13.3 (1H, m).

EXAMPLE 137

6-Carboxymethoxy-1-methyl-2-indoloylguanidine Hydrochloride

Yield: 53.0%, M.P.: 298° C.; $^1$H NMR (DMSO-$d_6$) δ: 3.97 (3H, s), 4.79 (2H, s), 6.85 (1H, dd, J=2.0, 8.9 Hz), 7.09 (1H, s), 7.63 (1H, t, J=8.9 Hz), 7.72 (1H, s), 8.34–8.51 (4H, m), 10–13 (2H, m).

EXAMPLE 138

Preparation of 1-methyl-7-(2-phenylethylamino)-2-indoloylguanidine Hydrochloride a) Preparation of Ethyl 1-methyl-7-(2-phenylethylamino)-2-indolecarboxylate A mixture of 0.10 g (0.46 mmol) of ethyl 7-amino-1-methyl-2-indolecarboxylate, 0.12 g (0.50 mmol) of phenylacetaldehyde as 50% isopropanol solution, 0.043 g (0.69 mmol) of sodium cyanogen borohydride and 0.1 ml of acetic acid in 5 ml of acetonitrile was stirred at room temperature for 15 minutes. Thereafter 0.2 ml of acetic acid was added to the reaction mixture. The resulting mixture was allowed to stand at room temperature for 15 hours. After 1N sodium hydroxide solution was added to the reaction mixture, the mixture was extracted three times with diethyl ether. The combined extracts were then washed with 1N potassium hydroxide solution. After drying over anhydrous magnesium sulfate, the solvent was distilled off under reduced pressure. The residue was purified by silica gel column chromatography to give 0.045 g (30.5%) of ethyl 1-methyl-7-(2-phenylethylamino)-2-indolecarboxylate.

b) Preparation of 1-methyl-7-(2-phenylethylamino)-2-indoloylquanidine Hydrochloride A mixture of 0.16 g (0.51 mmol) of ethyl 1-methyl-7-(2-phenylethylamino)-2-indolecarboxylate, 0.49 g (5.09 mmol) of guanidine hydrochloride and 0.28 g (5.09 mmol) of sodium methoxide in 10 ml of methanol was reacted in a manner similar to Example 1 to give 0.075 g (39.5%) of 1-methyl-7-(2-phenylethylamino)-2-indoloylguanidine hydrochloride.

M.P.: 220–223° C.; $^1$H NMR (DMSO-$d_6$) δ: 2.96–3.02 (2H, m), 3.29–3.35 (2H, m), 4.18 (3H, s), 6.60–6.95 (1H, m), 6.99 (1H, d, J=7.3 Hz), 7.06 (1H, d, J=7.3 Hz), 7.20–7.25 (1H, m), 7.31–7.33 (4H, m), 7.64 (1H, s), 8.42–8.59 (4H, m), 11.73 (1H, br-s).

The reaction was carried out in a manner similar to Example 138 to prepare the compound of Example 139.

EXAMPLE 139

1-Methyl-6-(2-phenylethylamino)-2-indoloylguanidine Hydrochloride

Yield: 26.6%, M.P.: 243–246° C.; $^1$H NMR (DMSO-$d_6$) δ: 2.91–2.97 (2H, m), 3.38–3.51 (2H, m), 3.92 (3H, s), 6.70 (1H, s), 6.79 (1H, d, J=7.9 Hz), 7.20–7.29 (1H, m), 7.31 (4H, m), 7.49 (1H, d, J=8.6 Hz), 7.76 (1H, s), 8.35–8.63 (4H, m), 11.64 (1H, br-s).

EXAMPLE 140

Preparation of 1-(3-aminopropyl)-4-trifluoromethyl-2-indoloylguanidine Dihydrochloride a) Preparation of Ethyl 1-(3-tert-butoxycarbonylaminopropyl)-4-trifluoromethyl-2-indolecarboxylate The reaction was carried out in a manner similar to Reference Example 5 (25) except for using 2.60 g (10.11 mmol) of ethyl 4-trifluoromethyl-2-indolecarboxylate, 0.445 g (11.12 mmol) of 60% sodium hydride, 4.32 g (15.17 mmol) of tert-butyl N-(3-iodopropyl)-carbamate and 100 ml of dimethylformamide. Ethyl 1-(3-tert-butoxycarbonylaminopropyl)-4-trifluoromethyl-2-indolecarboxylate was thus obtained in an amount of 2.81 g (67.1%).

b) Preparation of 1-(3-aminopropyl)-4-trifluoromethyl-2-indoloylquanidine Dihydrochloride The reaction was carried out in a manner similar to Example 1 except for using 2.81 g (6.78 mmol) of ethyl 1-(3-tert-butoxycarbonylaminopropyl)-4-trifluoromethyl-2-indolecarboxylate, 6.48 g (67.8 mmol) of guanidine hydrochloride and 100 ml of a methanol solution of 3.66 g (67.8 mmol) of sodium methoxide. 1-(3-tert-Butoxycarbonylaminopropyl)-4-trifluoromethyl-2-indoloylguanidine was thus obtained in an amount of 2.83 g. This compound, 2.72 g, was treated in a manner similar to Example 114 to give 1.45 g (57.0%) of 1-(3-aminopropyl)-4-trifluoromethyl-2-indoloylguanidine dihydrochloride.

M.P.: 245° C. (decompd.); $^1$H NMR (DMSO-$d_6$) δ: 1.99–2.20 (2H, m), 2.70–2.89 (2H, m), 4.72 (2H, t, J=6.9 Hz), 7.51–7.68 (2H, m), 8.06 (3H, br-s), 8.06–8.27 (2H, m), 8.71 (2H, br-s), 8.80 (2H, br-s), 12.30 (1H, br-s).

EXAMPLE 141

Preparation of 1-(3-dimethylaminopropyl)-4-trifluoromethyl-2-indoloylguanidine Dihydrochloride a) Preparation of Ethyl 1-(3-dimethylaminopropyl)-4-trifluoromethyl-2-indolecarboxylate Ethyl 1-(3-dimethylaminopropyl)-4-trifluoromethyl-2-indolecarboxylate was obtained in an amount of 1.77 g (74%) in a manner similar to Reference Example 5 except for using 2.07 g (4.84 mmol) of ethyl 4-trifluoromethyl-2-indolecarboxylate, 0.43 g (10.7 mmol) of 60% sodium hydride, 1.15 g (7.26 mmol) of 3-chloropropyldimethylamine hydrochloride and 80 ml of dimethylformamide.

b) Preparation of 1-(3-dimethylaminopropyl)-4-trifluoromethyl-2-indoloylquanidine Dihydrochloride 1-(3-Dimethylaminopropyl-4-trifluoromethyl-2-indoloylguanidine hydrochloride was obtained in an amount of 0.42 g (28%) in a manner similar to Example 1 except for using 1.77 g (3.45 mmol) of ethyl 1-(3-dimethylaminopropyl)-4-trifluoromethyl-2-indolecarboxylate, 3.30 g (34.5 mmol) of guanidine dihydrochloride and 100 ml of a methanol solution of 1.87 g (34.5 mmol) of sodium methoxide.

M.P.: 252–255° C.; $^1$H NMR (DMSO-$d_6$) δ: 2.07–2.30 (2H, m), 2.58–2.60 (6H, m), 3.00–3.19 (2H, m), 4.59–4.81 (2H, m), 7.49–8.67 (2H, m), 8.04–8.26 (2H, m), 8.71 (2H, br-s), 8.79 (2H, br-s), 10.69 (1H, br-s), 12.29 (1H, br-s).

The following compounds of Examples 142 to 147 were prepared in a manner similar to Example 141.

EXAMPLE 142

1-(3-Dimethylaminopropyl)-2-indoloylguanidine Dihydrochloride

Yield: 12.3%, M.P.: 240° C.; $^1$H NMR (DMSO-$d_6$) δ: 2.04–2.27 (2H, m), 2.60–2.78 (6H, m), 2.98–3.17 (2H, m), 4.51–4.72 (2H, m), 7.12–7.28 (1H, m), 7.37–7.49 (1H, m), 7.75 (1H, d, J=8.3 Hz), 8.07 (1H, s), 8.60 (2H, br-s), 8.81 (2H, br-s), 10.50 (1H, br-s), 12.15 (1H, br-s).

EXAMPLE 143

4-Chloro-1-(3-dimethylaminopropyl)-2-indoloylguanidine Dihydrochloride

Yield: 47.6%, M.P.; 237–240° C.; $^1$H NMR (DMSO-$d_6$) δ: 2.07–2.27 (2H, m), 2.70 (6H, d, J=1.3 Hz), 3.02–3.14 (2H, m), 4.55–4.72 (2H, m), 7.30 (1H, d, J=7.3 Hz), 7.38–7.48 (1H, m), 7.77 (1H, d, J=8.6 Hz), 8.06 (1H, s), 8.61 (2H, br-s), 8.68 (2H, br-s), 10.36 (1H, br-s), 12.11 (1H, br-s).

EXAMPLE 144

1-[2-[(N-Pyrrolidinyl)ethyl]-2-indoloylguanidine Dihydrochloride

Yield: 23.8%, M.P.: 236–239° C.; $^1$H NMR (DMSO-$d_6$) δ: 1.75–2.11 (4H, m), 2.88–3.13 (2H, m), 3.40–3.68 (4H, m), 4.85–5.04 (2H, m), 7.16–7.29 (1H, m), 7.40–7.54 (1H, m), 7.78 (1H, d, J=7.9 Hz), 7.87 (1H, d, J=7.9 Hz), 8.10 (1H, s), 8.62 (2H, br-s), 8.81 (2H, br-s), 11.17 (1H, br-s), 12.24 (1H, br-s).

EXAMPLE 145

4-Chloro-1-[2-(N-pyrrolidinyl)ethyl]-2-indoloylguanidine Dihydrochloride

Yield: 6.1%, M.P.: 220° C.; $^1$H NMR (DMSO-$d_6$) δ: 1.72–2.10 (4H, m), 2.83–3.13 (2H, m), 3.41–3.69 (4H, m), 4.86–5.05 (2H, m), 7.32 (1H, d, J=7.7 Hz), 7.45 (1H, dd, J=8.3, 7.7 Hz), 7.89 (1H, d, J=8.3 Hz), 8.14 (1H, br-s), 8.67 (2H, br-s), 8.74 (2H, br-s), 11.35 (1H, br-s), 12.28 (1H, br-s).

EXAMPLE 146

1-(3-Diethylaminopropyl)-4-trifluoromethyl-2-indoloylguanidine Dihydrochloride

Yield: 30.8%, M.P.: 222–225° C.; $^1$H NMR (DMSO-$d_6$) δ: 1.18 (6H, t, J=6.9 Hz), 2.08–2.30 (2H, m), 2.92–3.20 (6H, m), 4.57–4.80 (2H, m), 7.50–7.65 (2H, m), 8.07–8.24 (2H, m), 8.66 (2H, br-s), 8.78 (2H, br-s), 10.58 (1H, br-s), 12.30 (1H, br-s).

EXAMPLE 147

1-[2-(N-Morpholinyl)ethyl]-2-indoloylguanidine Dihydrochloride

Yield: 20.5%, M.P.: 180° C.; $^1$H NMR (DMSO-$d_6$) δ: 3.00–3.27 (2H, m), 3.27–3.70 (4H, m), 3.70–4.10 (4H, m), 4.88–5.14 (2H, m), 7.15–7.30 (1H, m), 7.39–7.52 (1H, m), 7.78 (1H, d, J=7.9 Hz), 7.90 (1H, d, J=8.9 Hz), 8.10 (1H, s), 8.65 (2H, br-s), 8.81 (2H, br-s), 11.85 (1H, br-s), 12.26 (1H, br-s).

EXAMPLE 148

Preparation of 6-(3-aminopropoxy)-1-methyl-4-trifluoromethyl-2-indoloylguanidine Dihydrochloride a) Preparation of Ethyl 6-benzyloxy-1-methyl-4-trifluoromethyl-2-indolecarboxylate Ethyl 6-benzyloxy-1-methyl-4-trifluoromethyl-2-indolecarboxylate was obtained in an amount of 2.25 g in a manner similar to Reference Example 5 except for using 2.20 g (6.06 mmol) of ethyl 6-benzyloxy-4-trifluoro-methyl-2-indolecarboxylate, 0.24 g (6.06 mmol) of 60% sodium hydride, 1.72 g (12.1 mmol) of methyl iodide and 50 ml of dimethylformamide.

b) Preparation of Ethyl 6-hydroxy-1-methyl-4-trifluoromethyl-2-indolecarboxylate The reaction was carried out in a manner similar to Reference Example 15 a) except for using 2.23 g (5.91 mmol) of ethyl 6-benzyloxy-1-methyl-4-trifluoromethyl-2-indolecarboxylate, 0.3 g of 10% palladium/carbon and 50 ml of tetrahydrofuran. Ethyl 6-hydroxy-1-methyl-4-trifluoromethyl-2-indolecarboxylate was thus obtained in an amount of 1.70 g.

c) Preparation of Ethyl 6-(3-tert-butoxycarbonylaminopropoxy)-1-methyl-4-trifluoromethyl-2-indolecarboxylate The reaction was carried out in a manner similar to Reference Example 5 except for using 1.00 g (3.48 mmol) of ethyl 6-hydroxy-1-methyl-4-trifluoromethyl-2-indolecarboxylate, 0.14 g (3.48 mmol) of 60% sodium hydride, 0.99 g (3.48 mmol) of tert-butyl N-(3-iodopropyl) carbamate and 40 ml of dimethylformamide. Ethyl 6-(3-tert-butoxycarbonylaminopropoxy)-1-methyl-4-trifluoromethyl-2-indolecarboxylate was thus obtained in an amount of 1.28 g.

d) Preparation of 6-(3-aminopropoxy)-1-methyl-4-trifluoromethyl-2-indoloylquanidine Dihydrochloride The reaction was carried out in a manner similar to Example 1 except for using 1.28 g (2.88 mmol) of ethyl 6-(3-tert-butoxycarbonylaminopropoxy)-1-methyl-4-trifluoromethyl-2-indolecarboxylate, 5.50 g (57.6 mmol) of guanidine hydrochloride and 60 ml of methanol solution of 3.11 g (57.6 mmol) of sodium methoxide. 6-(3-tert-Butoxycarbonylaminopropoxy)-1-methyl-4-trifluoromethyl-2-indoloylguanidine was thus obtained in an amount of 0.41 g. This compound, 0.41 g, was treated in a manner similar to Example 114 to give 0.27 g (21.8%) of 6-(3-aminopropoxy)-1-methyl-4-trifluoromethyl-2-indoloylguanidine dihydrochloride.

M.P.: 272–274° C.; $^1$H NMR (DMSO-$d_6$) δ: 2.08–2.13 (2H, m), 2.99–3.01 (2H, m), 4.05 (3H, s), 4.24–4.28 (2H, m), 7.21 (1H, s), 7.48 (1H, s), 7.97 (1H, s), 8.07 (3H, br-s), 8.56–8.70 (4H, m), 12.6 (1H, br-s).

The compound of Example 149 was obtained in a manner similar to Example 148.

EXAMPLE 149

6-(3-Aminopropoxy)-1,4-dimethyl-2-indoloylguanidine Dihydrochloride

M.P.: 265–267° C.; $^1$H NMR (DMSO-$d_6$) δ: 2.04–2.09 (2H, m), 2.46 (3H, s), 2.96–2.99 (2H, m), 3.98 (3H, s), 4.13–4.18 (2H, m), 6.65 (1H, s), 6.91 (1H, s), 8.00–8.04 (4H, m), 8.44 (2H, br-s), 8.73 (2H, br-s), 11.92 (1H, br-s).

EXAMPLE 150

Preparation of 6-(3-dimethylaminopropoxy)-1-methyl-4-trifluoromethyl-2-indoloylguanidine Dihydrochloride a) Preparation of Ethyl 6-(3-dimethylaminopropoxy)-1-methyl-4-trifluoromethyl-2-indolecarboxylate Ethyl 6-(3-dimethylaminopropoxy)-1-methyl-4-trifluoromethyl-2-indolecarboxylate was obtained in an amount of 0.72 g in a manner similar to Reference Example 4 except for using 1.00 g (3.48 mmol) of ethyl 6-hydroxy-1-methyl-4-trifluoromethyl-2-indolecarboxylate, 0.35 g (8.70 mmol) of 60% sodium hydride, 0.82 g (5.22 mmol) of 3-chloropropyldimethylamine hydrochloride and 40 ml of dimethylformamide.

b) Preparation of 6-(3-dimethylaminopropoxy)-1-methyl-4-trifluoromethyl-2-indoloylquanidine Dihydrochloride The reaction was carried out in a manner similar to Example 1 except for using 0.72 g (1.93 mmol) of ethyl 6-(3-dimethylaminopropoxy)-1-methyl-4-trifluoro-methyl-2-indolecarboxylate, 3.69 g (38.7 mmol) of guanidine hydrochloride and 50 ml of a methanol solution of 2.09 g (38.7 mmol) of sodium methoxide. 6-(3-dimethylaminopropoxy)-1-methyl-4-trifluoromethyl-2-indoloylguanidine was thus obtained in an amount of 0.40 g. This compound, 0.40 g, was treated in a manner similar to Example 1 to give 0.31 g (35.0%) of 6-(3-dimethylaminopropoxy)-1-methyl-4-trifluoro-methyl-2-indoloylguanidine dihydrochloride.

M.P.: 264–265° C.; $^1$H NMR (DMSO-$d_6$) δ: 2.17–2.23 (2H, m), 2.80 (6H, s), 3.2–3.4 (2H, m), 4.06 (3H, s), 4.23–4.27 (2H, m), 7.20 (1H, s), 7.50 (1H, s), 7.88 (1H, s), 8.5–8.7 (4H, m), 10.27 (1H, br-s), 11.90 (1H, br-s).

The compound of Example 151 was obtained in a manner similar to Example 150.

EXAMPLE 151

1,4-Dimethyl-6-(3-dimethylaminopropoxy)-2-indoloylquanidine Dihydrochloride

M.P.: 282–284° C.; $^1$H NMR (DMSO-$d_6$) δ: 2.14–2.20 (2H, m), 2.46 (3H, s), 2.79–2.80 (6H, m), 3.1–3.3 (2H, m), 3.98 (3H, s), 4.13–4.17 (2H, m), 6.66 (1H, s), 6.93 (1H, s), 7.99 (1H, s), 8.42–8.74 (4H, m), 10.26 (1H, br-s), 11.85 (1H, br-s).

EXAMPLE 152

Preparation of 7-[(3-aminopropyl)amino]-1-methyl-2-indoloylguanidine Dihydrochloride a) Preparation of Ethyl 7-[(3-aminopropyl)amino]-1-methyl-2-indolecarboxylate A mixture of 4.00 g (18.3 mmol) of ethyl 7-amino-1-methyl-2-indolecarboxylate, 7.60 g (37.6 mmol) of 3-(benzyloxycarbonylamino)propion aldehyde, 2.43 g (38.6 mmol) of sodium cyanoborohydride, 2.1 ml of acetic acid, 5.0 g of molecular sieves 3A and 200 ml of methanol was stirred at room temperature for 4.5 hours. After 28% ammonia water was added to the reaction solution to render the system alkaline, the reaction mixture was extracted three times with ethyl acetate. The combined extracts were then washed with saturated sodium chloride aqueous solution. After drying over anhydrous sodium sulfate, the solvent was distilled off under reduced pressure. The resulting residue was suspended in 100 ml of ethanol. After 6.40 g (101 mmol) of ammonium formate and 0.91 g of 10% palladium/carbon were added to the suspension, the mixture was heated to reflux for 8 hours. Insoluble matters were filtered off and the filtrate was concentrated under reduced pressure. The thus obtained residue was isolated and purified by silica gel column chromatography to give 1.04 g (24.6%) of ethyl 7-[(3-aminopropyl)amino]-1-methyl-2-indolecarboxylate.

b) Preparation of Ethyl 7-[(3-tert-butoxycarbonylaminopropyl)amino]-1-methyl-2-indolecarboxylate A mixture of 0.20 g (0.71 mmol) of ethyl 7-[(3-aminopropyl)amino]-1-methyl-2-indolecarboxylate, 0.17 g (0.79 mmol) of di-tert-butyl dicarbonate and 3 ml of dichloromethane was stirred at room temperature for an hour. The solvent was distilled off under reduced pressure. The residue was isolated and purified by silica gel column chromatography to give 0.25 g (91.6%) of ethyl 7-[(3-tert-butoxycarbonylaminopropyl)amino]-1-methyl-2-indolecarboxylate.

c) Preparation of 7-[(3-tert-butoxycarbonylaminopropyl)amino]-1-methyl-2-indolecarboxylic Acid A mixture of 0.12 g (0.31 mmol) of ethyl 7-[(3-tert-butoxycarbonylaminopropyl)amino]-1-methyl-2-indolecarboxylate, 2 ml of 5N potassium hydroxide aqueous solution and 5 ml of ethanol was stirred at room temperature for 2.5 hours. After 2N hydrochloric acid was gradually added to the reaction solution to render the pH 6, the reaction mixture was concentrated under reduced pressure. The residue was extracted three times with chloroform. The combined extracts were dried over anhydrous sodium sulfate. The solvent was then distilled off under reduced pressure. The resulting residue was isolated and purified by silica gel column chromatography to give 0.079 g (72.4%) of 7-[(3-tert-butoxycarbonylaminopropyl)amino]-1-methyl-2-indolecarboxylic acid.

d) Preparation of 7-[(3-tert-butoxycarbonylaminopropyl)amino]-1-methyl-2-indoloylquanidine A solution of 0.068 g (0.18 mmol) of 7-[(3-tert-butoxycarbonylaminopropyl)amino]-1-methyl-2-indolecarboxylic acid and 0.088 g (0.54 mmol) of carbonyldiimidazole in 5 ml of tetrahydrofuran was stirred for 2 hours at room temperature and then at 45 to 50° C. for an hour. After the temperature was reverted to ambient temperature, a solution of 0.10 g (1.08 mmol) of guanidine hydrochloride and 0.16 ml (1.15 mmol) of triethylamine in 5 ml of dimethylformamide was added to the reaction mixture followed by stirring at room temperature for 7 hours. The solvent was then distilled off under reduced pressure. The resulting residue was isolated and purified by silica gel column chromatography to give 0.043 g (61.2%) of 7-[(3-tert-butoxycarbonylaminopropyl)amino]-1-methyl-2-indoloylguanidine.

e) Preparation of 7-[(3-aminopropyl)amino]-1-methyl-2-indoloylquanidine Dihydrochloride After 0.04 g (0.10 mmol) of 7-[(3-tert-butoxycarbonylaminopropyl)amino]-1-methyl-2-indoloylguanidine was dissolved in 2 ml of hydrochloric acid/methanol, the solution was stirred at room temperature for 4 hours. The solvent was distilled off under reduced pressure. After 2N sodium hydroxide aqueous solution was added to the residue thus obtained, the mixture was extracted three times with chloroform. The combined extracts were dried over anhydrous sodium sulfate. The solvent was then distilled off under reduced pressure. The resulting residue was isolated and purified by silica gel column chromatography to give 0.023 g (80.0%) of 7-[(3-aminopropyl)amino]-1-methyl-2-indoloylguanidine. The guanidine derivative was converted into the hydrochloride with hydrochloric acid/methanol. Recrystallization from methanol gave 7-[(3-aminopropyl)amino]-1-methyl-2-indoloylguanidine dihydrochloride.

M.P.: 282–284° C. (decompd.); $^1$H NMR (DMSO-$d_6$) δ: 1.96 (2H, m), 2.96 (2H, m), 3.18 (2H, m), 4.27 (3H, s), 6.59 (1H, d, J=6.9 Hz), 6.96–7.09 (2H, m) 7.72 (1H, m), 8.49 (2H, m), 8.69 (2H, m).

The following compounds of Examples 153 to 169 were prepared in a manner similar to Example 150.

EXAMPLE 153

1,4-Dimethyl-7-(3-dimethylaminopropoxy)-2-indoloylquanidine Dihydrochloride

M.P.: 276–278° C.; $^1$H NMR (DMSO-$d_6$) δ: 2.20–2.26 (2H, m), 2.42 (3H, s), 2.80 (6H, d, J=4.62 Hz), 3.21–3.29 (2H, m), 4.13–4.18 (2H, m), 4.28 (3H, s), 6.75–6.89 (2H, m), 7.87 (1H, s), 8.46 (2H, brs), 8.64 (2H, br-s), 10.24 (1H, br-s), 11.88 (1H, s).

EXAMPLE 154

7-(3-Diethylaminopropoxy)-1,4-dimethyl-2-indoloylguanidine Dihydrochloride

M.P.: 235–236° C.; $^1$H NMR (DMSO-$d_6$) δ: 1.24 (6H, t, J=7.26 Hz), 2.20–2.30 (2H, m), 2.41 (3H, s), 3.14–3.28 (6H, m), 4.17 (2H, t, J=5.94 Hz), 4.29 (3H, s), 6.80 (2H, dd, J=7.92, 18.2 Hz), 7.91 (1H, s), 8.49 (2H, br-s), 8.69 (2H, br-s), 10.27 (1H, br-s), 11.94 (1H, br-s).

EXAMPLE 155

1,4-Dimethyl-7-[2-(N-pyrrolidinyl)ethoxy]-2-indoloylguanidine Dihydrochloride

M.P.: 287–288° C.; $^1$H NMR (DMSO-$d_6$) δ: 1.91–2.04 (4H, m), 2.42 (3H, s), 3.10–3.20 (2H, m), 3.62–3.70 (4H, m), 4.29 (3H, s), 4.46 (2H, t, J=4.95 Hz), 6.85 (2H, s), 7.94 (1H, s), 8.50 (2H, br-s), 8.70 (2H, br-s), 10.81 (1H, br-s), 11.97 (1H, br-s).

EXAMPLE 156

1,4-Dimethyl-7-(2-dimethylaminoethoxy)-2-indoloylguanidine Dihydrochloride

M.P.: 245° C.; $^1$H NMR (DMSO-$d_6$) δ: 2.42 (3H, s), 2.88 (6H, s), 3.60–3.70 (2H, m), 4.28 (3H, s), 4.45–4.48 (2H, m), 6.84 (2H, s), 7.93 (1H, s), 8.49 (2H, br-s), 8.70 (2H, br-s), 10.51 (1H, br-s), 11.98 (1H, br-s).

EXAMPLE 157

6-(3-Dimethylaminopropoxy)-4-methoxy-1-methyl-2-indoloylguanidine Dihydrochloride M.P.: 225° C.; $^1$H NMR (DMSO-$d_6$) δ: 2.10–2.28 (2H, m), 2.80 (6H, s), 3.12–3.37 (2H, m), 3.89 (3H, s), 3.95 (3H, s), 4.16 (1H, t, J=5.9 Hz), 6.27 (1H, d, J=1.7 Hz), 6.67–6.73 (1H, m), 7.77 (1H, br-s), 8.36 (2H, br-s), 8.50 (2H, br-s), 10.10–10.28 (1H, m), 11.57 (1H, br-s).

EXAMPLE 158

6-(3-Dimethylaminopropoxy)-4-isopropoxy-1-methyl-2-indoloylguanidine Dihydrochloride M.P.: 255° C.; $^1$H NMR (DMSO-$d_6$) δ: 1.33 (6H, d, J=5.9 Hz), 2.10–2.28 (2H, m), 2.78 (6H, d, J=4.0 Hz), 3.14–3.30 (2H, m), 3.94 (3H, s), 4.15 (2H, t, J=5.9 Hz), 4.76 (1H, sept, J=5.9 Hz), 6.28 (1H, d, J=1.1 Hz), 6.68 (1H, d, J=1.1 Hz), 7.70 (1H, s), 8.48 (4H, br-s), 10.44–10.65 (1H, m), 11.46 (1H, br-s).

EXAMPLE 159

7-(3-Dimethylaminopropoxy)-4-methoxy-1-methyl-2-indoloylguanidine Dihydrochloride M.P.: 243° C.; $^1$H NMR (DMSO-$d_6$) δ: 2.13–2.31 (2H, m), 2.79 (6H, d, J=4.6 Hz), 3.13–3.38 (2H, m), 3.85 (3H, s), 4.13 (2H, t, J=5.9 Hz), 4.26 (3H, s), 6.46 (1H, d, J=8.2 Hz), 6.79 (1H, d, J=8.2 Hz), 7.75 (1H, s), 8.51 (2H, br-s), 8.56 (2H, br-s), 10.33–10.55 (1H, m), 11.73 (1H, br-s).

EXAMPLE 160

7-(2-Dimethylaminoethoxy)-1-methyl-4-trifluoromethyl-2-indoloylguanidine Dihydrochloride M.P.: 278–280° C.; $^1$H NMR (DMSO-$d_6$) δ: 2.88 (6H, s), 3.67 (2H, br-s), 4.32 (3H, s), 4.59–4.63 (2H, m), 7.04 (1H, d, J=7.92 Hz), 7.49 (1H, d, J=8.25 Hz), 7.79 (1H, d, J=1.65 Hz), 8.60 (4H, br-s), 10.71 (1H, br-s), 12.00 (1H, br-s).

EXAMPLE 161

6-(2-Dimethylaminoethoxy)-1-methyl-4-trifluoromethyl-2-indoloylguanidine Dihydrochloride M.P.: 286–288° C.; $^1$H NMR (DMSO-$d_6$) δ: 2.86 (6H, s), 3.58 (2H, m), 4.07 (3H, s), 4.58 (2H, t, J=5.3 Hz), 7.28 (1H, d, J=1.0 Hz), 7.60 (1H, s), 8.07 (1H, d, J=1.0 Hz), 8.70–8.81 (4H, m), 10.95 (1H, br-s), 12.20 (1H, br-s).

EXAMPLE 162

6-(2-Diethylaminoethoxy)-1-methyl-4-trifluoromethyl-2-indoloylguanidine Dihydrochloride M.P.: 287–289° C.; $^1$H NMR (DMSO-$d_6$) δ: 1.29 (6H, t, J=7.5 Hz), 3.24 (4H, m), 3.56 (2H, m), 4.07 (3H, s), 4.58

(2H, t, J=4.8 Hz), 7.25 (1H, s), 7.59 (1H, s), 8.03 (1H, s), 8.63–8.76 (4H, m), 10.73 (1H, br-s), 12.16 (1H, br-s).

EXAMPLE 163

4-Chloro-6-(2-dimethylaminoethoxy)-1-methyl-2-indoloylguanidine Dihydrochloride

M.P.: 261–262° C.; $^1$H NMR (DMSO-$d_6$) δ: 2.86 (6H, s), 3.48–3.59 (2H, m), 4.02 (3H, s), 4.45–4.49 (2H, m), 7.04 (1H, d, J=1.98 Hz), 7.26 (1H, s), 7.82 (1H, s), 8.39–8.63 (4H, br-s), 10.14–10.32 (1H, m), 11.82 (1H, br-s).

EXAMPLE 164

4-Chloro-6-(3-dimethylaminopropoxy)-1-methyl-2-indoloylguanidine Dihydrochloride M.P.: 277–278° C.; $^1$H NMR (DMSO-$d_6$) δ: 2.16–2.21 (2H, m), 2.79 (6H, s), 3.23–3.26 (2H, m), 4.00 (3H, s), 4.19 (2H, t, J=5.94 Hz), 6.97 (1H, d, J=1.98 Hz), 7.17 (1H, s), 7.88 (1H, s), 8.50 (2H, br-s), 8.63 (2H, br-s), 10.36 (1H, br-s), 11.92 (1H, br-s).

EXAMPLE 165

4-Chloro-6-(2-diethylaminoethoxy)-1-methyl-2-indoloylguanidine Dihydrochloride

M.P.: 268–270° C.; $^1$H NMR (DMSO-$d_6$) δ: 1.24–1.30 (6H, m), 3.20–3.26 (4H, m), 3.45–3.55 (2H, m), 4.02 (3H, s), 4.48–4.51 (2H, m), 7.04 (1H, d, J=1.98 Hz), 7.25 (1H, br-s), 7.90 (1H, s), 8.50 (2H, br-s), 8.63 (2H, br-s), 10.27 (1H, br-s), 11.93 (1H, br-s).

EXAMPLE 166

4-Chloro-1-methyl-6-[2-(N-pyrrolidinyl)ethoxy]-2-indoloylguanidine Dihydrochloride M.P.: 272–274° C.; $^1$H NMR (DMSO-$d_6$) δ: 1.91 (2H, br-s), 2.03 (2H, br-s), 3.12–3.26 (2H, m), 3.62 (4H, br-s), 4.02 (3H, s), 4.45–4.49 (2H, m), 7.56 (1H, d, J=1.98 Hz), 7.25 (1H, br-s), 7.85 (1H, s), 8.50 (2H, br-s), 8.58 (2H, br-s), 10.60 (1H, br-s), 11.86 (1H, br-s).

EXAMPLE 167

4-Chloro-7-(3-diethylaminopropoxy)-1-methyl-2-indoloylguanidine Dihydrochloride

M.P.: 254–255° C.; $^1$H NMR (DMSO-$d_6$) δ: 1.24 (6H, t, J=7.26 Hz), 2.20–2.40 (2H, m), 3.11–3.28 (6H, m), 4.19–4.24 (2H, m), 4.29 (3H, s), 6.87 (1H, d, J=8.58 Hz), 7.14 (1H, d, J=8.25 Hz), 7.75 (1H, s), 8.56 (4H, br-s), 10.26 (1H, br-s), 11.90 (1H, br-s).

EXAMPLE 168

1-Methyl-6-[2-(N-pyrrolidinyl)ethoxy]-4-trifluoromethyl-2-indoloylguanidine Dihydrochloride M.P.: 320° C.; $^1$H NMR (DMSO-$d_6$) δ: 1.94–2.03 (4H, m), 3.15 (2H, m), 3.64 (4H, m), 4.07 (3H, s), 4.56 (1H, m), 7.27 (1H, s), 7.59 (1H, s), 8.05 (1H, s), 8.68–8.79 (4H, m), 11.21 (1H, br-s), 12.16 (1H, br-s).

EXAMPLE 169

7-(3-Dimethylaminopropoxy)-1-methyl-4-trifluoromethyl-2-indoloylguanidine Dihydrochloride M.P.: 250° C.; $^1$H NMR (DMSO-$d_6$) δ: 2.2–2.4 (2H, m), 2.79 (6H, d, J=4.62 Hz), 3.1–3.3 (2H, m), 4.28–4.32 (5H, m), 6.97 (1H, d, J=8.25 Hz), 7.47 (1H, d, J=8.25 Hz), 7.78 (1H, d, J=1.32 Hz), 8.61 (4H, br-s), 10.63 (1H, br-s), 12.00 (1H, br-s).

The following compounds of Examples 170 to 178 were prepared in a manner similar to Example 148.

EXAMPLE 170

6-(3-Aminopropoxy)-4-methoxy-1-methyl-2-indoloylguanidine Dihydrochloride

M.P.: 245° C.; $^1$H NMR (DMSO-$d_6$) δ: 2.00–2.15 (2H, m), 2.90–3.07 (2H, m), 3.89 (3H, s), 3.95 (3H, s), 4.17 (2H, t, J=6.3 Hz), 6.30 (1H, d, J=1.3 Hz), 6.65–6.73 (1H, m), 7.83 (1H, s), 7.98 (3H, br-s), 8.42 (2H, br-s), 8.60 (2H, br-s), 11.68 (1H, br-s).

EXAMPLE 171

6-(3-Aminopropoxy)-4-isopropoxy-1-methyl-2-indoloylguanidine Dihydrochloride

M.P.: 230° C.; $^1$H NMR (DMSO-$d_6$) δ: 1.33 (6H, d, J=5.9 Hz), 2.00–2.13 (2H, m), 2.90–3.07 (2H, m), 3.94 (3H, s), 4.15 (2H, t, J=5.9 Hz), 4.77 (1H, sept, J=5.9 Hz), 6.30 (1H, d, J=1.3 Hz), 6.63–6.70 (1H, m), 7.65 (1H, s), 7.98 (3H, br-s), 8.42 (4H, br-s), 11.37 (1H, br-s).

EXAMPLE 172

7-(3-Aminopropoxy)-1-methyl-4-trifluoromethyl-2-indoloylguanidine Dihydrochloride M.P.: 284–286° C.; $^1$H NMR (DMSO-$d_6$) δ: 2.16–2.18 (2H, m), 3.02–3.04 (2H, m), 4.28–4.31 (5H, m), 6.97 (1H, d, J=8.92 Hz), 7.48 (1H, d, J=8.25 Hz), 7.81 (1H, s), 8.07 (3H, br-s), 8.63 (4H, br-s), 12.03 (1H, br-s).

EXAMPLE 173

7-(2-Aminoethoxy)-1-methyl-4-trifluoromethyl-2-indoloylguanidine Dihydrochloride M.P.: 291–292° C.; $^1$H NMR (DMSO-$d_6$) δ: 3.2–3.5 (2H, m), 4.32 (3H, s), 4.44 (2H, t, J=4.95 Hz), 7.01 (1H, d, J=8.25 Hz), 7.47 (1H, d, J=8.25 Hz), 7.79 (1H, s), 8.30 (3H, br-s), 8.62 (4H, br-s), 12.02 (1H, br-s).

EXAMPLE 174

7-(2-Aminoethoxy)-1,4-dimethyl-2-indoloylguanidine Dihydrochloride

M.P.: 305–306° C.; $^1$H NMR (DMSO-$d_6$) δ: 2.49 (3H, s), 3.3–3.5 (2H, m), 4.29 (5H, m), 6.81–6.83 (2H, m), 7.89 (1H, s), 8.19 (3H, br-s), 8.50 (2H, br-s), 8.67 (2H, br-s), 11.92 (1H, br-s).

EXAMPLE 175

6-(2-Aminoethoxy)-4-chloro-1-methyl-2-indoloylguanidine Dihydrochloride

M.P.: 308–309° C.; $^1$H NMR (DMSO-$d_6$) δ: 3.1–3.3 (2H, m), 4.02 (3H, s), 4.32 (2H, t, J=4.95 Hz), 7.00 (1H, d, J=1.65 Hz), 7.23 (1H, br-s), 7.90 (1H, s), 8.19 (3H, br-s), 8.51 (2H, br-s), 8.65 (2H, br-s), 11.95 (1H, br-s).

EXAMPLE 176

7-(3-Aminopropoxy)-4-isopropoxy-1-methyl-2-indoloylguanidine Dihydrochloride

M.P.: 220° C.; $^1$H NMR (DMSO-$d_6$) δ: 1.31 (6H, d, J=6.3 Hz), 2.00–2.20 (2H, m), 2.90–3.10 (2H, m), 4.13 (2H, t,

J=5.9 Hz), 4.24 (1H, s), 4.67 (1H, sept, J=6.3 Hz), 6.50 (1H, d, J=8.6 Hz), 6.77 (1H, d, J=8.6 Hz), 7.55–7.64 (1H, m), 7.83–8.08 (3H, m), 8.32–8.56 (4H, m), 11.64 (1H, br-s).

EXAMPLE 177

6-(2-Aminoethoxy)-1-methyl-4-trifluoromethyl-2-indoloylguanidine Dihydrochloride M.P.: 289° C.; $^1$H NMR (DMSO-d$_6$) δ: 3.2–3.3 (2H, m), 4.07 (3H, s), 4.36–4.40 (2H, m), 7.23 (1H, s), 7.55 (1H, s), 7.99 (1H, s), 8.30 (3H, br-s), 8.57–8.72 (4H, m), 12.10 (1H, br-s).

EXAMPLE 178

7-(3-Aminopropoxy)-1,4-dimethyl-2-indoloylguanidine Dihydrochloride

M.P.: 318–320° C.; $^1$H NMR (DMSO-d$_6$) δ: 2.09–2.18 (2H, m), 2.41 (3H, s), 3.00 (2H, t) J=6.93 Hz), 4.16 (2H, t, J=5.94 Hz), 4.28 (3H, s), 6.75–6.87 (2H, m), 7.95 (1H, s), 8.01–8.05 (3H, br-s), 8.51 (2H, br-s), 8.72 (2H, br-s), 11.98 (1H, br-s).

The following compounds of Examples 179 to 180 were prepared in a manner similar to Example 141.

EXAMPLE 179

1-[3-(N-Pyrrolidinyl)propyl]-4-trifluoromethyl-2-indoloylguanidine Dihydrochloride M.P.: 180° C.; $^1$H NMR (DMSO-d$_6$) δ: 1.74–2.07 (4H, m), 2.08–2.32 (2H, m), 2.82–3.03 (2H, m), 3.08–3.25 (2H, m), 3.42–3.61 (2H, m), 4.72 (2H, t, J=5.3 Hz), 7.51–7.66 (2H, m), 8.04–8.13 (2H, m), 8.68 (2H, br-s), 8.75 (2H, br-s), 10.90 (1H, br-s), 12.23 (1H, br-s).

EXAMPLE 180

1-(3-Dimethylaminopropyl)-4-fluoro-2-indoloylguanidine Dihydrochloride

M.P.: 259–261° C.; $^1$H NMR (DMSO-d$_6$) δ: 2.14–2.25 (2H, m), 2.72 (6H, s), 3.10–3.12 (2H, m), 4.61–4.66 (2H, m), 7.00 (1H, dd, J=7.59, 10.23 Hz), 7.38–7.46 (1H, m), 7.61 (1H, d, J=8.58 Hz), 8.11 (1H, s), 8.58 (2H, br-s), 8.73 (2H, br-s), 10.34 (1H, br-s), 12.17 (1H, br-s).

The following compound of Example 181 was prepared in a manner similar to Example 114.

EXAMPLE 181

1-(3-Aminopropyl)-4-fluoro-2-indoloylguanidine Dihydrochloride

M.P.: 277–278° C.; $^1$H NMR (DMSO-d$_6$) δ: 2.04–2.09 (2H, m), 2.74–2.80 (2H, m), 4.63–4.68 (2H, m), 6.96–7.03 (1H, m), 7.38–7.46 (1H, m), 7.63 (1H, d, J=8.25 Hz), 7.98 (3H, br-s), 8.15 (1H, s), 8.63 (2H, br-s), 8.79 (2H, br-s), 12.25 (1H, br-s).

The following compounds of Examples 182 and 183 were prepared in a manner similar to Example 1.

EXAMPLE 182

6-Benzyloxy-1-methyl-4-trifluoromethyl-2-indoloylguanidine Hydrochloride

M.P.: 253–255° C.; $^1$H NMR (DMSO-d$_6$) δ: 4.05 (3H, s), 5.27 (2H, s), 7.26 (1H, s), 7.35–7.59 (6H, m), 7.80 (1H, s), 8.49 (4H, br-s), 11.74 (1H, br-s).

EXAMPLE 183

7-Benzyloxy-1-methyl-4-trifluoromethyl-2-indoloylguanidine Hydrochloride

M.P.: 255–257° C.; $^1$H NMR (DMSO-d$_6$) δ: 4.30 (3H, s), 5.36 (2H, s), 7.10 (1H, d, J=8.25 Hz), 7.37–7.57 (6H, m), 7.74 (1H, s), 8.54 (4H, br-s), 11.87 (2H, br-s).

The following compounds of Examples 184 and 185 were prepared in a manner similar to Example 91.

EXAMPLE 184

6-Hydroxy-1-methyl-4-trifluoromethyl-2-indoloylguanidine Hydrochloride

M.P.: 268° C.; $^1$H NMR (DMSO-d$_6$) δ: 3.96 (3H, s), 7.12 (1H, s), 7.16 (1H, s), 7.74 (1H, s), 8.46 (4H, br-s), 10.33 (1H, s), 11.64 (1H, br-s).

EXAMPLE 185

1,4-Dimethyl-7-hydroxy-2-indoloylguanidine Hydrochloride

M.P.: 267° C.; $^1$H NMR (DMSO-d$_6$) δ: 2.37 (3H, s), 4.29 (3H, s), 6.61 (1H, d, J=7.58 Hz), 6.69 (1H, d, J=7.59 Hz), 7.77 (1H, s), 8.44 (2H, br-s), 8.58 (2H, br-s), 9.84 (1H, s), 11.72 (1H, br-s).

EXAMPLE 186

Preparation of 6-(2-aminophenoxy)-4-chloro-1-methyl-2-indoloylguanidine Hydrochloride a) Preparation of Ethyl 4-chloro-1-methyl-6-(2-nitrophenoxy)-2-indolecarboxylate After 0.42 g (1.64 mmol) of ethyl 4-chloro-6-hydroxy-1-methyl-2-indolecarboxylate was added to a suspension of 0.066 g (1.64 mmol) of 60% sodium hydride and 5 ml of dimethylformamide, the suspension was stirred at room temperature until the mixture became an almost transparent solution. Then 0.35 g (2.49 mmol) of 1-fluoro-2-nitrobenzene was added to the solution at room temperature followed by stirring for 5 hours at the same temperature. The reaction mixture was poured onto ice water. The resulting mixture was then extracted three times with ethyl acetate. The combined extracts were washed with water. After drying over anhydrous magnesium sulfate, the solvent was distilled off under reduced pressure and the residue was isolated and purified by silica gel column chromatography to give 0.53 g (94.3%) of ethyl 4-chloro-1-methyl-6-(2-nitrophenoxy)-2-indolecarboxylate.

b) Preparation of 4-chloro-1-methyl-6-(2-nitrophenoxy)-2-indoloylguanidine

After 2.87 g (30.0 mmol) of guanidine hydrochloride was added to 25 ml of a methanol solution of 1.62 g (30.0 mmol) of sodium methoxide, the mixture was stirred at room temperature for 30 minutes. The precipitated sodium chloride was filtered off. To the obtained solution was added 0.51 g (1.50 mmol) of ethyl 4-chloro-1-methyl-6-(2-nitrophenoxy)-2-indolecarboxylate. Subsequently methanol was distilled off under reduced pressure. The resulting residue was heated at 130° C. for 5 minutes and then allowed to stand at room temperature for an hour. Thereafter water was poured onto the reaction solution and the mixture was extracted three times with ethyl acetate. The combined extracts were washed with water. After drying over anhydrous magnesium sulfate, the solvent was distilled off under reduced pressure. The resulting residue was isolated and purified by silica gel column chromatography to give 0.23 g (40.1%) of 4-chloro-1-methyl-6-(2-nitrophenoxy)-2-indoloylguanidine.

c) Preparation of 6-(2-aminophenoxy)-4-chloro-1-methyl-2-indoloylquanidine Hydrochloride A mixture of 0.23 g (0.60 mmol) of 4-chloro-1-methyl-6-(2-nitrophenoxy)-2-indoloylguanidine, 0.72 g (3.20 mmol) of tin (II) chloride dihydrate and 15 ml of ethanol was heated to reflux for 3 hours. After cooling, 28% ammonia water was added to the reaction mixture and ethanol was then distilled off under reduced pressure. The residue was extracted three times with ethyl acetate. The combined extracts were then washed with saturated sodium chloride aqueous solution. After drying over anhydrous magnesium sulfate, the solvent was distilled off under reduced pressure. The resulting residue was isolated and purified by silica gel column chromatography to give 0.11 g (51.6%) of 6-(2-aminophenoxy)-4-chloro-1-methyl-2-indoloylguanidine. The product was converted into the hydrochloride with hydrogen chloride/methanol to give 0.097 g of 6-(2-aminophenoxy)-4-chloro-1-methyl-2-indoloylguanidine hydrochloride.

M.P.: 302° C. (decompd.); $^1$H NMR (DMSO-$d_6$) δ: 3.97 (3H, s), 7.04 (1H, d, J=2.0 Hz), 7.11–7.17 (2H, m), 7.32–7.35 (3H, m), 7.94 (1H, s), 8.53–8.65 (4H, m).

EXAMPLE 187

Preparation of 7-(2-aminophenoxy)-1-methyl-2-indoloylguanidine Hydrochloride

The reaction was carried out in a manner similar to Example 186 except for using ethyl 7-hydroxy-1-methyl-2-indolecarboxylate as the starting material. 7-(2-Aminophenoxy)-1-methyl-2-indoloylguanidine hydrochloride was thus obtained.

M.P.: 255–257° C. (decompd.); $^1$H NMR (DMSO-$d_6$) δ: 4.21 (3H, s), 6.75–6.80 (2H, m), 6.91–6.97 (1H, m), 7.05–7.12 (2H, m), 7.23 (1H, d, J=7.25 Hz), 7.52 (1H, d, J=7.25 Hz), 7.85 (1H, s), 8.50 (2H, br-s), 8.67 (2H, br-s), 11.99 (1H, br-s).

EXAMPLE 188

Preparation of 7-(2-aminophenoxy)-4-chloro-1-methyl-2-indoloylquanidine Hydrochloride The reaction was carried out in a manner similar to Example 186 except for using ethyl 4-chloro-7-hydroxy-1-methyl-2-indolecarboxylate as the starting material. 7-(2-Aminophenoxy)-4-chloro-1-methyl-2-indoloylguanidine hydrochloride was thus obtained.

M.P.: 286–288° C. (decompd.); $^1$H NMR (DMSO-$d_6$) δ: 4.23 (3H, s), 6.73 (1H, d, J=8.25 Hz), 6.86 (1H, dd, J=1.32, 7.92 Hz), 6.95–7.01 (1H, m), 7.08–7.14 (1H, m), 7.18 (1H, d, J=8.25 Hz), 7.25–7.28 (1H, m), 7.89 (1H, s), 8.59 (2H, br-s), 8.65 (2H, br-s), 12.08 (1H, br-s).

EXAMPLE 189

Preparation of 7-(3-aminophenoxy)-4-chloro-1-methyl-2-indoloylguanidine Hydrochloride a) Preparation of Ethyl 4-chloro-1-methyl-7-(3-nitrophenoxy)-2-indolecarboxylate After 0.50 g (1.97 mmol) of ethyl 4-chloro-7-hydroxy-1-methyl-2-indolecarboxylate was added to a suspension of 0.16 g (3.94 mmol) of 60% sodium hydride and 10 ml of dimethylformamide, the suspension was stirred at room temperature for 30 minutes. Then 0.28 g (1.97 mmol) of 1-fluoro-3-nitrobenzene was added to the solution at room temperature followed by stirring for 3 hours at 150° C. After cooling, the reaction mixture was poured onto ice water. The resulting mixture was then extracted three times with ethyl acetate. The combined extracts were washed with saturated sodium chloride aqueous solution. After drying over anhydrous magnesium sulfate, the solvent was distilled off under reduced pressure. The residue was isolated and purified by silica gel column chromatography to give 0.18 g (24.3%) of ethyl 4-chloro-1-methyl-7-(3-nitrophenoxy)-2-indolecarboxylate.

b) Preparation of 4-chloro-1-methyl-7-(3-nitrophenoxy)-2-indoloylquanidine

The reaction was carried out in a manner similar to Example 186 b) except for using 0.17 g (0.45 mmol) of ethyl 4-chloro-1-methyl-7-(3-nitrophenoxy)-2-indolecarboxylate, 1.30 g of guanidine hydrochloride, 0.74 g (13.6 mmol) of sodium methoxide and 30 ml of methanol. 4-Chloro-1-methyl-7-(3-nitrophenoxy)-2-indoloylguanidine was obtained in the amount of 0.06 g (34.3%).

c) Preparation of 7-(3-aminophenoxy)-4-chloro-1-methyl-2-indoloylquanidine Hydrochloride The reaction was carried out in a manner similar to Example 186 c) except for using 0.055 g (0.14 mmol) of 4-chloro-1-methyl-7-(3-nitrophenoxy)-2-indoloylguanidine, 0.16 g (0.71 mmol) of tin (II) chloride dihydrate and 5 ml of ethanol. Thus, 0.036 g (59.0%) of 7-(3-aminophenoxy)-4-chloro-1-methyl-2-indoloylguanidine hydrochloride was obtained.

M.P.: 245° C. (decompd.); $^1$H NMR (DMSO-$d_6$) δ: 4.12 (3H, s), 6.27–6.59 (3H, m), 6.93 (1H, d, J=8.3 Hz), 7.08–7.20 (1H, m), 7.23 (1H, d, J=8.3 Hz), 7.71 (1H, s), 8.44 (4H, br-s), 11.75 (1H, m).

EXAMPLE 190

Preparation of 6-(3-aminophenoxy)-4-chloro-1-methyl-2-indoloylquanidine Hydrochloride The reaction was carried out in a manner similar to Example 189 except for using ethyl 6-hydroxy-1-methyl-2-indolecarboxylate as the starting material. Thus, 6-(3-aminophenoxy)-4-chloro-1-methyl-2-indoloylguanidine hydrochloride was obtained.

M.P.: 272° C. (decompd.); $^1$H NMR (DMSO-$d_6$) δ: 3.97 (3H, s), 6.62 (1H, s), 6.66 (1H, d, J=7.92 Hz), 6.76 (1H, d, J=8.57 Hz), 7.04 (1H, d, J=1.98 Hz), 7.25–7.31 (1H, m), 7.37 (1H, s), 7.87 (1H, s), 8.52 (4H, m), 11.88 (1H, br-s).

EXAMPLE 191

Preparation of 6-(4-aminophenoxy)-4-chloro-1-methyl-2-indolecarboxylate Dihydrochloride a) Preparation of Ethyl 4-chloro-1-methyl-6-(4-nitrophenoxy)-2-indolecarboxylate The reaction was carried out in a manner similar to Example 186 a) except for using 0.41 g (1.62 mmol) of ethyl 4-chloro-6-hydroxy-1-methyl-2-indolecarboxylate, 0.09 g (2.23 mmol) of 60% sodium hydride, 0.34 g (2.40 mmol) of 1-fluoro-4-nitrobenzene and 5 ml of dimethylformamide. Ethyl 4-chloro-1-methyl-6-(4-nitrophenoxy)-2-indolecarboxylate was thus obtained in an amount of 0.51 g (92.0%).

b) Preparation of 4-chloro-1-methyl-6-(4-nitrophenoxy)-2-indoloylquanidine

The reaction was carried out in a manner similar to Example 186 b) except for using 0.45 g (1.32 mmol) of ethyl 4-chloro-1-methyl-6-(4-nitrophenoxy)-2-indolecarboxylate, 2.52 g (26.4 mmol) of guanidine hydrochloride, 1.42 g (26.4 mmol) of sodium methoxide and 25 ml of methanol. Thus, 0.24 g (47.0%) of 4-chloro-1-methyl-6-(4-nitrophenoxy)-2-indoloylguanidine was obtained.

c) Preparation of 6-(4-aminophenoxy)-4-chloro-1-methyl-2-indoloylquanidine Dihydrochloride The reaction was carried out in a manner similar to Example 186 c) except for using 0.24 g (0.62 mmol) of 4-chloro-1-methyl-6-(4-nitrophenoxy)-2-indoloylguanidine, 0.72 g (3.20 mmol) of tin (II) chloride dihydrate and 15 ml of ethanol. Thus, 0.089 g of 6-(4-aminophenoxy)-4-chloro-1-methyl-2-indoloylquanidine dihydrochloride was obtained.

M.P.; 265–267° C.; $^1$H NMR (DMSO-d$_6$) δ: 3.97 (3H, s), 6.97 (1H, m), 7.06–7.19 (3H, m), 7.36 (1H, m), 8.01 (1H, d, J=0.7 Hz), 8.59–8.72 (4H, m), 12.13 (2H, br-s).

EXAMPLE 192

Preparation of 7-(4-aminophenoxy)-1-methyl-2-indoloylguanidine Hydrochloride

The reaction was carried out in a manner similar to Example 191 except for using ethyl 7-hydroxy-1-methyl-2-indolecarboxylate as the starting material. Thus, 7-(4-aminophenoxy)-1-methyl-2-indoloylguanidine hydrochloride was obtained.

M.P.: 286–288° C. (decompd.); $^1$H NMR (DMSO-d$_6$) δ: 4.12 (3H, s), 6.89–6.92 (1H, m), 7.07–7.17 (3H, m), 7.30–7.33 (2H, m), 7.56–7.59 (1H, m), 7.87 (1H, s), 8.50 (2H, br-s), 8.66 (2H, br-s), 9.50–10.20 (2H, m), 11.80–12.20 (1H, m).

EXAMPLE 193

Preparation of 7-(4-aminophenoxy)-4-chloro-1-methyl-2-indoloylguanidine Hydrochloride The reaction was carried out in a manner similar to Example 191 except for using ethyl 4-chloro-7-hydroxy-1-methyl-2-indolecarboxylate as the starting material. Thus, 7-(4-aminophenoxy)-4-chloro-1-methyl-2-indoloylguanidine hydrochloride was obtained.

M.P.: 276–278° C. (decompd.); $^1$H NMR (DMSO-d$_6$) δ: 4.14 (3H, s), 6.87 (1H, d, J=7.92 Hz), 7.11 (2H, d, J=8.91 Hz), 7.21 (1H, d, J=8.25 Hz), 7.31 (2H, d, J=8.91 Hz), 7.88 (1H, s), 8.60 (4H, br-s), 9.40–10.00 (2H, m), 11.80–12.20 (1H, m).

EXAMPLE 194

Preparation of 7-(4-aminophenoxy)-1-methyl-4-trifluoromethyl-2-indoloylguanidine Hydrochloride The reaction was carried out in a manner similar to Example 191 except for using ethyl 7-hydroxy-1-methyl-4-trifluoromethyl-2-indolecarboxylate as the starting material. Thus, 7-(4-aminophenoxy)-1-methyl-4-trifluoromethyl-2-indoloylguanidine hydrochloride was obtained.

M.P.: 264–266° C. (decompd.); $^1$H NMR (DMSO-d$_6$) δ; 4.27 (3H, s), 6.81 (1H, d, J=7.59 Hz), 7.19–7.31 (4H, m), 7.49 (1H, d, J=8.91 Hz), 7.83 (1H, d, J=1.64 Hz), 8.56 (4H, br-s).

EXAMPLE 195

Preparation of 7-(4-aminophenoxy)-1,4-dimethyl-2-indoloylguanidine Hydrochloride The reaction was carried out in a manner similar to Example 191 except for using ethyl 1,4-dimethyl-7-hydroxy-2-indolecarboxylate as the starting material. Thus, 7-(4-aminophenoxy)-1,4-dimethyl-2-indoloylguanidine hydrochloride was obtained.

M.P.: 285° C. (decompd.); $^1$H NMR (DMSO-d$_6$) δ: 4.08 (3H, s), 6.86 (1H, d, J=7.59 Hz), 6.95 (1H, d, J=8.57 Hz), 7.05 (2H, d, J=8.91 Hz), 7.33 (2H, d, J=8.91 Hz), 8.03 (1H, s), 8.50 (2H, br-s), 8.68 (2H, br-s), 10.0 (2H, br-s), 12.0 (1H, br-s).

EXAMPLE 196

Preparation of 6-[4-(aminomethyl)phenoxy]-4-chloro-1-methyl-2-indoloylguanidine Dihydrochloride a) Preparation of Ethyl 4-chloro-6-(4-formyl-phenoxy)-1-methyl-2-indolecarboxylate After 1.00 g (3.94 mmol) of ethyl 4-chloro-6-hydroxy-1-methyl-2-indolecarboxylate was added to a suspension of 0.16 g (3.94 mmol) of 60% sodium hydride and 30 ml of dimethylformamide, the suspension was stirred at room temperature until the mixture became an almost transparent solution. Then 0.54 g (4.34 mmol) of 4-fluoro-benzaldehyde was added to the solution at room temperature followed by stirring for 10 hours at 70° C. The reaction mixture was poured onto ice water. The resulting mixture was then extracted three times with ethyl acetate. The combined extracts were washed with water. After drying over anhydrous magnesium sulfate, the solvent was distilled off under reduced pressure and the residue was isolated and purified by silica gel column chromatography to give 0.91 g (64.5%) of ethyl 4-chloro-6-(4-formylphenoxy)-1-methyl-2-indolecarboxylate.

b) Preparation of Ethyl 4-chloro-6-[4-(hydroxymethyl)-phenoxy]-1-methyl-2-indolecarboxylate A mixture of 0.90 g (2.52 mmol) of ethyl 4-chloro-6-[4-formylphenoxy)-1-methyl-2-indolecarboxylate, 0.10 g (2.52 mmol) of sodium borohydride and 20 ml of ethanol was stirred at 0° C. for 2 hours. The reaction mixture was poured onto ice water. The resulting mixture was then extracted three times with ethyl acetate. The combined extracts were washed with saturated sodium chloride aqueous solution. After drying over anhydrous magnesium sulfate, the solvent was distilled off under reduced pressure to give 0.91 g (>99%) of ethyl 4-chloro-6-[4-(hydroxymethyl)phenoxy]-1-methyl-2-indolecarboxylate.

c) Preparation of Ethyl 4-chloro-6-[4-(chloromethyl)-phenoxy]-1-methyl-2-indolecarboxylate A mixture of 0.91 g (2.52 mmol) of ethyl 4-chloro-6-[4-(hydroxymethyl)phenoxy]-1-methyl-2-indolecarboxylate, 0.56 g (5.53 mmol) of triethylamine and 30 ml of dichloromethane was stirred under cooling at 0° C. and 0.35 g (3.02 mmol) of methanesulfonyl chloride was dropwise added to the mixture. Next, the reaction temperature was elevated from 0° C. to 20° C. and stirring was continued at 20° C. for further 5 hours. The reaction mixture was poured onto ice water. The resulting mixture was then extracted three times with ethyl acetate. The combined extracts were washed with saturated ammonium chloride aqueous solution, with saturated sodium hydrogencarbonate aqueous solution and finally with saturated sodium chloride aqueous solution. After drying over anhydrous magnesium sulfate, the solvent was distilled off under reduced pressure. The residue was isolated and purified by silica gel column chromatography to give 0.70 g (73.6%) of ethyl 4-chloro-6-[4-(hydroxymethyl)phenoxy]-1-methyl-2-indolecarboxylate.

d) Preparation of Ethyl 4-chloro-6-[4-(tert-butoxycarbonylaminomethyl)phenoxy]-1-methyl-2-indolecarboxylate A mixture of 0.67 g (1.77 mmol) of ethyl 4-chloro-6-[4-(chloromethyl)phenoxy]-1-methyl-2-indolecarboxylate, 0.17 g (2.66 mmol) of sodium azide and 30 ml of dimethylformamide was stirred at room temperature for 3 hours. The reaction mixture was poured onto ice water followed by extracting twice with ethyl acetate. The combined extracts were washed with saturated ammonium chloride aqueous solution and then with saturated sodium chloride aqueous solution. After drying over anhydrous magnesium sulfate, the solvent was distilled off under reduced pressure. To the residue were added 50 ml of ethyl acetate, 0.10 g of 10% palladium/carbon and 0.77 g (3.54 mmol) of di-tert-butyl dicarbonate. The mixture was catalytically hydrogenated at ambient temperature under normal pressure. After completion of the reaction, the catalyst was filtered off and the filtrate was concentrated under reduced pressure. The residue was isolated and purified by silica gel column chromatography to give 0.57 g (70.1%) of ethyl 4-chloro-6-[4-(tert-butoxycarbonylaminomethyl)phenoxy]-1-methyl-2-indolecarboxylate.

e) Preparation of 6-[4-(aminomethyl)phenoxy]-4-chloro-1-methyl-2-indoloylguanidine Dihydrochloride The reaction was carried out in a manner similar to Example 186 b) except for using 0.55 g (1.20 mmol) of ethyl 4-chloro-6-[4-(tert-butoxycarbonylaminoethyl)-phenoxy]-1-methyl-2-indolecarboxylate, 2.29 g (24.0 mmol) of guanidine hydrochloride, 1.29 g (24.0 mmol) of sodium methoxide and 50 ml of methanol. Thus, 0.70 g of ethyl 4-chloro-6-[4-(tert-butoxycarbonylaminomethyl)phenoxy]-1-methyl-2-indoloylguanidine was obtained. The product was added to a solution of 5 ml of trifluoroacetic acid in 30 ml of dichloromethane. The solution was stirred at room temperature for 2 hours. The reaction solution was concentrated under reduced pressure and ice water was poured to the residue. After 28% ammonia water was added to the reaction solution to render the system alkaline, the reaction mixture was extracted three times with ethyl acetate. The combined extracts were then washed with saturated sodium chloride aqueous solution. After drying over anhydrous sodium sulfate, the solvent was distilled off under reduced pressure. The resulting residue was treated with hydrogen chloride/methanol to give 0.28 g (52.5%) of 6-[4-(aminomethyl)phenoxy]-4-chloro-1-methyl-2-indoloylguanidine dihydrochloride.

M.P.: 287° C. (decompd.); $^1$H NMR (DMSO-$d_6$) δ: 3.97 (3H, s), 4.01 (2H, d, J=5.61 Hz), 6.96 (1H, d, J=1.65 Hz), 7.11 (2H, d, J=8.58 Hz), 7.35 (1H, s), 7.52 (2H, d, J=8.57 Hz), 7.95 (1H, s), 8.31 (3H, br-s), 8.54–8.65 (4H, m), 12.04 (1H, br-s).

EXAMPLE 197

Preparation of 7-[4-(aminomethyl)phenoxy]-4-chloro-1-methyl-2-indoloylguanidine Dihydrochloride The reaction was carried out in a manner similar to Example 196 except for using ethyl 4-chloro-7-hydroxy-1-methyl-2-indolecarboxylate as the starting material. Thus, 7-[4-(aminomethyl)phenoxy]-4-chloro-1-methyl-2-indoloylguanidine dihydrochloride was obtained.

M.P.: 290–291° C.; $^1$H NMR (DMSO-$d_6$) δ: 4.00–4.02 (2H, m), 4.12 (3H, s), 6.87 (1H, d, J=8.25 Hz), 7.07–7.10 (2H, m), 7.23 (1H, d, J=8.24 Hz), 7.49–7.52 (2H, m), 7.85 (1H, s), 8.25 (3H, br-s), 8.54 (4H, br-s), 11.98 (1H, br-s).

EXAMPLE 198

Preparation of 4-chloro-6-[4-(dimethylaminomethyl)-phenoxy]-1-methyl-2-indoloylguanidine Dihydrochloride a) Preparation of Ethyl 4-chloro-6-(4-dimethylaminomethyl)phenoxy)-1-methyl-2-indolecarboxylate A mixture of 1.34 g (3.53 mmol) of ethyl 4-chloro-6-[4-(chloromethyl)phenoxy]-1-methyl-2-indolecarboxylate, 8.0 g of dimethylamine and 80 ml of dimethylformamide was stirred at 0° C. for 3 hours. The reaction mixture was poured onto ice water. The resulting mixture was then extracted three times with ethyl acetate. The combined extracts were washed with saturated sodium chloride aqueous solution. After drying over anhydrous magnesium sulfate, the solvent was distilled off under reduced pressure and the residue was isolated and purified by silica gel column chromatography to give 0.29 g (21.2%) of ethyl 4-chloro-6-[4-(dimethylaminomethyl)phenoxy]-1-methyl-2-indolecarboxylate.

b) Preparation of 4-chloro-6-[4-(dimethylaminomethyl)-phenoxy]-1-methyl-2-indoloylquanidine Dihydrochloride The reaction was carried out in a manner similar to Example 186 b) except for using 0.29 g (0.75 mmol) of ethyl 4-chloro-6-[4-(dimethylaminomethyl)-phenoxy]-1-methyl-2-indolecarboxylate, 1.43 g (15.0 mmol) of guanidine hydrochloride, 0.81 g (15.0 mmol) of sodium methoxide and 30 ml of methanol. Thus, 0.23 g (66.0%) of 4-chloro-6-[4-(dimethylaminomethyl)phenoxy]-1-methyl-2-indoloylguanidine dihydrochloride was obtained.

M.P.: 275° C.; $^1$H NMR (DMSO-$d_6$) δ: 2.69 (6H, s), 3.98 (3H, s), 4.25 (2H, br-s), 7.04 (1H, d, J=1.98 Hz), 7.11 (2H, d, J=8.58 Hz), 7.40 (1H, d, J=1.65 Hz), 7.58 (2H, d, J=8.58 Hz), 7.96 (1H, s), 8.54–8.66 (1H, br-s), 10.55 (1H, br-s), 12.06 (1H, br-s).

EXAMPLE 199

Preparation of 4-chloro-7-[4-(dimethylaminomethyl)-phenoxy]-1-methyl-2-indoloylguanidine Dihydrochloride The reaction was carried out in a manner similar to Example 198 except for using ethyl 4-chloro-7-[4-(chloromethyl)phenoxy]-1-methyl-2-indolecarboxylate as the starting material. Thus, 4-chloro-7-[4-(dimethylaminomethyl)phenoxy]-1-methyl-2-indoloylguanidine dihydrochloride was obtained.

M.P.: 279–280° C.; $^1$H NMR (DMSO-$d_6$) δ: 2.68 (6H, d, J=3.63 Hz), 4.12 (3H, s), 4.24 (2H, d, J=3.96 Hz), 6.94 (1H, d, J=7.91 Hz), 7.11 (2H, d, J=8.91 Hz), 7.23 (1H, d, J=8.24 Hz), 7.59 (2H, d, J=8.58 Hz), 7.91 (1H, s), 8.5–8.8 (4H, m), 10.57 (1H, br-s), 12.09 (1H, br-s).

EXAMPLE 200

Preparation of 4-chloro-1-methyl-7-(4-nitrophenoxy)-2-indoloylguanidine Hydrochloride 4-Chloro-1-methyl-7-(4-nitrophenoxy)-2-indoloylguanidine obtained as the intermediate in Example 193 was converted into the hydrochloride with hydrogen chloride/methanol to give 4-chloro-1-methyl-7-(4-nitrophenoxy)-2-indoloylguanidine hydrochloride.

M.P.: 280–282° C.; $^1$H NMR (DMSO-$d_6$) δ: 4.04 (3H, s), 7.15 (1H, d, J=8.25 Hz), 7.19–7.23 (2H, m), 7.31 (1H, d, J=8.25 Hz), 7.86 (1H, s), 8.26–8.30 (2H, m), 8.52 (4H, br-s), 11.97 (1H, s).

EXAMPLE 201

Preparation of 4-chloro-1-methyl-7-(2-nitrophenoxy)-2-indoloylguanidine Hydrochloride 4-Chloro-1-methyl-7-(2-nitrophenoxy)-2-indoloylguanidine obtained as the intermediate in Example 188 was converted into the hydrochloride with hydrogen chloride/methanol to give 4-chloro-1-methyl-7-(2-nitrophenoxy)-2-indoloylguanidine hydrochloride.

M.P.: 176–178° C.; $^1$H NMR (DMSO-$d_6$) δ: 4.18 (3H, s), 6.87 (1H, d, J=8.25 Hz), 7.20–7.24 (2H, m), 7.40–7.46 (1H, m), 7.70–7.77 (2H, m), 8.15 (1H, dd, J=1.65, 8.24 Hz), 8.48 (4H, br-s), 11.84 (1H, s).

EXAMPLE 202

Preparation of 7-[4-(aminomethyl)benzyloxy]-4-chloro-1-methyl-2-indoloylguanidine Dihydrochloride a) Preparation of Ethyl 7-[4-tert-butoxycarbonylaminomethyl)benzyloxy-4-chloro-1-methyl-2-indolecarboxylate Dihydrochloride The reaction was carried out in a manner similar to Example 196 a) except for using 0.44 g (1.74 mmol) of ethyl 4-chloro-7-hydroxy-1-methyl-2-indolecarboxylate, 0.66 g (2.58 mmol) of 4-(tert-butoxycarbonylaminomethyl)-benzyl chloride, 0.07 9 (1.74 mmol) of 60% sodium hydride and 20 ml of dimethylformamide. Thus, 0.61 g (73.1%) of ethyl 7-[4-(tert-butoxycarbonylaminomethyl)benzyloxy]-4-chloro-1-methyl-2-indolecarboxylate was obtained.

b) Preparation of 7-[4-(aminomethyl)benzyloxy]-4-chloro-1-methyl-2-indoloylquanidine Dihydrochloride The reaction was carried out in a manner similar to Example 196 e) except for using 0.60 g (1.27 mmol) of ethyl 7-[4-(tert-butoxycarbonylaminomethyl)-benzyloxy]-4-chloro-1-methyl-2-indolecarboxylate, 2.42 g (25.4 mmol) of guanidine hydrochloride, 1.37 g (25.4 mmol) of sodium methoxide and 50 ml of methanol. Thus, 0.25 9 (43.0%) of 7-[4-(aminomethyl)benzyloxy]-4-chloro-1-methyl-2-indoloylguanidine dihydrochloride was obtained.

M.P.: 298° C.; $^1$H NMR (DMSO-$d_6$) δ: 4.02–4.04 (2H, m), 4.28 (3H, s), 5.29 (2H, s), 6.96 (1H, d, J=8.58 Hz), 7.12 (1H, d, J=8.25 Hz), 7.50–7.60 (4H, m), 7.77 (1H, s), 8.35 (3H, br-s), 8.57 (4H, br-s), 11.92 (1H, br-s).

EXAMPLE 203

Preparation of 6-[4-(aminomethyl)benzyloxy]-4-chloro-1-methyl-2-indoloylguanidine Dihydrochloride The reaction was carried out in a manner similar to Example 202 except for using ethyl 4-chloro-6-hydroxy-1-methyl-2-indolecarboxylate as the starting material. Thus, 6-[4-(aminomethyl)benzyloxy]-4-chloro-1-methyl-2-indoloylguanidine dihydrochloride was obtained.

M.P.: 267° C.; $^1$H NMR (DMSO-$d_6$) δ: 4.00–4.04 (5H, m), 5.24 (2H, s), 7.02–7.03 (1H, m), 7.27 (1H, s), 7.49–7.56 (4H, m), 7.91 (1H, s), 8.39–8.67 (7H, m), 11.97 (1H, br-s).

EXAMPLE 204

Preparation of 4-chloro-7-[4-(dimethylaminomethyl)-benzyloxy]-1-methyl-2-indoloylguanidine Dihydrochloride a) Preparation of Ethyl 7-[4-(aminomethyl)benzyloxy]-4-chloro-1-methyl-2-indolecarboxylate A mixture of 0.75 g (1.59 mmol) of ethyl 7-[4-(tert-butoxycarbonylaminomethyl)benzyloxy]-4-chloro-1-methyl-2-indolecarboxylate, 5 ml of trifluoroacetic acid and 50 ml of dichloromethane was stirred at 0° C. for 2 hours. The reaction mixture was concentrated under reduced pressure. Thereafter ice water was poured onto the resulting residue and 28% aqueous ammonia was added thereto to render alkaline (pH=9 to 10). The mixture was then extracted three times with ethyl acetate. The combined extracts were washed with saturated sodium chloride solution. After drying over anhydrous magnesium sulfate, the solvent was distilled off under reduced pressure to give 0.60 g (>99%) of ethyl 7-[4-(aminomethyl)benzyloxy]-4-chloro-1-methyl-2-indolecarboxylate.

b) Preparation of Ethyl 4-chloro-7-[4-(dimethylaminomethyl)benzyloxy]-1-methyl-2-indolecarboxylate A mixture of 0.54 g (1.45 mmol) of ethyl 7-[4-(aminomethyl)benzyloxy]-4-chloro-1-methyl-2-indolecarboxylate, 1.24 g (14.5 mmol) of 35% formaldehyde aqueous solution, 0.27 g (4.34 mmol) of sodium cyanogen borohydride and 20 ml of acetonitrile was stirred at room temperature for an hour. After acetic acid was added to the reaction solution to render the pH 6 to 7, the mixture was stirred for further an hour. The reaction mixture was concentrated under reduced pressure and ice water was poured onto the residue obtained. Then 28% ammonia water was added to render alkaline (pH=9 to 10). The mixture was then extracted three times with ethyl acetate. The combined extracts were then washed with saturated sodium chloride aqueous solution. After drying over anhydrous magnesium sulfate, the solvent was distilled off under reduced pressure. The resulting residue was isolated and purified by silica gel column chromatography to give 0.32 g (55.1%) of ethyl 4-chloro-7-[4-(dimethylaminomethyl)benzyloxy]-1-methyl-2-indolecarboxylate.

c) Preparation of 4-chloro-7-[4-(dimethylaminomethyl) benzyloxy]-1-methyl-2-indoloylquanidine Dihydrochloride The reaction was carried out in a manner similar to Example 186 b) except for using 0.28 g (0.70 mmol) of ethyl 4-chloro-7-[4-(dimethylaminomethyl)-benzyloxy]-1-methyl-2-indolecarboxylate, 1.52 g (16.0 mmol) of guanidine hydrochloride, 0.86 g (16.0 mmol) of sodium methoxide and 40 ml of methanol. Thus, 0.10 g (29.3%) of 4-chloro-7-[4-(dimethylaminomethyl)-benzyloxy]-1-methyl-2-indoloylguanidine dihydrochloride was obtained.

M.P.: 282° C. (decompd.); $^1$H NMR (DMSO-$d_6$) δ: 2.69 (6H, d, J=2.97 Hz), 4.2–4.4 (5H, m), 5.32 (2H, s), 6.97 (1H, d, J=8.58 Hz), 7.13 (1H, d, J=8.25 Hz), 7.61 (4H, s), 7.77 (1H, s), 8.4–8.7 (4H, m), 10.60 (1H, br-s), 11.92 (1H, br-s).

EXAMPLE 205

Preparation of 4-chloro-6-[4-(dimethylaminomethyl)-benzyloxy]-1-methyl-2-indoloylguanidine Dihydrochloride The reaction was carried out in a manner similar to Example 204 except for using ethyl 4-chloro-6-hydroxy-1-methyl-2-indolecarboxylate as the starting material. Thus, 4-chloro-6-[4-(dimethylaminomethyl)-benzyl-oxy]-1-methyl-2-indoloylguanidine dihydrochloride was obtained.

M.P.: 263° C.; $^1$H NMR (DMSO-$d_6$) δ: 2.70 (6H, s), 4.00 (3H, s), 4.28 (2H, s), 5.26 (2H, s), 7.05 (1H, d, J=1.65 Hz), 7.28 (1H, s), 7.5–7.7 (4H, m), 7.84 (1H, s), 8.4–8.6 (4H, m), 10.47 (1H, br-s), 11.84 (1H, br-s).

The following compounds of Examples 206 and 207 were prepared in a manner similar to Example 186.

EXAMPLE 206

7-(3-Aminobenzyloxy)-4-chloro-1-methyl-2-indoloylguanidine Hydrochloride

M.P.: 230° C.; $^1$H NMR (DMSO-$d_6$) δ: 4.30 (3H, s), 5.26 (2H, s), 6.96 (1H, d, J=8.3 Hz), 6.92–7.28 (3H, m), 7.15 (1H, d, J=8.3 Hz), 7.30–7.41 (1H, m), 7.67 (1H, s), 8.47 (1H, br-s), 11.75 (1H, br-s).

EXAMPLE 207

6-(3-Aminobenzyloxy)-4-chloro-1-methyl-2-indoloylguanidine Hydrochloride

M.P.: 237° C.; $^1$H NMR (DMSO-$d_6$) δ: 4.00 (3H, s), 5.24 (2H, s), 7.04 (1H, d, J=1.98 Hz), 7.15 (1H, d, J=7.92 Hz), 7.27–7.33 (3H, m), 7.40 (1H, t, J=7.59 Hz), 7.82 (1H, s), 8.45 (2H, br-s), 8.50 (2H, br-s), 11.80 (1H, br-s).

EXAMPLE 208

Preparation of 1,4-dimethyl-7-[(4-piperidino)methoxy]-2-indoloylguanidine Dihydrochloride a) Preparation of Ethyl 4-(1-tert-butoxycarbonyl)-piperidinecarboxylate A mixture of 25.0 g (159 mmol) of ethyl 4-piperidinecarboxylate, 34.7 g (159 mmol) of di-tert-butyl dicarbonate and 200 ml of dichloromethane was stirred at room temperature until the raw materials disappeared. Next, the reaction mixture was poured onto ice water. The mixture was then extracted twice with dichloromethane. After washing with 5% sodium chloride aqueous solution, the organic phase was dried over anhydrous magnesium sulfate. The solvent was distilled off under reduced pressure. The resulting residue was purified by silica gel column chromatography to give ethyl 4-(1-tert-butoxycarbonyl)piperidinecarboxylate.

b) Preparation of 4-(1-tert-butoxycarbonyl)piperidinemethanol

A mixture of 4.00 g (15.6 mmol) of ethyl 4-(1-tert-butoxycarbonyl)piperidinecarboxylate, 0.45 g (11.8 mmol) of lithium aluminum hydride and 50 ml of tetrahydrofuran was stirred at 0 to 5° C. for an hour. After completion of the reaction, excess lithium aluminum hydride was decomposed with hydrated tetrahydrofuran and then insoluble matters were filtered off. The filtrate was distilled off under reduced pressure to give 2.99 g of 4-(1-tert-butoxycarbonyl)-piperidinemethanol.

c) Preparation of 1-tert-butoxycarbonyl-4-methanesulfonyloxymethylpiperidine

To a mixture of 1.00 g (464 mmol) of 4-(1-tert-butoxycarbonyl)piperidinemethanol, 0.94 g (9.29 mmol) of triethylamine and 20 ml of dichloromethane was dropwise added 0.59 g (5.11 mmol) of methanesulfonyl chloride at 0 to 5° C. The mixture was stirred at 0 to 5° C. for a further hour. The reaction mixture was poured onto ice water. The mixture was then extracted with ethyl acetate. After washing with 5% sodium chloride aqueous solution, the extract was dried over anhydrous magnesium sulfate. The solvent was distilled off under reduced pressure to give 1-tert-butoxycarbonyl-4-methanesulfonyloxymethylpiperidine.

$^1$H NMR (CDCl$_3$) δ: 1.14–1.29 (2H, m), 1.46 (9H, s), 1.74 (2H, D, J=13.9 Hz), 1.90–1.92 (1H, m), 2.66–2.75 (2H, m), 3.01 (3H, s), 4.07 (2H, d, J=6.3 Hz), 4.13–4.20 (2H, m).

d) Preparation of Ethyl 1,4-dimethyl-7-[[(1-tert-butoxycarbonyl)piperidin-4-yl]methoxy]-2-indolecarboxylate After 0.20 g (0.86 mmol) of ethyl 1,4-dimethyl-7-hydroxy-2-indolecarboxylate, 0.034 g (0.86 mmol) of 60% sodium hydride and 10 ml of dimethylformamide were stirred at room temperature, 0.25 g (0.86 mmol) of 1-tert-butoxycarbonyl-4-methanesulfonyloxymethylpiperidine was added thereto. The mixture was stirred at 50° C. for 3 hours. The reaction mixture was poured onto ice water. The mixture was then extracted with ethyl acetate. After washing with 5% sodium chloride aqueous solution, the extract was dried over anhydrous magnesium sulfate. The solvent was distilled off under reduced pressure. The resulting residue was purified by silica gel column chromatography to give 0.32 g of ethyl 1,4-dimethyl-7-[[(1-tert-butoxycarbonyl)piperidin-4-yl]methoxy]-2-indolecarboxylate.

e) Preparation of 1,4-dimethyl-7-[[(1-tert-butoxycarbonyl)piperidin-4-yl]methoxy]-2-indoloylquanidine After 0.89 g (9.29 mmol) of guanidine hydrochloride was added to a solution of 0.50 g (9.29 mmol) of sodium methoxide in 10 ml of methanol, the mixture was stirred at room temperature for 30 minutes. The precipitated sodium chloride was filtered off. To the thus obtained solution was added 0.20 g (0.47 mmol) of ethyl 1,4-dimethyl-7-[[(1-tert-butoxycarbonyl)-piperidine-4-yl]methoxy]-2-indolecarboxylate. Subsequently methanol was distilled off under reduced pressure. The resulting residue was heated at 130° C. for 5 minutes and then allowed to stand at room temperature for an hour. Thereafter water was poured onto the reaction solution and the mixture was extracted with ethyl acetate. The extract was washed with water. After drying over anhydrous magnesium sulfate, the solvent was distilled off under reduced pressure. The resulting residue was purified by silica gel column chromatography to give 0.07 g of 1,4-dimethyl-7-[[(1-tert-butoxycarbonyl)piperidin-4-yl]methoxy]-2-indoloylguanidine.

f) Preparation of 1,4-dimethyl-7-[(4-piperidino)-methoxy]-2-indoloylquanidine Dihydrochloride A mixture of 0.07 g of 1,4-dimethyl-7-[[(1-tert-butoxycarbonyl)piperidin-4-yl]methoxy]-2-indoloylguanidine, 5 ml of trifluoroacetic acid and 30 ml of dichloromethane was stirred at room temperature for 2 hours. After 28% ammonia water was added to render the system alkaline, the reaction mixture was extracted with ethyl acetate. The extract was then washed with saturated sodium chloride aqueous solution. After drying over anhydrous magnesium sulfate, the solvent was distilled off under reduced pressure. The resulting residue was treated with hydrogen chloride/methanol to give 0.04 g of 1,4-dimethyl-7-[(4-piperidino)methoxy]-2-indoloylguanidine dihydrochloride.

M.P.: 313° C. (decompd.);

EXAMPLE 209

Preparation of 4-chloro-7-(4-dimethylaminophenoxy)-1-methyl-2-indoloylguanidine Hydrochloride a) Preparation of Ethyl 4-chloro-1-methyl-7-(4-nitrophenoxy)-2-indolecarboxylate A mixture of 1.00 g (3.94 mmol) of ethyl 4-chloro-7-hydroxy-1-methyl-2-indolecarboxylate, 0.56 g (3.94 mmol) of 1-fluoro-4-nitrobenzene, 0.16 g (3.94 mmol) of 60% sodium hydride and 30 ml of dimethylformamide was stirred at room temperature for 5 hours. The reaction mixture was poured onto ice water. The mixture was then extracted with ethyl acetate. After washing with water, the extract was dried over anhydrous magnesium sulfate. The solvent was distilled off under reduced pressure. The resulting residue was purified by silica gel column chromatography to give 1.25 g of ethyl 4-chloro-1-methyl-7-(4-nitrophenoxy)-2-indolecarboxylate.

b) Preparation of Ethyl 7-(4-aminophenoxy)-4-chloro-1-methyl-2-indolecarboxylate A mixture of 4.10 g (10.9 mmol) of ethyl 4-chloro-1-methyl-7-(4-nitrophenoxy)-2-indolecarboxylate, 12.34 g (54.7 mmol) of tin (II) chloride dihydrate and 150 ml of ethanol was stirred at 70° C. for 3 hours. After the reaction mixture was cooled to room temperature, 28% ammonia water was added to render alkaline and the mixture was extracted with ethyl acetate. Insoluble matters were filtered off. The filtrate was washed with 5% sodium chloride aqueous solution and then dried over anhydrous magnesium sulfate, the solvent was distilled off under reduced pressure. The resulting residue was purified by silica gel column chromatography to give 2.70 g of ethyl 7-(4-aminophenoxy)-4-chloro-1-methyl-2-indolecarboxylate.

c) Preparation of Ethyl 4-chloro-7-(4-dimethylaminophenoxy)-1-methyl-2-indolecarboxylate After 2.70 g (7.83 mmol) of ethyl 7-(4-aminophenoxy)-4-chloro-1-methyl-2-indolecarboxylate was dissolved in 100 ml of acetonitrile, 6.71 g (78.3 mmol) of 35% formaldehyde aqueous solution and 1.48 g (23.5 mmol) of sodium cyanogen borohydride were added to the solution at room temperature. Acetic acid was added to the mixture to maintain the pH of the reaction solution at about 4.0. The mixture was stirred for further 2 hours at room temperature. The solvent was distilled off under reduced pressure. Water and 28% ammonia water were added to the resulting residue to render alkaline. The mixture was then extracted with ethyl acetate. The extract was washed with 5% sodium chloride aqueous solution and then dried over anhydrous magnesium sulfate. The solvent was distilled off under reduced pressure. The resulting residue was purified by silica gel column chromatography to give 1.57 g of ethyl 4-chloro-7-(4-(dimethylaminophenoxy)-1-methyl-2-indolecarboxylate.

$^1$H NMR (CDCl$_3$) δ: 1.40–1.45 (3H, m), 2.93 (6H, s), 4.34–4.42 (5H, m), 6.57 (1H, d, J=8.3 Hz), 6.70–6.85 (2H, m), 6.92–6.97 (3H, m), 7.36 (1H, s).

d) Preparation of 4-chloro-7-(4-dimethylaminophenoxy)-1-methyl-2-indoloylquanidine Hydrochloride The reaction was carried out in a manner similar to Example 208 e) except for using 1.57 g (4.21 mmol) of ethyl 4-chloro-7-(4-dimethylaminophenoxy)-1-methyl-2-indolecarboxylate. Thus, 4-chloro-7-(4-dimethylaminophenoxy)-1-methyl-2-indoloylguanidine was obtained. The compound was further treated with hydrogen chloride/methanol to give 1.36 g of 4-chloro- 7-(4-dimethylaminophenoxy)-1-methyl-2-indoloylguanidine hydrochloride.

M.P.: 252° C. (decompd.);

The following compounds of Examples 210 to 213 were prepared in a manner similar to Example 186.

EXAMPLE 210

7-(2-Aminophenoxy)-1-methyl-4-trifluoromethyl-2-indoloylguanidine Dihydrochloride

M.P.: 187° C.;

EXAMPLE 211

7-(2-Aminophenoxy)-1-methyl-4-trifluoromethyl-2-indoloylguanidine Dimethanesulfonate The title compound was obtained by treating with methanesulfonic acid/hydrated isopropyl alcohol in Example 186, instead of treating with hydrogen chloride/methanol.

M.P.: 279–280° C. (decompd.);

EXAMPLE 212

7-(2-Aminophenoxy)-1-methyl-2-indoloylguanidine Dimethanesulfonate

M.P.: 260–261° C.;

EXAMPLE 213

7-(2-Aminophenoxy)-1,4-dimethyl-2-indoloylguanidine Dimethanesulfonate

M.P.: 279–280° C. (decompd.);

The following compound of Example 214 was prepared in a manner similar to Example 189.

EXAMPLE 214

7-(3-Aminophenoxy)-4-chloro-1-methyl-2-indoloylguanidine Dimethanesulfonate

M.P.: 284–285° C.;

EXAMPLE 215

Preparation of 7-[2-(1H-imidazol-1-yl)ethoxy]-1-methyl-4-trifluoromethyl-2-indoloylguanidine Dihydrochloride a) Preparation of Ethyl 7-(2-chloroethoxy)-1-methyl-4-trifluoromethyl-2-indolecarboxylate After 2.17 g (15.7 mmol) of potassium carbonate, 2.25 g (15.7 mmol) of 1-bromo-2-chloroethane and 0.05 g of potassium iodide were added to a solution of 3.00 g (10.4 mmol) of ethyl 7-hydroxy-1-methyl-4-trifluoromethyl-2-indolecarboxylate in 30 ml of dimethylformamide, the mixture was stirred at room temperature for 3 hours. Subsequently, 1.45 g (10.4 mmol) of potassium carbonate and 0.69 g (5.2 mmol) of 1-bromo-2-chloroethane were further added thereto. The mixture was stirred at 50° C. for an hour. After cooling to room temperature, the reaction mixture was poured into saturated sodium chloride aqueous solution and then extracted with ethyl acetate. The extract was washed with saturated sodium chloride aqueous solution and dried over anhydrous magnesium sulfate. The solvent was distilled off under reduced pressure. The resulting residue was purified by silica gel column chromatography to give 2.31 g of ethyl 7-(2-chloroethoxy)-1-methyl-4-trifluoromethyl-2-indolecarboxylate.

b) Preparation of Ethyl 7-[2-(1H-imidazol-1-yl)ethoxy]-1-methyl-4-trifluoromethyl-2-indolecarboxylate A mixture of 2.24 g (6.4 mmol) of ethyl (2-chloroethoxy)-1-methyl-4-trifluoromethyl-2-indolecarboxylate, 1.09 g (16.0 mmol) of imidazole, 0.36 g (9.0 mmol) of 60% sodium hydride and 30 ml of dimethylformamide was stirred at 60 to 70° C. for an hour. After cooling to room temperature, the reaction mixture was poured onto ice water. The resulting mixture was then extracted with ethyl acetate. The extract was washed with saturated sodium chloride aqueous solution. After drying over anhydrous magnesium sulfate, the solvent was distilled off under reduced pressure and the residue was purified by silica gel column chromatography to give 1.91 g of ethyl 7-[2-(1H-imidazol-1-yl)ethoxy]-1-methyl-4-trifluoromethyl-2-indolecarboxylate.

$^1$H NMR (CDCl$_3$) δ: 1.42 (3H, t, J=7.3 Hz), 4.27 (3H, s), 4.37 (2H, q, J=7.3 Hz), 4.42–4.53 (4H, m), 6.63 (1H, d, J=8.3 Hz), 6.99–7.07 (1H, m), 7.11 (1H, br-s), 7.31 (1H, dd, J=1.0 Hz, 8.3 Hz), 7.34–7.38 (1H, m), 7.59 (1H, br-s).

c) Preparation of 7-[2-(1H-imidazol-1-yl)ethoxy]-1-methyl-4-trifluoromethyl-2-indoloylquanidine Dihydrochloride The reaction was carried out in a manner similar to Example 208 e) except for using 1.84 g (4.82 mmol) of ethyl 7-[2-(1H-imidazol-1-yl)ethoxy]-1-methyl-4-trifluoromethyl-2-indolecarboxylate. Thus, 0.85 g of 7-[2-(1H-imidazol-1-yl)ethoxy]-1-methyl-4-trifluoromethyl-2-indoloylguanidine was obtained. This compound (0.50 g, 1.26 mmol) was converted into the hydrochloride with hydrochloric acid/isopropyl alcohol to give 0.58 g of 7-[2-(1H-imidazol-1-yl)ethoxy]-1-methyl-4-trifluoromethyl-2-indoloylguanidine dihydrochloride.

M.P.: 275° C. (decompd.).

The following compounds of Examples 216 to 220 were prepared in a manner similar to Example 215.

EXAMPLE 216

1-Methyl-7-[2-(1H-1,2,4-triazol-1-yl)ethoxy]-4-trifluoromethyl-2-indoloylguanidine Hydrochloride

M.P.; 270° C.

EXAMPLE 217

7-[2-(1H-Imidazol-1-yl)ethoxy]-1-methyl-4-trifluoroethyl-2-indoloylguanidine Dimethanesulfonate The title compound was obtained in a manner similar to Example 215 c) except that methanesulfonic acid was used instead of hydrochloric acid.

M.P.: 204–205° C.;

EXAMPLE 218

1-Methyl-7-[2-(1H-1,2,4-triazol-1-yl)ethoxy]-4-trifluoromethyl-2-indoloylguanidine Methanesulfonate

M.P.: 249–250° C.

EXAMPLE 219

1,4-Dimethyl-7-[3-(1H-imidazol-1-yl)propoxy]-2-indoloylguanidine Dimethanesulfonate

M.P.: 261–262° C.

EXAMPLE 220

1,4-Dimethyl-7-[2-(1H-imidazol-1-yl)ethoxy]-2-indoloylguanidine Dimethanesulfonate

M.P.: 238–240° C.

EXAMPLE 221

Preparation of 1,4-dimethyl-7-methoxy-2-indoloylguanidine Methanesulfonate a) Preparation of Ethyl 1,4-dimethyl-7-methoxy-2-indolecarboxylate A mixture of 3.50 g (15.5 mmol) of ethyl 1,4-dimethyl-7-hydroxy-2-indolecarboxylate, 4.14 g (30.0 mmol) of potassium carbonate, 4.26 g (30.0 mmol) of potassium iodide and dimethylformamide was stirred at room temperature for 2 hours. The reaction mixture was poured onto ice water followed by extraction with ethyl acetate. The extract was washed with saturated sodium chloride aqueous solution and dried over anhydrous magnesium sulfate. The solvent was distilled off under reduced pressure. The resulting residue was purified by silica gel column chromatography to give 3.21 g of ethyl 1,4-dimethyl-7-methoxy-2-indolecarboxylate.

$^1$H NMR (CDCl$_3$) δ: 1.41 (3H, t, J=7.3 Hz), 2.45 (3H, d, J=0.6 Hz), 3.88 (3H, s), 4.35 (2H, q, J=7.3 Hz), 4.36 (3H, s), 6.57 (1H, d, J=7.6 Hz), 6.76 (1H, dd, J=0.6 Hz, 7.6 Hz), 7.25 (1H, s).

b) Preparation of 1,4-dimethyl-7-methoxy-2-indoloylquanidine Methanesulfonate

The reaction was carried out in a manner similar to Example 208 e) except for using 3.21 g (13.0 mmol) of ethyl 1,4-dimethyl-7-methoxy-2-indolecarboxylate. Thus, 3.15 g of 1,4-dimethyl-7-methoxy-2-indoloylguanidine was obtained. The compound (3.15 g) was further treated with methanesulfonic acid/hydrated isopropyl alcohol to give 2.83 g of 1,4-dimethyl-7-methoxy-2-indoloylguanidine methanesulfonate.

M.P.: 256–258° C.

The following compounds of Examples 222 to 231 were prepared in a manner similar to Example 221.

EXAMPLE 222

7-Methoxy-1-methyl-4-trifluoromethyl-2-indoloylguanidine Hydrochloride

The title compound was obtained in a manner similar to Example 221 b) except that methanesulfonic acid was used instead of hydrochloric acid.

M.P.: 309–311° C. (decompd.).

EXAMPLE 223

7-Isopropoxy-1-methyl-4-trifluoromethyl-2-indoloylguanidine Hydrochloride

The title compound was obtained in a manner similar to Example 221 a) except that isopropyl iodide was used instead of methyl iodide.

M.P.: 258–259° C.

EXAMPLE 224

7-Methoxy-1-methyl-4-trifluoromethyl-2-indoloylguanidine Methanesulfonate

M.P.: 269–270° C. (decompd.).

EXAMPLE 225

7-Isopropoxy-1-methyl-4-trifluoromethyl-2-indoloylguanidine Methanesulfonate

M.P.: 238° C.

EXAMPLE 226

7-Methoxy-1-methyl-2-indoloylguanidine Methanesulfonate

M.P.: 215–216° C.

EXAMPLE 227

4-Chloro-7-methoxy-1-methyl-2-indoloylguanidine Methanesulfonate

M.P.: 240–242° C.

EXAMPLE 228

4-Chloro-6-methoxy-1-methyl-2-indoloylguanidine Methanesulfonate

M.P.: 271–273° C.

EXAMPLE 229

1,4-Dimethyl-7-isopropoxy-2-indoloylguanidine Methanesulfonate

M.P.: 193–195° C.

EXAMPLE 230

1,4-Dimethyl-7-methoxy-2-indoloylguanidine Hydrochloride

M.P.: 268–269° C.

EXAMPLE 231

1,4-Dimethyl-6-methoxy-2-indoloylguanidine Methanesulfonate

M.P.: 255–257° C.

EXAMPLE 232

7-Hydroxy-1-methyl-4-trifluoromethyl-2-indoloylguanidine Hydrochloride

The reaction was carried out in a manner similar to Example 191 to give 7-hydroxy-1-methyl-4-trifluoromethyl-2-indoloylguanidine hydrochloride.

M.P.: 272–273° C. (decompd.).

EXAMPLE 233

7-Hydroxy-1-methyl-4-trifluoromethyl-2-indoloylguanidine Methanesulfonate

The title compound was obtained in a manner similar to Example 232 except that methanesulfonic acid was used instead of hydrochloric acid.

M.P.: 274–275° C. (decompd.).

The following compounds of Examples 234 to 239 were prepared in a manner similar to Example 186.

EXAMPLE 234

7-(4-Aminobenzyloxy)-1-methyl-4-trifluoromethyl-2-indoloylguanidine Dimethanesulfonate M.P.: 194–195° C. (decompd.).

EXAMPLE 235

7-(2-Aminobenzyloxy)-1,4-dimethyl-2-indoloylguanidine Dimethanesulfonate

M.P.: 198–200° C.

EXAMPLE 236

7-(3-Aminobenzyloxy)-1,4-dimethyl-2-indoloylguanidine Dimethanesulfonate

M.P.: 233–234° C.

EXAMPLE 237

7-(4-Aminobenzyloxy)-1,4-dimethyl-2-indoloylguanidine Dimethanesulfonate

M.P.: 160–162° C.

EXAMPLE 238

7-(2-Aminobenzyloxy)-4-chloro-1-methyl-2-indoloylguanidine Dimethanesulfonate

M.P.: 202–203° C. (decompd.).

EXAMPLE 239

7-(3-Aminobenzyloxy)-4-chloro-1-methyl-2-indoloylguanidine Dimethanesulfonate

M.P.: 238–239° C. (decompd.).

EXAMPLE 240

1-Methyl-2-indoloylguanidine Methanesulfonate

The title compound was obtained by treating 1-methyl-2-indoloylguanidine obtained in Example 1 with methanesulfonic acid/hydrated isopropyl alcohol.

M.P.: 218° C.

EXAMPLE 241

Preparation of 1,4-dimethyl-2-indoloylguanidine Methanesulfonate

The title compound was obtained by treating 1,4-dimethyl-2-indoloylguanidine obtained in Example 9 with methanesulfonic acid/hydrated isopropyl alcohol.

M.P.: 251–252° C.

The following compounds of Examples 242 and 243 were prepared in a manner similar to Example 1.

EXAMPLE 242

1-Isopropyl-7-methoxy-4-methyl-2-indoloylguanidine Methanesulfonate

M.P.: 177–178° C.

EXAMPLE 243

1-Propyl-7-methoxy-4-methyl-2-indoloylguanidine Methanesulfonate

M.P.: 183–184° C.

EXAMPLE 244

1,4-Dimethyl-7-[(pyridin-2-yl)methoxy]-2-indoloylguanidine Dimethanesulfonate a) Preparation of Ethyl 1,4-dimethyl-7-[(pyridin-2-yl)methoxy]-2-indolecarboxylate A mixture of 2.00 g (8.57 mmol) of ethyl 1,4-dimethyl-7-hydroxy-2-indolecarboxylate, 4.74 g (34.3 mmol) of potassium carbonate, 1.55 g (9.43 mmol) of 2-picolyl chloride hydrochloride and 40 ml of dimethylformamide was stirred at 50° C. for 2 hours. The reaction mixture was poured into 5% sodium chloride aqueous solution. The mixture was extracted with ethyl acetate. After washing with 5% sodium hydrogencarbonate aqueous solution, the extract was dried over anhydrous magnesium sulfate. The solvent was distilled off under reduced pressure and the resulting residue was purified by silica gel column chromatography to give 2.54 g of ethyl 1,4-dimethyl-7-[(pyridin-2-yl)methoxy]-2-indolecarboxylate.

$^1$H NMR (CDCl$_3$) δ: 1.40–1.62 (3H, m), 2.46 (3H, d, J=1.0 Hz), 4.37 (2H, dd, J=7.3 Hz, 14.2 Hz), 4.45 (3H, s), 5.32 (2H, s), 6.65 (1H, d, J=7.6 Hz), 6.73–6.76 (1H, m), 7.23–7.27 (2H, m), 7.55 (1H, d, J=7.9 Hz), 7.70–7.77 (1H, m), 8.61–8.64 b) Preparation of 1,4-dimethyl-7-[(pyridin-2-yl)-methoxy]-2-indoloylquanidine Dimethanesulfonate The reaction was carried out in a manner similar to Example 208 e) except for using 2.50 g (7.71 mmol) of ethyl 1,4-dimethyl-7-[(pyridin-2-yl)methoxy]-2-indolecarboxylate. Thus, 2.10 g of 1,4-dimethyl-7-[(pyridin-2-yl)methoxy]-2-indoloylguanidine was obtained. The compound (2.10 g) was further treated with methanesulfonic acid/hydrated isopropyl alcohol to give 3.24 g of the title compound.

M.P.: 227–228° C.

The following compounds of Examples 245 to 248 were prepared in a manner similar to Example 244.

EXAMPLE 245

1,4-Dimethyl-7-[(pyridin-3-yl)methoxy]-2-indoloylguanidine Dimethanesulfonate

M.P.: 217–218° C.

EXAMPLE 246

1,4-Dimethyl-7-[(pyridin-4-yl)methoxy]-2-indoloylguanidine Dimethanesulfonate

M.P.: 154–155° C.

EXAMPLE 247

7-[(Furan-2-yl)methoxy]-1-methyl-4-trifluoromethyl-2-indoloylguanidine Hydrochloride

M.P.: 215° C.

EXAMPLE 248

7-[(Furan-2-yl)methoxy]-1-methyl-4-trifluoromethyl-2-indoloylguanidine Methanesulfonate

M.P.: 146° C.

The following compounds of Examples 249 to 252 were prepared in a manner similar to Example 84.

EXAMPLE 249

1-Methyl-7-(4-morpholino)-4-trifluoromethyl-2-indoloylguanidine Methanesulfonate

M.P.: 245–246° C.

EXAMPLE 250

4-Chloro-1-methyl-7-(4-morpholino)-2-indoloylguanidine Methanesulfonate

M.P.: 246–247° C.

EXAMPLE 251

1,4-Dimethyl-7-(4-morpholino)-2-indoloylguanidine Methanesulfonate

M.P.: 244–245° C.

EXAMPLE 252

4-Chloro-7-dimethylamino-1-methyl-2-indoloylguanidine Methanesulfonate

M.P.: 252–253° C.

EXAMPLE 253

Preparation of 1-methyl-7-[(1H-tetrazol-5-yl)methoxy]-4-trifluoromethyl-2-indoloylguanidine Hydrochloride a) Preparation of Ethyl 7-cyanomethoxy-1-methyl-4-trifluoromethyl-2-indolecarboxylate A mixture of 4.00 g (13.9 mmol) of ethyl 7-hydroxy-1-methyl-4-trifluoromethyl-2-indolecarboxylate, 4.23 g (30.6 mmol) of potassium carbonate, 1.26 g (16.7 mmol) of chloroacetonitrile and 60 ml of dimethylformamide was stirred at room temperature for 2 hours. Insoluble matters were filtered off. The filtrate was poured onto ice water followed by extraction with diethyl ether. The extract was washed with water and then dried over anhydrous magnesium sulfate. The solvent was distilled off under reduced pressure and the resulting residue was purified by silica gel column chromatography to give 4.50 g of ethyl 7-cyanomethoxy-1-methyl-4-trifluoromethyl-2-indolecarboxylate.

b) Preparation of Ethyl 1-methyl-7-[(1H-tetrazol-5-yl)methoxy-4-trifluoromethyl-2-indoloylquanidine A mixture of 1.00 g (3.1 mmol) of ethyl 7-cyanomethoxy-1-methyl-4-trifluoromethyl-2-indolecarboxylate, 0.20 g (3.1 mmol) of sodium azide, 0.16 g (3.1 mmol) of ammonium chloride and 6 ml of dimethylformamide was stirred at 80° C. for 5 hours. The reaction mixture was poured into water. After the mixture was rendered acidic with 2N hydrochloric acid, the mixture was extracted with ethyl acetate. The extract was washed with water and then dried over anhydrous magnesium sulfate. The solvent was distilled off under reduced pressure. By crystallizing the resulting residue from ethyl acetate, 1.00 g of ethyl 1-methyl-7-[(1H-tetrazol-5-yl)methoxy]-4-trifluoromethyl-2-indolecarboxylate.

$^1$H NMR (DMSO-$d_6$) δ: 1.32–1.38 (3H, m), 4.30–4.38 (5H, m), 5.75 (2H, s), 7.09 (1H, d, J=8.3 Hz), 7.18 (1H, dd, J=1.7 Hz, 3.3 Hz), 7.46 (1H, dd, J=1.0 Hz, 8.3 Hz).

c) Preparation of Ethyl 1-methyl-7-[(1H-(1-triphenylmethyl)tetrazol-5-yl)methoxy]-4-trifluoromethyl-2-indolecarboxylate A mixture of 1.00 g (2.7 mmol) of ethyl 1-methyl-7-[(1H-tetrazol-5-yl)methoxy]-4-trifluoromethyl-2-indolecarboxylate, 0.75 g (2.7 mmol) of chlorotriphenylmethane, 0.82 g (8.12 mmol) of triethylamine and 30 ml of tetrahydrofuran was stirred at room temperature for 2 hours. Insoluble matters were filtered off and the filtrate was distilled off under reduced pressure to give ethyl 1-methyl-7-[(1H-(1-triphenylmethyl)-tetrazol-5-yl)methoxy]-4-trifluoromethyl-2-indolecarboxylate. The product was employed without purification.

d) Preparation of 1-methyl-7-[(1H-(1-triphenylmethyl)-tetrazol-5-yl)methoxy]-4-trifluoromethyl-2-indolecarboxylic Acid Ethyl 1-methyl-7-[(1H-(1-triphenylmethyl)-tetrazol-5-yl)methoxy]-4-trifluoromethyl-2-indolecarboxylate obtained in c) above was added to a mixture of 10 ml of ethanol and 15 ml of 2N sodium hydroxide followed by stirring at room temperature for 2 hours. The reaction mixture was concentrated under reduced pressure and water was added to the resulting residue. The pH of the mixture was adjusted to 6 with acetic acid followed by extraction with ethyl acetate. The extract was washed with water and then dried over anhydrous magnesium sulfate. The solvent was distilled off under reduced pressure to give 1-methyl-7-[(1H-(1-triphenylmethyl)-tetrazol-5-yl)methoxy]-4-trifluoromethyl-2-indole-carboxylic acid.

$^1$H NMR (DMSO-$d_6$) δ: 4.19 (3H, s), 5.72 (2H, s), 6.98–7.43 (18H, m).

e) Preparation of 1-methyl-7-[(1H-tetrazol-5-yl)-methoxy]-4-trifluoromethyl-2-indoloylquanidine Hydrochloride The reaction was carried out in a manner similar to Example 84 except for using 1.60 g (2.7 mmol) of 1-methyl-7-[(1H-(1-triphenylmethyl)-tetrazol-5-yl)methoxy]-4-trifluoromethyl-2-indolecarboxylic acid. Thus, 1.26 g of 1-methyl-7-[(1H-(1-triphenylmethyl)-tetrazol-5-yl)methoxy]-4-trifluoromethyl-2-indoloylguanidine. The compound was added to hydrochloric acid/hydrated isopropyl alcohol. After the mixture was stirred at 80° C. for 30 minutes, insoluble matters were filtered off. The filtrate was cooled to precipitate solids. The solids were taken out by filtration and dried under reduced pressure to give 1-methyl-7-[(1H-tetrazol-5-yl)methoxy]-4-trifluoromethyl-2-indoloylguanidine hydrochloride.

M.P.: 288–290° C. (decompd.).

EXAMPLE 254

Preparation of 1-methyl-7-[2-(1H-pyrrol-1-yl)ethoxy]-4-trifluoromethyl-2-indoloylguanidine Methanesulfonate a) Preparation of Ethyl 1-methyl-7-[2-(1H-pyrrol-1-yl)ethoxy]-4-trifluoromethyl-2-indolecarboxylate After 1.28 g (9.69 mmol) of 2,5-dimethoxyfuran was added to a solution of 2.91 g (8.81 mmol) of ethyl 7-(2-aminoethoxy)-1-methyl-4-trifluoromethyl-2-indolecarboxylate in 30 ml of acetic acid, the mixture was stirred at 50° C. for 4 hours and at 70° C. for further an hour. Toluene was added to the reaction mixture followed by concentration under reduced pressure. Ice water was poured onto the resulting residue. The mixture was then extracted with ethyl acetate. The extract was washed with water and dried over magnesium sulfate. The solvent was distilled off under reduced pressure and the resulting residue was purified by silica gel column chromatography to give 1.96 g of ethyl 1-methyl-7-[2-(1H-pyrrol-1-yl)ethoxy]-4-trifluoromethyl-2-indolecarboxylate.

$^1$H NMR (CDCl$_3$) δ: 1.41 (3H, t, J=7.3 Hz), 4.28 (3H, s), 4.37 (2H, q, J=7.3 Hz), 4.40 (4H, br-s), 6.18 (1H, dd, J=2.0 Hz, 2.3 Hz), 6.61 (1H, d, J=8.3 Hz), 6.75 (1H, dd, J=2.0 Hz, 2.3 Hz), 7.28 (1H, dd, J=1.0 Hz, 8.3 Hz), 7.33–7.37 (1H, m).

b) Preparation of 1-methyl-7-[2-(1H-pyrrol-1-yl)ethoxy]-4-trifluoromethyl-2-indolecarboxylic Acid After 1.94 g (5.10 mmol) of ethyl 1-methyl-7-[2-(1H-pyrrol-1-yl)ethoxy]-4-trifluoromethyl-2-indolecarboxylate was dissolved in a mixture of 100 ml of ethanol and 50 ml of tetrahydrofuran, 10 ml of 3.75 N sodium hydroxide was added thereto. The mixture was stirred at room temperature for an hour. After completion of the reaction, the mixture was rendered acidic with 2 N hydrochloric acid and concentrated under reduced pressure. To the concentrate was added 100 ml of water. The mixture was then extracted with ethyl acetate. The extract was washed with water and dried over magnesium sulfate. The solvent was distilled off under reduced pressure. Crystallization of the resulting residue from chloroform/ethyl acetate gave 1.09 g of 1-methyl-7-[2-(1H-pyrrol-1-yl)ethoxy]-4-trifluoromethyl-2-indolecarboxylic acid.

$^1$H NMR (DMSO-d$_6$) δ: 4.16(3H, s), 4.34–4.52 (4H, m), 6.01 (1H, dd, J=2.0 Hz, 2.3 Hz), 6.88 (2H, dd, J=2.0 Hz, 2.3 Hz), 6.92 (1H, d, J=8.3 Hz), 7.09–7.14 (1H, m), 7.40 (1H, dd, J=1.0 Hz, 8.3 Hz), 13.26 (1H, br-s).

c) Preparation of 1-methyl-7-[2-(1H-pyrrol-1-yl)ethoxy]-4-trifluoromethyl-2-indoloylquanidine Methanesulfonate The reaction was carried out in a manner similar to Example 84 except for using 1.00 g (2.84 mmol) of 1-methyl-7-[2-(1H-pyrrol-1-yl)ethoxy]-4-trifluoromethyl-2-indolecarboxylic acid. Thus, 0.91 g of 1-methyl-7-[2-(1H-pyrrol-1-yl)ethoxy]-4-trifluoromethyl-2-indoloylguanidine was obtained. The compound was treated with methanesulfonic acid/hydrated isopropyl alcohol to give 0.70 g of 1-methyl-7-[2-(1H-pyrrol-1-yl)ethoxy]-4-trifluoromethyl-2-indoloylguanidine methanesulfonate.

M.P.: 216–217° C.

Experiment 1

Inhibition of Na$^+$/H$^+$ Exchanger Activity in Vitro

Method:

The experiment was performed by modifying the method of Yamori et al. described in J. Hypertension, 8, 153 (1990). That is, inhibition of the Na$^+$/H$^+$ exchanger activity was evaluated by the change in intracellular pH during acid loading, using the vascular smooth muscle cells isolated from the rat thoracic aorta.

Results:

The results of IC50 for the inhibition of the Na$^+$/H$^+$ exchanger activity tested are shown in Table 1 below.

TABLE 1

| Compound | $IC_{50}$ (-M) |
|---|---|
| Compound of Example 1 | 0.058 |
| Compound of Example 8 | 0.05 |
| Compound of Example 22 | 2.1 |
| Compound of Example 29 | 0.0009 |
| Compound of Example 55 | 0.02 |
| Compound of Example 118 | 0.01 |
| Dimethyl amiloride for comparison | 0.60 |
| 5-Hexamethylene amiloride for comparison | 0.14 |

Experiment 2

Inhibition of Na$^+$/H$^+$ Exchanger Activity in Vitro

Method:

The experiment was performed by modifying the method of Mungre et al. described in Exp. Cell Res., 193, 236 (1991). That is, inhibition of the Na$^+$/H$^+$ exchanger activity was evaluated by the change in cell viability during acid loading, using the vascular smooth muscle cells isolated from the rat thoracic aorta.

Results:

The compounds of the present invention shown in Examples were evaluated by the minimum effective concentration (MEC) for the inhibition of the Na$^+$/H$^+$ exchanger activity. The results are shown in Table 2.

TABLE 2

Inhibition of Na$^+$/H$^+$ Exchanger Activity

| Compound | Inhibition of Na$^+$/H$^+$ Exchanger MEC (μM) | Compound | Inhibition of Na$^+$/H$^+$ Exchanger MEC (μM) |
|---|---|---|---|
| Example 1 | 1.0 | Example 25 | 0.3 |
| Example 2 | 10 | Example 26 | 0.3 |
| Example 3 | >10 | Example 27 | 3.0 |
| Example 4 | >10 | Example 28 | >10 |
| Example 5 | 0.03 | Example 29 | 0.03 |
| Example 6 | 0.3 | Example 30 | 1.0 |
| Example 7 | 0.3 | Example 31 | >10 |
| Example 8 | 0.3 | Example 32 | >10 |
| Example 9 | 0.1 | Example 33 | 1.0 |
| Example 10 | 10 | Example 34 | 3.0 |
| Example 11 | 0.3 | Example 35 | 1.0 |
| Example 12 | 0.3 | Example 36 | 0.1 |
| Example 13 | 1.0 | Example 37 | * |
| Example 14 | >10 | Example 38 | 3.0 |
| Example 15 | 0.3 | Example 39 | 0.3 |
| Example 16 | 3.0 | Example 40 | 1.0 |
| Example 17 | 3.0 | Example 41 | 1.0 |
| Example 18 | 10 | Example 42 | 10 |
| Example 19 | >10 | Example 43 | 10 |

TABLE 2-continued

Inhibition of Na⁺/H⁺ Exchanger Activity

| Compound | Inhibition of Na⁺/H⁺ Exchanger MEC ($\mu$M) | Compound | Inhibition of Na⁺/H⁺ Exchanger MEC ($\mu$M) |
|---|---|---|---|
| Example 20 | 1.0 | Example 44 | >10 |
| Example 21 | 1.0 | Example 45 | >10 |
| Example 22 | 0.3 | Example 46 | * |
| Example 23 | 0.3 | Example 47 | 3.0 |
| Example 24 | 0.3 | Example 48 | 3.0 |
| Example 49 | 3.0 | Example 74 | 0.1 |
| Example 50 | 1.0 | Example 75 | 0.3 |
| Example 51 | 1.0 | Example 76 | 0.3 |
| Example 52 | 1.0 | Example 77 | 0.3 |
| Example 53 | 1.0 | Example 78 | >10 |
| Example 54 | 0.3 | Example 79 | 3.0 |
| Example 55 | 0.1 | Example 80 | 3.0 |
| Example 56 | 0.03 | Example 81 | >10 |
| Example 57 | 1.0 | Example 82 | 3.0 |
| Example 58 | 0.3 | Example 83 | 0.3 |
| Example 59 | 1.0 | Example 84 | 1.0 |
| Example 60 | * | Example 86 | 10 |
| Example 61 | 0.3 | Example 87 | 1.0 |
| Example 62 | >10 | Example 88 | >10 |
| Example 63 | 0.3 | Example 89 | >10 |
| Example 64 | 0.01 | Example 90 | 10 |
| Example 65 | 0.3 | Example 91 | 3.0 |
| Example 66 | 0.3 | Example 92 | 0.3 |
| Example 67 | 1.0 | Example 93 | 1.0 |
| Example 68 | * | Example 94 | 1.0 |
| Example 69 | 3.0 | Example 95 | 0.003 |
| Example 70 | 3.0 | Example 96 | 0.03 |
| Example 71 | 0.03 | Example 97 | >10 |
| Example 72 | 0.1 | Example 98 | >10 |
| Example 73 | 0.3 | Example 99 | 10 |
| Example 100 | 3.0 | Example 122 | 0.03 |
| Example 101 | >10 | Example 123 | 3.0 |
| Example 102 | 10 | Example 124 | 0.3 |
| Example 103 | >10 | Example 125 | 0.01 |
| Example 104 | >10 | Example 126 | 0.3 |
| Example 105 | * | Example 127 | 0.1 |
| Example 106 | * | Example 128 | 0.03 |
| Example 107 | 0.1 | Example 129 | 0.03 |
| Example 108 | >10 | Example 130 | 0.03 |
| Example 109 | 1.0 | Example 131 | 0.1 |
| Example 110 | 0.3 | Example 132 | 0.1 |
| Example 111 | 10 | Example 133 | 1.0 |
| Example 112 | >10 | Example 134 | 0.3 |
| Example 113 | 3.0 | Example 135 | 0.1 |
| Example 114 | 1.0 | Example 136 | 1.0 |
| Example 115 | >10 | Example 137 | >1 |
| Example 116 | >10 | Example 138 | 3.0 |
| Example 117 | 0.3 | Example 139 | 3.0 |
| Example 118 | 0.01 | Example 140 | 1.0 |
| Example 119 | 0.1 | Example 141 | 0.3 |
| Example 120 | 0.1 | Example 142 | 3 |
| Example 121 | 0.1 | Example 143 | 0.3 |
| Example 144 | >10 | Example 166 | 0.1 |
| Example 145 | 10 | Example 167 | 0.03 |
| Example 146 | 10 | Example 168 | 0.03 |
| Example 147 | >10 | Example 169 | 0.03 |
| Example 148 | 0.1 | Example 170 | 0.3 |
| Example 149 | 0.3 | Example 171 | 0.3 |
| Example 150 | 0.1 | Example 172 | 0.01 |
| Example 151 | 0.3 | Example 173 | 0.03 |
| Example 152 | 0.3 | Example 174 | 0.1 |
| Example 153 | 0.3 | Example 175 | 0.03 |
| Example 154 | 0.3 | Example 176 | 0.1 |
| Example 155 | 0.3 | Example 177 | 0.01 |
| Example 156 | 0.3 | Example 178 | 0.1 |
| Example 157 | 0.3 | Example 179 | 0.3 |
| Example 158 | 0.1 | Example 180 | 1 |
| Example 159 | 1.0 | Example 181 | 1 |
| Example 160 | 0.1 | Example 182 | 0.3 |
| Example 161 | 0.03 | Example 183 | * |
| Example 162 | 0.1 | Example 184 | 0.003 |
| Example 163 | 0.1 | Example 185 | 0.1 |
| Example 164 | 0.03 | Example 186 | 0.003 |
| Example 165 | 0.1 | Example 187 | 0.1 |
| Example 188 | 0.03 | Example 199 | 0.01 |
| Example 189 | 0.01 | Example 200 | 0.01 |
| Example 190 | 0.01 | Example 201 | 0.01 |
| Example 191 | 0.01 | Example 202 | 0.003 |
| Example 192 | 0.01 | Example 203 | 0.001 |
| Example 193 | 0.003 | Example 204 | 0.003 |
| Example 194 | 0.1 | Example 205 | 0.003 |
| Example 195 | 0.01 | Example 206 | 0.03 |
| Example 196 | 0.001 | Example 207 | 0.01 |
| Example 197 | 0.003 | Dimethyl amiloride | 3.0 |
| Example 198 | 0.001 | 5-Hexamethylene amiloide | 0.3 |

*: not measurable due to cytotoxicity

Experiment 3

Inhibition of Ischemia- and Reperfusion-induced Arrhythmia in Vivo

Method:

The experiment was performed by modifying the method of Crome et al. described in J. Cardiovasc. Pharmacol., 8, 1249 (1986). That is, the prevention of arrhythmia induced by reperfusion after rat coronary artery occlusion was evaluated by the incidence of ventricular tachycardia and ventricular fibrillation as well as the mortality.

Results:

The compound of Example 1 in the present invention was evaluated by the method described above, with respect to the incidence of ventricular tachycardia and ventricular fibrillation, and mortality. The results are shown in Table 3 below.

TABLE 3

Inhibition of Reperfusion-induced Arrhythmia

| Compound | Dose (mg/kg) | Incidence of Ventricular Tachycardia (%) | Incidence of Ventricular Fibrillation (%) | Mortality (%) |
|---|---|---|---|---|
| Example 1 | 0.3 | 50 | 0 | 0 |
|  | 0.1 | 70 | 10 | 10 |
| EIPA* | 1 | 43 | 0 | 0 |
|  | 0.3 | 100 | 56 | 44 |
| Control** | — | 100 | 95 | 76 |

*EIPA: 5-N-ethyl-N-isopropyl amiloride
**Control: untreated

The indoloylguanidine derivatives of formula (1) inhibit the Na⁺/H⁺ exchanger activity and are useful for the prevention and treatment of diseases caused by the increased Na⁺/H⁺ exchanger activity, e.g., hypertension, arrhythmia, angina pectoris, cardiac hypertrophy, diabetes mellitus, organ disorders associated with ischemia or cardiac ischemic reperfusion injury, disorders associated with cerebral ischemia, etc.

What is claimed is:

1. An indoloylguanidine derivative represented by formula (1)

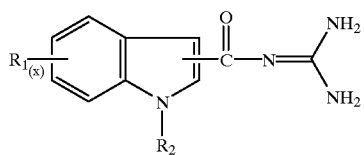

(1)

wherein:

the guanidinocarbonyl group may be located at any open position on either the 5-membered or 6-membered rings comprising the indole nucleus, x=5 so that $R_1$ is located at each position on the indole nucleus not occupied by the guanidinocarbonyl group, and each $R_1$ independently represents a hydrogen atom, a $C_1$–$C_8$ alkyl group, a substituted $C_1$–$C_8$ alkyl group, a $C_2$–$C_6$ alkenyl group, a $C_2$–$C_6$ alkynyl group, a $C_3$–$C_7$ cycloalkyl group, a halogen atom, nitro, a $C_2$–$C_8$ alkanoyl group, an arylalkanoyl group having carbon atoms up to 10, an aroyl group having carbon atoms up to 11, carboxyl, a $C_2$–$C_6$ alkoxycarbonyl group, an aromatic group, a group shown by formula: —$OR_3$, —$NR_6R_7$, —$SO_2NR_6R_7$ or —$S(O)_nR_{40}$, and a group shown by formula:

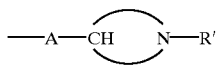

wherein A represents an oxygen atom or a group shown by formula: —$S(O)_n$— or —$N(R_{50})$— (in which $R_{50}$ is a hydrogen atom or a $C_1$–$C_8$ alkyl group; R' represents a hydrogen atom, a $C_1$–$C_8$ alkyl group or a substituted $C_1$–$C_8$ alkyl group); and

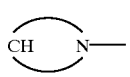

represents a saturated 3 to 8-membered hetero ring containing one nitrogen atom;

$R_2$ represents a hydrogen atom, a $C_1$–$C_8$ alkyl group, a substituted $C_1$–C8 alkyl group, a $C_3$–$C_7$ cycloalkyl group, hydroxy, a $C_1$–$C_6$ alkoxy group, an aromatic group or a group shown by formula: —$CH_2R_{20}$;

$R_3$ represents a hydrogen atom, a $C_1$–$C_8$ alkyl group, a substituted $C_1$–$C_8$ alkyl group, a $C_3$–$C_7$ cycloalkyl group, an aromatic group or a group shown by formula: —$CH_2R_{30}$, in which $R_{30}$ represents an $C_2$–$C_6$ alkenyl group or an $C_2$–$C_6$ alkynyl group;

each of $R_6$ and $R_7$ independently represents a hydrogen atom, a $C_1$–$C_8$ alkyl group, a substituted $C_1$–$C_8$ alkyl group, a $C_3$–$C_7$ cycloalkyl group, a $C_2$–$C_8$ alkanoyl group, an arylalkanoyl group having carbon atoms up to 10, an aroyl group having carbon atoms up to 11, an aromatic group or a group shown by formula: —$CH_2R_{60}$ (in which $R_{60}$ represents a $C_2$–$C_6$ alkenyl group or a $C_2$–$C_6$ alkynyl group); or $R_6$ and $R_7$ are combined together to form a saturated 5- to 7-membered cyclic amino group which may contain other hetero atom(s) in the ring thereof;

$R_{40}$ represents a $C_1$–$C_8$ alkyl group, a substituted $C_1$–$C_8$ alkyl group or an aromatic group;

n represents 0, 1 or 2; and, $R_{20}$ represents a $C_2$–$C_6$ alkenyl group or a $C_2$–$C_6$ alkynyl group;

in which:

the substituent(s) of said substituted $C_1$–$C_8$ alkyl group means a halogen atom, hydroxy, a $C_1$–$C_6$ alkoxy group, cyano, carboxyl, a $C_2$–$C_6$ alkoxycarbonyl group, a $C_2$–$C_8$ alkanoyl group, an arylalkanoyl group having carbon atoms up to 10, an aroyl group having carbon atoms up to 11, an aromatic group, and —$CONR_4R_5$ in which each of $R_4$ and $R_5$ independently represents a hydrogen atom or a $C_1$–$C_8$ alkyl group or $R_4$ and $R_5$ are combined together to form a saturated 5- to 7-membered cyclic amino group which may contain other hetero atom(s) in the ring; —$NR_6R_7$ or a group shown by:

in which:

E represents a nitrogen atom or a CH group and

R" represents a hydrogen atom, a $C_1$–$C_8$ alkyl group or a substituted $C_1$–$C_8$ alkyl group substituted with hydroxy, a $C_1$–$C_6$ alkoxy group, cyano, carboxyl, a $C_2$–$C_6$ alkoxycarbonyl group, a $C_2$–$C_8$ alkanoyl group, an arylalkanoyl group having carbon atoms up to 10, an aroyl group having carbon atoms up to 11, an aromatic group, a group shown by —$NR_6R_7$, or a group shown by —$CONR_4R_5$, in which each of $R_4$ and $R_5$ independently represents a hydrogen atom or a $C_1$–$C_8$ alkyl group or $R_4$ and $R_5$ are combined together to form a saturated 5- to 7-membered cyclic amino group which may contain other hetero atom(s) therein; and the ring of

is a 3- to 8-membered saturated aliphatic ring or saturated hetero ring containing one nitrogen atom;

each of the aromatic groups being selected from the group consisting of (a) an aryl group having carbon atoms up to 10, (b) a 5- or 6-membered hetero-aryl group containing 1 to 4 nitrogen atom(s), (c) a 5- or 6-membered hetero-aryl group containing 1 to 2 nitrogen atom(s) and one oxygen atom or one sulfur atom, and (d) a furyl group; and, each of the aromatic groups may be substituted with a substituent selected from the group consisting of a $C_1$–$C_8$ alkyl group, a substituted $C_1$–$C_8$ alkyl group, a halogen atom, nitro, a $C_2$–$C_6$ alkoxy-carbonyl group, carboxyl and a group selected from the group shown by formulae: —$OR_3$, —$NR_6R_7$, —$CONR_6R_7$, —$SO_2NR_6R_7$ and —$S(O)_nR_{40}$;

provided that said indoloylguanidine derivative does not include 1-methyl-2-indoloylguanidine; and at least one of $R_1$ or $R_2$ is a substituted $C_1$–$C_8$ alkyl group wherein the substituent is carboxyl or a $C_2$–$C_6$ alkoxycarbonyl group; or, a pharmaceutically acceptable acid addition salt thereof.

2. An indoloylguanidine derivative represented by formula (1):

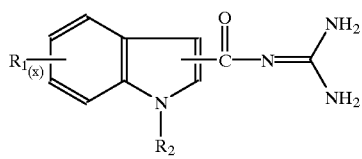

wherein:
the guanidinocarbonyl group may be located at any open position on either the 5-membered or 6-membered rings comprising the indole nucleus, x=5 so that $R_1$ is located at each position on the indole nucleus not occupied by the guanidinocarbonyl group, and each $R_1$ independently represents a hydrogen atom, a $C_1$–$C_8$ alkyl group, a substituted $C_1$–$C_8$ alkyl group, a $C_2$–$C_6$ alkenyl group, a $C_2$–$C_6$ alkynyl group, a $C_3$–$C_7$ cycloalkyl group, a halogen atom, nitro, a $C_2$–$C_8$ alkanoyl group, an arylalkanoyl group having carbon atoms up to 10, an aroyl group having carbon atoms up to 11, carboxyl, a $C_2$–$C_6$ alkoxycarbonyl group, an aromatic group, and a group shown by formula: —$OR_3$, —$NR_6R_7$, —$SO_2NR_6R_7$ or —$S(O)_nR_{40}$;

$R_2$ represents a hydrogen atom, a $C_1$–$C_8$ alkyl group, a substituted $C_1$–$C_8$ alkyl group, a $C_3$–$C_7$ cycloalkyl group, hydroxy, a $C_1$–$C_6$ alkoxy group, an aromatic group or a group shown by formula: —$CH_2R_{20}$;

$R_3$ represents a hydrogen atom, a $C_1$–$C_8$ alkyl group, a substituted $C_1$–$C_8$ alkyl group, a $C_3$–$C_7$ cycloalkyl group, an aromatic group or a group shown by formula: —$CH_2R_{30}$ in which $R_{30}$ represents an alkenyl group or an alkynyl group;

each of $R_6$ and $R_7$ independently represents a hydrogen atom, a $C_1$–$C_8$ alkyl group, a substituted $C_1$–$C_8$ alkyl group, a $C_3$–$C_7$ cycloalkyl group, a $C_2$–$C_8$ alkanoyl group, an arylalkanoyl group having carbon atoms up to 10, an aroyl group having carbon atoms up to 11, an aromatic group, or a group shown by formula: —$CH_2R_{60}$ (in which $R_{60}$ represents a $C_2$–$C_6$ alkenyl group or a $C_2$–$C_6$ alkynyl group); or $R_6$ and $R_7$ are combined together to form a saturated 5- to 7-membered cyclic amino group which may contain other hetero atom(s) in the ring thereof;

$R_{40}$ represents a $C_1$–$C_8$ alkyl group, a substituted $C_1$–$C_8$ alkyl group or an aromatic group;

n represents 0, 1 or 2; and, $R_{20}$ represents a $C_2$–$C_6$ alkenyl group or a $C_2$–$C_6$ alkynyl group;

in which:
the substituent(s) of said substituted $C_1$–$C_8$ alkyl group means a halogen atom, hydroxy, a $C_1$–$C_6$ alkoxy group, cyano, carboxyl, a $C_2$–$C_6$ alkoxycarbonyl group, a $C_2$–$C_8$ alkanoyl group, an arylalkanoyl group having carbon atoms up to 10, an aroyl group having carbon atoms up to 11, an aromatic group, and —$CONR_4R_5$ in which each of $R_4$ and $R_5$ independently represents a hydrogen atom or a $C_1$–$C_8$ alkyl group or $R_4$ and $R_5$ are combined together to form a saturated 5- to 7-membered cyclic amino group which may contain other hetero atom(s) in the ring; —$NR_6R_7$; or a group shown by:

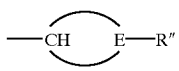

in which:
E represents a nitrogen atom or a CH group and
R″ represents a hydrogen atom, a $C_1$–$C_8$ alkyl group or a substituted $C_1$–$C_8$ alkyl group substituted with hydroxy, a $C_1$–$C_6$ alkoxy group, cyano, carboxyl, a $C_2$–$C_6$ alkoxycarbonyl group, a $C_2$–$C_8$ alkanoyl group, an arylalkanoyl group having carbon atoms up to 10, an aroyl group having carbon atoms up to 11, an aromatic group, a group shown by —$NR_6R_7$, or a group shown by —$CONR_4R_5$, in which each of $R_4$ and $R_5$ independently represents a hydrogen atom or a $C_1$–$C_8$ alkyl group or $R_4$ and $R_5$ are combined together to form a saturated 5- to 7-membered cyclic amino group which may contain other hetero atom(s) therein; and the ring of

is a 3- to 8-membered saturated aliphatic ring or saturated hetero ring containing one nitrogen atom;

each of the aromatic groups being selected from the group consisting of (a) an aryl group having carbon atoms up to 10, (b) a 5- or 6-membered hetero-aryl group containing 1 to 4 nitrogen atom(s), (c) a 5- or 6-membered hetero-aryl group containing 1 to 2 nitrogen atom(s) and one oxygen atom or one sulfur atom, and (d) a furyl group; and, each of the aromatic groups may be substituted with a substituent selected from the group consisting of a $C_1$–$C_8$ alkyl group, a substituted $C_1$–$C_8$ alkyl group, a halogen atom, nitro, a $C_2$–$C_6$ alkoxy-carbonyl group, carboxyl and a group selected from the group shown by formulae: —$OR_3$, —$NR_6R_7$, —$CONR_6R_7$, —$SO_2NR_6R_7$ and —$S(O)_nR_{40}$;

provided that said indoloylguanidine derivative does not include 1-methyl-2-indoloylguanidine; and at least one of $R_1$ or $R_2$ is a substituted $C_1$–$C_8$ alkyl group wherein the substituent is carboxyl or a $C_2$–$C_6$ alkoxycarbonyl group; or, a pharmaceutically acceptable acid addition salt thereof.

3. An indoloylguanidine derivative or a pharmaceutically acceptable acid addition salt thereof, wherein said indoloylguanidine derivative is represented by general formula (2):

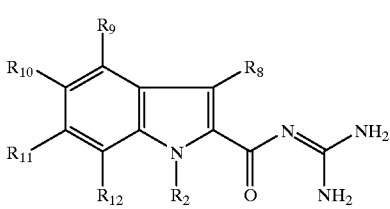

wherein:
each of $R_8$, $R_9$, $R_{10}$, $R_{11}$ and $R_{12}$ independently represents a hydrogen atom, a $C_1$–$C_8$ alkyl group, a substituted $C_1$–$C_8$ alkyl group, a $C_2$–$C_8$ alkenyl group, a $C_2$–$C_6$ alkynyl group, a $C_3$–$C_7$ cycloalkyl group, a halogen atom, nitro, a $C_2$–$C_8$ alkanoyl group, an arylalkanoyl group having carbon atoms up to 10, an aroyl group having carbon atoms up to 11, carboxyl, a $C_2$–$C_6$ alkoxycarbonyl group, an aromatic group, a group shown by formula: —$OR_3$, —$NR_6R_7$, —$SO_2NR_6R_7$ or —$S(O)_nR_{40}$, and a group shown by formula:

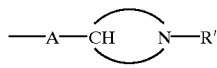

wherein A represents an oxygen atom or a group shown by formula: —$S(O)_n$— or $N(R_{50})$— (in which $R_{50}$ is a hydrogen atom or a $C_1$–$C_8$ alkyl group; R' represents a hydrogen atom, a $C_1$–$C_8$ alkyl group or a substituted $C_1$–$C_8$ alkyl group); and

represents a saturated 3 to 8- membered hetero ring containing one nitrogen atom;

$R_2$ represents a hydrogen atom, a $C_1$–$C_8$ alkyl group, a substituted $C_1$–$C_8$ alkyl group, a $C_3$–$C_7$ cycloalkyl group, hydroxy, a $C_1$–$C_6$ alkoxy group, an aromatic group or a group shown by formula: —$CH_2R_{20}$;

$R_3$ represents a hydrogen atom, a $C_1$–$C_8$ alkyl group, a substituted $C_1$–$C_8$ alkyl group, a $C_3$–$C_7$ cycloalkyl group, an aromatic group or a group shown by formula: —$CH_2R_{30}$ in which $R_{30}$ represents a $C_2$–$C_6$ alkenyl group or an alkynyl group;

each of $R_6$ and $R_7$ independently represents a hydrogen atom, a $C_1$–$C_8$ alkyl group, a substituted $C_1$–$C_8$ alkyl group, a $C_3$–$C_7$ cycloalkyl group, a $C_2$–$C_8$ alkanoyl group, an arylalkanoyl group having carbon atoms up to 10, an aroyl group having carbon atoms up to 11, an aromatic group, or a group shown by formula: —$CH_2R_{60}$ (in which $R_{60}$ represents a $C_2$–$C_6$ alkenyl group or a $C_2$–$C_6$ alkynyl group); or $R_6$ and $R_7$ are combined together to form a saturated 5- to 7-membered cyclic amino group which may contain other hetero atom(s) in the ring thereof;

$R_{40}$ represents a $C_1$–$C_8$ alkyl group or a substituted $C_1$–$C_8$ alkyl group;

n represents 0, 1 or 2; and, $R_{20}$ represents a $C_2$–$C_6$ alkenyl group or a $C_2$–$C_6$ alkynyl group; in which:

the substituent(s) of said substituted $C_1$–$C_8$ alkyl group means a halogen atom, hydroxy, a $C_1$–$C_6$ alkoxy group, cyano, carboxyl, a $C_2$–$C_6$ alkoxycarbonyl group, a $C_2$–$C_8$ alkanoyl group, an arylalkanoyl group having carbon atoms up to 10, an aroyl group having carbon atoms up to 11, an aromatic group, or —$CONR_4R_5$ in which each of $R_4$ and $R_5$ independently represents a hydrogen atom or a $C_1$–$C_8$ alkyl group or $R_4$ and $R_5$ are combined together to form a saturated 5- to 7-membered cyclic amino group which may contain other hetero atom(s) in the ring; —$NR_6R_7$; or a group shown by:

in which:

E represents a nitrogen atom or a CH group and

R" represents a hydrogen atom, a $C_1$–$C_8$ alkyl group or a substituted $C_1$–$C_8$ alkyl group substituted with hydroxy, a $C_1$–$C_6$ alkoxy group, cyano, carboxyl, a $C_2$–$C_6$ alkoxycarbonyl group, a $C_2$–$C_8$ alkanoyl group, an arylalkanoyl group having carbon atoms up to 10, an aroyl group having carbon atoms up to 11, an aromatic group, a group shown by —$NR_6R_7$, or a group shown by —$CONR_4R_5$, in which each of $R_4$ and $R_5$ independently represents a hydrogen atom or a $C_1$–$C_8$ alkyl group or $R_4$ and $R_5$ are combined together to form a saturated 5- to 7-membered cyclic amino group which may contain other hetero atom(s) therein; and the ring of

is a 3- to 8-membered saturated aliphatic ring or saturated hetero ring containing one nitrogen atom;

each of the aromatic groups being selected from the group consisting of (a) an aryl group having carbon atoms up to 10, (b) a 5- or 6-membered hetero-aryl group containing 1 to 4 nitrogen atom(s), (c) a 5- or 6-membered hetero-aryl group containing 1 to 2 nitrogen atom(s) and one oxygen atom or one sulfur atom, and (d) a furyl group; and, each of the aromatic groups may be substituted with a substituent selected from the group consisting of a $C_1$–$C_8$ alkyl group, a substituted $C_1$–$C_8$ alkyl group, a halogen atom, nitro, a $C_2$–$C_6$ alkoxy-carbonyl group, carboxyl and a group selected from the group shown by formulae: —$OR_3$, —$NR_6R_7$, —$CONR_6R_7$, —$SO_2NR_6R_7$ and —$S(O)_nR_{40}$;

provided that said indoloylguanidine derivative does not include 1-methyl-2-indoloylguanidine; and at least one of $R_8$–$R_{12}$ or $R_2$ is a substituted $C_1$–$C_8$ alkyl group wherein the substituent is a carboxyl or a $C_2$–$C_6$ alkoxycarbonyl group.

4. An indoloylguanidine derivative or a pharmaceutically acceptable acid addition salt thereof according to claim 3, wherein $R_8$ represents a hydrogen atom, and $R_{10}$ represents a hydrogen atom or a halogen atom.

5. An indoloylguanidine derivative represented by general formula (3):

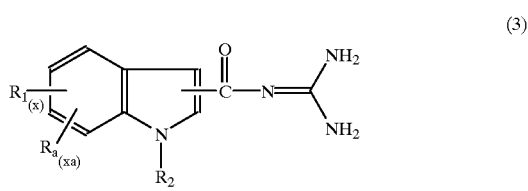

wherein:

the guanidinocarbonyl group may be located at any open position on either the 5- membered or 6-membered rings comprising the indole nucleus, x+xa=5 wherein x is 3 or 4 and xa is 1 or 2 such that each $R_1$ and each $R_a$ is located at the positions on the indole nucleus not occupied by the guanidinocarbonyl group, and each $R_1$ independently represents a hydrogen atom, a $C_1$–$C_8$ alkyl group, a substituted $C_1$–$C_8$ alkyl group, a $C_2$–$C_6$ alkenyl group, a $C_2$–$C_6$ alkynyl group, a $C_3$–$C_7$ cycloalkyl group, a halogen atom, nitro, a $C_2$–$C_8$ alkanoyl group, an arylalkanoyl group having carbon atoms up to 10, an aroyl group having carbon atoms up to 11, carboxyl, a $C_2$–$C_6$ alkoxycarbonyl group, an aromatic group, a group shown by formula: —$OR_3$, —$NR_6R_7$, —$SO_2NR_6R_7$ or —$S(O)_nR_{40}$, and a group shown by formula:

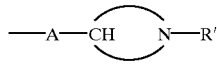

wherein A represents an oxygen atom or a group shown by formula: —$S(O)_n$— or —$N(R_{50})$— (in which $R_{50}$ is a hydrogen atom or a $C_1$–$C_8$ alkyl group); R' represents a hydrogen atom, a $C_1$–$C_8$ alkyl group or a substituted $C_1$–$C_8$ alkyl group); and

represents a saturated 3 to 8-membered hetero ring containing one nitrogen atom;

$R_2$ represents a hydrogen atom, a $C_1$–$C_8$ alkyl group, a substituted $C_1$–$C_8$ alkyl group, a $C_3$–$C_7$ cycloalkyl group, hydroxy, a $C_1$–$C_6$ alkoxy group, a group shown by formula: —$CH_2R_{20}$ or an aromatic group;

when $R_2$ is an aromatic group, $R_a$ represents $R_1$;

when $R_2$ is a hydrogen atom, a $C_1$–$C_8$ alkyl group, a substituted $C_1$–$C_8$ alkyl group, a $C_3$–$C_7$ cycloalkyl group, hydroxy, a $C_1$–$C_6$ alkoxy group or —$CH_2R_{20}$;

$R_a$ may be one or two substituent(s), which may be the same or different and represents an aryl-$C_1$–$C_8$ alkyl group or a hetero-aryl-$C_1$–$C_8$ alkyl group, in which the aryl moiety in these groups contains a substituent(s) selected from the group consisting of a $C_1$–$C_8$ alkyl group, a substituted $C_1$–$C_8$ alkyl group, a $C_2$–$C_6$ alkoxycarbonyl group, carboxyl, —$CONR_6R_7$, —$SO_2NR_6R_7$ and —$S(O)_nR_{40}$; or $R_a$ represents a group shown by formula: —A—$R_b$, in which A represents an oxygen atom or a group shown by formula: —$S(O)_n$— or —$N(R_{50})$— (in which $R_{50}$ is a hydrogen atom or a $C_1$–$C_8$ alkyl group); $R_b$ represents an aryl group or a hetero-aryl group in which the aryl moiety and the hetero-aryl group may contain a substituent(s) selected from the group consisting of a $C_1$–$C_8$ alkyl group, a substituted $C_1$–$C_8$ alkyl group, a halogen atom, nitro, a $C_2$–$C_6$ alkoxycarbonyl group, carboxy, —$OR_3$, —$NR_6R_7$, —$CONR_6R_7$, —$SO_2NR_6R_7$ and —$S(O)_nR_{40}$ or, Ra represents a group shown by formula:

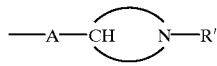

wherein A represents an oxygen atom or a group shown by formula: —$S(O)_n$— or —$N(R_{50})$— (in which $R_{50}$ is a hydrogen atom or a $C_1$–$C_8$ alkyl group); R' represents a hydrogen atom, a $C_1$–$C_8$ alky group or a substituted $C_1$–$C_8$ alkyl group; and

represents a saturated 3 to 8-membered hetero ring containing one nitrogen atom; or, $R_a$ represents a group shown by formula:

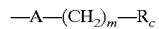

wherein A represents an oxygen atom or a group shown by formula: —$S(O)_n$— or —$N(R_{50})$— (in which $R_{50}$ is a hydrogen atom or a $C_1$–$C_8$ alkyl group); $R_c$ represents an aryl group or a heteroaryl group in which the aryl moiety and the hetero-aryl group contain a substituent (s) selected from the group consisting of a $C_1$–$C_8$ alkyl group, a substituted $C_1$–$C_8$ alkyl group, a $C_2$–$C_6$ alkoxycarbonyl group, carboxyl, —$CONR_6R_7$, —$OR_{31}$, —$SO_2NR_6R_7$ and —$S(O)_nR_{40}$; m represents 1 to 8; and $R_{31}$ represents a substituted $C_1$–$C_8$ alkyl group, a $C_3$–$C_7$ cycloalkyl group or —$CH_2R_{30}$ (in which $R_{30}$ represents a $C_2$–$C_6$ alkenyl group or a $C_2$–$C_6$ alkynyl group);

$R_3$ represents a hydrogen atom, a $C_1$–$C_8$ alkyl group, a substituted $C_1$–$C_8$ alkyl group, a $C_3$–$C_7$ cycloalkyl group, an aromatic group or a group shown by formula: —$CH_2R_{30}$ in which $R_{30}$ represents a $C_2$–$C_6$ alkenyl group or a $C_2$–$C_6$ alkynyl group;

each of $R_6$ and $R_7$ independently represents a hydrogen atom, a $C_1$–$C_8$ alkyl group, a substituted $C_1$–$C_8$ alkyl group, a $C_3$–$C_7$ cycloalky group, a $C_2$–$C_8$ alkanoyl group, an arylalkanoyl group having carbon atoms up to 10, an aroyl group having carbon atoms up to 11, an aromatic group or a group shown by formula: —$CH_2R_{60}$ (in which $R_{60}$ represents a $C_2$–$C_6$ alkeny group or a $C_2$–$C_6$ alkynyl group); or $R_6$ and $R_7$ are combined together to form a saturated 5-to 7-membered cyclic amino group which may contain other hetero atom(s) in the ring thereof;

$R_{40}$ represents a $C_1$–$C_8$ alkyl group or a substituted $C_1$–$C_8$ alkyl group;

n represents 0, 1 or 2; and, $R_{20}$ represents a $C_2$–$C_6$ alkenyl group or a $C_2$–$C_6$ alkynyl group;

in which:

the substituent(s) of said substituted $C_1$–$C_8$ alkyl group means a halogen atom, hydroxy, a $C_1$–$C_6$ alkoxy group, cyano, carboxyl, a $C_2$–$C_6$ alkoxycarbonyl group, a $C_2$–$C_8$ alkanoyl group, an arylalkanoyl group having carbon atoms up to 10, an aroyl group having carbon atoms up to 11, an aromatic group, and —$CONR_4R_5$ in which each of $R_4$ and $R_5$ independently represents a hydrogen atom or a $C_1$–$C_8$ alkyl, group or $R_4$ and $R_5$ are combined together to form a saturated 5- to 7-membered cyclic amino group which may contain other hetero atom(s) in the ring; —$NR_6R_7$; or a group shown by:

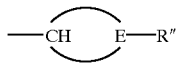

in which:

E represents a nitrogen atom or a CH group and

R″ represents a hydrogen atom, a $C_1$–$C_8$ alkyl group or a substituted $C_1$–$C_8$ alkyl group substituted with hydroxy, a $C_1$–$C_6$ alkoxy group, cyano, carboxyl, a $C_2$–$C_6$ alkoxycarbonyl group, a $C_2$–$C_8$ alkanoyl group, an arylalkanoyl group having carbon atoms up to 10, an aroyl group having carbon atoms up to 11, an aromatic group, a group shown by —$NR_6R_7$, or a group shown by —$CONR_4R_5$, in which each of $R_4$ and $R_5$ independently represents a hydrogen atom or a $C_1$–$C_8$ alkyl group or $R_4$ and $R_5$ are combined together to form a saturated 5- to 7-membered cyclic amino group which may contain other hetero atom(s) therein; and the ring of

is a 3- to 8-membered saturated aliphatic ring or saturated hetero ring containing one nitrogen atom;

each of the aromatic groups being selected from the group consisting of (a) an aryl group having carbon atoms up to 10, (b) a 5- or 6-membered hetero-aryl group containing 1 to 4 nitrogen atom(s), (c) a 5- or 6-membered hetero-aryl group containing 1 to 2 nitrogen atom(s) and one oxygen atom or one sulfur atom, and (d) a furyl group; and, each of the aromatic groups may be substituted with a substituent selected from the group consisting of a $C_1$–$C_8$ alkyl group, a substituted $C_1$–$C_8$ alkyl group, a halogen atom, nitro, a $C_2$–$C_6$ alkoxy-carbonyl group, carboxyl and a group selected from the group shown by formulae: —$OR_3$, —$NR_6R_7$, —$CONR_6R_7$, —$SO_2NR_6R_7$, and —$S(O)_nR_{40}$;

provided that at least one of $R_1$, $R_a$ or $R_2$ is a substituted $C_1$–$C_8$ alkyl group wherein the substituent is a carboxyl or a $C_2$–$C_6$ alkoxycarbonyl group; or, a pharmaceutically acceptable acid addition salt thereof.

6. An indoloylguanidine derivative or a pharmaceutically acceptable acid addition salt thereof according to claim 5, wherein:

$R_1$ represents a hydrogen atom, a $C_1$–$C_8$ alkyl group, a substituted $C_1$–$C_8$ alkyl group, a $C_2$–$C_6$ alkenyl group, a $C_2$–$C_6$ alkynyl group, a $C_3$–$C_7$ cycloalkyl group, a halogen atom, nitro, a $C_2$–$C_8$ alkanoyl group, an arylalkanoyl group having carbon atoms up to 10, an aroyl group having carbon atoms up to 11, carboxyl, a $C_2$–$C_6$ alkoxycarbonyl group, an aromatic group, a group shown by formula: —$OR_3$, —$NR_6R_7$, —$SO_2NR_6R_7$ or —$S(O)_nR_{40}$;

$R_2$ represents a hydrogen atom, a $C_1$–$C_8$ alkyl group, a substituted $C_1$–$C_8$ alkyl group, a $C_3$–$C_7$ cycloalkyl group, hydroxy, a $C_1$–$C_6$ alkoxy group, a group shown by formula: —$CH_2R_{20}$ or an aromatic group;

when $R_2$ is an aromatic group, $R_a$ represents $R_1$;

when $R_2$ is a hydrogen atom, a $C_1$–$C_8$ alkyl group, a substituted $C_1$–$C_8$ alkyl group, a $C_3$–$C_7$ cycloalkyl group, hydroxy, a $C_1$–$C_6$ alkoxy group or —$CH_2R_{20}$;

$R_a$ represents an aryl-$C_1$–$C_8$ alkyl group or a hetero-aryl-$C_1$–$C_8$ alkyl group, in which the aryl moiety in these groups contains a substituent(s) selected from the group consisting of a $C_1$–$C_8$ alkyl group, a substituted $C_1$–$C_8$ alkyl group, a $C_2$–$C_6$ alkoxycarbonyl group, carboxyl, —$CONR_6R_7$, —$SO_2NR_6R_7$ and —$S(O)_nR_{40}$; or, $R_a$ represents a group shown by formula: —A—$R_b$, in which A represents an oxygen atom or a group shown by formula: —$S(O)_n$— or —$N(_{50})$— (in which $R_{50}$ is a hydrogen atom or a $C_1$–$C_8$ alkyl group); $R_b$ represents an aryl group or a hetero-aryl group in which the aryl moiety and the hetero-aryl group may contain a substituent(s) selected from the group consisting of a $C_1$–$C_8$ alkyl group, a substituted $C_1$–$C_8$ alkyl group, a halogen atom, nitro, a $C_2$–$C_6$ alkoxycarbonyl group, carboxyl —$OR_3$, —$NR_6R_7$, —$CONR_6R_7$, —$SO_2NR_6R_7$ and —$S(O)_nR_{40}$; or, $R_a$ represents a group shown by formula:

—A—$(CH_2)_m$—$R_c$ wherein A represents an oxygen atom or a group shown by formula: —$S(O)_n$— or —$N(R_{50})$— (in which $R_{50}$ is a hydrogen atom or a $C_1$–$C_8$ alkyl group); $R_c$ represents an aryl group or a hetero-aryl group in which the aryl moiety and the hetero-aryl group contain a substituent (s) selected from the group consisting of a $C_1$–$C_8$ alkyl group, a substituted $C_1$–$C_8$ alkyl group, a $C_2$–$C_6$ alkoxycarbonyl group, carboxyl, —$CONR_6R_7$, —$OR_{31}$, —$SO_2NR_6R_7$ and —$S(O)_nR_{40}$; m represents 1 to 8; and $R_{31}$ represents a substituted $C_1$–$C_8$ alkyl group, a $C_3$–$C_7$ cycloalkyl group or —$CH_2R_{30}$ (in which $R_{30}$ represents a $C_2$–$C_6$ alkenyl group or a $C_2$–$C_6$ alkynyl group);

$R^3$ represents a hydrogen atom, a $C_1$–$C_8$ alkyl group, a substituted $C_1$–$C_8$ alkyl group, a $C_3$–$C_7$ cycloalkyl group, an aromatic group or a group shown by formula: —$CH_2R_{30}$ in which $R_{30}$ represents a $C_2$–$C_6$ alkenyl group or a $C_2$–$C_6$ alkynyl group;

each of $R_6$ and $R_7$ independently represents a hydrogen atom, a $C_1$–$C_8$ alkyl group, a substituted $C_1$–$C_8$ alkyl group, a $C_3$–$C_7$ cycloalkyl group, a $C_2$–$C_8$ alkanoyl group, an arylalkanoyl group having carbon atoms up to 10, an aroyl group having carbon atoms up to 11, an aromatic group or a group shown by formula: —$CH_2R_{60}$ (in which $R_{60}$ represents a $C_2$–$C_6$ alkenyl group or a $C_2$–$C_6$ alkynyl group); or $R_6$ and $R_7$ are combined together to form a saturated 5-to 7-membered cyclic amino group which may contain other hetero atom(s) in the ring thereof;

$R_{40}$ represents a $C_1$–$C_8$ alkyl group or a substituted $C_1$–$C_8$ alkyl group;

n represents 0, 1 or 2; and, $R_{20}$ represents a $C_2$–$C_6$ alkenyl group or a $C_2$–$C_6$ alkynyl group;

in which:

the substituent(s) of said substituted $C_1$–$C_8$ alkyl group means a halogen atom, hydroxy, a $C_1$–$C_6$ alkoxy group, cyano, carboxyl, a $C_2$–$C_6$ alkoxycarbonyl group, a $C_2$–$C_8$ alkanoyl group, an arylalkanoyl group having carbon atoms up to 10, an aroyl group having carbon atoms up to 11, an aromatic group, and —$CONR_4R_5$ in which each of $R_4$ and $R_5$ independently represents a hydrogen atom or a $C_1$–$C_8$ alkyl group or $R_4$ and $R_5$ are combined together to form a saturated 5- to 7-membered cyclic amino group which may contain other hetero atom(s) in the ring; —NR$_6$R$_7$; or a group shown by:

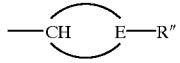

in which:

E represents a nitrogen atom or a CH group and

R" represents a hydrogen atom, a C$_1$–C$_8$ alkyl group or a substituted C$_1$–C$_8$ alkyl group substituted with hydroxy, a C$_1$–C$_6$ alkoxy group, cyano, carboxyl, a C$_2$–C$_6$ alkoxycarbonyl group, a C$_2$–C$_8$ alkanoyl group, an arylalkanoyl group having carbon atoms up to 10, an aroyl group having carbon atoms up to 11, an aromatic group, a group shown by —NR$_6$R$_7$, or a group shown by —CONR$_4$R$_5$, in which each of R$_4$ and R$_5$ independently represents a hydrogen atom or a C$_1$–C$_8$ alkyl group or R$_4$ and R$_5$ are combined together to form a saturated 5- to 7-membered cyclic amino group which may contain other hetero atom(s) therein; and the ring of

is a 3- to 8-membered saturated aliphatic ring or saturated hetero ring containing one nitrogen atom;

each of the aromatic groups being selected from the group consisting of (a) an aryl group having carbon atoms up to 10, (b) a 5- or 6-membered hetero-aryl group containing 1 to 4 nitrogen atom(s), (c) a 5- or 6-membered hetero-aryl group containing 1 to 2 nitrogen atom(s) and one oxygen atom or one sulfur atom, and (d) a furyl group; and, each of the aromatic groups may be substituted with a substituent selected from the group consisting of a C$_1$–C$_8$ alkyl group, a substituted C$_1$–C$_8$ alkyl group, a halogen atom, nitro, a C$_2$–C$_6$ alkoxy-carbonyl group, carboxyl and a group selected from the group shown by formulae: —OR$_3$, —NR$_6$R$_7$, —CONR$_6$R$_7$, —SO$_2$NR$_6$R$_7$ and —S(O)$_n$R$_{40}$.

7. An indoloylguanidine derivative or a pharmaceutically acceptable acid addition salt thereof according to claim 6, which is represented by general formula (3):

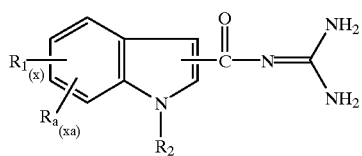

(3)

wherein:

the guanidinocarbonyl group may be located at any open position on either the 5- membered or 6-membered rings comprising the indole nucleus, x+xa=5 wherein x is 3 or 4 and xa is 1 or 2 such that each R$_1$ and each Ra is located at the positions on the indole nucleus not occupied by the guanidinocarbonyl group, and each R$_1$ independently represents a hydrogen atom, a C$_1$–C$_8$ alkyl group, a substituted C$_1$–C$_8$ alkyl group, a C$_2$–C$_6$ alkenyl group, a C$_2$–C$_6$ alkynyl group, a C$_3$–C$_7$ cycloalkyl group, a halogen atom, nitro, a C$_2$–C$_8$ alkanoyl group, an arylalkanoyl group having carbon atoms up to 10, an aroyl group having carbon atoms up to 11, carboxyl, a C$_2$–C$_6$ alkoxycarbonyl group, an aromatic group, a group shown by formula: —OR$_3$, —NR$_6$R$_7$, —SO$_2$NR$_6$R$_7$ or —S(O)$_n$R$_{40}$;

R$_2$ represents a hydrogen atom, a C$_1$–C$_8$ alkyl group, a substituted C$_1$–C$_8$ alkyl group, a C$_3$–C$_7$ cycloalkyl group, hydroxy, a C$_1$–C$_6$ alkoxy group, a group shown by formula: —CH$_2$R$_{20}$ or an aromatic group;

R$_a$ contains one or two substituent(s), which may be the same or different and represents an aryl-C$_1$–C$_8$ alkyl group or a hetero-aryl-C$_1$–C$_8$ alkyl group, in which the aryl moiety in these groups contains a substituent(s) selected from the group consisting of a C$_1$–C$_8$ alkyl group, a substituted C$_1$–C$_8$ alkyl group, a C$_2$–C$_6$ alkoxycarbonyl group, carboxyl, —CONR$_6$R$_7$ and —SO$_2$NR$_6$R$_7$; or R$_a$ represents a group shown by formula: —A—R$_b$, in which A represents an oxygen atom or a group shown by formula: —S(O)$_n$— or —N(R$_{50}$)— (in which R$_{50}$ is a hydrogen atom or a C$_1$–C$_8$ alkyl group); R$_b$ represents an aryl group or a hetero-aryl group in which the aryl moiety and the hetero-aryl group contain a substituent (s) selected from the group consisting of a C$_1$–C$_8$ alkyl group, a C$_1$–C$_8$ alkyl group substituted with —NR$_6$R$_7$, a halogen atom, nitro, a C$_2$–C$_6$ alkoxycarbonyl group, carboxyl, —OR$_3$, —NR$_6$R$_7$, —CONR$_6$R$_7$, —SO$_2$NR$_6$R$_7$ or, R$_a$ represents a group shown by formula:

wherein A represents an oxygen atom or a group shown by formula: —S(O)$_n$— or —N(R$_{50}$)— (in which R$_{50}$ is a hydrogen atom or a C$_1$–C$_8$ alkyl group); R$_c$ represents an aryl group or a heteroaryl group in which the aryl moiety and the hetero-aryl group contain a substituent (s) selected from the group consisting of a C$_1$–C$_8$ alkyl group, a C$_1$–C$_8$ alkyl group substituted with —NR$_6$R$_7$, a C$_2$–C$_6$ alkoxycarbonyl group, carboxyl, —CONR$_6$R$_7$—, —OR$_{31}$ and —SO$_2$NR$_6$R$_7$; m represents 1 to 8; and, R$_{31}$ represents a substituted C$_1$–C$_8$ alkyl group, a C$_3$–C$_7$ cycloalkyl group or —CH$_2$R$_{30}$ (in which R$_{30}$ represents a C$_2$–C$_6$ alkenyl group or a C$_2$–C$_6$ alkynyl group);

R$_3$ represents a hydrogen atom, a C$_1$–C$_8$ alkyl group, a substituted C$_1$–C$_8$ alkyl group, a C$_3$–C$_7$ cycloalkyl group, or a group shown by formula: —CH$_2$R$_{30}$, in which R$_{30}$ represents a C$_2$–C$_6$ alkenyl group or a C$_2$–C$_6$ alkynyl group;

each of R$_6$ and R$_7$ independently represents a hydrogen atom, a C$_1$–C$_8$ alkyl group, a substituted C$_1$–C$_8$ alkyl group, a C$_3$–C$_7$ cycloalkyl group, a C$_2$–C$_8$ alkanoyl group, an arylalkanoyl group having carbon atoms up to 10, an aroyl group having carbon atoms up to 11, or a group shown by formula: —CH$_2$R$_{60}$ (in which R$_{60}$ represents a C$_2$–C$_6$ alkenyl group or a C$_2$–C$_6$ alkynyl group); or R$_6$ and R$_7$ are combined together to form a saturated 5- to 7-membered cyclic amino group which may contain other hetero atom(s) in the ring thereof;

R$_{40}$ represents a C$_1$–C$_8$ alkyl group or a substituted C$_1$–C$_8$ alkyl group;

n represents 0, 1 or 2; and,

R$_{20}$ represents a C$_2$–C$_6$ alkenyl group or a C$_2$–C$_6$ alkynyl group.

8. An indoloylguanidine derivative represented by formula (1):

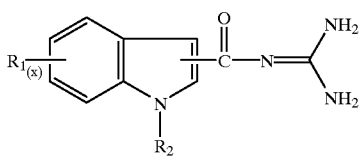

wherein:
the guanidinocarbonyl group may be located at any open position on either the 5-membered or 6-membered rings comprising the indole nucleus, x=5 so that $R_1$ is located at each position on the indole nucleus not occupied by the guanidinocarbonyl group, and each $R_1$ independently represents
a hydrogen atom,
a $C_1$–$C_8$ alkyl group,
an substituted $C_1$–$C_8$ alkyl group in which the substituent means a cycloalkyl group having 3 to 7 carbon atoms, a halogen atom, hydroxy, an alkoxy group having carbon atoms up to 6, cyano, carboxyl, a $C_2$–$C_6$ alkoxycarbonyl group, an alkanoyl group having carbon atom up to 8, an aryl group having carbon atoms up to 10 which may be substituted with hydroxy, an alkoxy group having carbon atoms up to 6, a halogen atom, nitro or a group shown by formula: —$NR_6R_7$; a 5 or 6-membered heteroaryl group containing 1 to 4 nitrogen atoms which may be substituted with hydroxy, an alkoxy group having carbon atoms up to 6, a halogen atom, nitro or a group shown by formula: —$NR_6R_7$; a 5 or 6-membered heteroaryl group containing 1 to 2 nitrogen atoms and one oxygen atom or one sulfur atom which may be substituted with hydroxy, an alkoxy group having carbon atoms up to 6, a halogen atom, nitro or a group shown by formula: —$NR_6R_7$; 2-furyl, 3-furyl, 2-thienyl, 3-thienyl or a group shown by formula: —$CONR_4R_5$ or —$NR_6R_7$,
an alkenyl group having carbon atoms up to 6,
an alkynyl group having 2 to 4 carbon atoms,
a cycloalkyl group having 3 to 7 carbon atoms,
a halogen atom,
a nitro group,
an alkanoyl group having carbon atoms up to 8,
an arylalkanoyl group having carbon atoms up to 10, an aroyl group having carbon atoms up to 11,
a carboxyl group,
an alkoxycarbonyl group having carbon atoms up to 6,
an aryl group having carbon atoms up to 10 which may be substituted with hydroxy, an alkoxy group having carbon atoms up to 6, a halogen atom, nitro or a group shown by formula: —$NR_6R_7$;
a 5 or 6-membered heteroaryl group containing 1 to 4 nitrogen atoms which may be substituted with hydroxy, an alkoxy group having carbon atoms up to 6, a halogen atom, nitro or a group shown by formula: —$NR_6R_7$;
a 5 or 6-membered hetoroaryl group containing 1 to 2 nitrogen atoms and one oxygen atom or one sulfur atom which may be substituted with hydroxy, an alkoxy group having carbon atoms up to 6, a halogen atom, nitro or a group shown by formula: —$NR_6R_7$; 2-furyl, 3-furyl, 2-thienyl, 3-thienyl or
a group shown by formula: —$OR_3$, —$NR_6R_7$, —$SO_2NR_6R_7$ or —$S(O)_nR_{40}$;

$R_2$ represents
a hydrogen atom,
an alkyl group having carbon atoms up to 8,
a substituted $C_1$–$C_8$ alkyl group as defined above,
a cycloalkyl group having 3 to 7 carbon atoms,
a hydroxy group,
an alkoxy group having carbon atoms up to 6, or
a group shown by formula: —$CH_2R_{20}$;

$R_3$ represents
a hydrogen atom,
an alkyl group having carbon atoms up to 8,
a substituted $C_1$–$C_8$ alkyl group as defined above,
a cycloalkyl group having 3 to 7 carbon atoms, or
a group shown by formula: —$CH_2R_{30}$, wherein $R_{30}$ represents an alkenyl group having carbon atoms up to 6, or an alkynyl group having 2 to 6 carbon atoms;

each of $R_4$ and $R_5$ independently represents hydrogen atom or an alkyl group having carbon atoms up to 8, or $R_4$ and $R_5$ are combined together to form a saturated 5- to 7-membered cyclic group containing 1 to 3 nitrogen atoms and a saturated 5- to 7-membered cyclic group containing one nitrogen atom and one oxygen atom;

each of $R_6$ and $R_7$ independently represents
a hydrogen atom,
an alkyl group having carbon atoms up to 8,
a substituted $C_1$–$C_8$ alkyl group in which the substituent means a cycloalkyl group having 3 to 7 carbon atoms, hydroxy, an alkoxy group having carbon atoms up to 6, carboxyl, an alkoxycarbonyl group having carbon atoms up to 6, an alkanoyl group having carbon atom up to 8, an aryl group having carbon atoms up to 10 or a group shown by formula: —$CONR_4R_5$ or —$NR_4R_5$,
a cycloalkyl group having 3 to 7 carbon atoms,
an alkanoyl group having carbon atoms up to 8,
an arylalkanoyl group having carbon atoms up to 10,
an aroyl group having carbon atoms up to 11,
a group shown by formula: —$CH_2R_{60}$, wherein $R_{60}$ represents an alkenyl group having carbon atoms up to 6, or an alkynyl group having 2 to 6 carbon atoms, or $R_6$ and $R_7$ are combined together to form a saturated 5- to 7-membered cyclic group containing 1 to 3 nitrogen atoms or a saturated 5- to 7-membered cyclic group containing one nitrogen atom and one oxygen atom;

$R_{40}$ represents an alkyl group having carbon atoms up to 8, or a substituted $C_1$–$C_8$ alkyl group as defined above, n represents 0, 1 or 2; and, $R_{20}$ represents an alkenyl group having carbon atoms up to 6 or an alkynyl group having 2 to 6 carbon atoms;

provided that said indoloylguanidine derivative does not include 1-methyl-2-indoloylguanidine; and at least one of $R_1$ or $R_2$ is a substituted $C_1$–$C_8$ alkyl group wherein the substituent is a carboxyl or a $C_2$–$C_6$ alkoxycarbonyl group;

or, a pharmaceutically acceptable acid addition salt thereof.

9. An indoloylguanidine derivative or a pharmaceutically acceptable acid addition salt thereof according to claim 8, which is a 2-indoloylguanidine compound.

10. An indoloylguanidine derivative represented by formula (2):

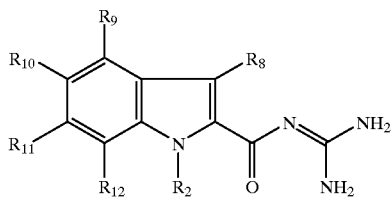

wherein:
each of $R_8$, $R_9$, $R_{10}$, $R_{11}$ and $R_{12}$ independently represents
a hydrogen atom,
an alkyl group having carbon atoms up to 8,
a substituted $C_1$–$C_8$ alkyl group in which the substituent means a cycloalkyl group having 3 to 7 carbon atoms, a halogen atom, hydroxy, an alkoxy group having carbon atoms up to 6, cyano, carboxyl, a $C_2$–$C_6$ alkoxycarbonyl group, an alkanoyl group having carbon atom up to 8, an aryl group having carbon atoms up to 10 which may be substituted with hydroxy, an alkoxy group having carbon atoms up to 6, a halogen atom, nitro or a group shown by formula: —$NR_6R_7$;
a 5 or 6-membered heteroaryl group containing 1 to 4 nitrogen atoms which may be substituted with hydroxy, an alkoxy group having carbon atoms up to 6, a halogen atom, nitro or a group shown by formula: —$NR_6R_7$; a 5 or 6-membered heteroaryl group containing 1 to 2 nitrogen atoms and one oxygen atom or one sulfur atom which may be substituted with hydroxy, an alkoxy group having carbon atoms up to 6, a halogen atom, nitro or a group shown by formula: —$NR_6R_7$; 2-furyl, 3-furyl, 2-thienyl, 3-thienyl or a group shown by formula: —$CONR_4R_5$ or —$NR_6R_7$,
an alkenyl group having carbon atoms up to 6,
an alkynyl group having 2 to 6 carbon atoms,
a cycloalkyl group having 3 to 7 carbon atoms,
a halogen atom,
a nitro group,
an alkanoyl group having carbon atoms up to 8,
an arylalkanoyl group having carbon atoms up to 10,
an aroyl group having carbon atoms up to 11,
a carboxyl group,
an alkoxycarbonyl group having carbon atoms up to 6,
an aryl group having carbon atoms up to 10 which may be substituted with hydroxy, an alkoxy group having carbon atoms up to 6, a halogen atom, nitro and a group shown by formula: —$NR_6R_7$;
a 5 or 6-membered heteroaryl group containing 1 to 4 nitrogen atoms which may be substituted with hydroxy, an alkoxy group; having carbon atoms up to 6, a halogen atom, nitro or a group shown by formula: —$NR_6R_7$;
a 5 or 6-membered hetoroaryl group containing 1 to 2 nitrogen atoms and one oxygen atom or one sulfur atom which may be substituted with hydroxy, an alkoxy group having carbon atoms up to 6, a halogen atom, nitro or a group shown by formula: —$NR_6R_7$; 2-furyl, 3-furyl, 2-thienyl, 3-thienyl or
a group shown by formula: $OR_3$, —$NR_6R_7$, —$SO_2NR_6R_7$ or —$S(O)_nR_{40}$;

$R_2$ represents
a hydrogen atom,
an alkyl group; having carbon atoms up to 8,
a substituted $C_1$–$C_8$ alkyl group as defined above,
a cycloalkyl group having 3 to 7 carbon atoms,
a hydroxy group,
an alkoxy group having carbon atoms up to 6, or
a group shown by formula: —$CH_2R_{20}$;
$R_3$ represents
a hydrogen atom,
an alkyl group having carbon atoms up to 8,
a substituted $C_1$–$C_8$ alkyl group as defined above,
a cycloalkyl group having 3 to 7 carbon atoms, or
a group shown by formula: —$CH_2R_{30}$, wherein $R_{30}$ represents an alkenyl group having carbon atoms up to 6, or an alkynyl group having 2 to 6 carbon atoms;
each of $R_4$ and $R_5$ independently represents hydrogen atom or an alkyl group having carbon atoms up to 8, or $R_4$ and $R_5$ are combined together to form a saturated 5- to 7-membered cyclic group containing 1 to 3 nitrogen atoms and a saturated 5- to 7-membered cyclic group containing one nitrogen atom and one oxygen atom;
each of $R_6$ and $R_7$ independently represents a hydrogen atom, an alkyl group having carbon atoms up to 8, a substituted $C_1$–$C_8$ alkyl group in which the substituent means a cycloalkyl group having 3 to 7 carbon atoms, hydroxy, an alkoxy group having carbon atoms up to 6, carboxyl, an alkoxycarbonyl group having carbon atoms up to 6, or an alkanoyl group having carbon atom up to 8, an aryl group having carbon atoms up to 10,
a cycloalkyl group having 3 to 7 carbon atoms,
an alkanoyl group having carbon atoms up to 8, an arylalkanoyl group having carbon atoms up to 10, or an aroyl group having carbon atoms up to 11, or
a group shown by formula: —$CH_2R_{60}$, wherein $R_{60}$ represents an alkenyl group having carbon atoms up to 6 or an alkynyl group having 2 to 6 carbon atoms; or
$R_6$ and $R_7$ are combined together to form a saturated 5- to 7-membered cyclic group containing 1 to 3 nitrogen atoms or a saturated 5- to 7-membered cyclic group containing one nitrogen atom and one oxygen atom;
$R_{40}$ represents an alkyl group having carbon atoms up to 8, or a substituted $C_1$–$C_8$ alkyl group as defined above,
n represents 0, 1 or 2; and,
$R_{20}$ represents an alkenyl group having carbon atoms up to 6 or an alkynyl group having 2 to 6 carbon atoms;
provided that said indoloylguanidine derivative does not include 1-methyl-2-indoloylguanidine; and at least one of $R_8$–$R_{12}$ and $R_2$ is a substituted $C_1$–$C_8$ alkyl group wherein the substituent is a carboxyl or a $C_2$–$C_6$ alkoxycarbonyl group; or,
a pharmaceutically acceptable acid addition salt thereof.

11. An indoloylguanidine derivative or a pharmaceutically acceptable acid addition salt thereof according to claim 10, wherein $R_8$ represents a hydrogen atom, and $R_{10}$ represents a hydrogen atom or a halogen atom.

12. An indolylguanidine derivative or a pharmaceutically acceptable acid addition salt thereof according to claim 1, wherein:
$R_1$ represents
a hydrogen atom,
an alkyl group having carbon atoms up to 8,
a cycloalkyl group having 3 to 7 carbon atoms,
a halogen atom,
a nitro group, and
a group shown by formula: —$OR_3$, or —$NR_6R_7$, $R_2$ represents
- a hydrogen atom,
- an alkyl group having carbon atoms up to 8,
- a substituted $C_1$–$C_8$ alkyl group in which the substituent means hydroxy, cyano, carboxyl, a $C_2$–$C_6$ alkoxycarbonyl group, an aryl group having carbon atoms up to 10 or carbamoyl, $R_3$ represents
- a hydrogen atom,
- an alkyl group having carbon atoms up to 8,
- a substituted $C_1$–$C_8$ alkyl group in which the substituent means a cycloalkyl group having 3 to 7 carbon atoms, an aryl group having carbon atoms up to 10, a 5 or 6-membered heteroaryl group containing 1 to 4 nitrogen atoms, a 5 or 6-membered heteroaryl group containing 1 to 2 nitrogen atoms and one oxygen atom or one sulfur atom,
- a cycloalkyl group having 3 to 7 carbon atoms or
- a group shown by formula: —$CH_2R_{30}$, wherein $R_{30}$ represents an alkenyl group having carbon atoms up to 6, or an alkynyl group having 2 to 6 carbon atoms;

each of $R_6$ and $R_7$ independently represents
- a hydrogen atom,
- an alkyl group having carbon atoms up to 8,
- a substituted $C_1$–$C_8$ alkyl group in which the substituent means a cycloalkyl group having 3 to 7 carbon atoms, an aryl group having carbon atoms up to 10, a 5 or 6 membered heteroaryl group containing 1 to 4 nitrogen atoms, a 5 or 6-membered heteroaryl group containing 1 to 2 nitrogen atoms and one oxygen atom or one sulfur atom,
- a cycloalkyl group having 3 to 7 carbon atoms,
- a group shown by formula: —$CH_2R_{60}$, wherein $R_{60}$ represents an alkenyl group having carbon atoms up to 6, or an alkynyl group having 2 to 6 carbon atoms, or $R_6$ and $R_7$, are combined together to form a saturated 5- to 7-membered cyclic group containing 1 to 3 nitrogen atoms or a saturated 5- to 7-membered cyclic group containing one nitrogen atom and one oxygen atom.

13. A pharmaceutical composition comprising as an active ingredient an effective amount of an indoloylguanidine derivative or a pharmaceutically acceptable acid addition salt thereof according to any one of claims 1–12 and a pharmaceutically acceptable carrier.

14. A method for treating a disease caused by increased $Na^+/H^+$ exchanger activity, which comprises administering to a patient a pharmaceutically effective dose of a compound according to any one of claims 1–12, or a pharmaceutically acceptable acid addition salt thereof.

15. A method according to claim 14, wherein the disease is selected from the group consisting of hypertension, arrhythmia, angina pectoris, cardiac hypertrophy, diabetes, disorders associated with ischemia or ischemic reperfusion, cerebroishemic disorders, and diseases caused by excessive cell proliferation.

* * * * *